US012502434B2

(12) United States Patent
Yu et al.

(10) Patent No.: US 12,502,434 B2
(45) Date of Patent: Dec. 23, 2025

(54) COMPOUND COMPRISING EZH2 INHIBITOR AND E3 LIGASE BINDER AND PHARMACEUTICAL COMPOSITION FOR PREVENTING OR TREATING EZH2-ASSOCIATED DISEASE COMPRISING SAME AS ACTIVE INGREDIENT

(71) Applicant: DAEGU-GYEONGBUK MEDICAL INNOVATION FOUNDATION, Daegu (KR)

(72) Inventors: Ji-Hoon Yu, Daegu (KR); Chun Young Im, Daegu (KR); So Young Kim, Daegu (KR); Ye Ri Han, Daegu (KR); Doohyun Lee, Daegu (KR); Hui-Jeon Jeon, Daegu (KR); Sang-Hyun Min, Daegu (KR); Bae Jun Oh, Daegu (KR); Sang-Wook Park, Daegu (KR); Dong-Kyu Choi, Daegu (KR); Young-Kyu Kim, Daegu (KR); Sung Hwan Kim, Daegu (KR); Yuri Lee, Daegu (KR); Seungyeon Lee, Daegu (KR); Nam Hui Kim, Daegu (KR); Sang Bum Kim, Daegu (KR); Ju-Sik Min, Daegu (KR)

(73) Assignee: DAEGU-GYEONGBUK MEDICAL INNOVATION FOUNDATION, Daegu (KR)

( * ) Notice: Subject to any disclaimer, the term of this patent is extended or adjusted under 35 U.S.C. 154(b) by 826 days.

(21) Appl. No.: 17/773,325

(22) PCT Filed: Oct. 29, 2020

(86) PCT No.: PCT/KR2020/014936
§ 371 (c)(1),
(2) Date: Apr. 29, 2022

(87) PCT Pub. No.: WO2021/086069
PCT Pub. Date: May 6, 2021

(65) Prior Publication Data

US 2023/0010508 A1 Jan. 12, 2023

(30) Foreign Application Priority Data

Oct. 31, 2019 (KR) ........................ 10-2019-0137938

(51) Int. Cl.

*A61K 47/55* (2017.01)
*A61K 47/54* (2017.01)
*A61P 35/00* (2006.01)
*C07D 405/14* (2006.01)

(52) U.S. Cl.
CPC ............ *A61K 47/55* (2017.08); *A61K 47/545* (2017.08); *A61P 35/00* (2018.01); *C07D 405/14* (2013.01)

(58) Field of Classification Search
CPC ........ A61K 47/55; A61K 47/545; A61P 35/00
See application file for complete search history.

(56) References Cited

U.S. PATENT DOCUMENTS

2018/0177750 A1* 6/2018 Crew .................. A61K 31/351

FOREIGN PATENT DOCUMENTS

| | | | | |
|---|---|---|---|---|
| CN | 111303133 | A | 6/2020 | |
| KR | 10-2018-0029061 | A | 3/2018 | |
| KR | 10-2019-0084063 | A | 7/2019 | |
| WO | WO 2017-210395 | A1 | 12/2017 | |
| WO | WO-2018081530 | A1 * | 5/2018 | ............ A61K 47/55 |
| WO | WO 2018-119357 | A1 | 6/2018 | |
| WO | WO 2021/238007 | A1 | 12/2021 | |

OTHER PUBLICATIONS

Itoh, Journal of the American Chemical Society, 132, 16, Apr. 28, 2010, pp. 5820-5826 (Year: 2010).*
Duan, Journal of Hematology and Oncology, 2020, 13:104 (Year: 2020).*
International Search Report from parent PCT Application No. PCT/KR2020/014936, 5 pages (mailed Feb. 9, 2021).

* cited by examiner

*Primary Examiner* — Andrew D Kosar
*Assistant Examiner* — Phillip Matthew Rzeczycki
(74) *Attorney, Agent, or Firm* — Klarquist Sparkman, LLP

(57) ABSTRACT

The present invention relates to a compound comprising an EZH2 inhibitor and an E3 ligase binder, and a pharmaceutical composition for preventing or treating EZH2-associated disease and a pharmaceutical composition for selective protein degradation containing the same as an active ingredient. Since the compound of the present invention can selectively degrade EZH2, it can be effectively used for the treatment of EZH2-related diseases and cancers, particularly, cancers in which EZH2 is overexpressed, and can be usefully used for the selective degradation of EZH2.

7 Claims, 4 Drawing Sheets

COMPOUND COMPRISING EZH2 INHIBITOR AND E3 LIGASE BINDER AND PHARMACEUTICAL COMPOSITION FOR PREVENTING OR TREATING EZH2-ASSOCIATED DISEASE COMPRISING SAME AS ACTIVE INGREDIENT

CROSS REFERENCE TO RELATED APPLICATIONS

This is the U.S. National Stage of International Application No. PCT/KR2020/014936, filed on Oct. 29, 2020, which claims the benefit of Korean Patent Application No. 10-2019-0137938, filed on Oct. 31, 2019

BACKGROUND OF THE INVENTION

1. Field of the Invention

The present invention relates to a compound comprising an EZH2 inhibitor and an E3 ligase binder, and a pharmaceutical composition for preventing or treating EZH2-associated disease and a pharmaceutical composition for selective protein degradation containing the same as an active ingredient.

2. Description of the Related Art

Polycomb Group (PcG) protein was first known to inhibit Hox gene transcription, which plays an important role in the early development of *Drosophila*, through a mutation experiment using *Drosophila*. It is known that this function is opposite to that of Trithorax Group (TrxG) proteins found in *Drosophila*, which promotes specific gene transcription. It was demonstrated that the functions of PcG proteins were well conserved in vertebrates as spinal malformations appeared in the mutants in which the functions of PcG proteins were suppressed. It is known that the gene transcriptional repression by PcG protein is caused by changing the structure of histone that is bound to a specific gene. Methods used for the structural change of histone by these PcG proteins are largely based on methylation and a method of attaching ubiquitin to specific histones. PcG proteins can be referred to as enzyme complexes that play the role of methyltransferase and ubiquitin ligase. In addition, some PcG proteins induce histone deacetylation or induce DNA methylation. Therefore, transcription of a specific gene is suppressed according to the activity of PcG proteins, and a phenotypic change of a specific cell occurs by this function.

PcG proteins form two well-conserved complexes in eukaryotes, and divided into polycomb repressive complex 1 (PRC1) and polycomb repressive complex 2 (PRC2). There are four types of proteins that make up the complex in PRC1, and these include BMI-1, CBX2, RING1A/B, and EDR1 (PHC1). There are three types of proteins that make up the complex in PRC2, and these include EED, SUZ12 and EZH2 (ENX2).

Specifically, the EZH2 (enhancer of zeste homolog 2) is a major catalytic subunit of polycomb repressive complex 2 (PRC2) that promotes methylation of histone H3 lysine 27 (H3K27), and trimethylation of H3K27 (H3K27me3) is a transcriptionally repressive epigenetic mark that regulates gene expression, differentiation and development. In addition to EZH2, dysregulation of other PRC2 components (eg EED and SUZ12) and/or H3K27 trimethylation is associated with a number of cancers.

For example, EZH2 is overexpressed in a wide range of cancers including prostate cancer, breast cancer, myeloma and lymphoma, and it has been known that high EZH2 expression is associated with a bad prognosis of cancer. Hyper-trimethylation of H3K27 catalyzed by PRC2 induces tumorigenesis and progression of cancers including diffused large B cell lymphoma (DLBCL) and malignant rhabdoid tumor (MRT).

Therefore, pharmacological inhibition of EZH2 has been pursued as a targeted therapy to treat these cancers. Indeed, EZH2 inhibitors that effectively inhibit the methyltransferase activity of EZH2 have been demonstrated to exhibit robust antiproliferative activity in DLBCL and MRT cells and animal models, and many EZH2 inhibitors have been reported. Among them, EPZ-6438, GSK126, CPI-1205 and PF-06821497 are in the I/II clinical trial stage to treat lymphoma and several subtypes of MRT.

In addition, EZH2 has been shown to downregulate the tumor/metastasis suppressor RKIP (Raf-1 kinase inhibitor protein), the tumor suppressor KLF2 (Kruppel-like factor), the forkhead box transcription factor FOXC1 (Forkhead box 01), and the tumor suppressor RUNX3 (Runt-related transcription factor 3).

In addition, until now, low-molecular compounds have focused on inhibiting the function of disease-related proteins, but recent research trends are targeting undruggable target proteins for new therapeutic agents and the development of a selective proteolysis method that removes disease-related proteins themselves. This is expected the removal of the "target" and also to be able to overcome the resistance of previously developed drugs.

As part of the development of the selective proteolysis method, PROTAC (Proteolysis-targeting chimaera) technology was devised. PROTAC is a method that can selectively remove target proteins using the ubiquitin-proteasome pathway, and is a low-molecular compound-based drug development platform technology.

Intracellular protein degradation occurs through two pathways by lysosomes and proteasomes. Most (80%) of cellular proteins are labeled with ubiquitin and then degraded in the cytoplasm and nucleus by the proteasome. This process is called ubiquitin-proteasome system (UPS). A series of enzymes (E1, E2 and E3) are involved in the ubiquitination process in which ubiquitin is labeled to selectively degrade proteins, and the labeled protein is degraded by the 26S proteasome, an ATP-dependent protease complex.

In humans, it is estimated that there are 2 types of E1, 40 types of E2, and 600-700 types of E3. In particular, E3 is divided into HECT, RING-finger, U-Box, and PHD-finger according to the structure and function. Importantly, E3 binds to both E2 and substrate proteins, providing specificity for recognizing substrate proteins to be labeled with ubiquitin. That is, the selection of the target protein to be degraded is determined by the E3 enzyme in the ubiquitination process. At this time, all substrate proteins have a recognition site by a specific E3 enzyme and an ubiquitin linkage site. By E2 complexed with E3 ligase, polyubiquitination is induced on the lysine residue of the target protein, and the target protein is degraded by the proteosome.

PROTAC technology is a bifunctional small molecule composed of E3 ligase binding module-connector-target protein binding module, and by the above mechanism, in vivo degradation of disease-causing target proteins is induced through ubiquitination. The PROTAC-based low-molecular compound used in this way has the advantage that it can be reused.

Accordingly, the present inventors have developed a pharmaceutical composition having the configuration of E3 ligase binding module-connector-EZH2 inhibitor by targeting EZH2 as a target protein.

SUMMARY OF THE INVENTION

It is an object of the present invention to provide a compound comprising an EZH2 inhibitor and an E3 ligase binder.

It is another object of the present invention to provide a method for preparing a compound comprising an EZH2 inhibitor and an E3 ligase binder.

It is another object of the present invention to provide a pharmaceutical composition for preventing or treating EZH2-related diseases, which contains a compound comprising an EZH2 inhibitor and an E3 ligase binder as an active ingredient.

To achieve the above objects, in one aspect of the present invention, the present invention provides a compound represented by formula 1, an isomer thereof, a solvate thereof, a hydrate thereof or a pharmaceutically acceptable salt thereof.

[Formula 1]

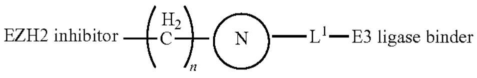

(In formula 1,
EZH2 inhibitor, E3 Ligase binder, n,

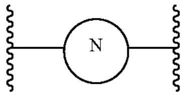

and $L^1$ are as defined in this specification).

In another aspect of the present invention, the present invention provides a compound represented by formula 2, an isomer thereof, a solvate thereof, a hydrate thereof or a pharmaceutically acceptable salt thereof.

[Formula 2]

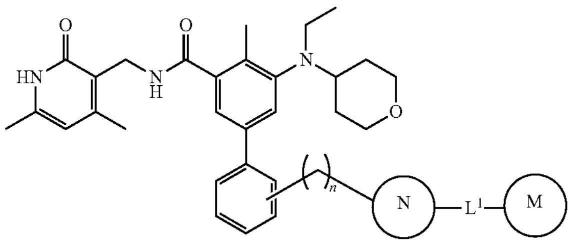

(In formula 2,
n,

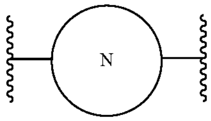

and $L^1$ are as defined in formula 1,

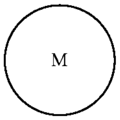

is any one selected from the group consisting of

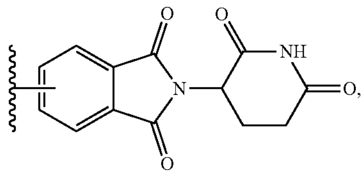

,

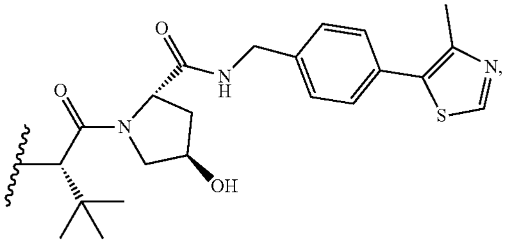

, and

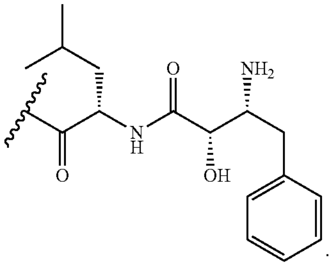

.)

In another aspect of the present invention, the present invention provides a pharmaceutical composition comprising a compound represented by formula 1 or formula 2, an isomer thereof, a solvate thereof, a hydrate thereof or a pharmaceutically acceptable salt thereof as an active ingredient for the prevention or treatment of cancer.

In another aspect of the present invention, the present invention provides a pharmaceutical composition comprising a compound represented by formula 1 or formula 2, an isomer thereof, a solvate thereof, a hydrate thereof or a pharmaceutically acceptable salt thereof as an active ingredient for the selective degradation of EZH2 protein.

In another aspect of the present invention, the present invention provides a health functional food comprising a compound represented by formula 1 or formula 2, an isomer thereof, a solvate thereof, a hydrate thereof or a pharmaceutically acceptable salt thereof as an active ingredient for the prevention or amelioration of cancer.

In another aspect of the present invention, the present invention provides a method for preventing or treating cancer, which comprises a step of administering a pharmaceutical composition or a health functional food comprising a compound represented by formula 1 or formula 2, an isomer thereof, a solvate thereof, a hydrate thereof or a pharmaceutically acceptable salt thereof as an active ingredient to a subject in need.

In another aspect of the present invention, the present invention provides a use of the pharmaceutical composition or the health functional food above comprising a compound represented by formula 1 or formula 2, an isomer thereof, a solvate thereof, a hydrate thereof or a pharmaceutically acceptable salt thereof as an active ingredient for the prevention or treatment of cancer.

Advantageous Effect

The compound comprising an EZH2 inhibitor and an E3 ligase binder of the present invention can selectively degrade EZH2. Therefore, the compound of the present invention can be effectively used for the treatment of EZH2-related diseases and cancers, particularly, cancers in which EZH2 is overexpressed, and can be usefully used for the selective degradation of EZH2.

DESCRIPTION OF THE PREFERRED EMBODIMENTS

Figure 1:
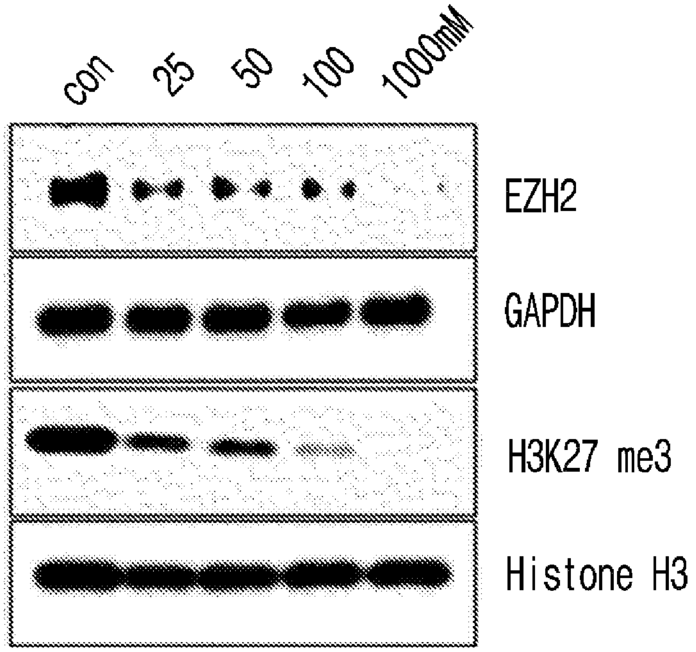
FIG. 1 is an image confirming the EZH2 proteolytic effect of the compound of Example 21 by Western blotting.
Figure 2:
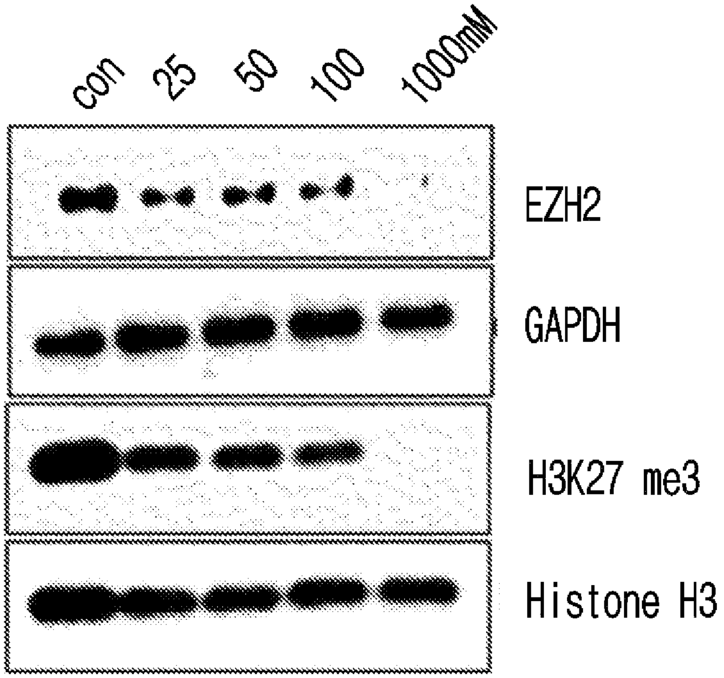
FIG. 2 is an image confirming the EZH2 proteolytic effect of the compound of Example 30 by Western blotting.
Figure 3:
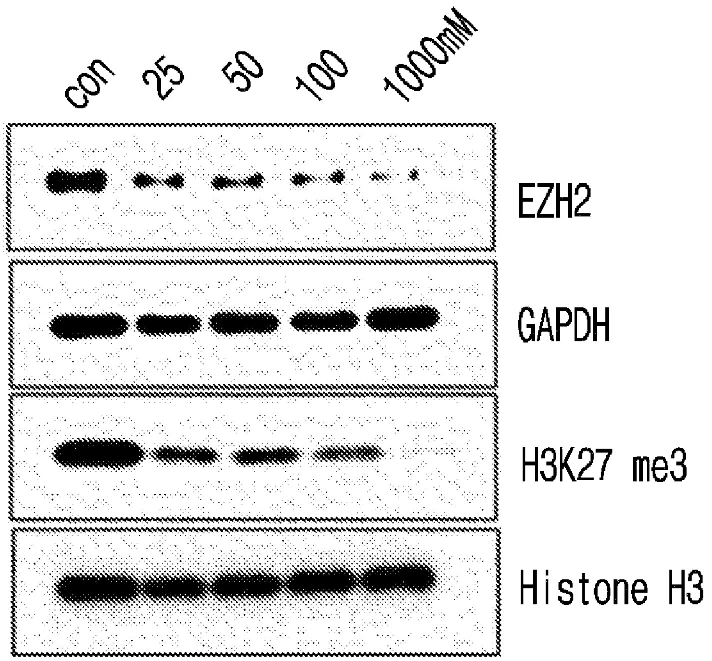
FIG. 3 is an image confirming the EZH2 proteolytic effect of the compound of Example 33 by Western blotting.
Figure 4:
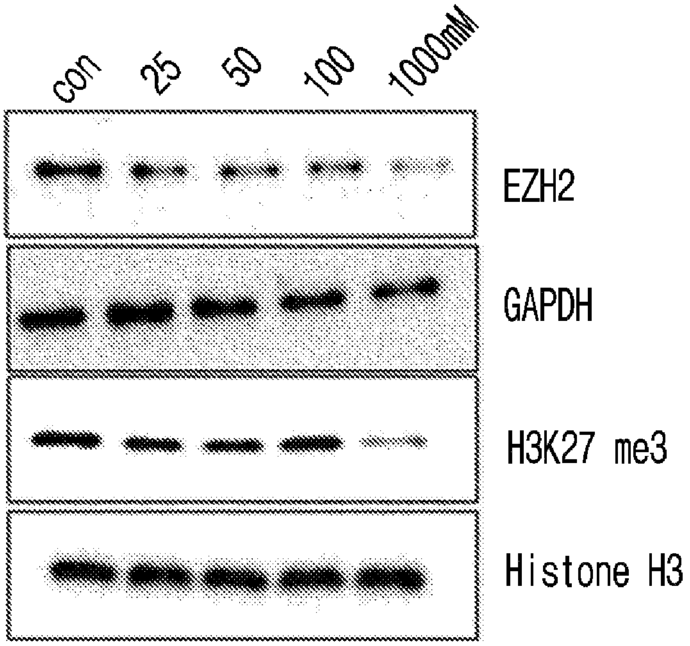
FIG. 4 is an image confirming the EZH2 proteolytic effect of the compound of Example 46 by Western blotting.
Figure 5:
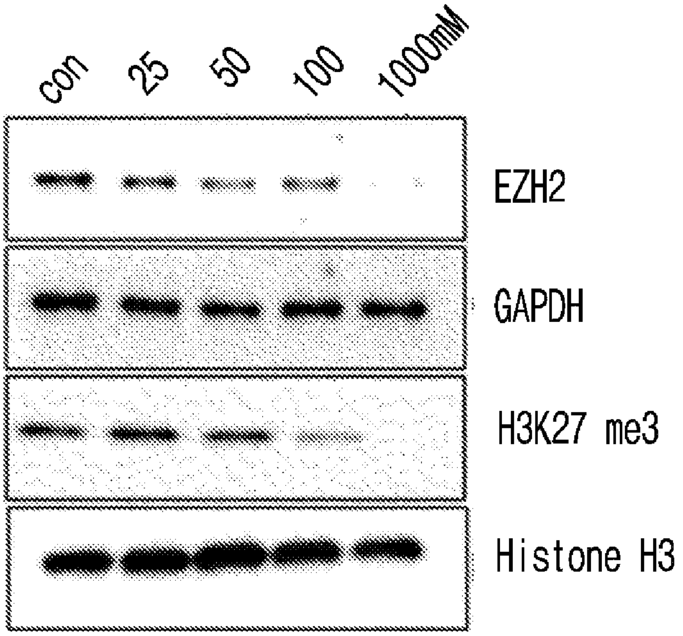
FIG. 5 is an image confirming the EZH2 proteolytic effect of the compound of Example 49 by Western blotting.

Hereinafter, the present invention is described in detail.

The embodiments of this invention can be modified in various other forms, and the scope of the present invention is not limited to the embodiments described below. It is well understood by those in the art who has the average knowledge on this field that the embodiments of the present invention are given to explain the present invention more precisely. In addition, the "inclusion" of an element throughout the specification does not exclude other elements, but may include other elements, unless specifically stated otherwise.

The present invention provides a compound represented by formula 1, an isomer thereof, a solvate thereof, a hydrate thereof or a pharmaceutically acceptable salt thereof.

[ Formula 1 ]

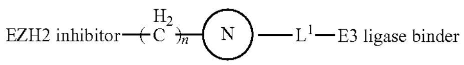

(In formula 1,

EZH2 inhibitor is a low molecular binding residue that can bind to EZH2 (enhancer of zeste homolog 2) and inhibit the activity of EZH2;

Ligase binder is a low molecular binding residue capable of binding to E3 ligase;

N is an integer of 1-5;

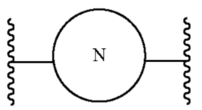

is —NH— or

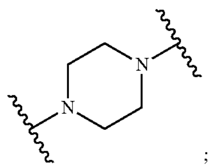 [SMILES: *N1CCN(*)CC1]

;

and $L^1$ is a spacer).

The compound represented by formula 1 of the present invention is intended to be introduced into PROTAC technology, and targets EZH2 as a target protein, and is not limited as long as it is a compound having a residue capable of binding to EZH2. In the present invention, an EZH2 inhibitor was introduced.

Specifically, in formula 1, the EZH2 inhibitor can be a low molecular weight compound known as an EZH2 inhibitor or a derivative thereof, and can be a compound selected from the following compound group or a derivative thereof. In one embodiment of the present invention, a derivative of tazemethostat (epz6438, EZH-6438, E-7438), which is widely known as an EZH2 inhibitor, was introduced, but this is only an example and is not limited thereto.

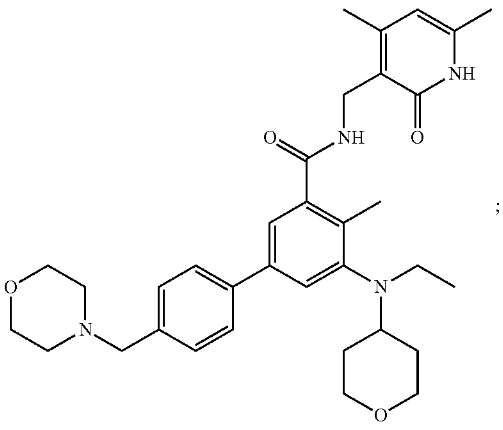

;

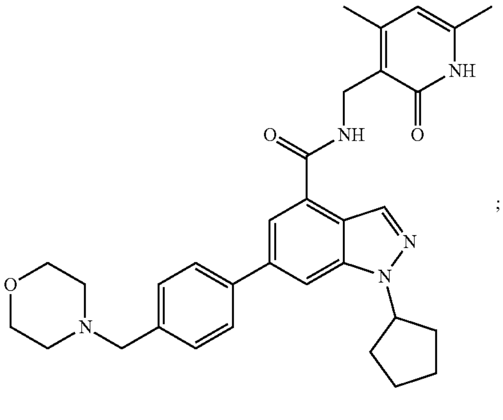

;

-continued

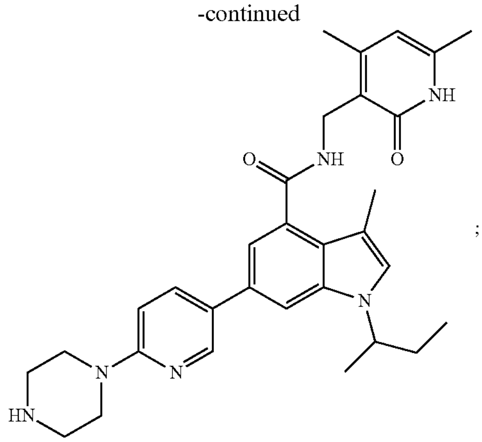

;

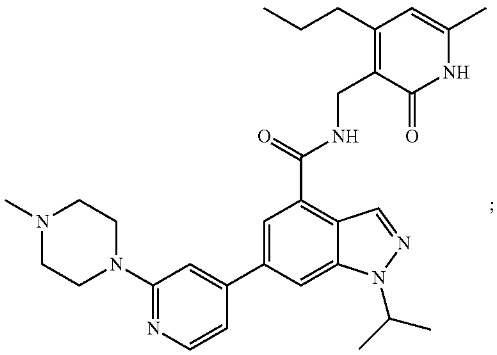

;

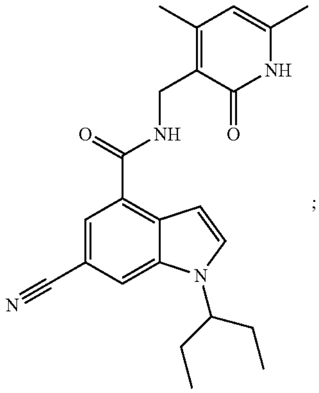

;

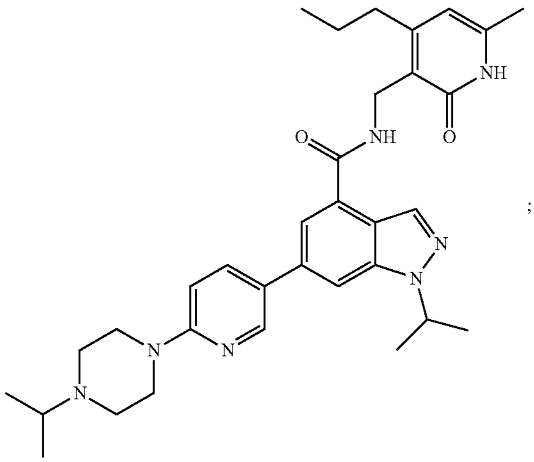

;

-continued

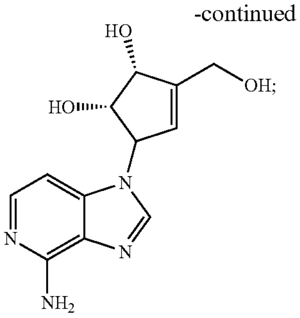

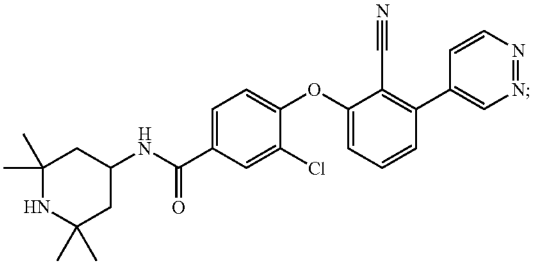

and

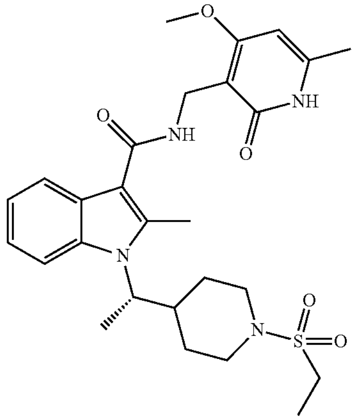 [SMILES: CCS(=O)(=O)N1CCC([C@H](C)n2c(C)c(C(=O)NCc3c(OC)cc(C)[nH]c3=O)c3ccccc32)CC1]

In addition, as the EZH2 inhibitor, an EZH1/EZH2 dual inhibitor can be used, and Valemetostat (DS-3201), which is widely known as an EZH1/EZH2 dual inhibitor, or a derivative thereof can be used, but not always limited thereto.

[Valemetostat]

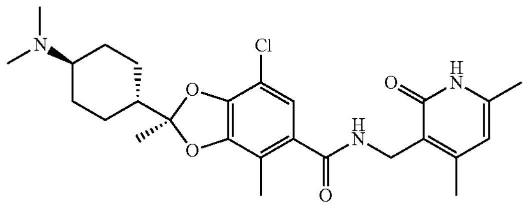

In addition, the compound represented by formula of the present invention is intended to be introduced into PROTAC technology, and is not limited as long as it is a compound having a residue capable of binding to E3 ligase. In the present invention, an E3 ligase binder was introduced.

In the present invention, the E3 ligase binder can be any one selected from the group consisting of a β-TRCP binder, a MDM2 binder, a cIAP/XIAP binder, a VHL binder, a HyT binder, an IAP binder, a Bestatin amido binder and a CRBN binder. In one embodiment of the present invention, thalidomide as a CRBN binder, (S,R,S)-AHPC hydrochloride as a VHL binder, and bestatin as an IAP binder were introduced, but this is only an example, but is not limited thereto.

In the compound represented by formula 1 of the present invention, an EZH2 inhibitor and an E3 ligase binder are connected by a linker containing —$CH_2$— and

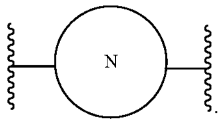

$L^1$ is a spacer and represents a site where

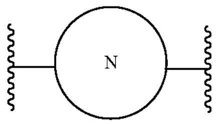

and an E3 ligase binder are connected. $L^1$ can be absent, or can be a linker consisting of a combination of one or more linkers selected from the group consisting of straight or branched $C_{1-20}$ alkylene, straight or branched $C_{2-20}$ alkenylene, straight or branched $C_{2-20}$ alkynylene, —O—, —S—. S(═O)— —$SO_2$—, —NH—, —N═, —C(═S)— and —C(═O)—.

In addition, the spacer can be a linker consisting of a combination of one or more linkers selected from the group consisting of straight or branched $C_{1-10}$ alkylene, —O—, —NH—, and —C(═O)—.

In addition, the spacer is

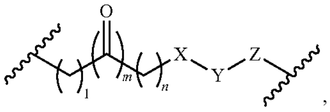, l, m, and n are each independently an integer of 0 to 6;

X is a single bond, or is selected from the group consisting of —NH—,

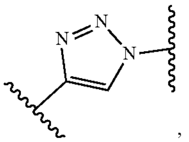,

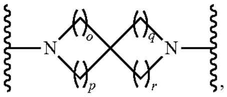, or

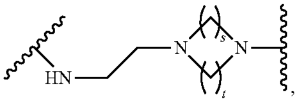, wherein o, p, q, r, s, and t are each independently an integer of 1 or 2;

Y is unsubstituted or oxo-substituted $C_{1-15}$ alkylene, wherein the alkylene can be substituted with —O—; and Z can be selected from the group consisting of —NH—, —O—, or —$NH(CH_2)_2NH$—.

In addition, the spacer can be any one selected from the group consisting of

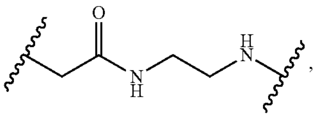, 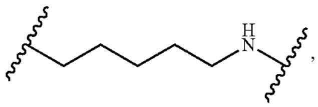, 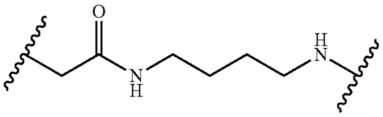,

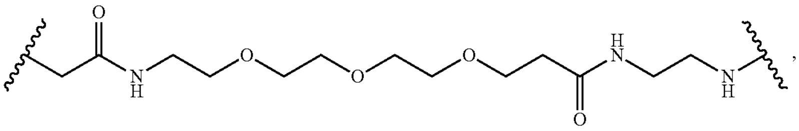, 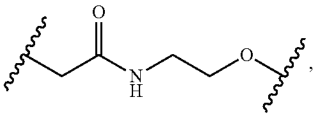,

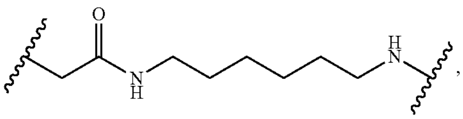, 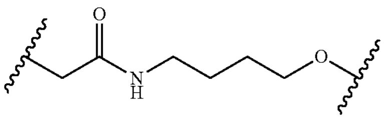,

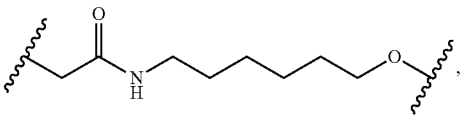, 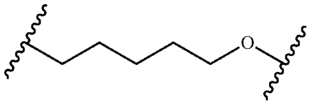,

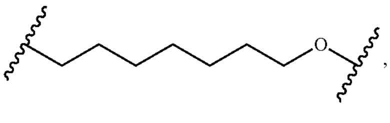, 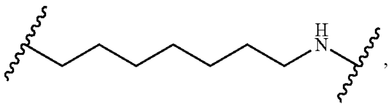, 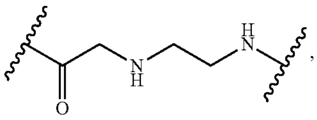,

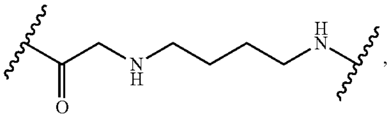, 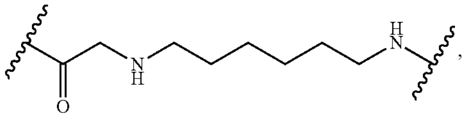,

-continued
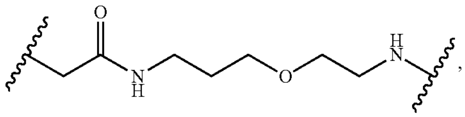 , 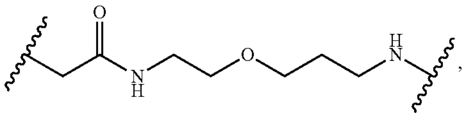 ,
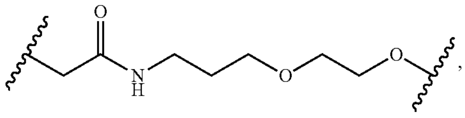 , 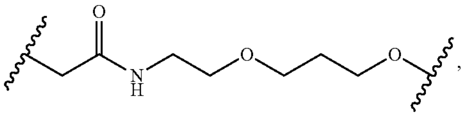 ,
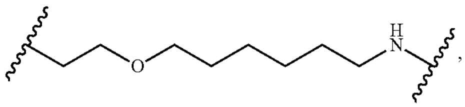 , 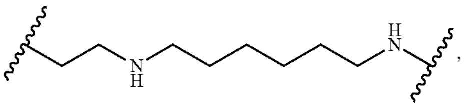 ,
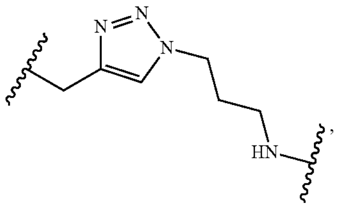 , 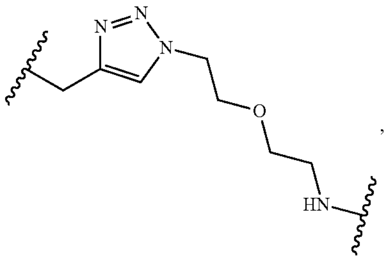 , 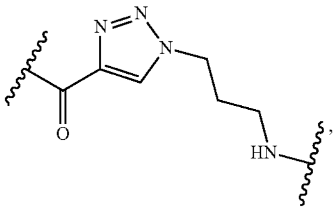 ,
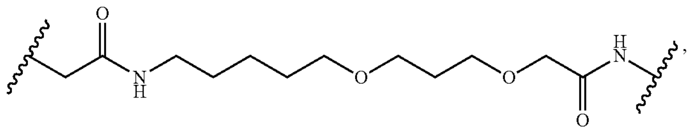 ,
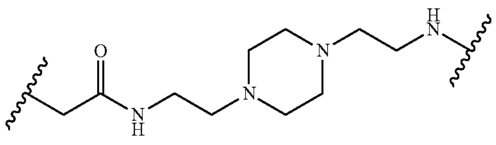 , 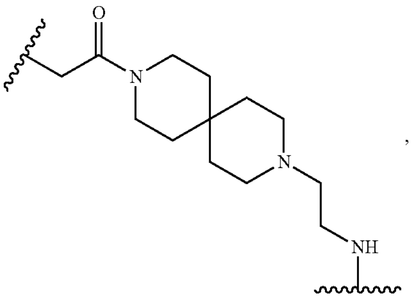 ,
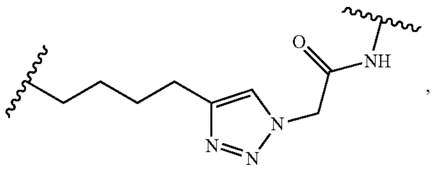 , 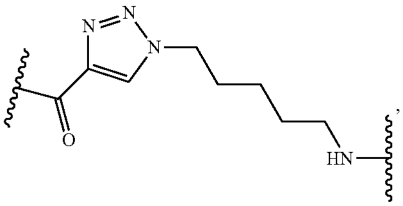 ,
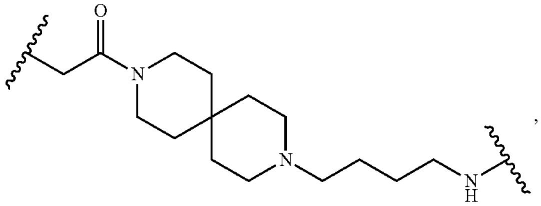 , 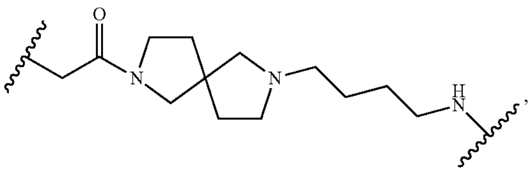 ,
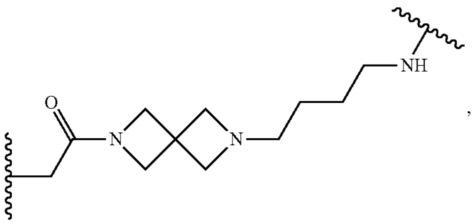 , 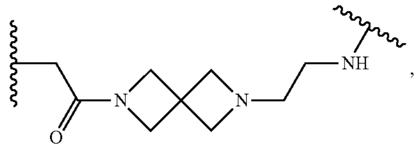 , -continued

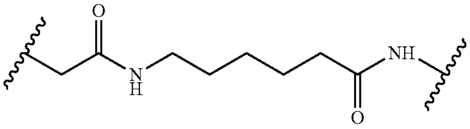
,
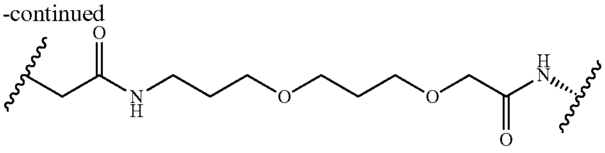
,
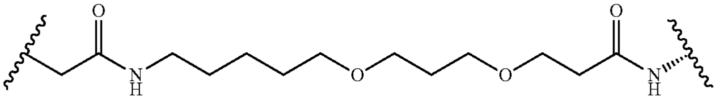
,
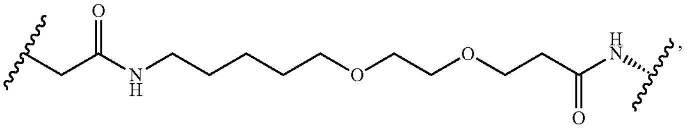
,
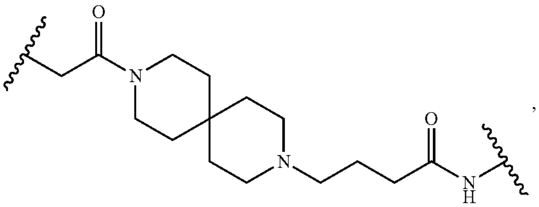
,
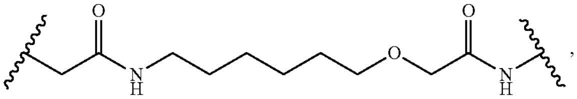
,
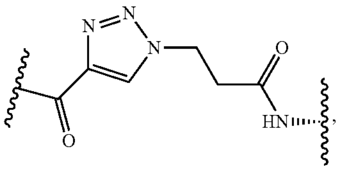
,
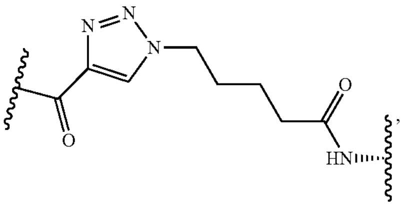
,
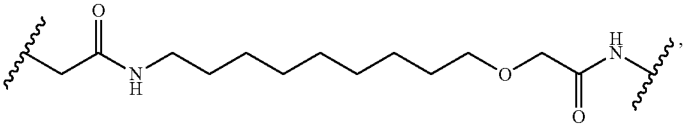
, and
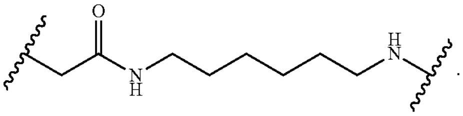
.

In formula 1 above, n can be an integer of 1-3, can be an integer of 1-2, and can be 1.

In another aspect of the present invention, the present invention provides a compound represented by formula 2, an isomer thereof, a solvate thereof, a hydrate thereof or a pharmaceutically acceptable salt thereof.

[ Formula 2 ]

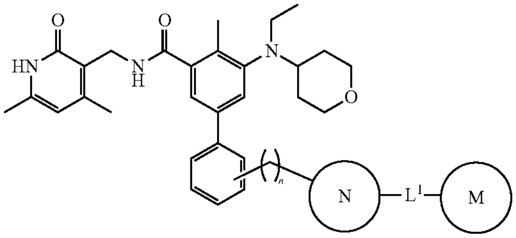

(In formula 2, n,

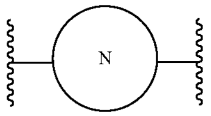

and $L^1$ are as defined in formula 1,

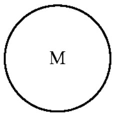

is any one selected from the group consisting of

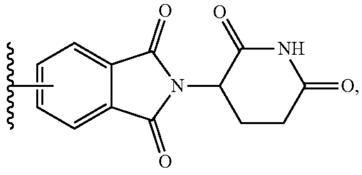
,

-continued

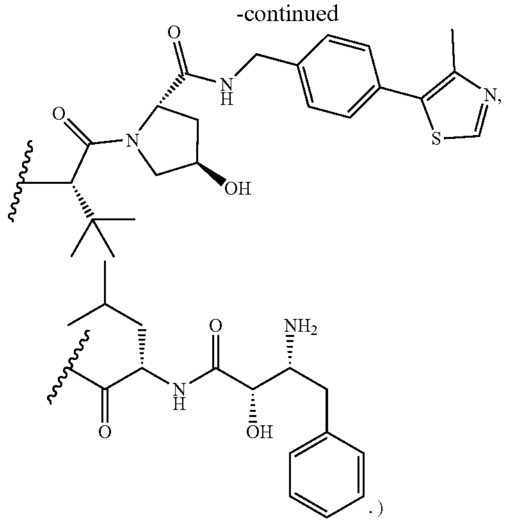

and

.)

Examples of the compound represented by formula 1 or formula 2 according to the present invention include the following compounds:

(1) N-((4,6-dimethyl-2-oxo-1,2-dihydropyridine-3-yl)methyl)-4'-((4-(2-((2-((2-(2,6-dioxopiperidine-3-yl)-1,3-dioxoisoindoline-4-yl)amino)ethyl)amino)-2-oxoethyl)piperazine-1-yl)methyl)-5-(ethyl(tetrahydro-2H-pyran-4-yl)amino)-4-methyl-[1,1'-biphenyl]-3-carboxamide (2) N-((4,6-dimethyl-2-oxo-1,2-dihydropyridine-3-yl)methyl)-4'-((4-(5-((2-(2,6-dioxopiperidine-3-yl)-1,3-dioxoisoindoline-4-yl)amino)pentyl)piperazine-1-yl)methyl)-5-(ethyl(tetrahydro-2H-pyran-4-yl)amino)-4-methyl-[1,1'-biphenyl]-3-carboxamide (3) N-((4,6-dimethyl-2-oxo-1,2-dihydropyridine-3-yl)methyl)-4'-((4-(2-((4-((2-(2,6-dioxopiperidine-3-yl)-1,3-dioxoisoindoline-4-yl)amino)butyl)amino)-2-oxoethyl)piperazine-1-yl)methyl)-5-(ethyl(tetrahydro-2H-pyran-4-yl)amino)-4-methyl-[1,1'-biphenyl]-3-carboxamide (4) N-((4,6-dimethyl-2-oxo-1,2-dihydropyridine-3-yl)methyl)-4'-((4-(18-((2-(2,6-dioxopiperidine-3-yl)-1,3-dioxoisoindoline-4-yl)amino)-2,15-dioxo-6,9,12-trioxa-3,16-diazaoctadecyl)piperazine-1-yl)methyl)-5-(ethyl(tetrahydro-2H-pyran-4-yl)amino)-4-methyl-[1,1'-biphenyl]-3-carboxamide (5) N-((4,6-dimethyl-2-oxo-1,2-dihydropyridine-3-yl)methyl)-4'-((4-(2-((2-((2-(2,6-dioxopiperidine-3-yl)-1,3-dioxoisoindoline-4-yl)oxy)ethyl)amino)-2-oxoethyl)piperazine-1-yl)methyl)-5-(ethyl(tetrahydro-2H-pyran-4-yl)amino)-4-methyl-[1,1'-biphenyl]-3-carboxamide (6) N-((4,6-dimethyl-2-oxo-1,2-dihydropyridine-3-yl)methyl)-4'-((4-(2-((6-((2-(2,6-dioxopiperidine-3-yl)-1,3-dioxoisoindoline-4-yl)amino)hexyl)amino)-2-oxoethyl)piperazine-1-yl)methyl)-5-(ethyl(tetrahydro-2H-pyran-4-yl)amino)-4-methyl-[1,1'-biphenyl]-3-carboxamide (7) N-((4,6-dimethyl-2-oxo-1,2-dihydropyridine-3-yl)methyl)-4'-((4-(2-((4-((2-(2,6-dioxopiperidine-3-yl)-1,3-dioxoisoindoline-4-yl)oxy)butyl)amino)-2-oxoethyl)piperazine-1-yl)methyl)-5-(ethyl(tetrahydro-2H-pyran-4-yl)amino)-4-methyl-[1,1'-biphenyl]-3-carboxamide (8) N-((4,6-dimethyl-2-oxo-1,2-dihydropyridine-3-yl)methyl)-4'-((4-(2-((6-((2-(2,6-dioxopiperidine-3-yl)-1,3-dioxoisoindoline-4-yl)oxy)hexyl)amino)-2-oxoethyl)piperazine-1-yl)methyl)-5-(ethyl(tetrahydro-2H-pyran-4-yl)amino)-4-methyl-[1,1'-biphenyl]-3-carboxamide (9) N-((4,6-dimethyl-2-oxo-1,2-dihydropyridine-3-yl)methyl)-4'-((4-(5-((2-(2,6-dioxopiperidine-3-yl)-1,3-dioxoisoindoline-4-yl)oxy)pentyl)piperazine-1-yl)methyl)-5-(ethyl(tetrahydro-2H-pyran-4-yl)amino)-4-methyl-[1,1'-biphenyl]-3-carboxamide

(10) N-((4,6-dimethyl-2-oxo-1,2-dihydropyridine-3-yl)methyl)-4'-((4-(7-((2-(2,6-dioxopiperidine-3-yl)-1,3-dioxoisoindoline-4-yl)oxy)heptyl)piperazine-1-yl)methyl)-5-(ethyl(tetrahydro-2H-pyran-4-yl)amino)-4-methyl-[1,1'-biphenyl]-3-carboxamide

(11) N-((4,6-dimethyl-2-oxo-1,2-dihydropyridine-3-yl)methyl)-4'-((4-(7-((2-(2,6-dioxopiperidine-3-yl)-1,3-dioxoisoindoline-4-yl)amino)heptyl)piperazine-1-yl)methyl)-5-(ethyl(tetrahydro-2H-pyran-4-yl)amino)-4-methyl-[1,1'-biphenyl]-3-carboxamide

(12) N-((4,6-dimethyl-2-oxo-1,2-dihydropyridine-3-yl)methyl)-4'-((4-((2-((2-(2,6-dioxopiperidine-3-yl)-1,3-dioxoisoindoline-4-yl)amino)ethyl)glycyl)piperazine-1-yl)methyl)-5-(ethyl(tetrahydro-2H-pyran-4-yl)amino)-4-methyl-[1,1'-biphenyl]-3-carboxamide

(13) N-((4,6-dimethyl-2-oxo-1,2-dihydropyridine-3-yl)methyl)-4'-((4-((4-((2-(2,6-dioxopiperidine-3-yl)-1,3-dioxoisoindoline-4-yl)amino)butyl)glycyl)piperazine-1-yl)methyl)-5-(ethyl(tetrahydro-2H-pyran-4-yl)amino)-4-methyl-[1,1'-biphenyl]-3-carboxamide

(14) N-((4,6-dimethyl-2-oxo-1,2-dihydropyridine-3-yl)methyl)-4'-((4-((6-((2-(2,6-dioxopiperidine-3-yl)-1,3-dioxoisoindoline-4-yl)amino)hexyl)glycyl)piperazine-1-yl)methyl)-5-(ethyl(tetrahydro-2H-pyran-4-yl)amino)-4-methyl-[1,1'-biphenyl]-3-carboxamide

(15) N-((4,6-dimethyl-2-oxo-1,2-dihydropyridine-3-yl)methyl)-4'-((4-(2-((3-(2-((2-(2,6-dioxopiperidine-3-yl)-1,3-dioxoisoindoline-4-yl)amino)ethoxy)propyl)amino)-2-oxoethyl)piperazine-1-yl)methyl)-5-(ethyl(tetrahydro-2H-pyran-4-yl)amino)-4-methyl-[1,1'-biphenyl]-3-carboxamide

(16) N-((4,6-dimethyl-2-oxo-1,2-dihydropyridine-3-yl)methyl)-4'-((4-(2-((2-(3-((2-(2,6-dioxopiperidine-3-yl)-1,3-dioxoisoindoline-4-yl)amino)propoxy)ethyl)amino)-2-oxoethyl)piperazine-1-yl)methyl)-5-(ethyl(tetrahydro-2H-pyran-4-yl)amino)-4-methyl-[1,1'-biphenyl]-3-carboxamide

(17) N-((4,6-dimethyl-2-oxo-1,2-dihydropyridine-3-yl)methyl)-4'-((4-(2-((3-(2-((2-(2,6-dioxopiperidine-3-yl)-1,3-dioxoisoindoline-4-yl)oxy)ethoxy)propyl)amino)-2-oxoethyl)piperazine-1-yl)methyl)-5-(ethyl(tetrahydro-2H-pyran-4-yl)amino)-4-methyl-[1,1'-biphenyl]-3-carboxamide

(18) N-((4,6-dimethyl-2-oxo-1,2-dihydropyridine-3-yl)methyl)-4'-((4-(2-((2-(3-((2-(2,6-dioxopiperidine-3-yl)-1,3-dioxoisoindoline-4-yl)oxy)propoxy)ethyl)amino)-2-oxoethyl)piperazine-1-yl)methyl)-5-(ethyl(tetrahydro-2H-pyran-4-yl)amino)-4-methyl-[1,1'-biphenyl]-3-carboxamide

(19) N-((4,6-dimethyl-2-oxo-1,2-dihydropyridine-3-yl)methyl)-4'-((4-(2-((6-((2-(2,6-dioxopiperidine-3-yl)-1,3-dioxoisoindoline-4-yl)amino)hexyl)oxy)ethyl)piperazine-1-yl)methyl)-5-(ethyl(tetrahydro-2H-pyran-4-yl)amino)-4-methyl-[1,1'-biphenyl]-3-carboxamide

(20) N-((4,6-dimethyl-2-oxo-1,2-dihydropyridine-3-yl)methyl)-4'-((4-(2-((6-((2-(2,6-dioxopiperidine-3-yl)-1-oxoisoindoline-4-yl)amino)hexyl)amino)-2-oxoethyl)piperazine-1-yl)methyl)-5-(ethyl(tetrahydro-2H-pyran-4-yl)amino)-4-methyl[1,1'-biphenyl]-3-carboxamide

(21) N-((4,6-dimethyl-2-oxo-1,2-dihydropyridine-3-yl)methyl)-4'-((4-(2-((6-((2-(2,6-dioxopiperidine-3-yl)-1,3-dioxoisoindoline-4-yl)amino)hexyl)amino)ethyl)piperazine-1-yl)methyl)-5-(ethyl(tetrahydro-2H-pyran-4-yl)amino)-4-methyl-[1,1'-biphenyl]-3-carboxamide

(22) N-((4,6-dimethyl-2-oxo-1,2-dihydropyridine-3-yl)methyl)-4'-((4-(2-((6-((2-(2,6-dioxopiperidine-3-yl)-3-oxoisoindoline-4-yl)amino)hexyl)amino)-2-oxoethyl)piperazine-1-yl)methyl)-5-(ethyl(tetrahydro-2H-pyran-4-yl)amino)-4-methyl-[1,1'-biphenyl]-3-carboxamide

(23) N-((4,6-dimethyl-2-oxo-1,2-dihydropyridine-3-yl)methyl)-4'-((4-((1-(3-((2-(2,6-dioxopiperidine-3-yl)-1,3-dioxoisoindoline-4-yl)amino)propyl)-1H-1,2,3-triazole-4-yl)methyl)piperazine-1-yl)methyl)-5-(ethyl(tetrahydro-2H-pyran-4-yl)amino)-4-methyl-[1,1'-biphenyl]-3-carboxamide

(24) N-((4,6-dimethyl-2-oxo-1,2-dihydropyridine-3-yl)methyl)-4'-((4-((1-(2-(2-((2-(2,6-dioxopiperidine-3-yl)-1,3-dioxoisoindoline-4-yl)amino)ethoxy)ethyl)-1H-1,2,3-triazole-4-yl)methyl)piperazine-1-yl)methyl)-5-(ethyl(tetrahydro-2H-pyran-4-yl)amino)-4-methyl-[1,1'-biphenyl]-3-carboxamide

(25) N-((4,6-dimethyl-2-oxo-1,2-dihydropyridine-3-yl)methyl)-4'-((4-(1-(3-((2-(2,6-dioxopiperidine-3-yl)-1,3-dioxoisoindoline-4-yl)amino)propyl)-1H-1,2,3-triazole-4-carbonyl)piperazine-1-yl)methyl)-5-(ethyl(tetrahydro-2H-pyran-4-yl)amino)-4-methyl[1,1'-biphenyl]-3-carboxamide

(26) N-((4,6-dimethyl-2-oxo-1,2-dihydropyridine-3-yl)methyl)-4'-((4-(2-((6-((2-(2,6-dioxopiperidine-3-yl)-1,3-dioxoisoindoline-5-yl)oxy)hexyl)amino)-2-oxoethyl)piperazine-1-yl)methyl)-5-(ethyl(tetrahydro-2H-pyran-4-yl)amino)-4-methyl-[1,1'-biphenyl]-3-carboxamide

(27) N-((4,6-dimethyl-2-oxo-1,2-dihydropyridine-3-yl)methyl)-4'-((4-(2-((5-(3-(2-((2-(2,6-dioxopiperidine-3-yl)-1-oxoisoindoline-4-yl)amino)-2-oxoethoxy)propoxy)pentyl)amino)-2-oxoethyl)piperazine-1-yl)methyl)-5-(ethyl(tetrahydro-2H-pyran-4-yl)amino)-4-methyl-[1,1'-biphenyl]-3-carboxamide

(28) N-((4,6-dimethyl-2-oxo-1,2-dihydropyridine-3-yl)methyl)-4'-((4-(2-((5-(3-(2-((2-(2,6-dioxopiperidine-3-yl)-1,3-dioxoisoindoline-4-yl)amino)-2-oxoethoxy)propoxy)pentyl)amino)-2-oxoethyl)piperazine-1-yl)methyl)-5-(ethyl(tetrahydro-2H-pyran-4-yl)amino)-4-methyl-[1,1'-biphenyl]-3-carboxamide

(29) N-((4,6-dimethyl-2-oxo-1,2-dihydropyridine-3-yl)methyl)-4'-((4-(2-((2-(4-(2-((2-(2,6-dioxopiperidine-3-yl)-1,3-dioxoisoindoline-4-yl)amino)ethyl)piperazine-1-yl)ethyl)amino)-2-oxoethyl)piperazine-1-yl)methyl)-5-(ethyl(tetrahydro-2H-pyran-4-yl)amino)-4-methyl-[1,1'-biphenyl]-3-carboxamide

(30) N-((4,6-dimethyl-2-oxo-1,2-dihydropyridine-3-yl)methyl)-4'-((4-(2-(9-(2-((2-(2,6-dioxopiperidine-3-yl)-1,3-dioxoisoindoline-4-yl)amino)ethyl)-3,9-diazaspiro[5.5]undecane-3-yl)-2-oxoethyl)piperazine-1-yl)methyl)-5-(ethyl(tetrahydro-2H-pyran-4-yl)amino)-4-methyl-[1,1'-biphenyl]-3-carboxamide

(31) N-((4,6-dimethyl-2-oxo-1,2-dihydropyridine-3-yl)methyl)-4'-((4-(4-(1-(2-((2-(2,6-dioxopiperidine-3-yl)-1,3-dioxoisoindoline-4-yl)amino)-2-oxoethyl)-1H-1,2,3-triazole-4-yl)butyl)piperazine-1-yl)methyl)-5-(ethyl(tetrahydro-2H-pyran-4-yl)amino)-4-methyl-[1,1'-biphenyl]-3-carboxamide

(32) N-((4,6-dimethyl-2-oxo-1,2-dihydropyridine-3-yl)methyl)-4'-((4-(1-(5-((2-(2,6-dioxopiperidine-3-yl)-1,3-dioxoisoindoline-4-yl)amino)pentyl)-1H-1,2,3-triazole-4-carbonyl)piperazine-1-yl)methyl)-5-(ethyl(tetrahydro-2H-pyran-4-yl)amino)-4-methyl-[1,1'-biphenyl]-3-carboxamide

(33) N-((4,6-dimethyl-2-oxo-1,2-dihydropyridine-3-yl)methyl)-4'-((4-(2-(9-(4-((2-(2,6-dioxopiperidine-3-yl)-1,3-dioxoisoindoline-4-yl)amino)butyl)-3,9-diazaspiro[5.5]undecane-3-yl)-2-oxoethyl)piperazine-1-yl)methyl)-5-(ethyl(tetrahydro-2H-pyran-4-yl)amino)-4-methyl-[1,1'-biphenyl]-3-carboxamide

(34) N-((4,6-dimethyl-2-oxo-1,2-dihydropyridine-3-yl)methyl)-4'-((4-(2-(7-(4-((2-(2,6-dioxopiperidine-3-yl)-1,3-dioxoisoindoline-4-yl)amino)butyl)-2,7-diazaspiro[4.4]nonane-2-yl)-2-oxoethyl)piperazine-1-yl)methyl)-5-(ethyl(tetrahydro-2H-pyran-4-yl)amino)-4-methyl-[1,1'-biphenyl]-3-carboxamide

(35) N-((4,6-dimethyl-2-oxo-1,2-dihydropyridine-3-yl)methyl)-4'-((4-(2-(6-(4-((2-(2,6-dioxopiperidine-3-yl)-1,3-dioxoisoindoline-4-yl)amino)butyl)-2,6-diazaspiro[3.3]heptane-2-yl)-2-oxoethyl)piperazine-1-yl)methyl)-5-(ethyl(tetrahydro-2H-pyran-4-yl)amino)-4-methyl-[1,1'-biphenyl]-3-carboxamide

(36) N-((4,6-dimethyl-2-oxo-1,2-dihydropyridine-3-yl)methyl)-4'-((4-(2-(6-(2-((2-(2,6-dioxopiperidine-3-yl)-1,3-dioxoisoindoline-4-yl)amino)ethyl)-2,6-diazaspiro[3.3]heptane-2-yl)-2-oxoethyl)piperazine-1-yl)methyl)-5-(ethyl(tetrahydro-2H-pyran-4-yl)amino)-4-methyl-[1,1'-biphenyl]-3-carboxamide

(37) (2S,4R)-1-((S)-2-(tert-butyl)-18-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-biphenyl]-4-yl)methyl)piperazine-1-yl)-4,17-dioxo-6,10-dioxa-3,16-diazaoctadecanoyl)-4-hydroxy-N-(4-(4-methylthiazole-5-yl)benzyl)pyrrolidine-2-carboxamide

(38) (2S,4R)-1-((S)-2-((6-(2-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-biphenyl]-4-yl)methyl) piperazine-1-yl) acetamido) hexyl)amino)-3,3-dimethylbutanoyl)-4-hydroxy-N-(4-(4-methylthiazole-5-yl)benzyl)pyrrolidine-2-carboxamide

(39) (2S,4R)-1-((S)-2-((2-(3-(2-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-biphenyl]-4-yl)methyl)piperazine-1-yl)acetamido)propoxy)ethyl)amino)-3,3-dimethylbutanoyl)-4-hydroxy-N-(4-(4-methylthiazole-5-yl)benzyl)pyrrolidine-2-carboxamide

(40) (2S,4R)-1-((S)-2-((3-(2-(2-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-biphenyl]-4-yl)methyl)piperazine-1-yl) acetamido)ethoxy) propyl)amino)-3,3-dimethylbutanoyl)-4-hydroxy-N-(4-(4-methylthiazole-5-yl)benzyl)pyrrolidine-2-carboxamide

(41) (2S,4R)-1-((S)-2-(6-(2-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-biphenyl]-4-yl)methyl)piperazine-1-yl)acetamido)hexanamido)-3,3-dimethylbutanoyl)-4-hydroxy-N-(4-(4-methylthiazole-5-yl)benzyl)pyrrolidine-2-carboxamide

(42) (2S,4R)-1-((S)-2-(tert-butyl)-16-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-biphenyl]-4-yl)methyl)piperazine-1-yl)-4,15-dioxo-6,10-dioxa-3,14-diazahexadecanoyl)-4-hydroxy-N-(4-(4-methylthiazole-5-yl)benzyl)pyrrolidine-2-carboxamide

(43) (2S,4R)-1-((S)-2-(tert-butyl)-19-(4-((3'-(((4,6-dimethyl-2-oxo-1,2-dihydropyridine-3-yl)methyl)carbamoyl)-5'-(ethyl(tetrahydro-2H-pyran-4-yl)amino)-4'- methyl-[1,1'-biphenyl]-4-yl)methyl)piperazine-1-yl)-4,18-dioxo-7,11-dioxa-3,17-diazanonadecanoyl)-4-hydroxy-N-(4-(4-methylthiazole-5-yl)benzyl)pyrrolidine-2-carboxamide

(44) (2S,4R)-1-((S)-2-(tert-butyl)-18-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-biphenyl]-4-yl)methyl)piperazine-1-yl)-4,17-dioxo-7,10-dioxa-3,16-diazaoctadecanoyl)-4-hydroxy-N-(4-(4-methylthiazole-5-yl)benzyl)pyrrolidine-2-carboxamide

(45) (2S,4R)-1-((S)-2-(4-(9-(2-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-biphenyl]-4-yl)methyl)piperazine-1-yl)acetyl)-3,9-diazaspiro[5.5]undecane-3-yl)butanamido)-3,3-dimethylbutanoyl)-4-hydroxy-N-(4-(4-methylthiazole-5-yl)benzyl)pyrrolidine-2-carboxamide

(46) (2S,4R)-1-((S)-2-(2-((6-(2-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-biphenyl]-4-yl)methyl)piperazine-1-yl) acetamido) hexyl)oxy) acetamido)-3,3-dimethylbutanoyl)-4-hydroxy-N-(4-(4-methylthiazole-5-yl)benzyl)pyrrolidine-2-carboxamide

(47) (2S,4R)-1-((S)-2-(3-(4-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-biphenyl]-4-yl)methyl)piperazine-1-carbonyl)-1H-1,2,3-triazole-1-yl)propanamido)-3,3-dimethylbutanoyl)-4-hydroxy-N-(4-(4-methylthiazole-5-yl)benzyl)pyrrolidine-2-carboxamide

(48) (2S,4R)-1-((S)-2-(5-(4-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-biphenyl]-4-yl)methyl)piperazine-1-carbonyl)-1H-1,2,3-triazole-1-yl)pentanamido)-3,3-dimethylbutanoyl)-4-hydroxy-N-(4-(4-methylthiazole-5-yl)benzyl)pyrrolidine-2-carboxamide

(49) (2S,4R)-1-((S)-2-(2-((9-(2-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-biphenyl]-4-yl)methyl)piperazine-1-yl) acetamido) nonyl)oxy) acetamido)-3,3-dimethylbutanoyl)-4-hydroxy-N-(4-(4-methylthiazole-5-yl)benzyl)pyrrolidine-2-carboxamide

(50) 4'-((4-(2-((6-((S)-2-((2S,3R)-3-amino-2-hydroxy-4-phenylbutanamido)-4-methylpentanamido)hexyl)amino)-2-oxoethyl)piperazine-1-yl)methyl)-N-((4,6-dimethyl-2-oxo-1,2-dihydropyridine-3-yl)methyl)-5-(ethyl(tetrahydro-2H-pyran-4-yl)amino)-4-methyl-[1,1'-biphenyl]-3-carboxamide The compound represented by formula 1 or formula 2 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, β-hydroxybutylate, glycolate, malate, tartrate, methanesulfonate, propanesulfonate, naphthalene-1-sulfonate, naphthalene-2-sulfonate, and mandelate.

The acid addition salt according to the present invention can be prepared by the conventional method known to those in the art. For example, the compound represented by formula 1 or formula 2 is dissolved in an organic solvent such as methanol, ethanol, acetone, methylenechloride, and acetonitrile, to which organic acid or inorganic acid is added to induce precipitation. Then, the precipitate is filtered and dried to give the salt. Or the solvent and the excessive acid are distillated under reduced pressure, and dried to give the salt. Or the precipitate is crystallized in an organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding salt is prepared by the reaction of alkali metal or alkali earth metal salt with proper silver salt (ex; silver nitrate).

In addition, the present invention includes not only the compound represented by formula 1 or formula 2 but also a pharmaceutically acceptable salt thereof, and a solvate, an optical isomer, or a hydrate possibly produced from the same.

The term "hydrate" refers to a compound or a salt thereof of the present invention containing a stoichiometric or non-stoichiometric amount of water bound by a non-covalent intermolecular force. The hydrate of the compound represented by formula 1 or formula 2 of the present invention can contain a stoichiometric or non-stoichiometric amount of water bonded by a non-covalent intermolecular force. The hydrate can contain 1 equivalent or more of water, preferably 1 to 5 equivalents of water. The hydrate can be prepared by crystallizing the compound represented by formula 1 or formula 2, the isomer thereof, or the pharmaceutically acceptable salt thereof from water or the solvent containing water.

The term "solvate" refers to a compound or a salt thereof of the present invention containing a stoichiometric or non-stoichiometric amount of solvent bound by a non-covalent intermolecular force. Preferred solvents therefor include volatile, non-toxic, and/or solvents suitable for administration to human.

The term "isomer" refers to a compound or a salt thereof of the present invention having the same chemical formula or molecular formula, but structurally or sterically different. Such isomers include structural isomers such as tautomers, R or S isomers having an asymmetric carbon center, stereoisomers such as geometric isomers (trans, cis), and optical isomers (enantiomers). All these isomers and mixtures thereof are also included in the scope of the present invention.

The compound represented by formula 1 or formula of the present invention can be prepared according to the preparation method shown in the following examples, but this is only an example and is not limited thereto. For each preparation step, the method well known to those skilled in the art can be used.

In another aspect of the present invention, the present invention provides a pharmaceutical composition comprising a compound represented by formula 1 or formula 2, an isomer thereof, a solvate thereof, a hydrate thereof or a pharmaceutically acceptable salt thereof as an active ingredient for the prevention or treatment of cancer.

The cancer can be at least one selected from the group consisting of pseudomyxoma, intrahepatic biliary tract cancer, hepatoblastoma, liver cancer, thyroid cancer, colon cancer, testis cancer, myelodysplastic syndrome, glioblastoma, oral cancer, lib cancer, mycosis fungoides, acute myeloid leukemia, acute lymphoid leukemia, basal cell carcinoma, ovarian epithelial cancer, ovarian germ cell cancer, male breast cancer, brain cancer, pituitary adenoma, multiple myeloma, gallbladder cancer, biliary tract cancer, colorectal cancer, chronic myelogenous leukemia, chronic lymphocytic leukemia, retinoblastoma, choroidal melanoma, ampullar of vater cancer, bladder cancer, peritoneal cancer, parathyroid cancer, adrenal cancer, nasal cavity cancer, non-small cell lung cancer, tongue cancer, astrocytoma, small cell lung cancer, pediatric brain cancer, pediatric lymphoma, pediatric leukemia, small intestine cancer, meningioma, esophageal cancer, glioma, renal pelvic cancer, kidney cancer, heart cancer, duodenal cancer, malignant soft tissue cancer, malignant bone cancer, malignant lymphoma, malignant mesothelioma, malignant melanoma, eye cancer, vulvar cancer, ureteral cancer, urethral cancer, primary site unknown cancer, gastric lymphoma, stomach cancer, gastric carcinoid tumor, gastrointestinal stromal tumor, Wilms cancer, breast cancer, sarcoma, penile cancer, pharyngeal cancer, gestational trophoblastic disease, cervical cancer, endometrial cancer, uterine sarcoma, prostate cancer, metastatic bone cancer, metastatic brain cancer, mediastinal cancer, rectal cancer, rectal carcinoma, vaginal cancer, spinal cord cancer, acoustic tumor, pancreatic cancer, salivary gland cancer, Kaposi's sarcoma, Paget's disease, tonsil cancer, squamous cell carcinoma, lung adenocarcinoma, lung cancer, lung squamous cell carcinoma, skin cancer, anal cancer, rhabdomyosarcoma, laryngeal cancer, pleura cancer, blood cancer and thymus cancer.

In another aspect of the present invention, the present invention provides a pharmaceutical composition comprising a compound represented by formula 1 or formula 2, an isomer thereof, a solvate thereof, a hydrate thereof or a pharmaceutically acceptable salt thereof as an active ingredient for the selective degradation of EZH2 protein.

The compound represented by formula 1 or formula of the present invention targets EZH2 as a target protein, and has tazemethostat (epz6438, EZH-6438, E-7438) as the EZH2 inhibitor having a residue capable of binding to EZH2, and thalidomide (cereblon), (S,R,S)-AHPC hydrochloride and bestatin as the E3 ligase binders. As demonstrated in Experimental Example 1 of the present invention, the compound of the present invention can selectively degrade EZH2.

Therefore, the compound represented by formula 1 or formula 2 of the present invention can be effectively used for the treatment of EZH2-related diseases and cancers, particularly, cancers in which EZH2 is overexpressed, and can be usefully used for the selective degradation of EZH2.

The pharmaceutical composition for preventing or treating cancer of the present invention can be administered alone or in combination with an existing anticancer agent.

In the pharmaceutical composition according to the present invention, the compound represented by formula 1 or formula 2 or the pharmaceutically acceptable salt thereof can be administered in various oral and parenteral formulations during clinical administration, more preferably can be a parenteral formulation. In the case of formulation, it is prepared using diluents or excipients such as generally used fillers, extenders, binders, wetting agents, disintegrants, and surfactants. Solid formulations for oral administration are tablets, pills, powders, granules and capsules. These solid formulations are prepared by mixing one or more compounds with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions and emulsions. Water insoluble excipients and suspensions can contain, in addition to the active compound or compounds, propylene glycol, polyethylene glycol, vegetable oil like olive oil, injectable ester like ethylolate, etc.

The pharmaceutical composition comprising the compound represented by formula 1 or formula 2 or the pharmaceutically acceptable salt thereof as an active ingredient can be administered by parenterally and the parenteral administration includes subcutaneous injection, intravenous injection, intramuscular injection, or intrathoracic injection.

At this time, to prepare the compound represented by formula 1 or formula 2 or the pharmaceutically acceptable salt thereof as a formulation for parenteral administration, the compound represented by formula 1 or formula 2 or the pharmaceutically acceptable salt thereof is mixed with a stabilizer or a buffering agent in water to produce a solution or suspension, which is then formulated as ampoules or vials. The composition herein can be sterilized and additionally contains preservatives, stabilizers, wettable powders or emulsifiers, salts and/or buffers for the regulation of osmotic pressure, and other therapeutically useful materials, and the composition can be formulated by the conventional mixing, granulating or coating method.

The formulations for oral administration are exemplified by tablets, pills, hard/soft capsules, solutions, suspensions, emulsions, syrups, granules, elixirs, and troches, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavours, and sweeteners can be additionally included thereto.

In another aspect of the present invention, the present invention provides a health functional food comprising a compound represented by formula 1 or formula 2, an isomer thereof, a solvate thereof, a hydrate thereof or a pharmaceutically acceptable salt thereof as an active ingredient for the prevention or amelioration of cancer.

In another aspect of the present invention, the present invention provides a method for preventing or treating cancer, which comprises a step of administering a pharmaceutical composition or a health functional food comprising a compound represented by formula 1 or formula 2, an isomer thereof, a solvate thereof, a hydrate thereof or a pharmaceutically acceptable salt thereof as an active ingredient to a subject in need.

In another aspect of the present invention, the present invention provides a use of the pharmaceutical composition or the health functional food above comprising a compound represented by formula 1 or formula 2, an isomer thereof, a solvate thereof, a hydrate thereof or a pharmaceutically acceptable salt thereof as an active ingredient for the prevention or treatment of cancer.

Hereinafter, the present invention will be described in detail by the following examples and experimental examples.

However, the following examples and experimental examples are only for illustrating the present invention, and the contents of the present invention are not limited thereto.

Analysis and Purification Conditions

HPLC Analysis Conditions (A)

Device name: Shimadzu

Column: YMC-pack pro C18, 150×4.6 mm I.D., 5 m, 40° C.

Moving phase: 5%→100% acetonitrile/$H_2O$+0.1% trifluoroacetic acid,

Analysis time: 9 minutes,

Flow rate: 1 ml/min

UV detector: 254 nm

HPLC Analysis Conditions (B)

Device name: Thermo Scientific Ultimate 3000RSLC

Column: Kinetex®2.6 M biphenyl 100 Å, 100×2.1 mm

Moving phase: 5%→100% acetonitrile/$H_2O$+0.1% trifluoroacetic acid,

Analysis time: 8 minutes,

Flow rate: 0.7 ml/min

UV detector: 254 nm

LC-MS Analysis Conditions

Device name: Shimadzu LCMS-2020

Column: ACE Excel2 C18, 75×2.1 mm

Moving phase: acetonitrile/$H_2O$+0.1% trifluoroacetic acid

Flow rate: 1 mL/min

UV detector: 254 nm

MPLC Purification Conditions

Device name: CombiFlash® Rf+

UV detector: 254 nm

Prep-HPLC Purification Conditions

Device name: Gilson GX-281, 321 pump, UV/VIS-155

Column: Luna®10 M C18 (2) 100 Å, 250×21.2 mm

Moving phase: acetonitrile/0.1% trifluoroacetic acid $H_2O$

Flow rate: 15 mL/min

UV detector: 254 nm

1H NMR

Device name: Bruker Avance (400 MHz)

Example 1

Preparation of N-((4,6-dimethyl-2-oxo-1,2-dihydropyridine-3-yl)methyl)-4'-((4-(2-((2-((2-(2,6-dioxopiperidine-3-yl)-1,3-dioxoisoindoline-4-yl)amino)ethyl)amino)-2-oxoethyl)piperazine-1-yl)methyl)-5-(ethyl(tetrahydro-2H-pyran-4-yl)amino)-4-methyl-[1,1'-biphenyl]-3-carboxamide

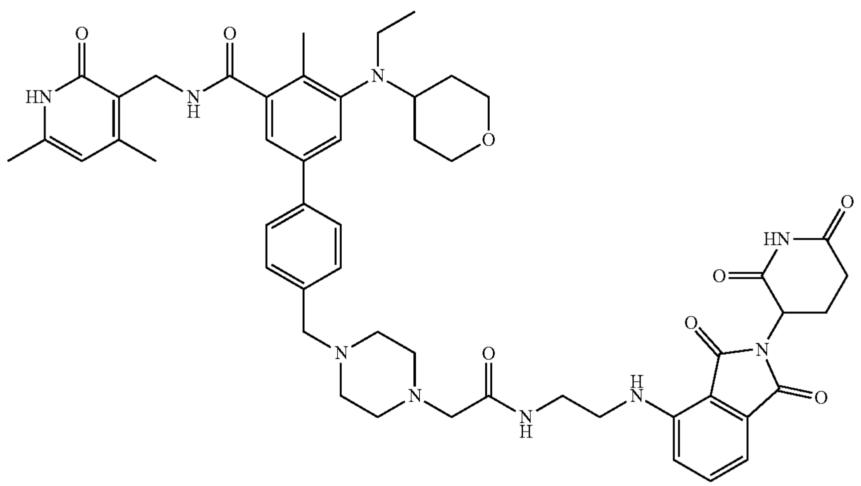 [SMILES: CCN(c1cc(-c2ccc(CN3CCN(CC(=O)NCCNc4cccc5c4C(=O)N(C4CCC(=O)NC4=O)C5=O)CC3)cc2)cc(C(=O)NCc2c(C)cc(C)[nH]c2=O)c1C)C1CCOCC1]

Step 1: Preparation of tert-butyl (2-((2-(2,6-dioxopiperidine-3-yl)-1,3-dioxoisoindoline-4-yl)amino)ethyl)carbamate

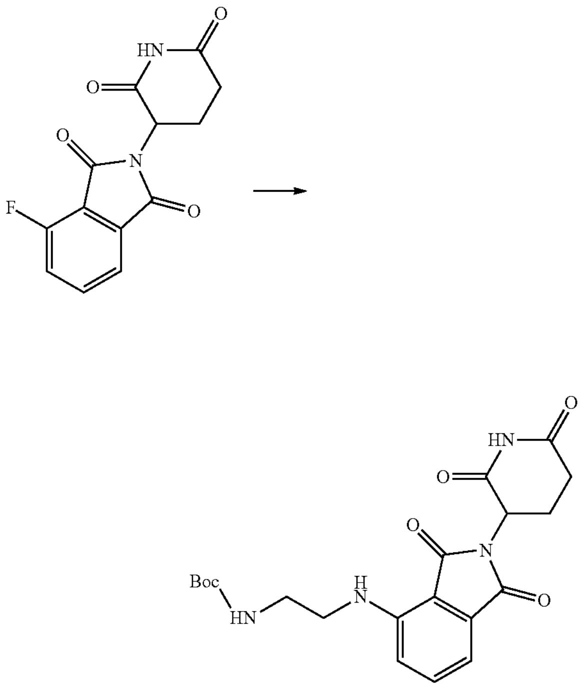

2-(2,6-Dioxopiperidine-3-yl)-4-fluoroisoindoline-1,3-dione (0.5 g, 1.810 mmol) was dissolved in N-methyl-2-pyrrolidone, mixed with tert-butyl(2-aminoethyl)carbamate (0.31 g, 1.991 mmol) and N,N-diisopropylethylamine (0.63 ml, 3.62 mmol), and then heated at 90° C. for 12 hours. Upon completion of the reaction, the temperature of the reaction mixture was lowered to room temperature, diluted with ethyl acetate, and washed with water and brine. The residue of the organic layer was dried over anhydrous sodium sulfate, filtered and concentrated, and then purified by MPLC to give a target compound (0.3 g, 41%, green solid).

LC/MS (ESI) m/z: 417[M+H]$^+$

Step 2: Preparation of 4-((2-aminoethyl)amino)-2-(2,6-dioxopiperidine-3-yl)isoindoline-1,3-dione, 2,2,2-trifluoroacetic acid salt

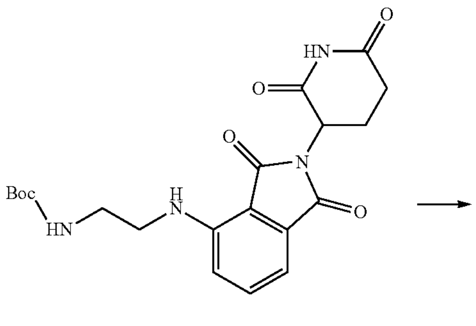

-continued

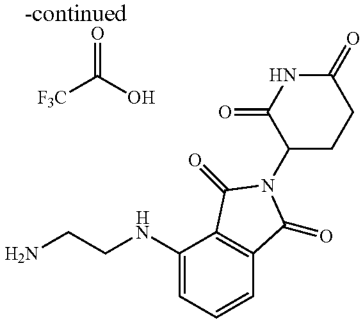

The compound prepared in step 1 (0.07 g, 0.168 mmol) was dissolved in dichloromethane (2 ml), trifluoroacetic acid (1 ml, 12.98 mmol) was added thereto, and the mixture was stirred at room temperature for 1 hour. Upon completion of the reaction, the reaction mixture was concentrated under reduced pressure to give a target compound, and the obtained compound was used in the next step without further purification.

LC/MS (ESI) m/z: 317[M+H]$^+$

Step 3: Preparation of tert-butyl 4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-pipenyl]-4-yl)methyl)piperazine-1-carboxylate

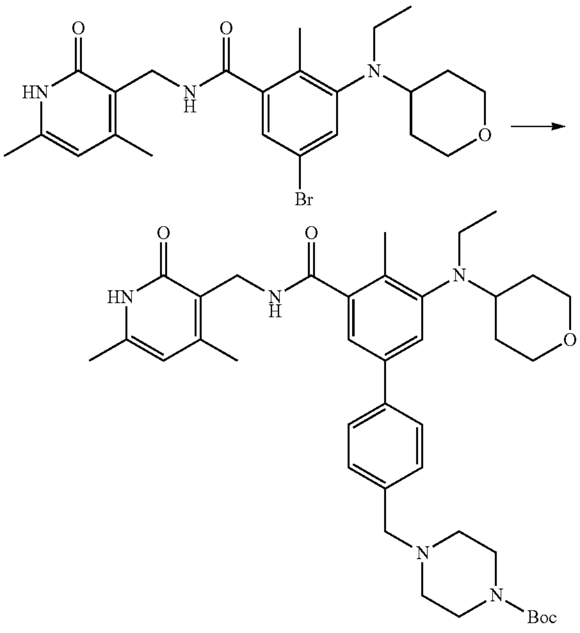

5-Bromo-N-((4,6-dimethyl-2-oxo-1,2-dihydropyridine-3-yl)methyl)-3-(ethyl(tetrahydro-2H-pyran-4-yl)amino)-2-methylbenzamide (3 g, 6.30 mmol) was dissolved in 1,4-dioxane (63 ml), to which (4-((4-(tert-butoxycarbonyl)piperazine-1-yl)methyl)phenyl)boronic acid (2.21 g, 6.93 mmol), tetrakis(triphenylphosphine)palladium(0) (0.73 g, 0.630 mmol), and 1 M sodium carbonate aqueous solution (18 ml, 18.89 mmol) were added, followed by heating at 100° C. for 1 hour. Upon completion of the reaction, the temperature of the reaction mixture was lowered to room temperature, diluted with dichloromethane, and washed with water and brine. The residue of the organic layer was dried over anhydrous sodium sulfate, filtered and concentrated, and then purified by MPLC to give a target compound (3.84 g, 91%, yellow solid).

LC/MS (ESI) m/z: 672[M+H]$^+$

Step 4: Preparation of N-((4,6-dimethyl-2-oxo-1,2-dihydropyridine-3-yl)methyl)-5-(ethyl(tetrahydro-2H-pyran-4-yl)amino)-4-methyl-4'-(piperazine-1-ylmethyl)-[1,1'-pipenyl]-3-carboxamide

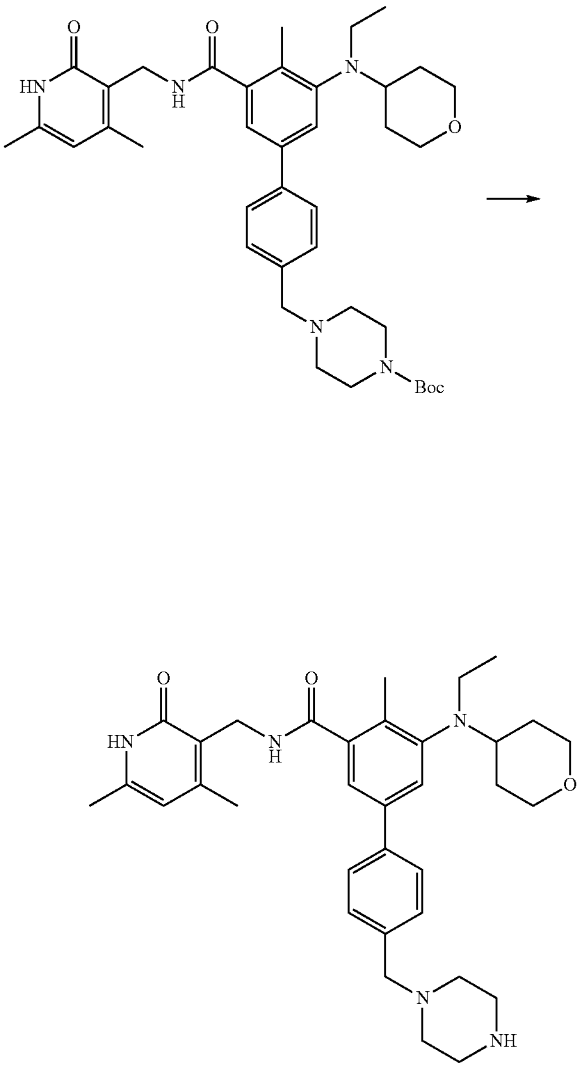

The compound prepared in step 3 (3.84 g, 5.72 mmol) was dissolved in dichloromethane (16 ml), trifluoroacetic acid (8 ml, 104 mmol) was added thereto, and the mixture was stirred at room temperature for 1 hour. Upon completion of the reaction, the mixture was diluted with dichloromethane and neutralized by addition of a sodium hydrogen carbonate aqueous solution. After washing with water and brine, the residue of the organic layer was dried over anhydrous sodium sulfate, filtered and concentrated, and then purified by MPLC to give a target compound (2.87 g, 88%, yellow solid).

LC/MS (ESI) m/z: 572[M+H]$^+$

Step 5: Preparation of ethyl 2-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-pipenyl]-4-yl)methyl)piperazine-1-yl)acetate

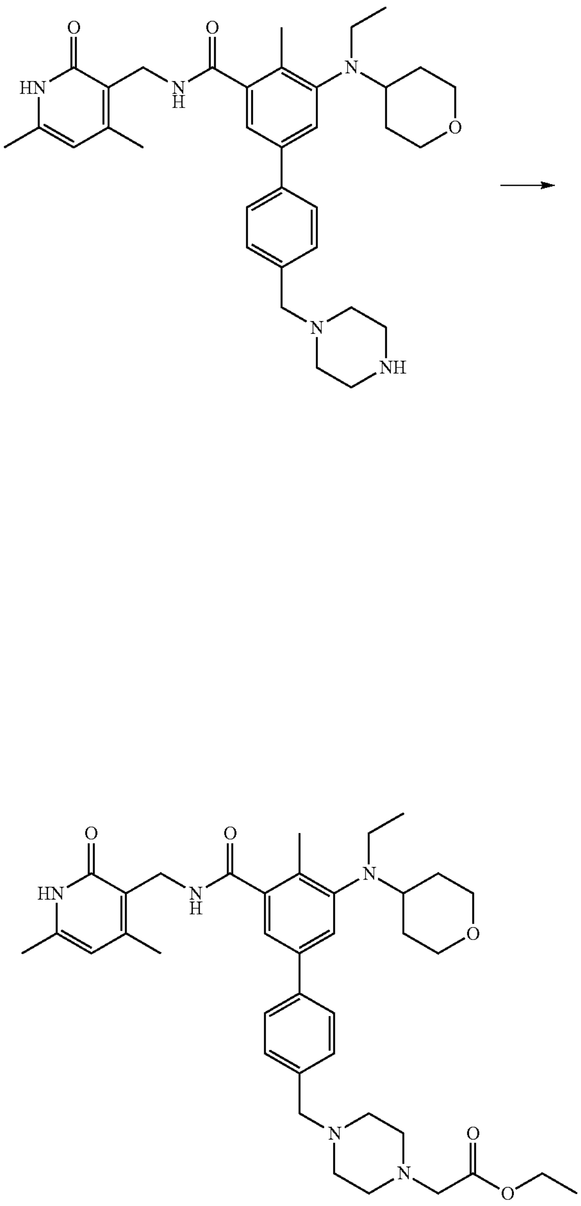

The compound prepared in step 4 (2 g, 3.50 mmol) was dissolved in toluene (2.3 mL), to which triethylamine (0.975 ml, 7.00 mmol) and ethyl 2-bromoacetate (0.701 g, 4.20 mmol) were added at 0° C., followed by stirring at room temperature for 4 hours. Upon completion of the reaction, the reaction mixture was diluted with dichloromethane and washed with water and brine. The residue of the organic layer was dried over anhydrous sodium sulfate, filtered and concentrated, and then purified by MPLC to give a target compound (1.97 g, 86%, yellow solid).

LC/MS (ESI) m/z: 658[M+H]$^+$

Step 6: Preparation of 2-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-pipenyl]-4-yl)methyl)piperazine-1-yl)acetic acid

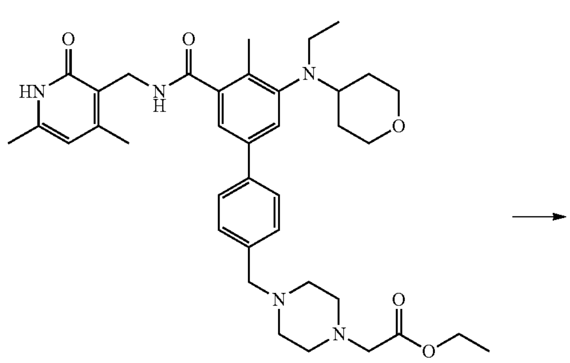

-continued

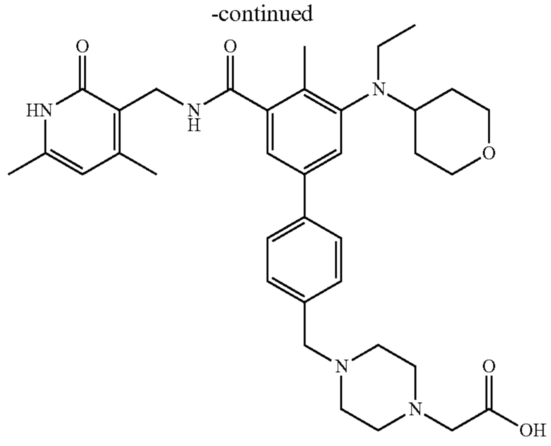

The compound prepared in step 5 (2.97 g, 4.52 mmol) was dissolved in tetrahydrofuran/methanol (1:1, ml), to which lithium hydroxide (0.32 g, 13.57 mmol) dissolved in water (15 ml) was added, followed by stirring at room temperature for 1 hour. Upon completion of the reaction, 1N hydrochloric acid solution was added until the pH of the reaction mixture reached 7, the mixture was diluted with dichloromethane, and washed several times with water and brine. The residue of the organic layer was dried over anhydrous sodium sulfate, filtered and concentrated to give a target compound. The obtained compound was used in the next step without further purification.

LC/MS (ESI) m/z: 630[M+H]$^+$

Step 7: Preparation of 2-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-pipenyl]-4-yl)methyl)piperazine-1-yl)acetic acid

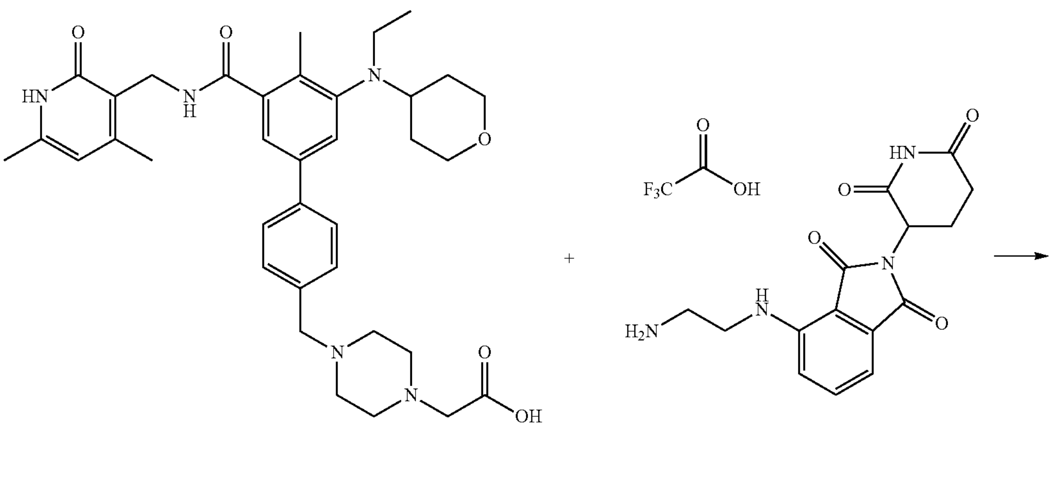

-continued

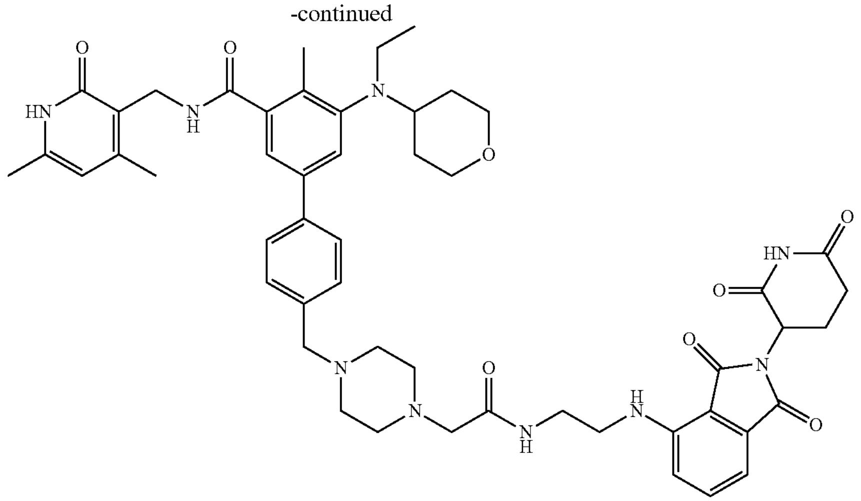

The compound prepared in step 6 (0.1 g, 0.159 mmol) was dissolved in N,N-dimethylformamide (2 ml), to which HATU (0.091 g. diisopropylethylamine (0.083 ml, 0.476 mmol) and the compound prepared in step 2 (0.072 g, 0.167 mmol) were added, followed by stirring at room temperature for 12 hours. Upon completion of the reaction, the reaction mixture was purified by Prep HPLC, and neutralized by adding sodium hydrogen carbonate aqueous solution to give a target compound (0.038 g, 26%, yellow solid).

LC/MS (ESI) m/z: 929[M+H]$^+$

Example 2

Preparation of N-((4,6-dimethyl-2-oxo-1,2-dihydropyridine-3-yl)methyl)-4'-((4-(5-((2-(2,6-dioxopiperidine-3-yl)-1,3-dioxoisoindoline-4-yl)amino)pentyl)piperazine-1-yl)methyl)-5-(ethyl(tetrahydro-2H-pyran-4-yl)amino)-4-methyl-[1,1'-biphenyl]-3-carboxamide

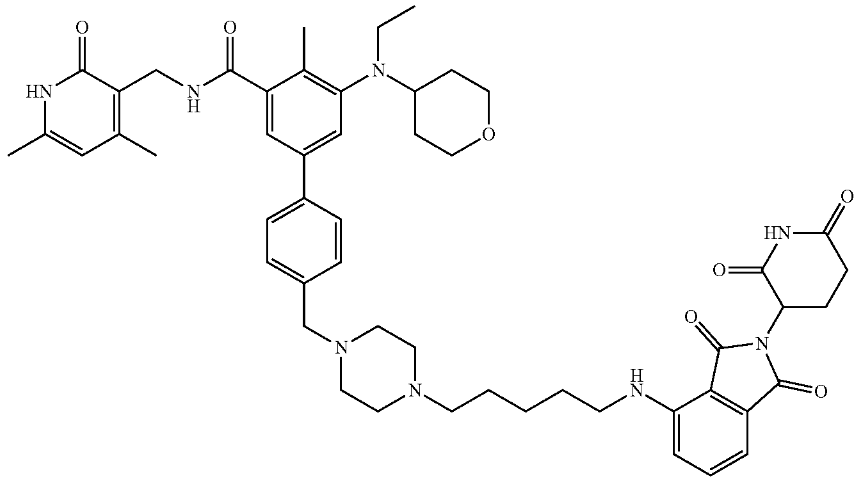 [SMILES: CCN(c1cc(-c2ccc(CN3CCN(CCCCCNc4cccc5c4C(=O)N(C4CCC(=O)NC4=O)C5=O)CC3)cc2)cc(C(=O)NCc2c(C)cc(C)[nH]c2=O)c1C)C1CCOCC1]

Step 1: Preparation of N-((4,6-dimethyl-2-oxo-1,2-dihydropyridine-3-yl)methyl)-4'-((4-(5-(1,3-dioxoisoindoline-2-yl)pentyl)piperazine-1-yl)methyl)-5-(ethyl(tetrahydro-2H-pyran-4-yl)amino)-4-methyl-[1,1'-pipenyl]-3-carboxamide
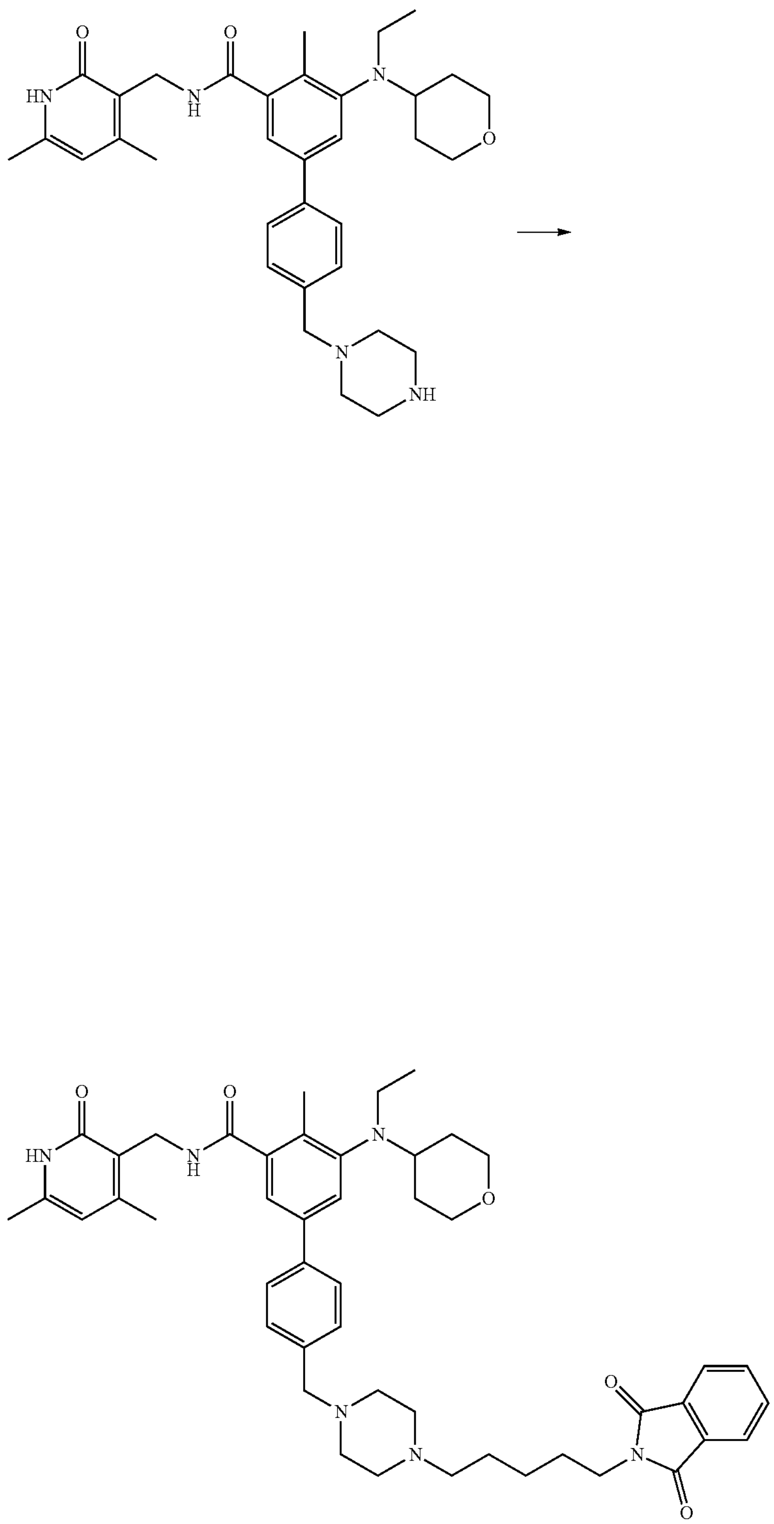

The compound (0.2 g, 0.350 mmol) prepared in [Example 1-Step 4] was dissolved in N,N-dimethylformamide (3.5 ml), to which potassium carbonate (0.097 g, 0.700 mmol) and 2-(5-bromopentyl)isoindoline-1,3-dione (0.135 g, 0.455 mmol) were added, followed by heating at 70° C. for 1 hour. Upon completion of the reaction, the temperature of the reaction mixture was lowered to room temperature, the mixture was diluted with ethyl acetate, and washed with water and brine. The residue of the organic layer was dried over anhydrous sodium sulfate, filtered and concentrated, and then purified by MPLC to give a target compound (0.13 g, 49%, yellow liquid).

LC/MS (ESI) m/z: 788[M+H]$^+$

Step 2: Preparation of 4'-((4-(5-aminopentyl)piperazine-1-yl)methyl)-N-((4,6-dimethyl-2-oxo-1,2-dihydropyridine-3-yl)methyl)-5-(ethyl(tetrahydro-2H-pyran-4-yl)amino)-4-methyl-[1,1'-pipenyl]-3-carboxamide

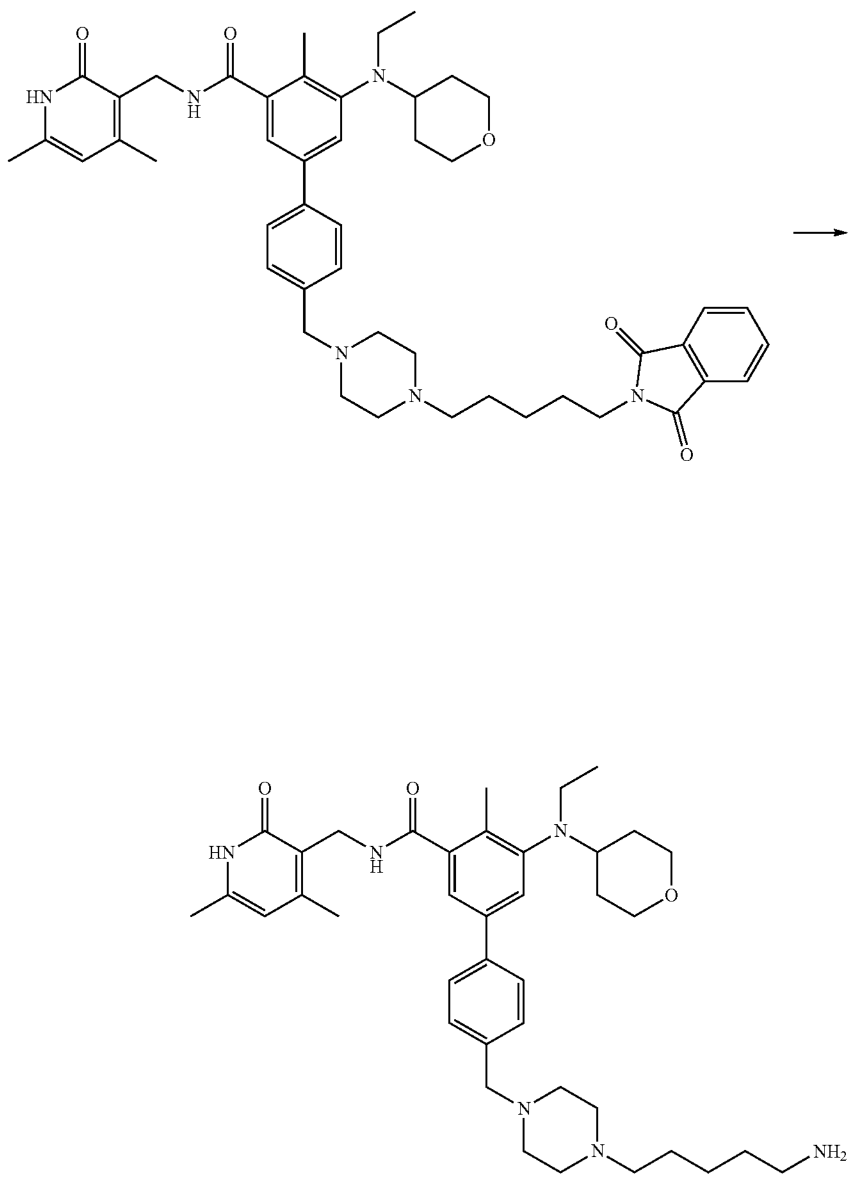

The compound prepared in step 1 (0.134 g, 0.171 mmol) was dissolved in ethanol (2 ml), to which hydrazinyl hydrate (0.042 ml, 0.857 mmol) was added, followed by stirring at room temperature for 12 hours.

Upon completion of the reaction, the reaction mixture was concentrated under reduced pressure and purified by MPLC to give a target compound (0.085 g, 76%, yellow solid).

LC/MS (ESI) m/z: 657[M+H]+

Step 3: Preparation of N-((4,6-dimethyl-2-oxo-1,2-dihydropyridine-3-yl)methyl)-4'-((4-(5-((2-(2,6-dioxopiperidine-3-yl)-1,3-dioxoisoindoline-4-yl)amino)pentyl)piperazine-1-yl)methyl)-5-(ethyl(tetrahydro-2H-pyran-4-yl)amino)-4-methyl-[1,1'-biphenyl]-3-carboxamide

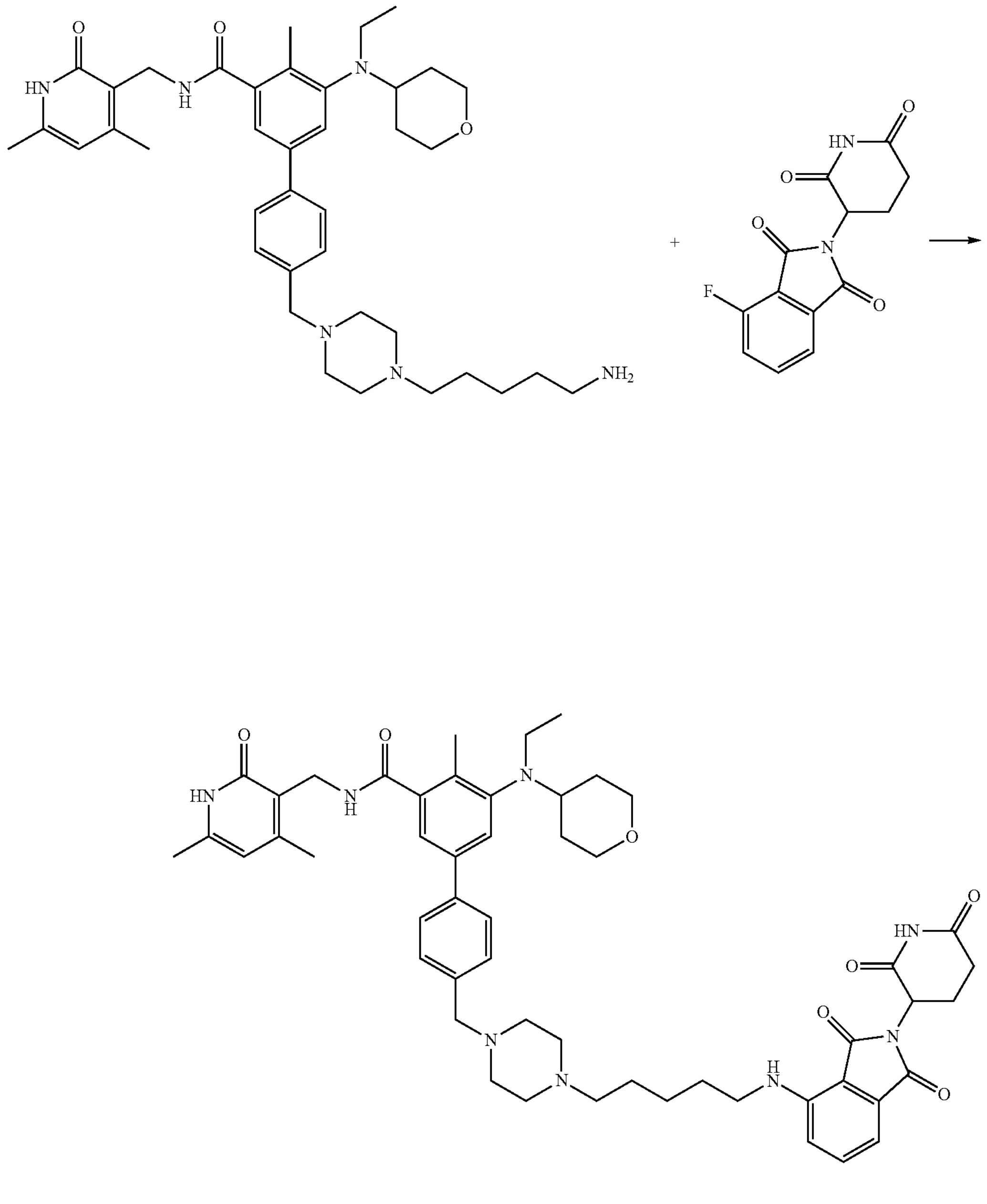

The compound prepared in step 2 (0.040 g, 0.061 mmol) was dissolved in N-methyl-2-pyrrolidone (1 ml), to which 2-(2,6-dioxopiperidine-3-yl)-4-fluoroisoindoline-1,3-dione (0.015 g, 0.055 mmol) and N,N-diisopropylethylamine (0.019 ml, 0.111 mmol) were added, followed by heating at 90° C. for 1 hour. Upon completion of the reaction, the temperature of the reaction mixture was lowered to room temperature, the mixture was diluted with ethyl acetate, and washed with water and brine. The residue of the organic layer was dried over anhydrous sodium sulfate, filtered and concentrated, purified by Prep HPLC, and neutralized by addition of a sodium hydrogen carbonate aqueous solution to give a target compound (0.004 g, 10%, yellow solid).

LC/MS (ESI) m/z: $914[M+H]^+$

Example 3

A target compound was prepared in the same manner as described in Example 1.

Example 4

Preparation of N-((4,6-dimethyl-2-oxo-1,2-dihydropyridine-3-yl)methyl)-4'-((4-(18-((2-(2,6-dioxopiperidine-3-yl)-1,3-dioxoisoindoline-4-yl)amino)-2,15-dioxo-6,9,12-trioxa-3,16-diazaoctadecyl)piperazine-1-yl)methyl)-5-(ethyl(tetrahydro-2H-pyran-4-yl)amino)-4-methyl-[1,1'-biphenyl]-3-carboxamide

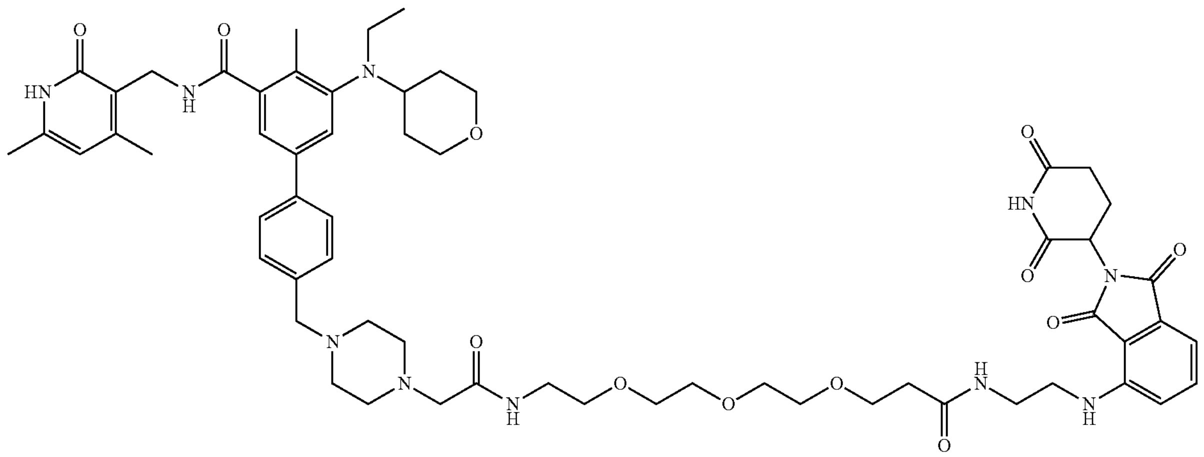 [SMILES: CCN(c1cc(-c2ccc(CN3CCN(CC(=O)NCCOCCOCCOCCC(=O)NCCNc4cccc5c4C(=O)N(C4CCC(=O)NC4=O)C5=O)CC3)cc2)cc(C(=O)NCc2c(C)cc(C)[nH]c2=O)c1C)C1CCOCC1]

Step 1: Preparation of tert-butyl1-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-pipenyl]-4-yl)methyl)piperazine-1-yl)-2-oxo-6,9,12-trioxa-3-azapentadecane-15-oate

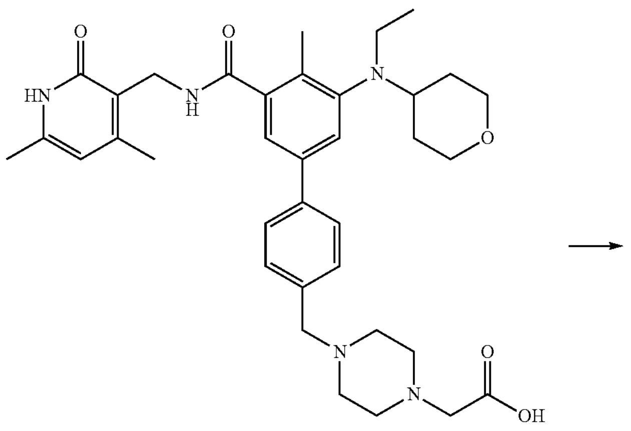

-continued

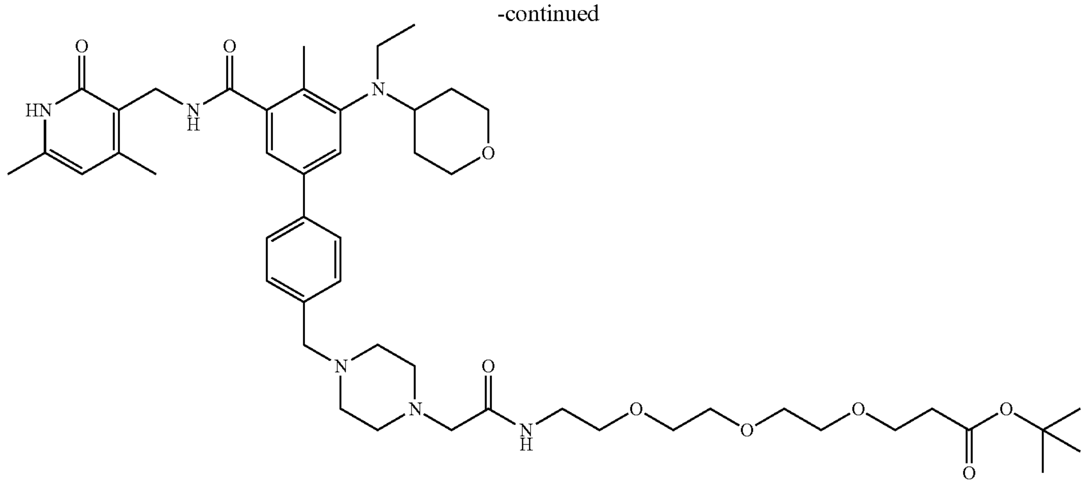

The compound (0.2 g, 0.318 mmol) prepared in [Example 1-Step 6] was dissolved in N,N-dimethylformamide (3 ml), to which tert-butyl-3-(2-(2-(2-aminoethoxy)ethoxy)ethoxy) propanoate (0.088 g, 0.318 mmol), N,N-diisopropylethylamine (0.166 ml, 0.953 mmol) and HATU (0.181 g, 0.476 mmol) were added, followed by stirring at room temperature for 12 hours. Upon completion of the reaction, the reaction mixture was diluted with ethylacetate, and washed with water and brine. The residue of the organic layer was dried over anhydrous sodium sulfate, filtered and concentrated under reduced pressure to give a target compound, and the obtained compound was used in the next step without further purification.

LC/MS (ESI) m/z: 890[M+H]$^+$

Step 2: Preparation of 1-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-pipenyl]-4-yl)methyl)piperazine-1-yl)-2-oxo-6,9,12-trioxa-3-azapentadecane-15-oic acid

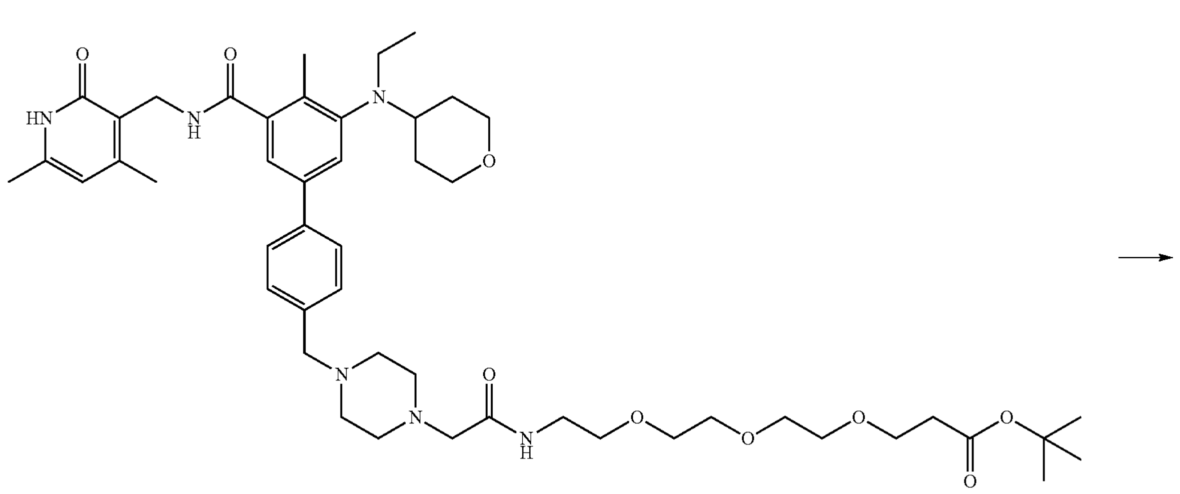

-continued

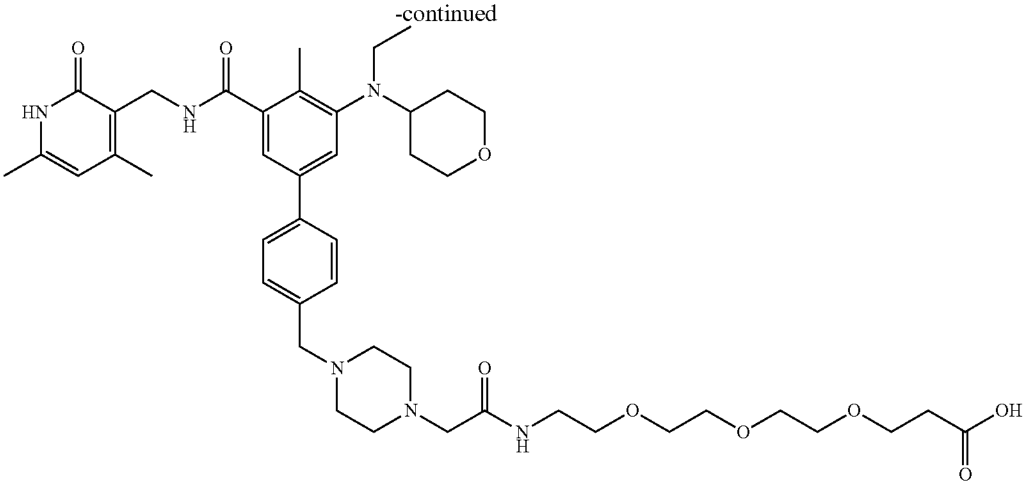

The compound prepared in step 1 (0.282 g, 0.317 mmol) was dissolved in dichloromethane (4 ml), to which trifluoroacetic acid (2 ml, 26.0 mmol) was added, followed by stirring at room temperature for 1 hour. Upon completion of the reaction, the reaction mixture was concentrated under reduced pressure, diluted with dichloromethane, and neutralized by addition of a sodium hydrogen carbonate aqueous solution to give a target compound. The obtained compound was used in the next step without further purification.

LC/MS (ESI) m/z: 834[M+H]+

Step 3: Preparation of N-((4,6-dimethyl-2-oxo-1,2-dihydropyridine-3-yl)methyl)-4'-((4-(18-((2-(2,6-dioxopiperidine-3-yl)-1,3-dioxoisoindoline-4-yl)amino)-2,15-dioxo-6,9,12-trioxa-3,16-diazaoctadecyl)piperazine-1-yl)methyl)-5-(ethyl(tetrahydro-2H-pyran-4-yl)amino)-4-methyl-[1,1'-biphenyl]-3-carboxamide

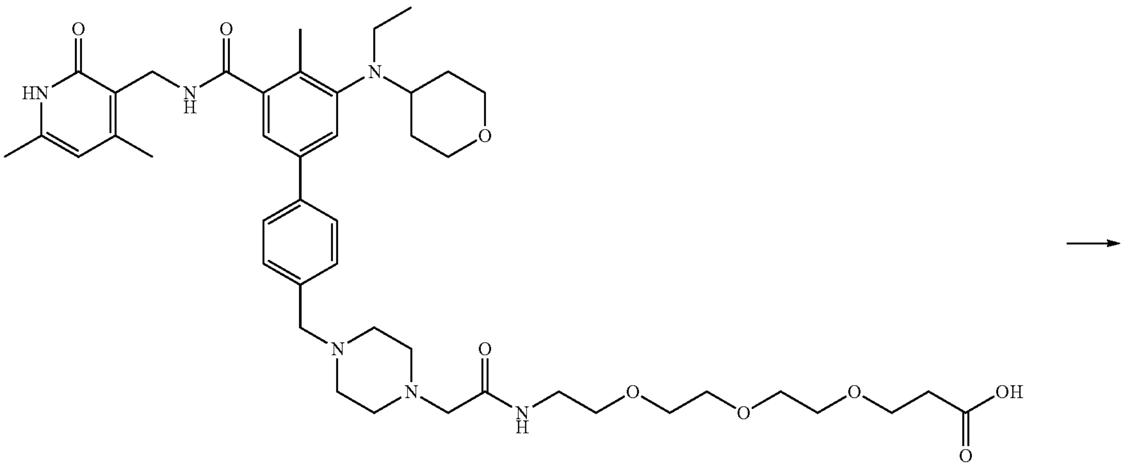

-continued

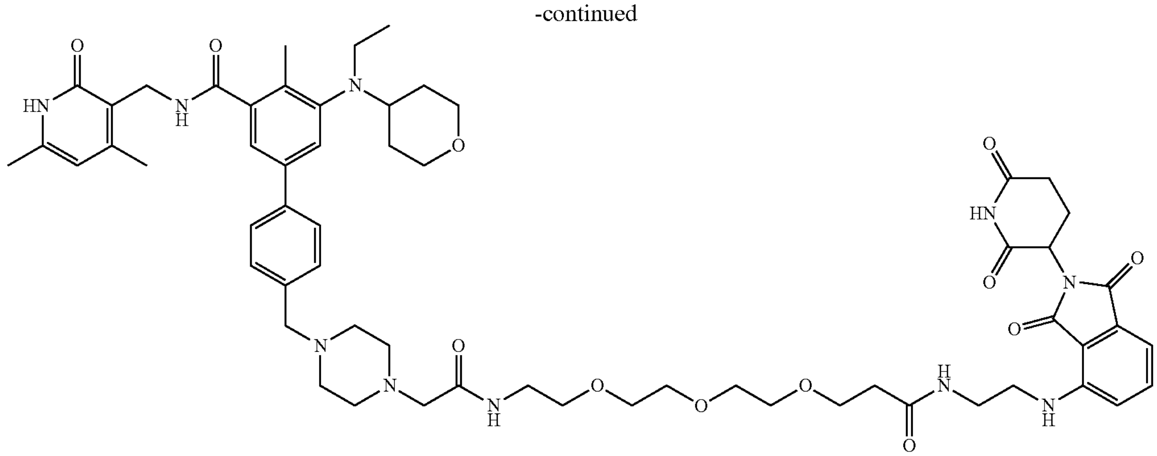

The compound prepared in step 3 (0.060 g, 0.072 mmol) was dissolved in N,N-dimethylformamide (1 ml), to which the compound prepared in [Example 1-Step 2] (0.031 g, 0.072 mmol), N,N-diisopropylethylamine (0.038 ml, 0.216 mmol) and HATU (0.041 g, 0.108 mmol) were added, followed by stirring at room temperature for 12 hours. Upon completion of the reaction, the reaction mixture was purified by Prep HPLC, and neutralized by adding a sodium hydrogen carbonate aqueous solution to give a target compound (0.046 g, 57%, yellow solid).

LC/MS (ESI) m/z: 1132[M+H]$^+$

Example 5

Preparation of N-((4,6-dimethyl-2-oxo-1,2-dihydropyridine-3-yl)methyl)-4'-((4-(2-((2-((2-(2,6-dioxopiperidine-3-yl)-1,3-dioxoisoindoline-4-yl)oxy)ethyl)amino)-2-oxoethyl)piperazine-1-yl)methyl)-5-(ethyl(tetrahydro-2H-pyran-4-yl)amino)-4-methyl-[1,1'-biphenyl]-3-carboxamide

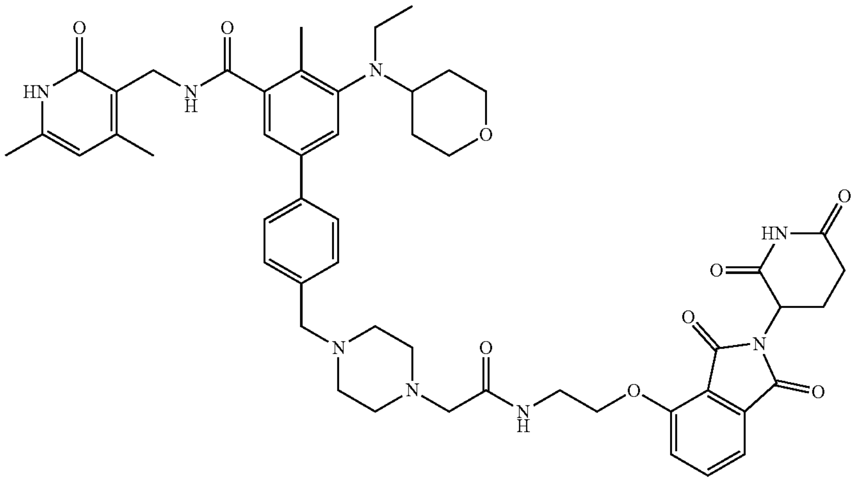 [SMILES: CCN(c1cc(-c2ccc(CN3CCN(CC(=O)NCCOc4cccc5c4C(=O)N(C4CCC(=O)NC4=O)C5=O)CC3)cc2)cc(C(=O)NCc2c(C)cc(C)[nH]c2=O)c1C)C1CCOCC1]

Step 1: Preparation of tert-butyl (2-((2-(2,6-dioxopiperidine-3-yl)-1,3-dioxoisoindoline-4-yl)oxy) ethyl)carbamate

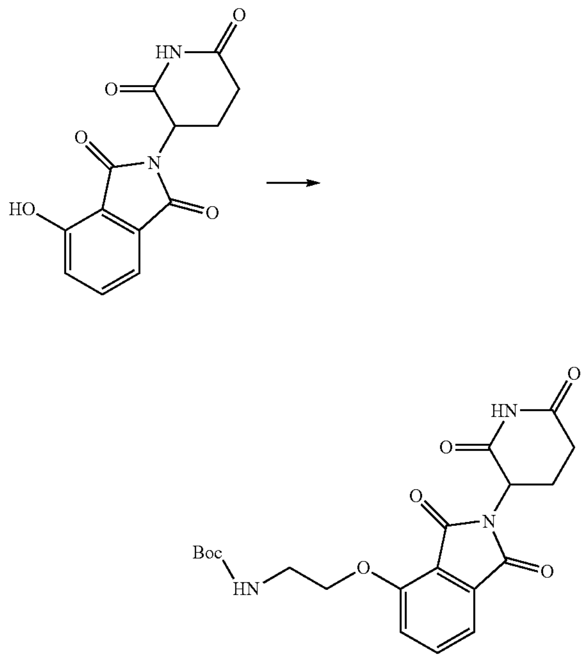

2-(2,6-Dioxopiperidine-3-yl)-4-hydroxyisoindoline-1,3-dione (0.2 g, 0.729 mmol) was dissolved in N,N-dimethylformamide (2 ml), to which tert-butyl(2-bromoethyl)carbamate (0.136 g, 0.608 mmol) and potassium carbonate (0.126 g, 0.912 mmol) were added, followed by heating at 60° C. for 7 hours. Upon completion of the reaction, the reaction mixture was diluted with dichloromethane, and washed with water and brine. The residue of the organic layer was dried over anhydrous sodium sulfate, filtered and concentrated, and then purified by MPLC to give a target compound (0.084 g, 33%, yellow solid).

LC/MS (ESI) m/z: 418[M+H]$^+$

Step 2: Preparation of 4-(2-aminoethoxy)-2-(2,6-dioxopiperidine-3-yl)isoindoline-1,3-dione, 2,2,2-trifluoroacetic acid salt

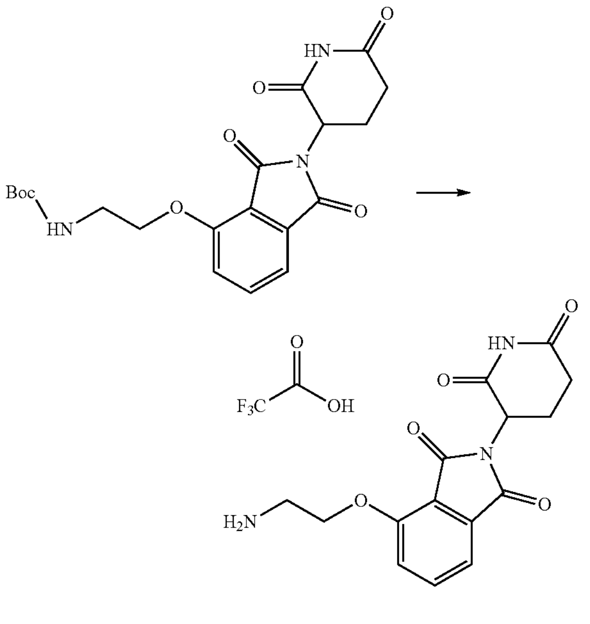

The compound prepared in step 1 (0.0418 g, 0.070 mmol) was dissolved in dichloromethane (2 ml), to which trifluoroacetic acid (1 ml, 12.98 mmol) was added, followed by stirring at room temperature for 1 hour. Upon completion of the reaction, the reaction mixture was concentrated under reduced pressure to give a target compound, and the obtained compound was used in the next step without further purification.

LC/MS (ESI) m/z: 318[M+H]$^+$

Step 3: Preparation of N-((4,6-dimethyl-2-oxo-1,2-dihydropyridine-3-yl)methyl)-4'-((4-(2-((2-((2-(2,6-dioxopiperidine-3-yl)-1,3-dioxoisoindoline-4-yl) oxy)ethyl)amino)-2-oxoethyl)piperazine-1-yl) methyl)-5-(ethyl(tetrahydro-2H-pyran-4-yl)amino)-4-methyl-[1,1'-biphenyl]-3-carboxamide

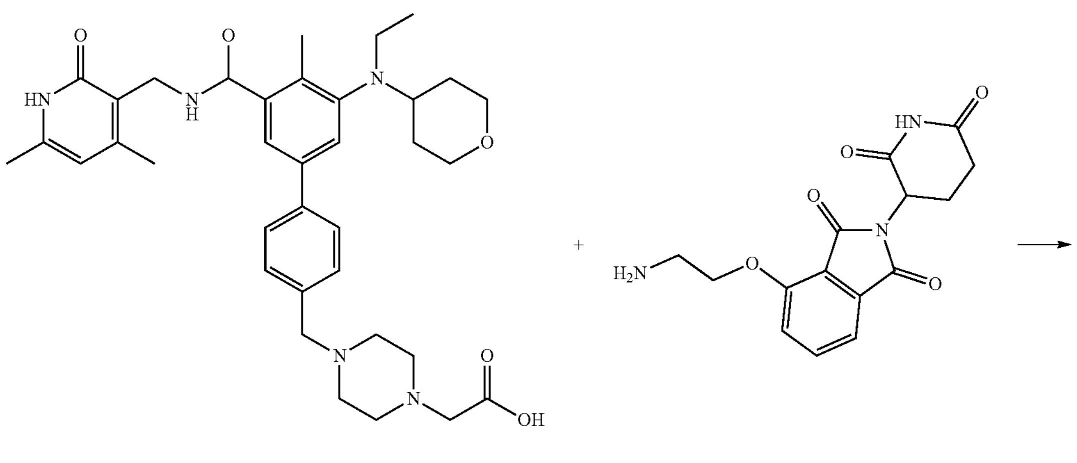

-continued

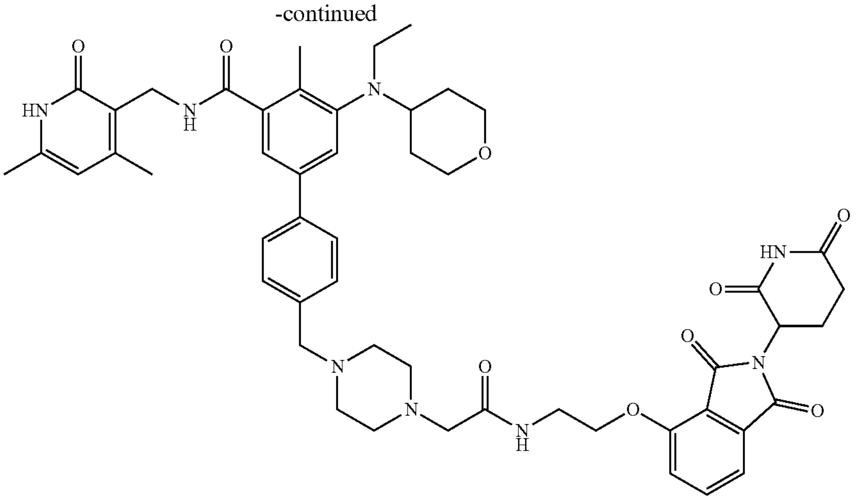

The compound (0.044 g, 0.070 mmol) prepared in [Example 1-Step 6] was dissolved in N,N-dimethylformamide (2 ml), to which the compound prepared in step 2 (0.030 g, 0.070 mmol), N,N-diisopropylethylamine (0.036 ml, 0.209 mmol) and HATU (0.040 g, 0.104 mmol) were added, followed by stirring at room temperature for 12 hours. Upon completion of the reaction, the reaction mixture was purified by Prep HPLC, and neutralized by adding a sodium hydrogen carbonate aqueous solution to give a target compound (0.022 g, 34%, yellow solid).

LC/MS (ESI) m/z: 930[M+H]$^+$

Example 6

A target compound was prepared in the same manner as described in Example 1.

Example 7, 8

Target compound were prepared in the same manner as described in Example 5.

Example 9

Preparation of N-((4,6-dimethyl-2-oxo-1,2-dihydropyridine-3-yl)methyl)-4'-((4-(5-((2-(2,6-dioxopiperidine-3-yl)-1,3-dioxoisoindoline-4-yl)oxy)pentyl)piperazine-1-yl)methyl)-5-(ethyl(tetrahydro-2H-pyran-4-yl)amino)-4-methyl-[1,1'-biphenyl]-3-carboxamide

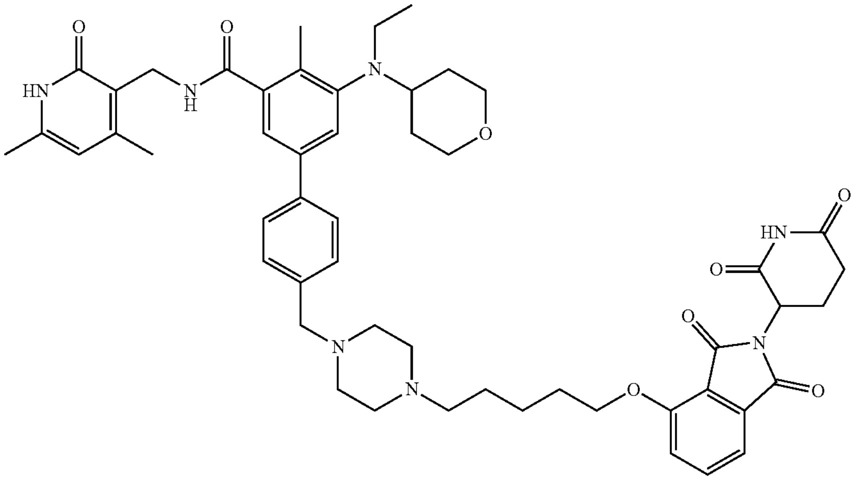 [SMILES: CCN(c1cc(-c2ccc(CN3CCN(CCCCCOc4cccc5c4C(=O)N(C4CCC(=O)NC4=O)C5=O)CC3)cc2)cc(C(=O)NCc2c(C)cc(C)[nH]c2=O)c1C)C1CCOCC1]

Step 1: Preparation of 4-((5-(benzyloxy)pentyl)oxy)-2-(2,6-dioxopiperidine-3-yl)isoindoline-1,3-dione

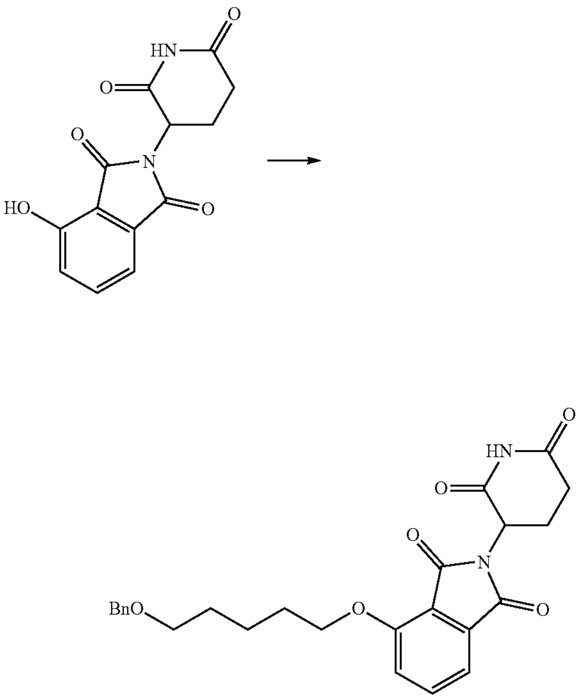

2-(2,6-Dioxopiperidine-3-yl)-4-hydroxyisoindoline-1,3-dione (0.4 g, 1.459 mmol) was dissolved in N,N-dimethylformamide (4 ml), to which (((5-bromopentyl)oxy)methyl)benzene (0.313 g, 1.216 mmol) and potassium carbonate (0.252 g, 1.823 mmol) were added, followed by heating at 60° C. for 16 hours. Upon completion of the reaction, the reaction mixture was diluted with dichloromethane, and washed with water and brine. The residue of the organic layer was dried over anhydrous sodium sulfate, filtered and concentrated, and then purified by MPLC to give a target compound (0.327 g, 60%, yellow solid).

LC/MS (ESI) m/z: 451[M+H]$^+$

Step 2: Preparation of 2-(2,6-dioxopiperidine-3-yl)-4-((5-hydroxypentyl)oxy)isoindoline-1,3-dione

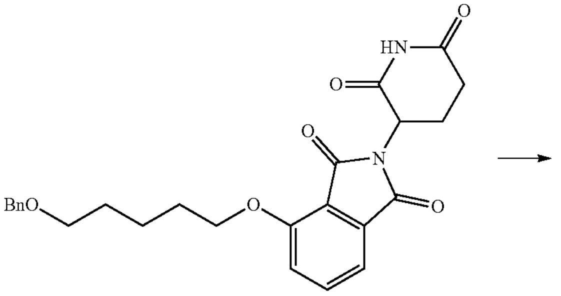

-continued

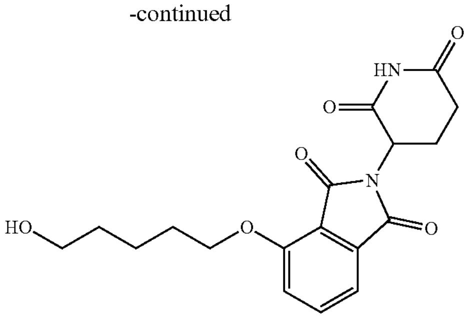

The compound prepared in step 1 (0.3277 g, 0.727 mmol) was dissolved in tetrahydrofuran (4 ml) and methanol (1 ml), to which $Pd(OH)_2/C$ (0.163 g, 1.164 mmol) and two drops of concentrated hydrochloric acid were added, followed by stirring at room temperature for 1 hour under a hydrogen atmosphere. Upon completion of the reaction, the reaction mixture was filtered through Celite. The separated filtrate was concentrated under reduced pressure to give a target compound, and the obtained compound was used in the next step without further purification.

LC/MS (ESI) m/z: 361[M+H]$^+$

Step 3: Preparation of 5-((2-(2,6-dioxopiperidine-3-yl)-1,3-dioxoisoindoline-4-yl)oxy)pentanal

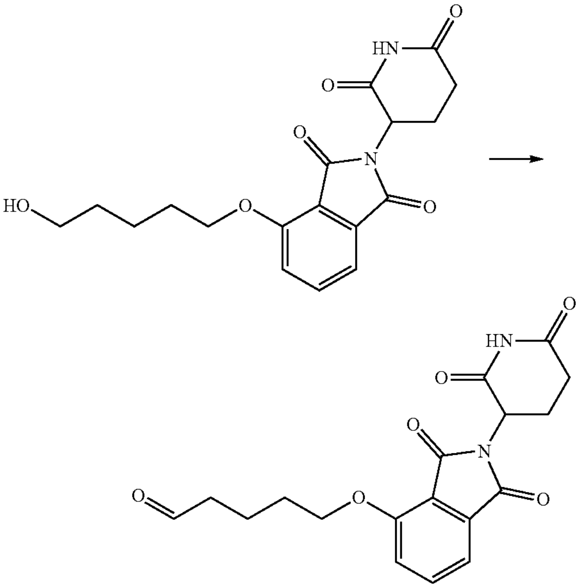

The compound prepared in step 2 (0.262 g, 0.727 mmol) was dissolved in dichloromethane (3.6 ml), to which Dess-MartinPeriodinane (0.401 g, 0.945 mmol) was added at 0° C., followed by stirring at room temperature for 4 hours. Upon completion of the reaction, the reaction mixture was diluted with dichloromethane, and washed with water and a sodium hydrogen carbonate aqueous solution. The residue of the organic layer was dried over anhydrous sodium sulfate, filtered and concentrated, and then purified by MPLC to give a target compound (0.093 g, 36%, yellow solid).

LC/MS (ESI) m/z: 359[M+H]$^+$

Step 4: Preparation of N-((4,6-dimethyl-2-oxo-1,2-dihydropyridine-3-yl)methyl)-4'-((4-(5-((2-(2,6-dioxopiperidine-3-yl)-1,3-dioxoisoindoline-4-yl)oxy)pentyl)piperazine-1-yl)methyl)-5-(ethyl(tetrahydro-2H-pyran-4-yl)amino)-4-methyl-[1,1'-biphenyl]-3-carboxamide
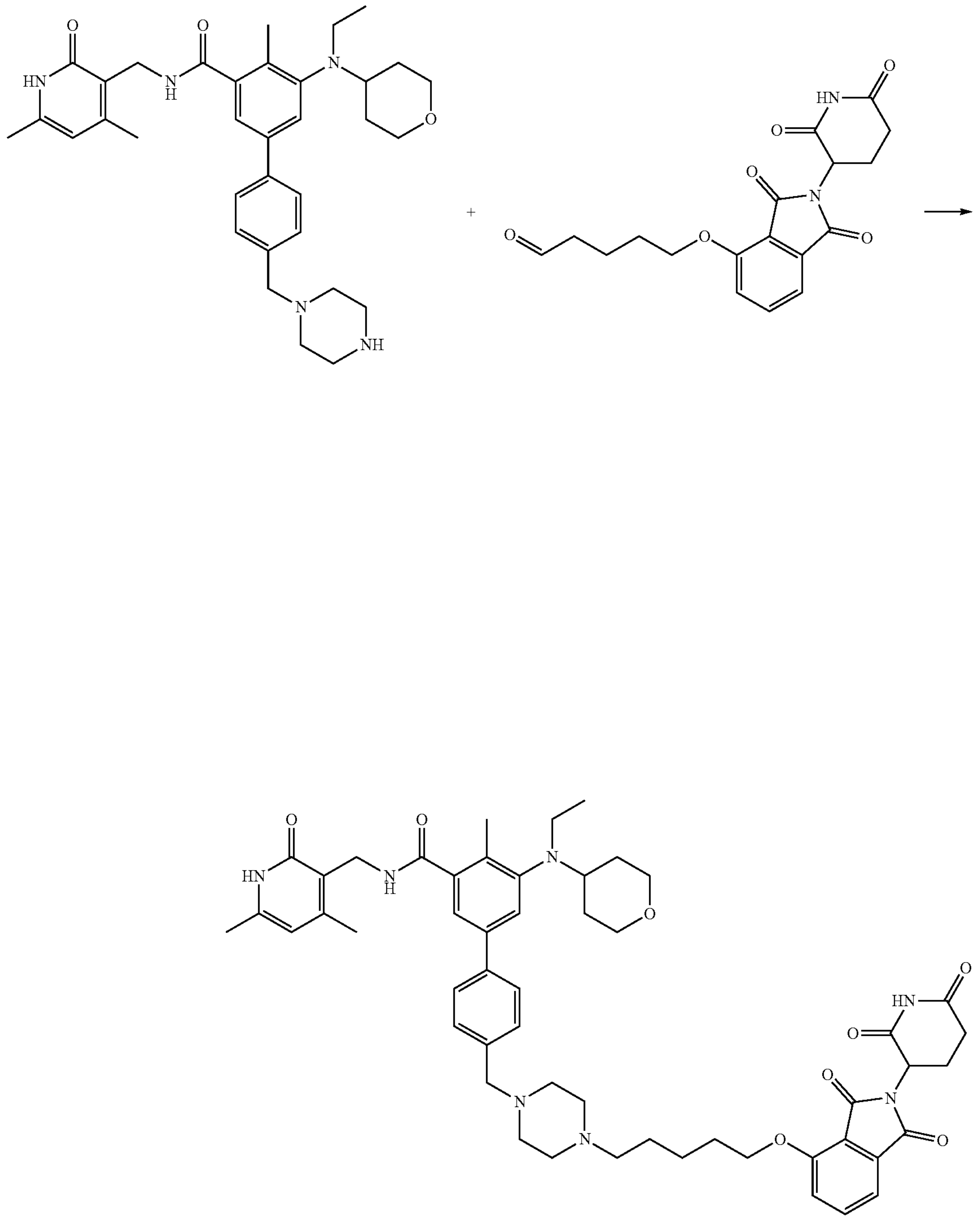

The compound (0.149 g, 0.261 mmol) prepared in [Example 1-Step 4] was dissolved in methanol (2.6 ml), to which the compound prepared in step 3 (0.0936 g, 0.261 mmol), two drops of acetic acid and $NaBH_3CN$ (0.049 g, 0.784 mmol) were added, followed by stirring at room temperature for 2 hours. Upon completion of the reaction, the reaction mixture was diluted with dichloromethane, and washed with water and brine. The residue of the organic layer was dried over anhydrous sodium sulfate, filtered and concentrated, purified by Prep HPLC, and neutralized by adding a sodium hydrogen carbonate aqueous solution to give a target compound (0.056 g, 24%, yellow solid).

LC/MS (ESI) m/z: $915[M+H]^+$

Example 10

A target compound was prepared in the same manner as described in Example 9.

Example 11

A target compound was prepared in the same manner as described in Example 2.

Example 12

Preparation of N-((4,6-dimethyl-2-oxo-1,2-dihydropyridine-3-yl)methyl)-4'-((4-((4-((2-(2,6-dioxopiperidine-3-yl)-1,3-dioxoisoindoline-4-yl)amino)butyl)glycyl)piperazine-1-yl)methyl)-5-(ethyl(tetrahydro-2H-pyran-4-yl)amino)-4-methyl-[1,1'-biphenyl]-3-carboxamide

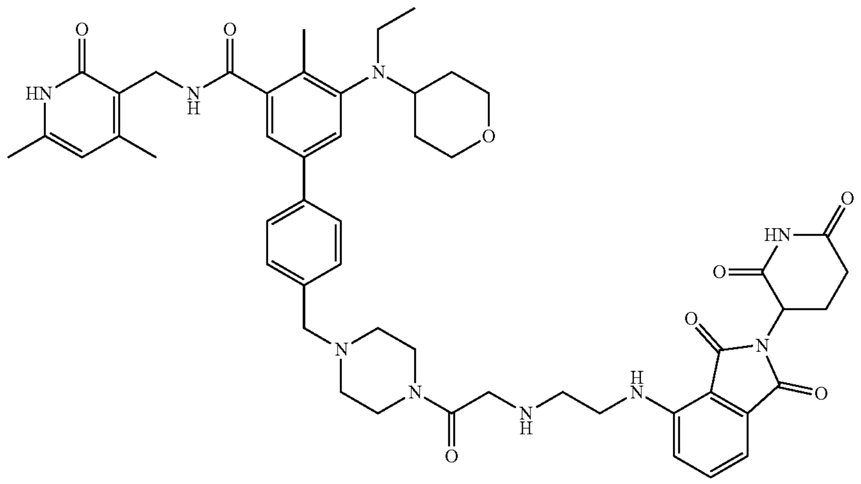 [SMILES: CCN(c1cc(-c2ccc(CN3CCN(C(=O)CNCCNc4cccc5c4C(=O)N(C4CCC(=O)NC4=O)C5=O)CC3)cc2)cc(C(=O)NCc2c(C)cc(C)[nH]c2=O)c1C)C1CCOCC1]

Step 1: Preparation of 4'-((4-(2-bromoacetyl)piperazine-1-yl)methyl)-N-((4,6-dimethyl-2-oxo-1,2-dihydropyridine-3-yl)methyl)-5-(ethyl(tetrahydro-2H-pyran-4-yl)amino)-4-methyl-[1,1'-biphenyl]-3-carboxamide

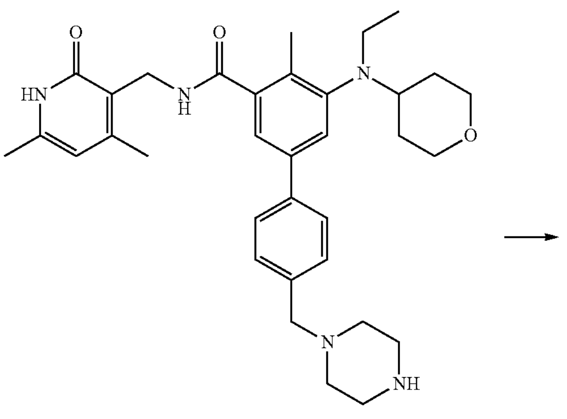

-continued

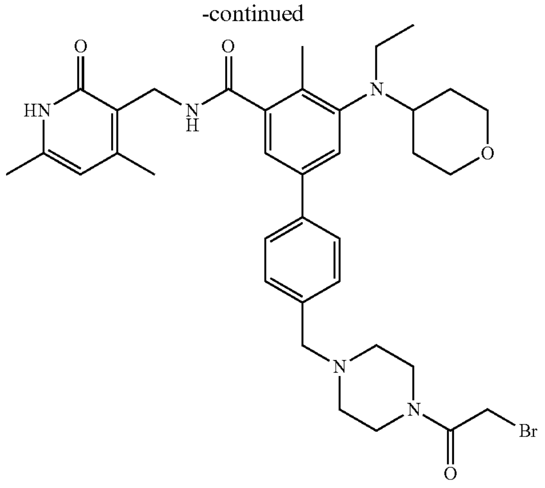

The compound (0.4 g, 0.583 mmol) prepared in [Example 1-Step 4] was dissolved in dichloromethane (3 mL), to which triethylamine (0.244 mL, 1.750 mmol) and 2-bromoacetylbromide (0.141 g, 0.700 mmol) were added at 0° C., followed by stirring for 1 hour. Upon completion of the reaction, the reaction mixture was diluted with dichloromethane, and washed with water and brine. The residue of the organic layer was dried over anhydrous sodium sulfate, filtered and concentrated, and purified by MPLC to give a target compound (0.11 g, 28%).

LC/MS (ESI) m/z: 693[M+H]$^+$

Step 2: Preparation of N-((4,6-dimethyl-2-oxo-1,2-dihydropyridine-3-yl)methyl)-4'-((4-((4-((2-(2,6-dioxopiperidine-3-yl)-1,3-dioxoisoindoline-4-yl)amino)butyl)glycyl)piperazine-1-yl)methyl)-5-(ethyl(tetrahydro-2H-pyran-4-yl)amino)-4-methyl-[1,1'-biphenyl]-3-carboxamide

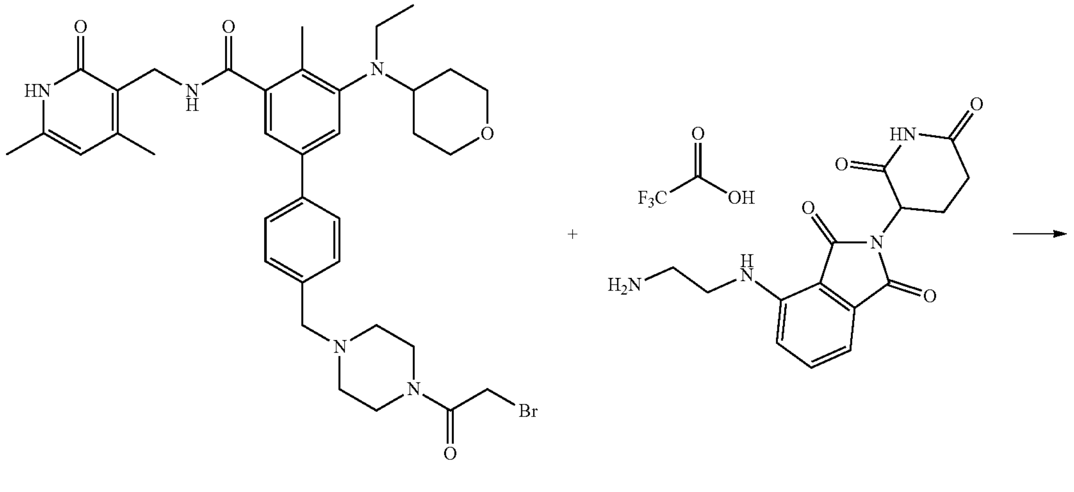

-continued

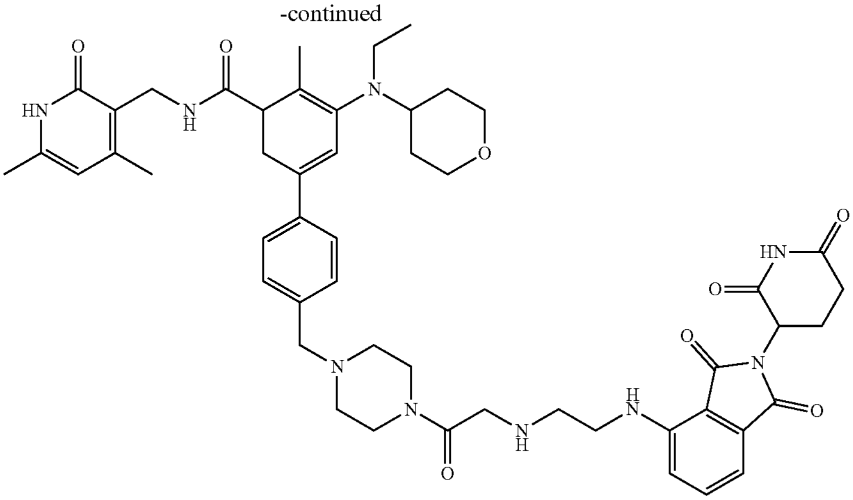

The compound prepared in step 1 (0.044 g, 0.064 mmol) was dissolved in N,N-dimethylformamide (1 mL), to which the compound (0.041 g, 0.095 mmol) prepared in [Example 1-Step 2] and triethylamine (0.027 mL, 0.191 mmol) were added, followed by stirring at room temperature for 1 hour. Upon completion of the reaction, the reaction mixture was purified by Prep HPLC, and neutralized by adding a sodium hydrogen carbonate aqueous solution to give a target compound (0.015 g, 26%, yellow solid).

LC/MS (ESI) m/z: 929[M+H]$^+$

Example 13, 14

Target compounds were prepared in the same manner as described in Example 12.

Example 15

Preparation of N-((4,6-dimethyl-2-oxo-1,2-dihydropyridine-3-yl)methyl)-4'-((4-(2-((3-(2-((2-(2,6-dioxopiperidine-3-yl)-1,3-dioxoisoindoline-4-yl)amino)ethoxy)propyl)amino)-2-oxoethyl)piperazine-1-yl)methyl)-5-(ethyl(tetrahydro-2H-pyran-4-yl)amino)-4-methyl-[1,1'-biphenyl]-3-carboxamide

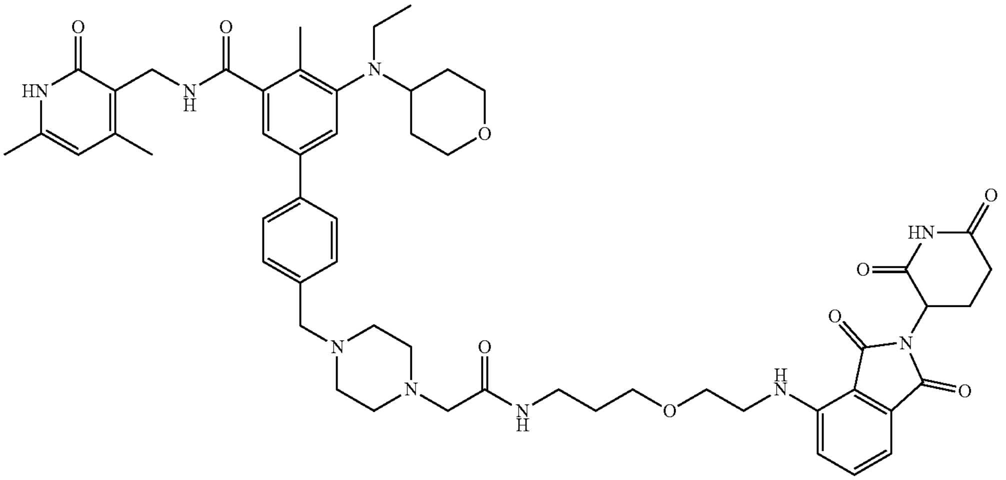 [SMILES: CCN(c1cc(-c2ccc(CN3CCN(CC(=O)NCCCOCCNc4cccc5c4C(=O)N(C4CCC(=O)NC4=O)C5=O)CC3)cc2)cc(C(=O)NCc2c(C)cc(C)[nH]c2=O)c1C)C1CCOCC1]

Step 1: Preparation of tert-butyl(2-(3-bromopropoxy)ethyl)carbamate

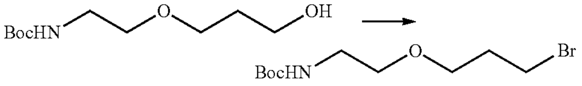

Tert-butyl(2-(3-hydroxypropoxy)ethyl)carbamate (2 g, 9.12 mmol) was dissolved in dichloromethane (22 mL), to which carbon tetrabromide (3.63 g, 10.95 mmol) and triphenylphosphine (2.87 g, 10.95 mmol) were added, followed by stirring for 30 minutes and further stirring at room temperature for 4 hours. Upon completion of the reaction, the reaction mixture was concentrated under reduced pressure and purified by MPLC to give a target compound (0.98 g, 77%).

LC/MS (ESI) m/z: 283$[M+H]^+$

Step 2: Preparation of tert-butyl(2-(3-azidopropoxy)ethyl)carbamate

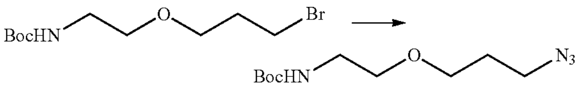

The compound prepared in step 1 (1 g, 3.54 mmol) was dissolved in N,N-dimethylformamide (6 mL), to which sodium azide (1.15 g, 17.72 mmol) was added, followed by stirring at room temperature for 4 hours. Upon completion of the reaction, the reaction mixture was diluted with dichloromethane, and washed with water and brine. The residue of the organic layer was dried over anhydrous sodium sulfate, filtered and concentrated, and then purified by MPLC to give a target compound (0.86 g, 100%).

LC/MS (ESI) m/z: 245$[M+H]^+$

Step 3: Preparation of 2-(3-azidopropoxy)ethane-1-amine 2,2,2-trifluoroacetic acid salt

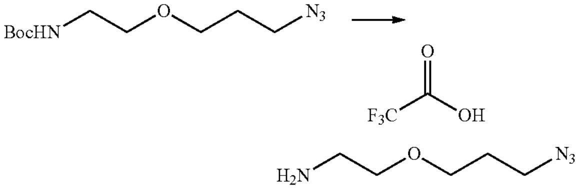

The compound prepared in step 2 (0.2 g, 0.819 mmol) was dissolved in dichloromethane (5 mL), to which trifluoroacetic acid (2 mL, 26.0 mmol) was added, followed by stirring at room temperature for 1 hour. Upon completion of the reaction, the reaction mixture was concentrated under reduced pressure to give a target compound, and the obtained compound was used in the next step without further purification.

LC/MS (ESI) m/z: 145$[M+H]^+$

Step 4: Preparation of 4-((2-(3-azidopropoxy)ethyl)amino)-2-(2,6-dioxopiperidine-3-yl)isoindoline-1,3-dione

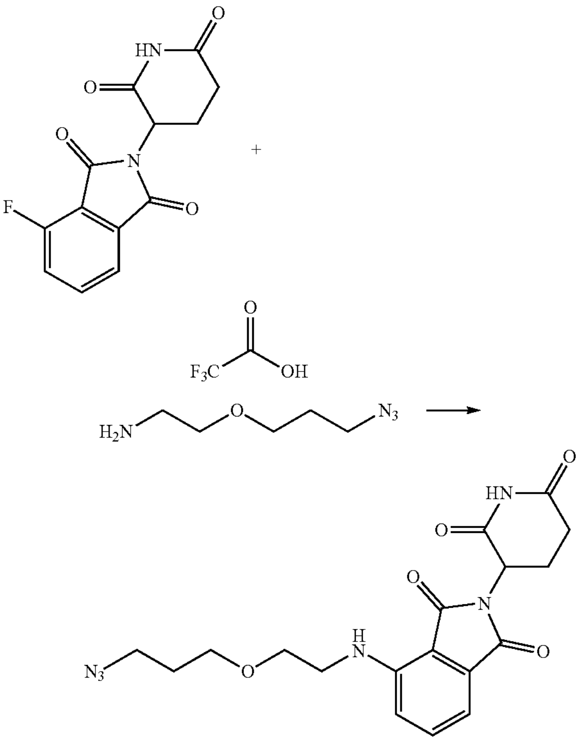

2-(2,6-Dioxopiperidine-3-yl)-4-fluoroisoindoline-1,3-dione (0.226 g, 0.817 mmol) was dissolved in N-methyl-2-pyrrolidone (8 mL), to which the compound prepared in step 3 (0.211 g, 0.817 mmol) and N,N-diisopropylethylamine (0.714 mL, 4.09 mmol) were added, followed by stirring at 90° C. for 16 hours. Upon completion of the reaction, the reaction mixture was diluted with dichloromethane, and washed with water and brine. The residue of the organic layer was dried over anhydrous sodium sulfate, filtered and concentrated, and then purified by MPLC to give a target compound (0.28 g, 86%).

LC/MS (ESI) m/z: 401$[M+H]^+$

Step 5: Preparation of 4-((2-(3-aminopropoxy)ethyl)amino)-2-(2,6-dioxopiperidine-3-yl)isoindoline-1,3-dione

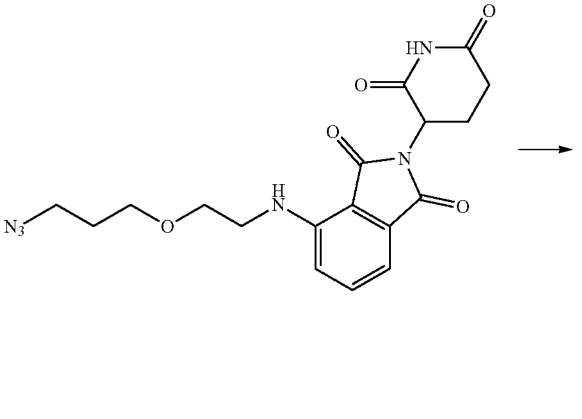

-continued

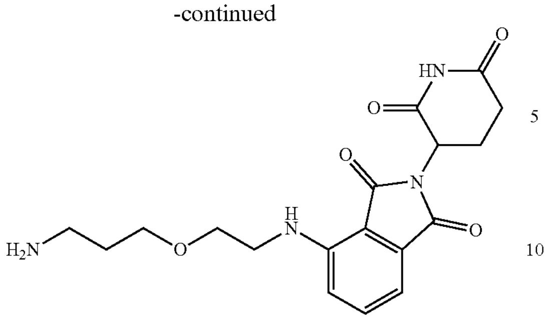

The compound prepared in step 4 (0.28 g, 0.699 mmol) was dissolved in methanol (7 ml), to which Pd/C (0.074 g, 0.070 mmol) was added, followed by stirring at room temperature for 48 hours under a hydrogen atmosphere. Upon completion of the reaction, the reaction mixture was filtered through Celite. The separated filtrate was concentrated under reduced pressure to give a target compound, and the obtained compound was used in the next step without further purification.

LC/MS (ESI) m/z: 375[M+H]+

Step 6: Preparation of N-((4,6-dimethyl-2-oxo-1,2-dihydropyridine-3-yl)methyl)-4'-((4-(2-((3-(2-((2-(2,6-dioxopiperidine-3-yl)-1,3-dioxoisoindoline-4-yl)amino)ethoxy)propyl)amino)-2-oxoethyl)piperazine-1-yl)methyl)-5-(ethyl(tetrahydro-2H-pyran-4-yl)amino)-4-methyl-[1,1'-biphenyl]-3-carboxamide

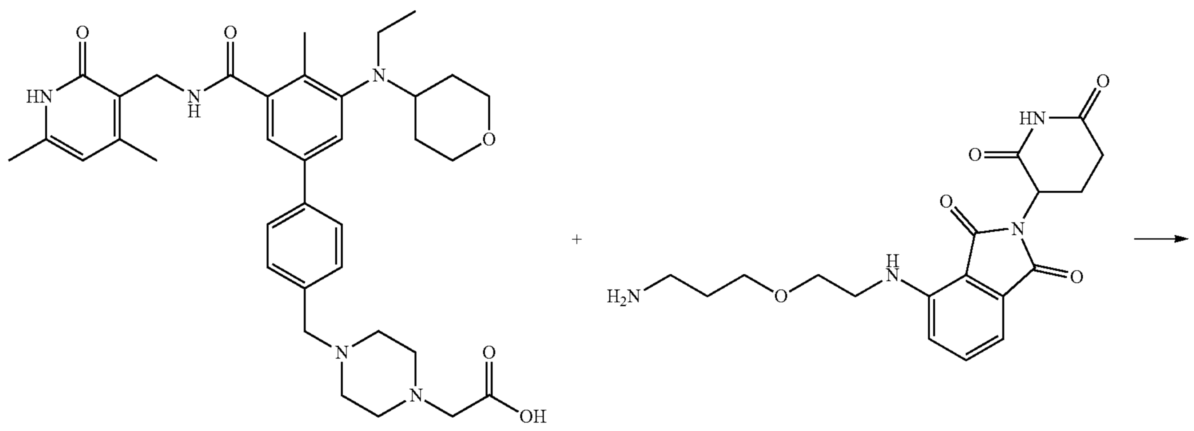

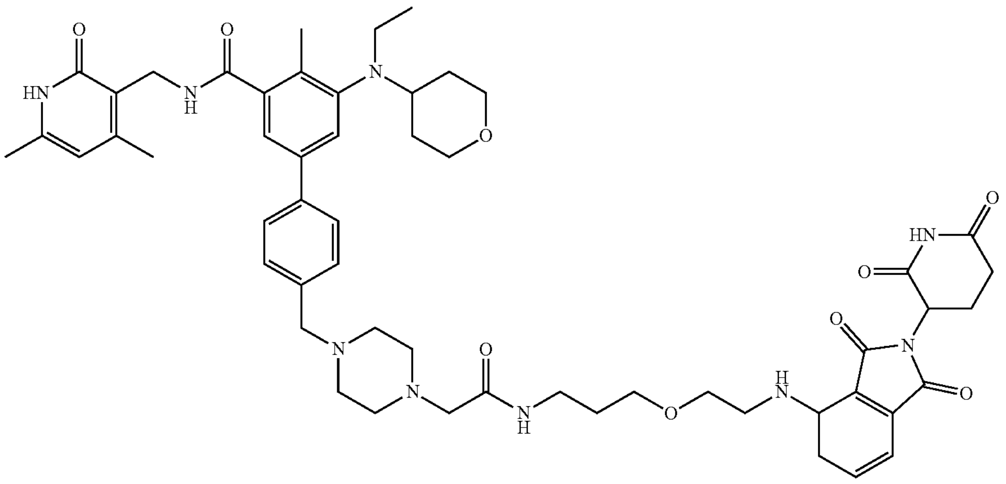

The compound (0.078 g, 0.104 mmol) prepared in [Example 1-Step 6] was dissolved in N,N-dimethylformamide (2 mL), to which the compound prepared in step 5 (0.030 g, 0.070 mmol), N,N-diisopropylethylamine (0.091 mL, 0.522 mmol) and HATU (0.060 g, 0.157 mmol) were added, followed by stirring at room temperature for 16 hours. Upon completion of the reaction, the reaction mixture was purified by Prep HPLC, and neutralized by adding a sodium hydrogen carbonate aqueous solution to give a target compound (8.5 mg, 8%, yellow solid).

LC/MS (ESI) m/z: 987[M+H]$^+$

Example 16

A target compound was prepared in the same manner as described in Example 15.

Example 17, 18

Target compounds were prepared in the same manner as described in Example 5.

Example 19

Preparation of N-((4,6-dimethyl-2-oxo-1,2-dihydropyridine-3-yl)methyl)-4'-((4-(2-((6-((2-(2,6-dioxopiperidine-3-yl)-1,3-dioxoisoindoline-4-yl)amino)hexyl)oxy)ethyl)piperazine-1-yl)methyl)-5-(ethyl(tetrahydro-2H-pyran-4-yl)amino)-4-methyl-[1,1'-biphenyl]-3-carboxamide

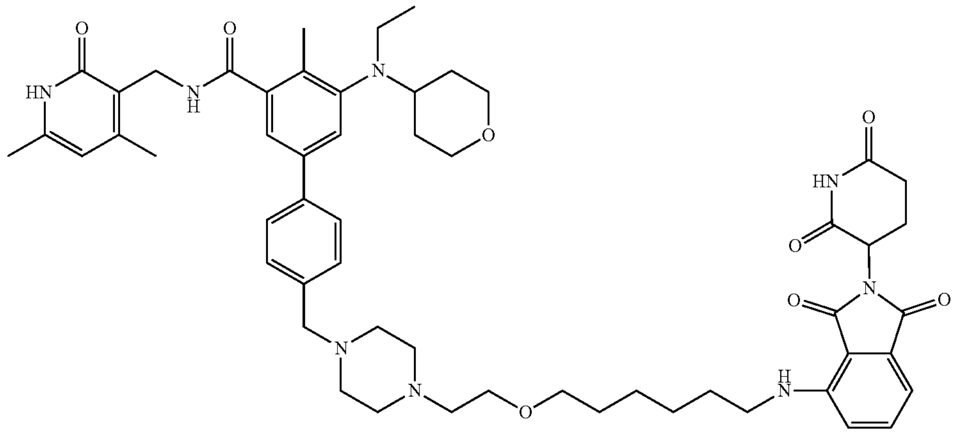 [SMILES: CCN(c1cc(-c2ccc(CN3CCN(CCOCCCCCCNc4cccc5c4C(=O)N(C4CCC(=O)NC4=O)C5=O)CC3)cc2)cc(C(=O)NCc2c(C)cc(C)[nH]c2=O)c1C)C1CCOCC1]

Step 1: Preparation of 2-(6-(2-(benzyloxy)ethoxy)hexyl)isoindoline-1,3-dione

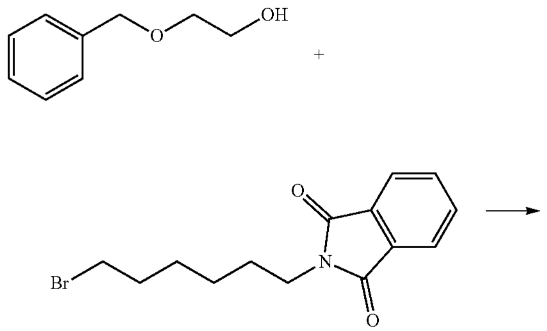

-continued

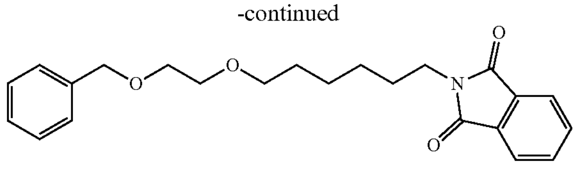

2-(Benzyloxy)ethanol (0.368 g, 2.42 mmol) was dissolved in N,N-dimethylformamide (5 ml), to which sodium hydride (0.13 g, 3.22 mmol) was added at 0° C. Then, 2-(6-bromohexyl)isoindoline-1,3-dione (0.5 g, 1.6 mmol) was added to the reaction mixture while stirring at 0° C., followed by stirring at room temperature for 15 hours. Upon completion of the reaction, the reaction mixture was diluted with ethyl acetate and an aqueous ammonium chloride solution and washed with water and brine. The residue of the organic layer was dried over anhydrous sodium sulfate, filtered and concentrated, and then purified by MPLC to give a target compound (94 mg, 16%, colorless liquid).

LC/MS (ESI) m/z: 382[M+H]+

Step 2: Preparation of 2-(6-(2-hydroxyethoxy)hexyl)isoindoline-1,3-dione

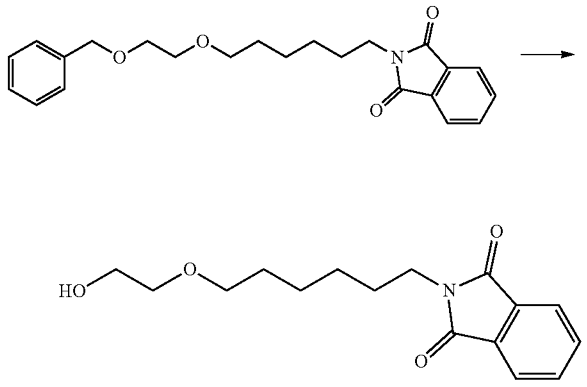

The compound prepared in step 1 (94 mg, 0.25 mmol) was dissolved in a 3:1 solution (3 ml) of ethyl acetate and methanol, followed by stirring under palladium and hydrogen for 3 hours. Upon completion of the reaction, the reaction mixture was filtered and concentrated to give a target compound (70 mg, 98%, colorless liquid).

LC/MS (ESI) m/z: 292 [M+H]+

Step 3: Preparation of 2-(6-(2-bromoethoxy)hexyl)isoindoline-1,3-dione

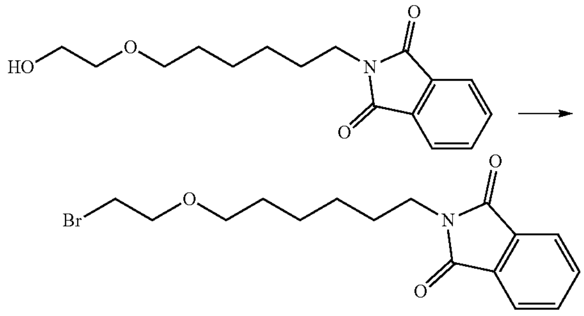

The compound prepared in step 2 (70 mg, 0.24 mmol) was dissolved in dichloromethane (1.2 ml), to which carbon tetrabromide (88 mg, 0.26 mmol) and triphenylphosphine (107 mg, 0.41 mmol) were added, followed by stirring at room temperature for 20 hours. Then, the reaction mixture was diluted with hexane, filtered and concentrated, and then purified by MPLC to give a target compound (69 mg, 81%, colorless liquid).

LC/MS (ESI) m/z: 354[M+H]+

Step 4: Preparation of N-((4,6-dimethyl-2-oxo-1-2-dihydropyridine-3-yl)methyl)-4'-((4-(2-((6-(1,3-dioxoisoindoline-2-yl)hexyl)oxy)ethyl)piperazine-1-yl)methyl)-5-(ethyl(tetrahydro-2H-pyran-4-yl)amino)-4-methyl-[1,1'-biphenyl]-3-carboxamide

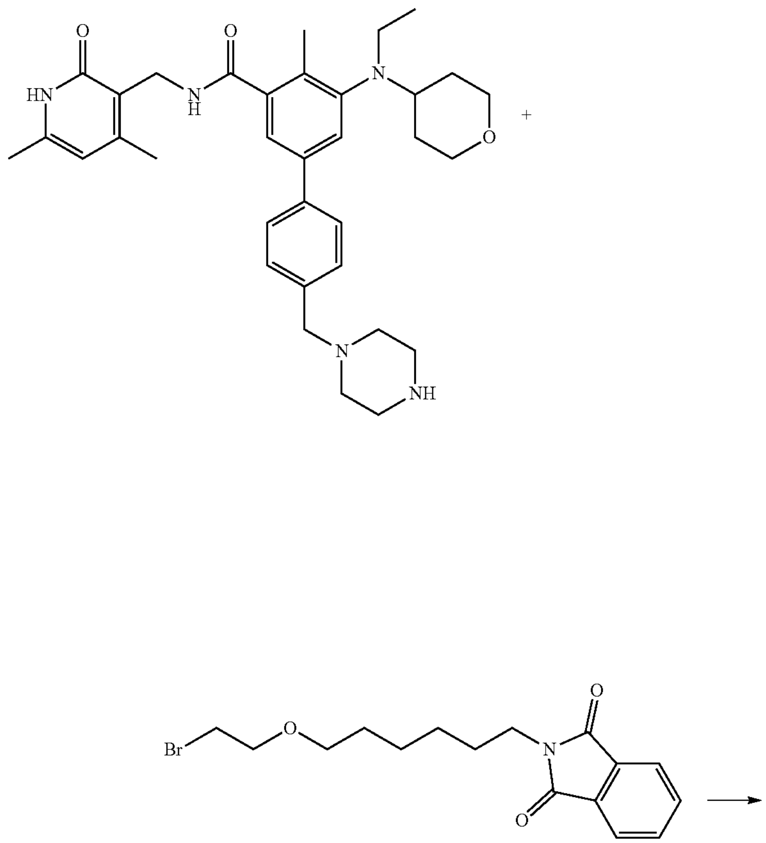

-continued

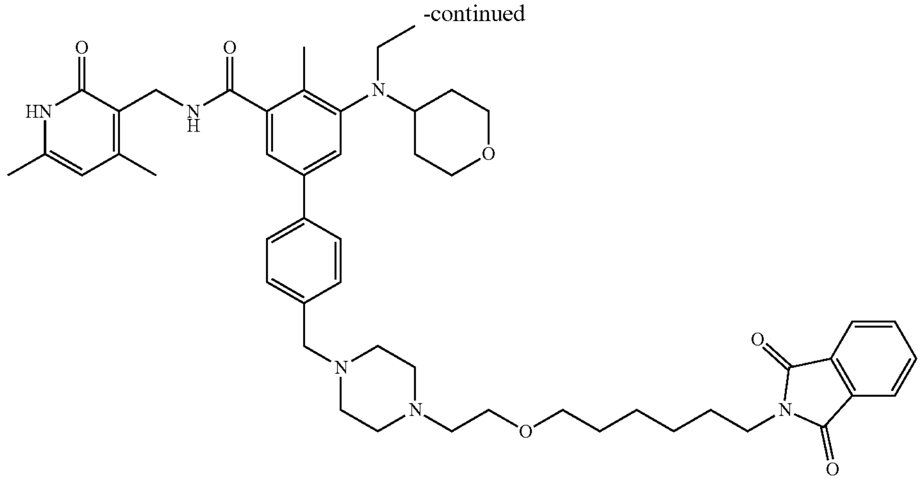

The compound prepared in step 3 (69 mg, 0.195 mmol) was dissolved in N,N-dimethylformamide (5 ml), to which the compound (101 mg, 0.177 mmol) prepared in [Example 1—step 4] and potassium carbonate (122 mg, 0.88 mmol) were added, followed by stirring at 70° C. for 3 hours. Upon completion of the reaction, the reaction mixture was diluted with ethyl acetate, and washed with water. The residue of the organic layer was dried over anhydrous sodium sulfate, filtered and concentrated, and then purified by MPLC to give a target compound (60 mg, 40%, yellow liquid).

LC/MS (ESI) m/z: $845[M+H]^+$

Step 5: Preparation of 4'-((4-(2-((6-aminohexyl)oxy)ethyl)piperazine-1-yl)methyl)-N-((4,6-dimethyl-2-oxo-1,2-dihydropyridine-3-yl)methyl)-5-(ethyl(tetrahydro-2H-pyran-4-yl)amino)-4-methyl-[1,1'-biphenyl]-3-carboxamide

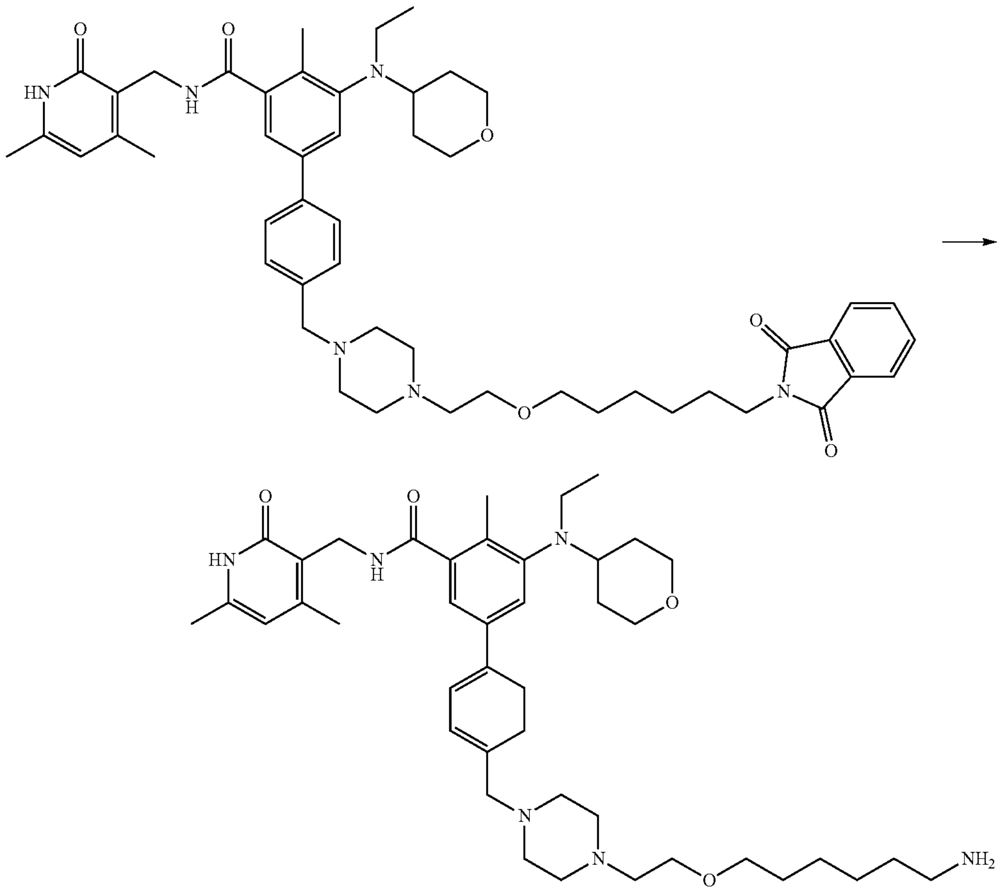

The compound prepared in step 4 (60 mg, 0.071 mmol) was dissolved in ethanol (1 ml), to which hydrazinyl hydrate (0.017 ml, 0.35 mmol) was added, followed by stirring at room temperature for 3 hours. Upon completion of the reaction, the reaction mixture was concentrated under reduced pressure and purified by MPLC to give a target compound (48 mg, 95%, yellow liquid).

LC/MS (ESI) m/z: 715[M+H]$^+$

Step 6: Preparation of N-((4,6-dimethyl-2-oxo-1,2-dihydropyridine-3yl)methyl)-4'-((4-(2-((6-((2-(2,6-dioxopiperidine-3-yl)-1,3-dioxoisoindoline-4-yl)amino)hexyl)oxy)ethyl)piperazine-1-yl)methyl)-5-(ethyl(tetrahydro-2H-pyran-4-yl)amino)-4-methyl-[1,1'-biphenyl]-3-carboxamide

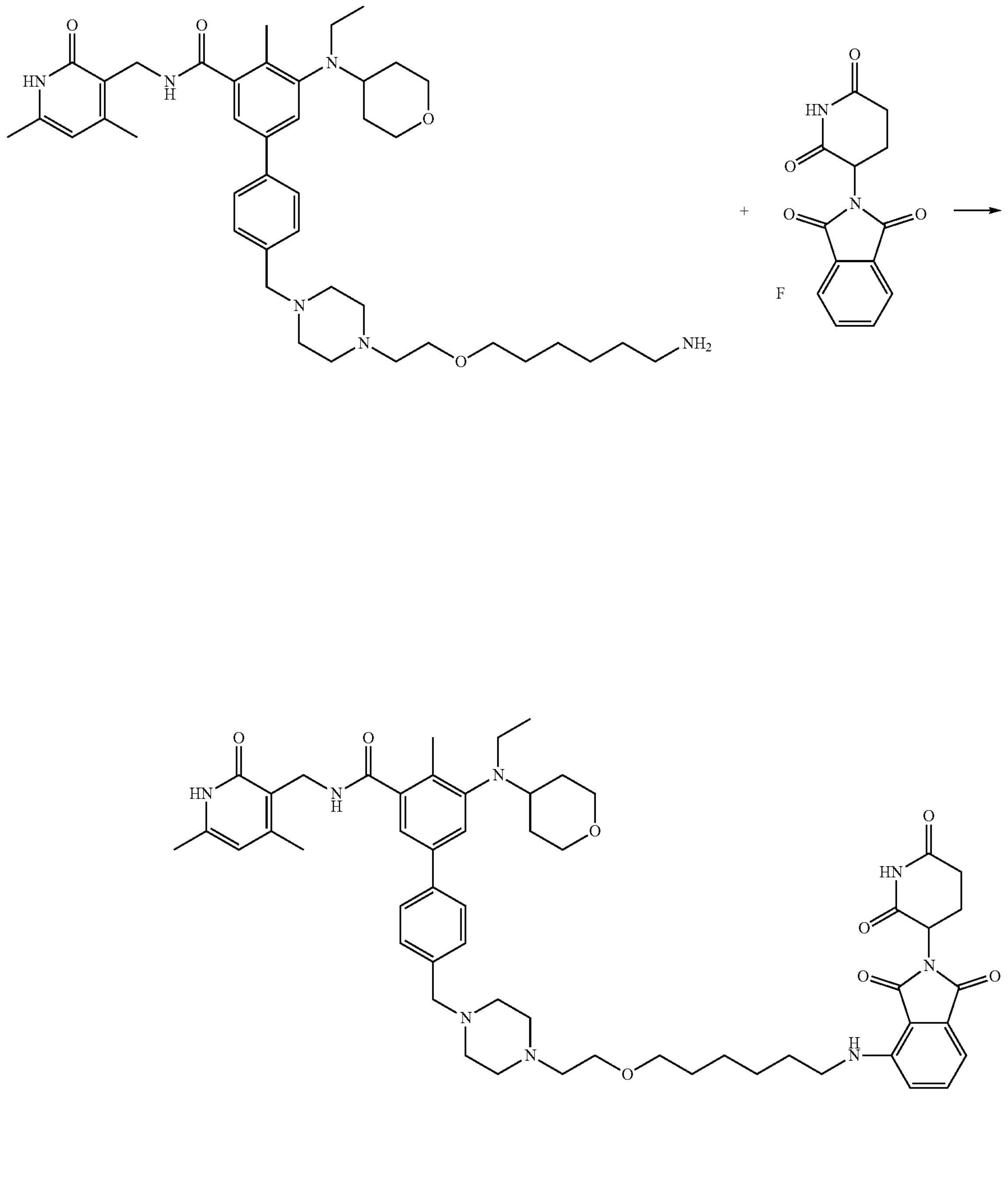

The compound prepared in step 5 (48 mg, 0.067 mmol) was dissolved in N,N-dimethylformamide (1 ml), to which 2-(2,6-dioxopiperidine-3-yl)-4-fluoroisoindoline-1,3-dione (0.028 g, 0.101 mmol) and N,N-diisopropylethylamine (0.035 ml, 0.20 mmol) were added, followed by stirring at 90° C. for 4 hours. Upon completion of the reaction, the temperature of the reaction mixture was lowered to room temperature, diluted with ethyl acetate, and washed with water and brine. The residue of the organic layer was dried over anhydrous sodium sulfate, filtered and concentrated, purified by Prep HPLC, and neutralized by adding a sodium hydrogen carbonate aqueous solution to give a target compound (11.8 mg, 17%, yellow solid).

LC/MS (ESI) m/z: $971[M+H]^+$

Example 20

A target compound was prepared in the same manner as described in Example 1.

Example 21

Preparation of N-((4,6-dimethyl-2-oxo-1,2-dihydropyridine-3-yl)methyl)-4'-((4-(2-((6-((2-(2,6-dioxopiperidine-3-yl)-1,3-dioxoisoindoline-4-yl)amino)hexyl)amino)ethyl)piperazine-1-yl)methyl)-5-(ethyl(tetrahydro-2H-pyran-4-yl)amino)-4-methyl-[1,1'-biphenyl]-3-carboxamide

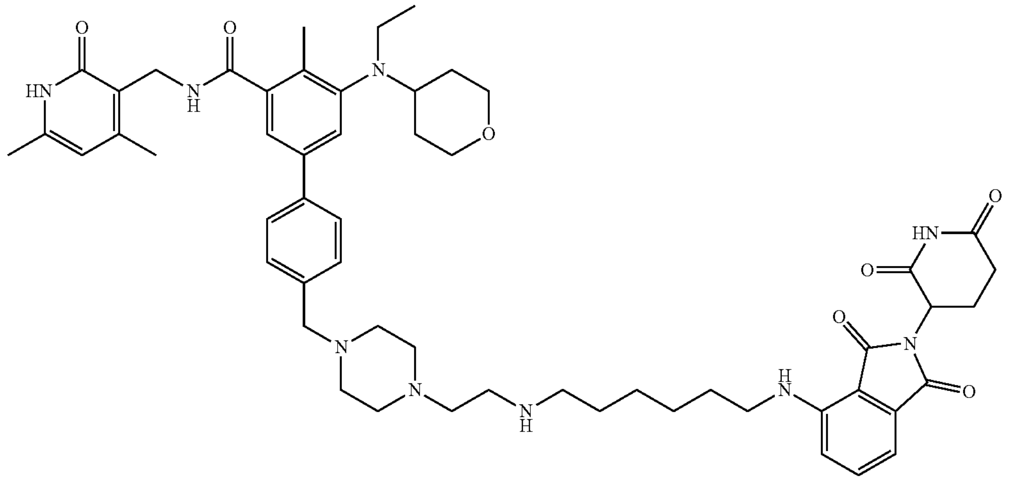 [SMILES: CCN(c1cc(-c2ccc(CN3CCN(CCNCCCCCCNc4cccc5c4C(=O)N(C4CCC(=O)NC4=O)C5=O)CC3)cc2)cc(C(=O)NCc2c(C)cc(C)[nH]c2=O)c1C)C1CCOCC1]

Step 1: Preparation of 2-(2,6-dioxopiperidine-3-yl)-4-((6-hydroxyhexyl)amino)isoindoline-1,3-dione

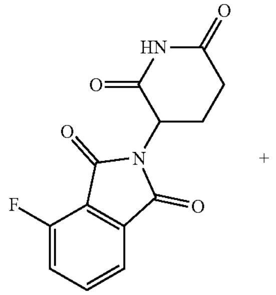

-continued

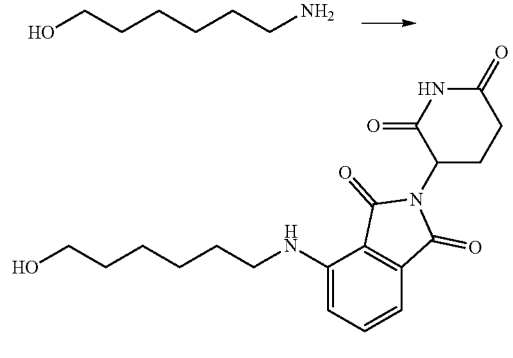

2-(2,6-Dioxopiperidine-3-yl)-4-fluoroisoindoline-1,3-dione (0.2 g, 0.724 mmol) was dissolved in N-methyl-2-pyrrolidone (7 mL), to which 6-aminohexan-1-ol (0.085 g, 0.724 mmol) and N,N-diisopropylethylamine (0.253 mL, 1.448 mmol) were added, followed by stirring at 90° C. for 16 hours. Upon completion of the reaction, the reaction mixture was diluted with dichloromethane, and washed with water and brine. The residue of the organic layer was dried over anhydrous sodium sulfate, filtered and concentrated, and then purified by MPLC to give a target compound (0.12 g, 45%).

LC/MS (ESI) m/z: 374[M+H]+

Step 2: Preparation of 6-((2-(2,6-dioxopiperidine-3-yl)-1,3-dioxoisoindoline-4-yl)amino)hexanal

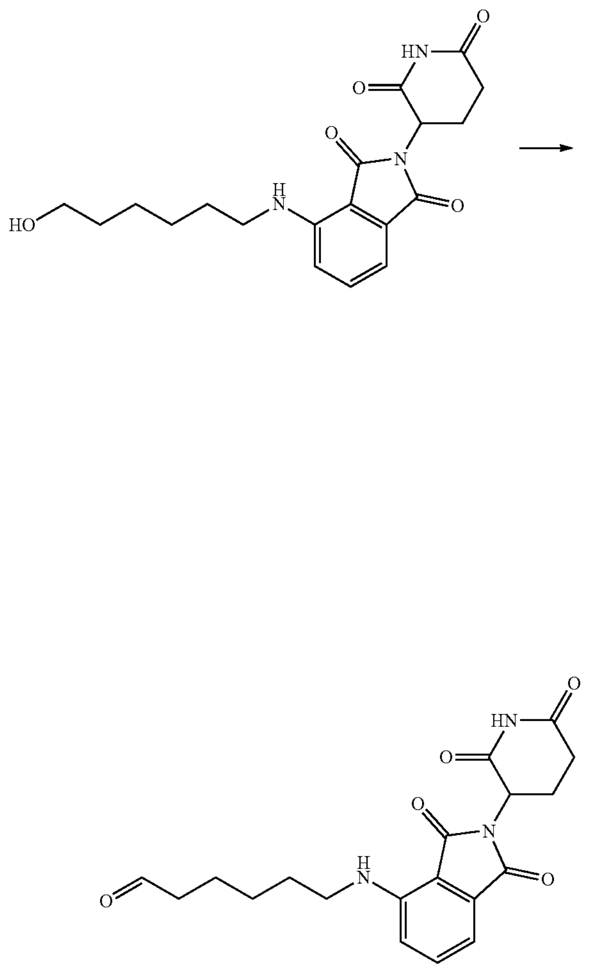

The compound prepared in step 1 (0.1215 g, 0.325 mmol) was dissolved in dichloromethane (2 mL), to which Dess-MartinPeriodinane (0.179 g, 0.423 mmol) was added at 0° C., followed by stirring at room temperature for 4 hours. Upon completion of the reaction, the reaction mixture was diluted with dichloromethane, and washed with water and brine. The residue of the organic layer was dried over anhydrous sodium sulfate, filtered and concentrated, and then purified by MPLC to give a target compound (0.124 g, 100%).

LC/MS (ESI) m/z: 372[M+H]+

Step 3: Preparation of tert-butyl(2-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-biphenyl]-4-yl)methyl)piperazine-1-yl)ethyl)carbamate

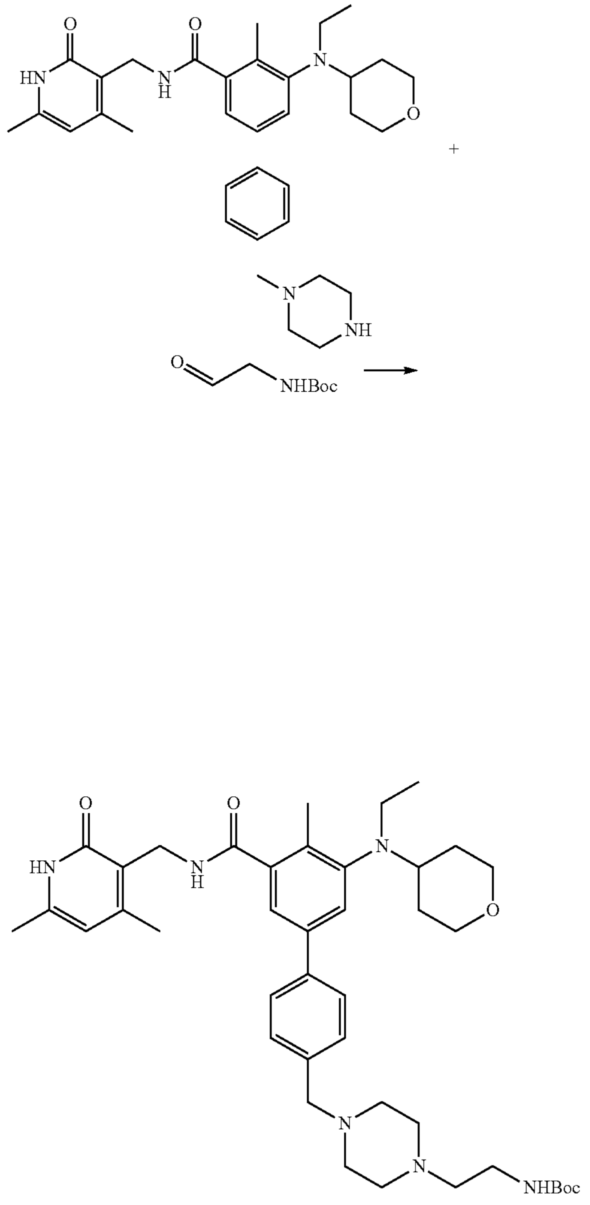

The compound (0.3 g, 0.525 mmol) prepared in [Example 1-Step 4] was dissolved in N,N-dimethylformamide (5 mL), to which tert-butyl(2-oxoethyl)carbamate (0.134 g, 0.840 mmol) and $NaBH_3CN$ (0.222 g, 1.049 mmol) were added, and acetic acid (0.300 mL, 5.25 mmol) was added at 0° C. Then, the mixture was stirred at room temperature for 16 hours. Upon completion of the reaction, the reaction mixture was diluted with dichloromethane, and washed with water and a sodium hydrogen carbonate aqueous solution. The residue of the organic layer was dried over anhydrous sodium sulfate, filtered and concentrated, and then purified by MPLC to give a target compound (0.10 g, 28%).

LC/MS (ESI) m/z: 715[M+H]+

Step 4: Preparation of 4'-((4-(2-aminoethyl)piperazine-1-yl)methyl)-N-((4,6-dimethyl-2-oxo-1,2-dihydropyridine-3-yl)methyl)-5-(ethyl(tetrahydro-2H-pyran-4-yl)amino)-4-methyl-[1,1'-biphenyl]-3-carboxamide2,2,2-trifluoroacetic acid salt

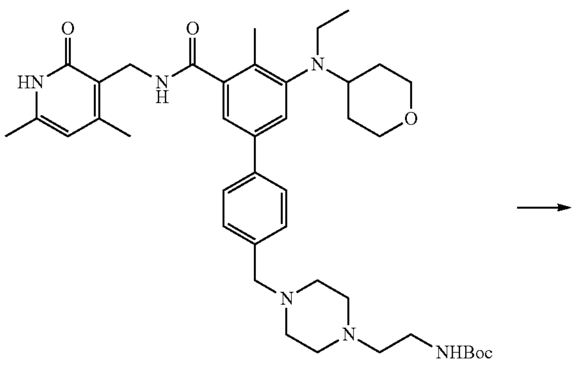

-continued

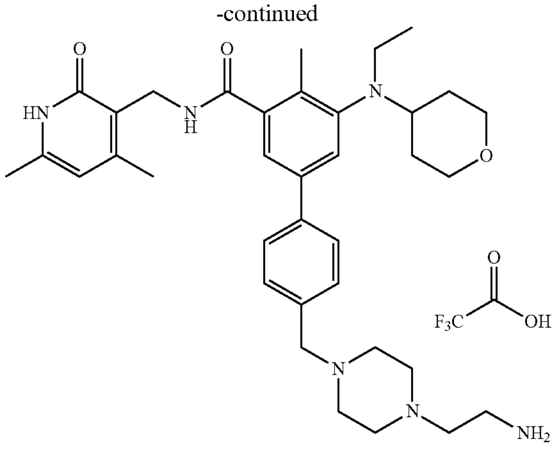

The compound prepared in step 3 (0.1044 g, 0.146 mmol) was dissolved in dichloromethane (2 mL), to which trifluoroacetic acid (1 mL, 26.0 mmol) was added, followed by stirring at room temperature for 1 hour. Upon completion of the reaction, the reaction mixture was concentrated under reduced pressure to give a target compound, and the obtained compound was used in the next step without further purification.

LC/MS (ESI) m/z: 615[M+H]$^+$

Step 5: Preparation of N-((4,6-dimethyl-2-oxo-1,2-dihydropyridine-3-yl)methyl)-4'-((4-(2-((6-((2-(2,6-dioxopiperidine-3-yl)-1,3-dioxoisoindoline-4-yl)amino)hexyl)amino)ethyl)piperazine-1-yl)methyl)-5-(ethyl(tetrahydro-2H-pyran-4-yl)amino)-4-methyl-[1,1'-biphenyl]-3-carboxamide

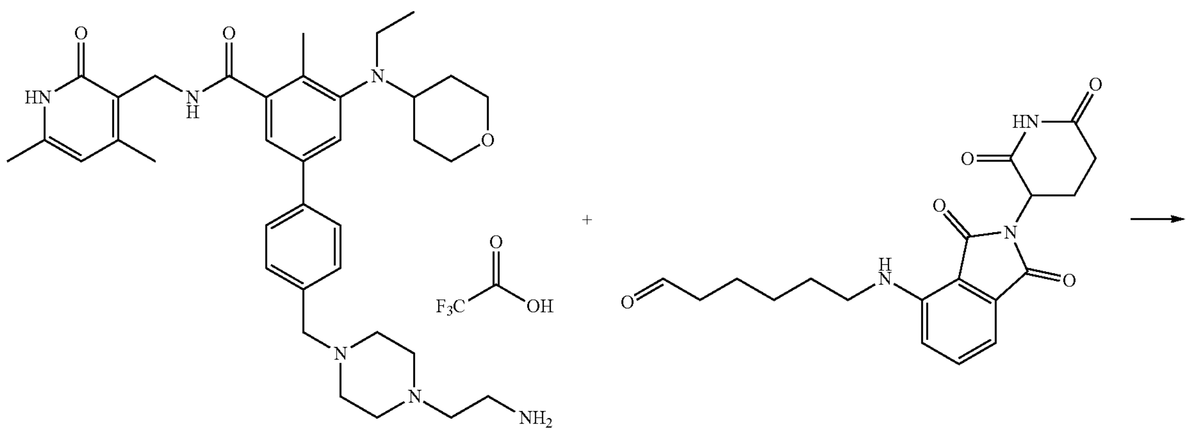

-continued

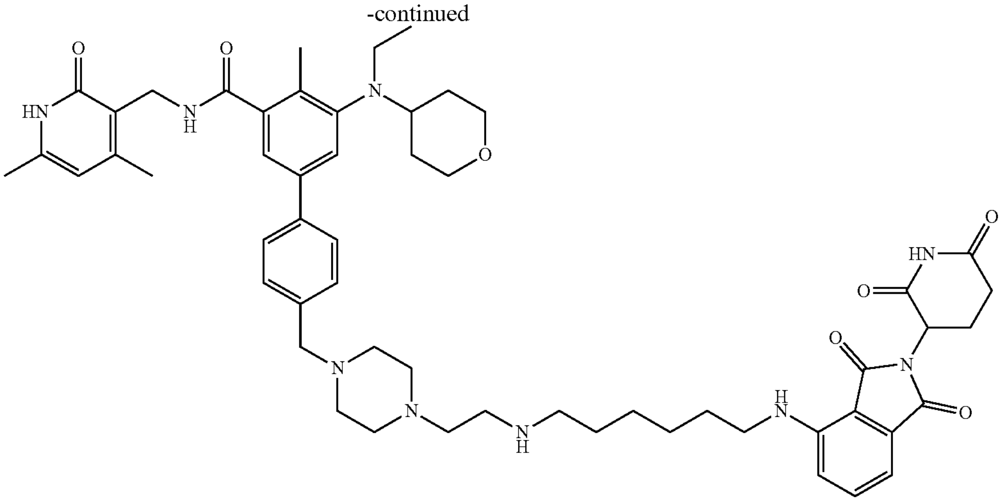

The compound prepared in step 4 (0.0341 g, 0.055 mmol) was dissolved in dichloroethane (2 ml), to which the compound prepared in step 2 (0.021 g, 0.055 mmol), $NaBH_3CN$ (0.024 g, 0.111 mmol) and two drops of acetic acid were added at 0° C., followed by stirring at room temperature for 6 hours. Upon completion of the reaction, the reaction mixture was diluted with dichloromethane, and washed with water and a sodium hydrogen carbonate aqueous solution. The residue of the organic layer was dried over anhydrous sodium sulfate, filtered and concentrated, purified by Prep HPLC, and neutralized by adding a sodium hydrogen carbonate aqueous solution to give a target compound (6.1 mg, 11%, yellow solid).

LC/MS (ESI) m/z: 971[M+H]+

Example 22

A target compound was prepared in the same manner as described in Example 1.

Example 23

Preparation of N-((4,6-dimethyl-2-oxo-1,2-dihydropyridine-3-yl)methyl)-4'-((4-((1-(3-((2-(2,6-dioxopiperidine-3-yl)-1,3-dioxoisoindoline-4-yl)amino)propyl)-1H-1,2,3-triazole-4-yl)methyl)piperazine-1-yl)methyl)-5-(ethyl(tetrahydro-2H-pyran-4-yl)amino)-4-methyl-[1,1'-biphenyl]-3-carboxamide

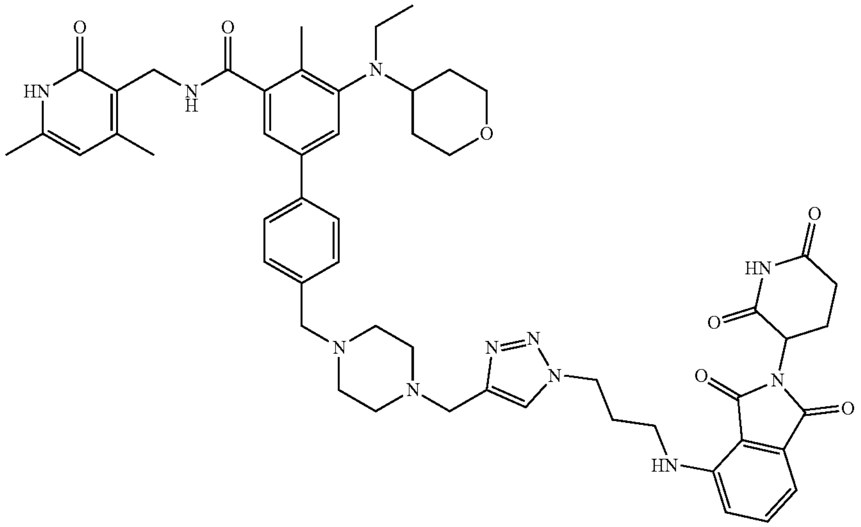 [SMILES: CCN(c1cc(-c2ccc(CN3CCN(Cc4cn(CCCNc5cccc6c5C(=O)N(C5CCC(=O)NC5=O)C6=O)nn4)CC3)cc2)cc(C(=O)NCc2c(C)cc(C)[nH]c2=O)c1C)C1CCOCC1]

Step 1: Preparation of 4-((3-azidopropyl)amino)-2-(2,6-dioxopiperidine-3-yl)isoindoline-1,3-dione

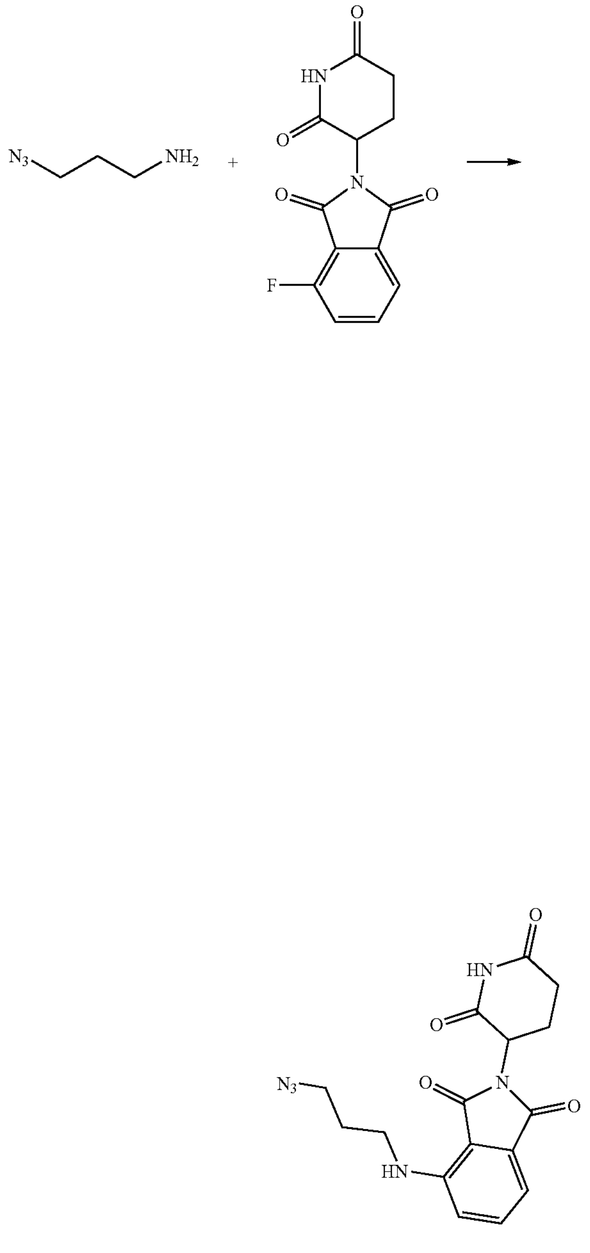

3-Azidopropane-1-amine (0.435 g, 4.34 mmol) was dissolved in N,N-dimethylformamide (12 ml), to which 2-(2,6-dioxopiperidine-3-yl)-4-fluoroisoindoline-1,3-dione (1 g, 3.62 mmol) and N,N-diisopropylethylamine (1.26 ml, 7.24 mmol) were added, followed by heating at 90° C. for 2 hours. Upon completion of the reaction, the temperature of the reaction mixture was lowered to room temperature, diluted with ethyl acetate, and washed with water and brine. The residue of the organic layer was dried over anhydrous sodium sulfate, filtered and concentrated, and then purified by MPLC to give a target compound (0.3 g, 23%, yellow solid).

LC/MS (ESI) m/z: 357[M+H]$^+$

Step 2: Preparation of N-((4,6-dimethyl-2-oxo-1,2-dihydropyridine-3-yl)methyl)-5-(ethyl(tetrahydro-2H-pyran-4-yl)amino)-4-methyl-4'-((4-prop-2-yn-1-yl)piperazine-1-yl)methyl)-[1,1'-biphenyl]-3-carboxamide

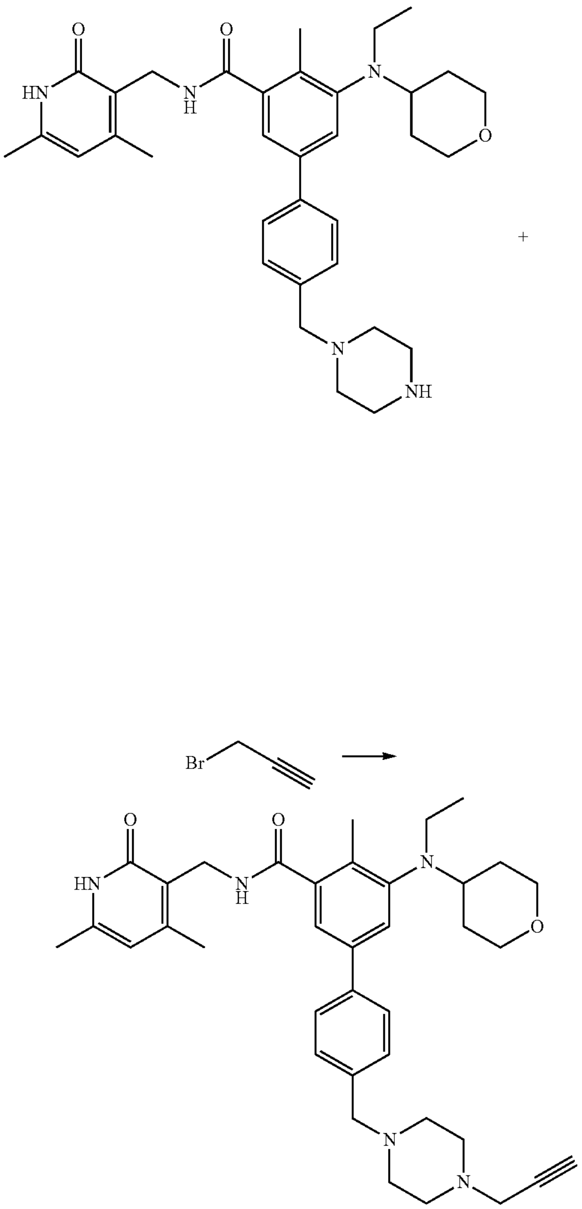

The compound (0.3 g, 0.437 mmol) prepared in [Example 1—Step 4] was dissolved in N,N-dimethylformamide (4 ml), to which potassium carbonate (0.3 g, 2.2 mmol) and 3-bromoprop-1-yn (0.104 g, 0.875 mmol) were added, followed by stirring at 70° C. for 3 hours. Upon completion of the reaction, the temperature of the reaction mixture was lowered to room temperature, diluted with ethyl acetate, and washed with water and brine. The residue of the organic layer was dried over anhydrous sodium sulfate, filtered and concentrated, and then purified by MPLC to give a target compound (0.1 g, 38%, white solid).

LC/MS (ESI) m/z: 610[M+H]$^+$

Step 3: Preparation of N-((4,6-dimethyl-2-oxo-1,2-dihydropyridine-3-yl)methyl)-4'-((4-((1-(3-((2-(2,6-dioxopiperidine-3-yl)-1,3-dioxoisoindoline-4-yl)amino)propyl)-1H-1,2,3-triazole-4-yl)methyl)piperazine-1-yl)methyl)-5-(ethyl(tetrahydro-2H-pyran-4-yl)amino)-4-methyl-[1,1'-biphenyl]-3-carboxamide
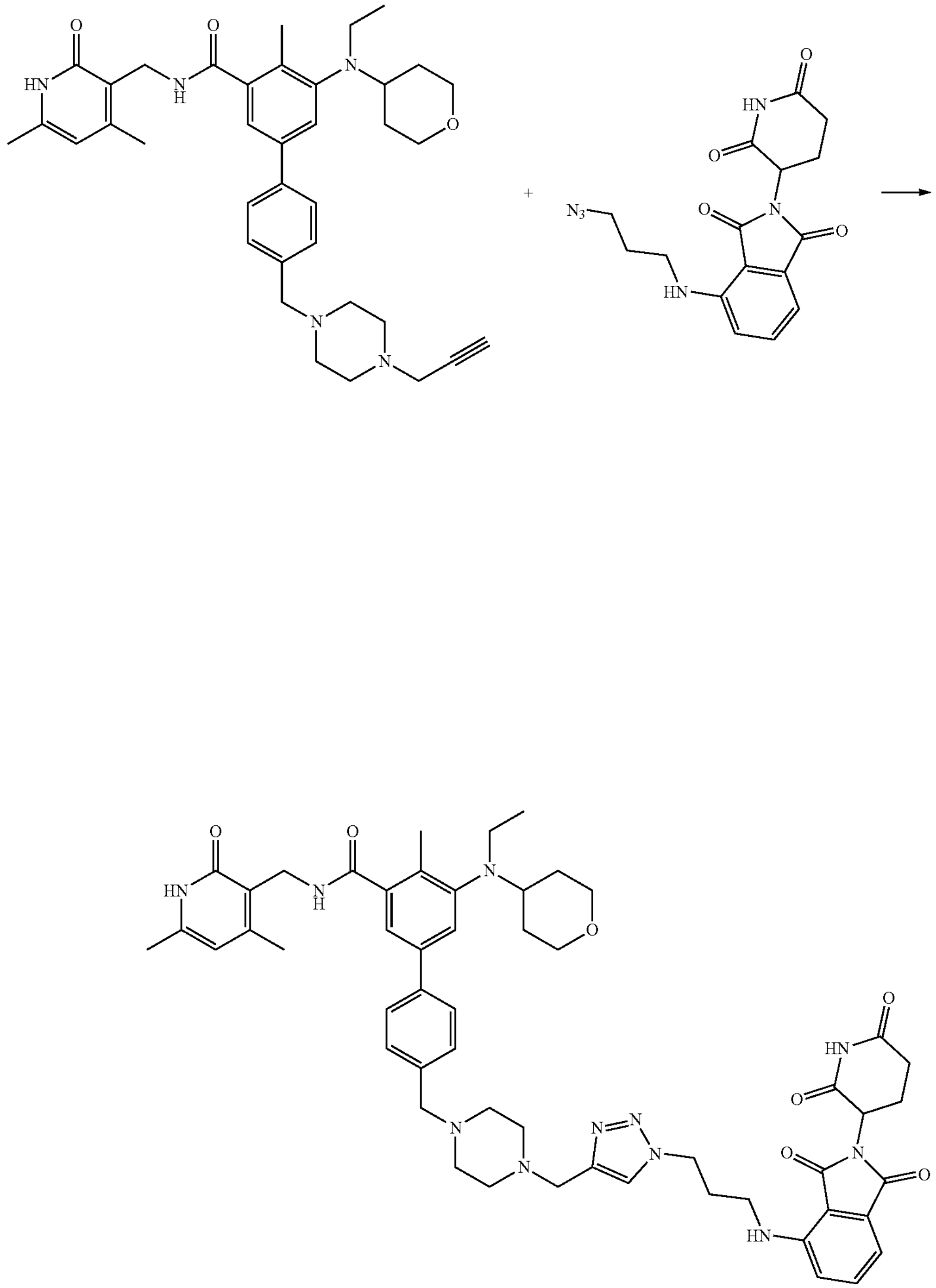

The compound prepared in step 1 (23.4 mg, 0.066 mmol) and the compound prepared in step 2 (20 mg, 0.033 mmol) were dissolved in tetrahydrofuran (1 ml), to which copper sulfate (0.52 mg, 0.003 mmol), sodium ascorbate (1.3 mg, 0.006 mmol) and water (0.2 ml) were added, followed by stirring at room temperature for 12 hours. Upon completion of the reaction, the reaction mixture was diluted with ethyl acetate, and washed with water. The residue of the organic layer was dried over anhydrous sodium sulfate, filtered and concentrated, purified by Prep HPLC, and neutralized by adding a sodium hydrogen carbonate aqueous solution to give a target compound (7.6 mg, 23%, yellow solid).

LC/MS (ESI) m/z: 966$[M+H]^+$

Example 24

A target compound was prepared in the same manner as described in Example 23.

Example 25

Preparation of N-((4,6-dimethyl-2-oxo-1,2-dihydropyridine-3-yl)methyl)-4'-((4-(1-(3-((2-(2,6-dioxopiperidine-3-yl)-1,3-dioxoisoindoline-4-yl)amino)propyl)-1H-1,2,3-triazole-4-carbonyl)piperazine-1-yl)methyl)-5-(ethyl(tetrahydro-2H-pyran-4-yl)amino)-4-methyl-[1,1'-biphenyl]-3-carboxamide

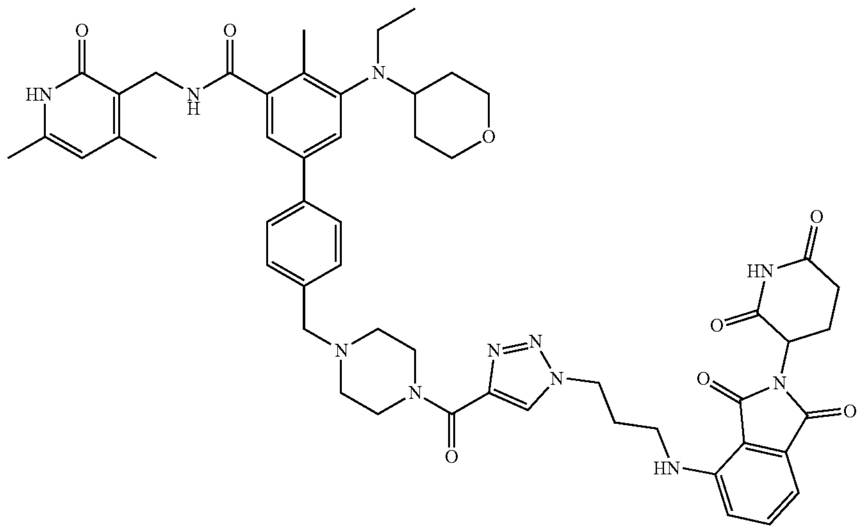 [SMILES: CCN(c1cc(-c2ccc(CN3CCN(C(=O)c4cn(CCCNc5cccc6c5C(=O)N(C5CCC(=O)NC5=O)C6=O)nn4)CC3)cc2)cc(C(=O)NCc2c(C)cc(C)[nH]c2=O)c1C)C1CCOCC1]

Step 1: Preparation of N-((4,6-dimethyl-2-oxo-1,2-dihydropyridine-3-yl)methyl)-5-(ethyl(tetrahydro-2H-pyran-4-yl)amino)-4-methyl-4'-((4-propioloylpiperazine-1-yl)methyl)-[1,1'-biphenyl]-3-carboxamide

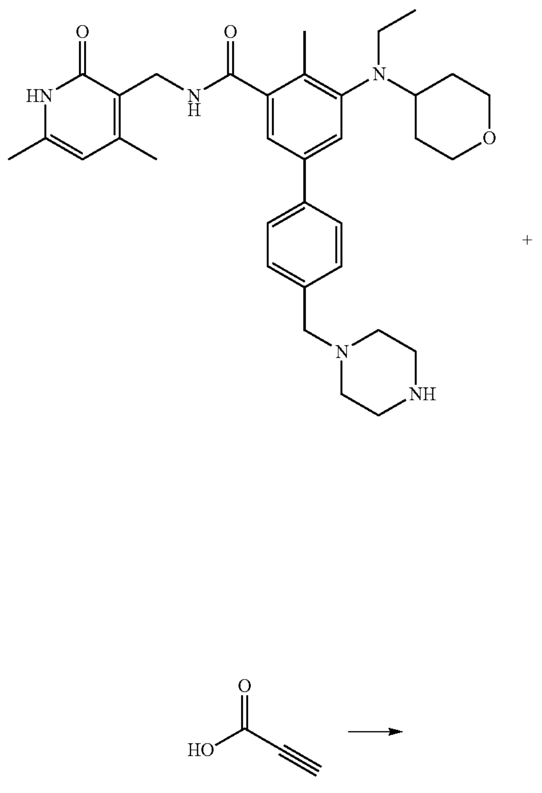

-continued

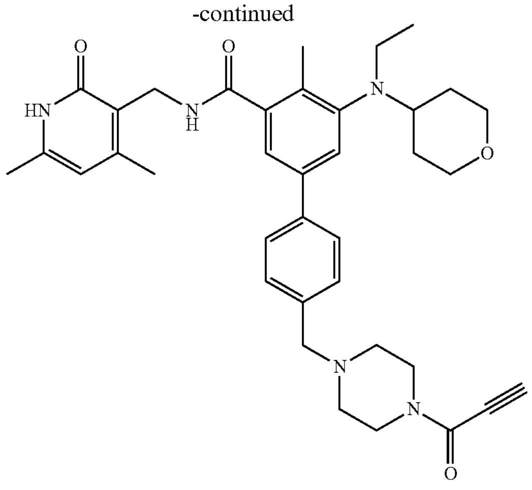

The compound (0.2 g, 0.29 mmol) prepared in [Example 1—Step 4] was dissolved in N,N-dimethylformamide (1.5 ml), to which propiolic acid (0.036 ml, 0.58 mmol), N,N-diisopropylethylamine (0.254 ml, 1.5 mmol)) and HATU (0.22 g, 0.58 mmol) were added, followed by stirring at room temperature for 12 hours. Upon completion of the reaction, the reaction mixture was diluted with ethyl acetate, and washed with water. The residue of the organic layer was dried over anhydrous sodium sulfate, filtered and concentrated, and then purified by MPLC to give a target compound (65 mg, 36%, white solid).

LC/MS (ESI) m/z: 624[M+H]$^+$

Step 2: Preparation of N-((4,6-dimethyl-2-oxo-1,2-dihydropyridine-3-yl)methyl)-4'-((4-(1-(3-((2-(2,6-dioxopiperidine-3-yl)-1,3-dioxoisoindoline-4-yl)amino)propyl)-1H-1,2,3-triazole-4-carbonyl)piperazine-1-yl)methyl)-5-(ethyl(tetrahydro-2H-pyran-4-yl)amino)-4-methyl-[1,1'-biphenyl]-3-carboxamide

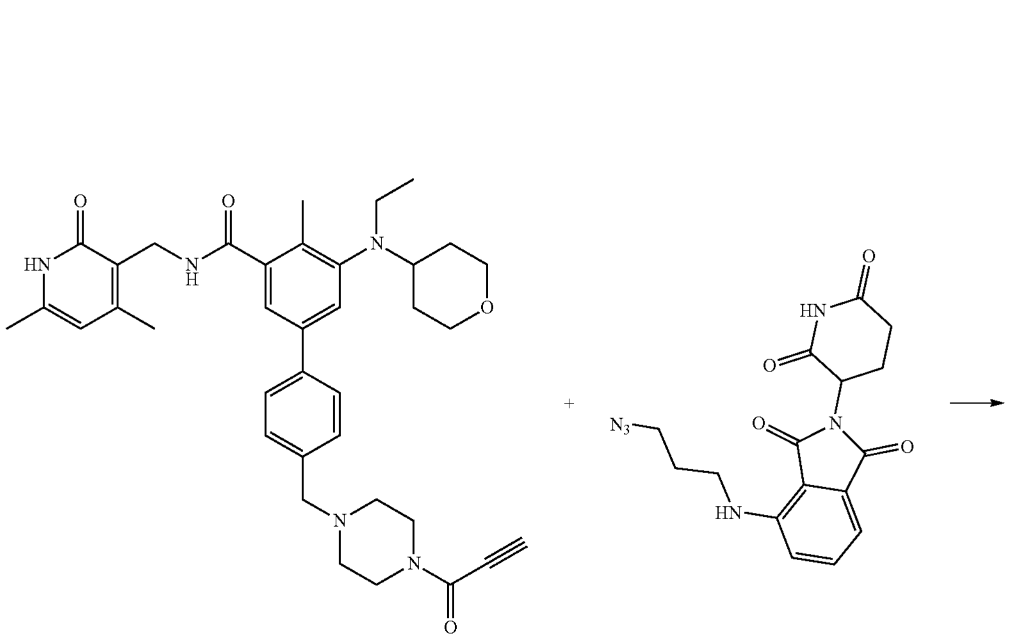

-continued

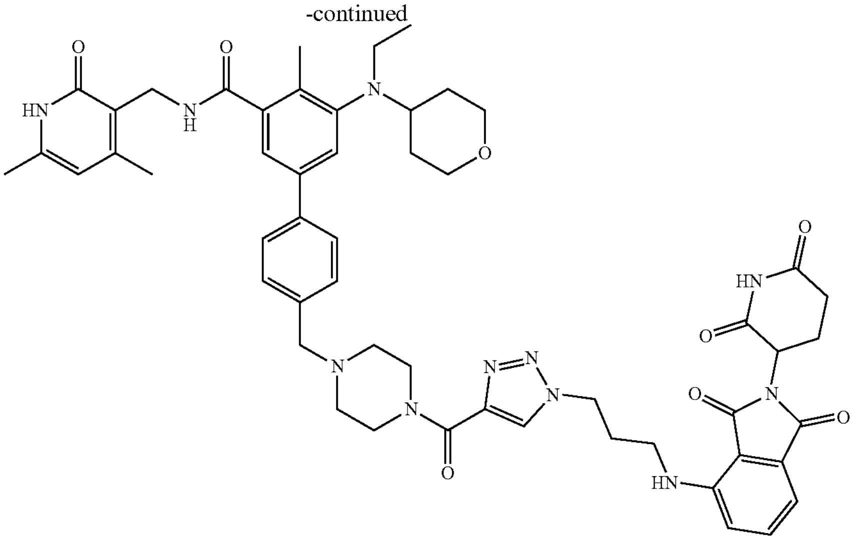

The compound prepared in step 1 (50 mg, 0.08 mmol) and the compound prepared in [Example 23—Step 1] (57.1 mg, 0.16 mmol) were dissolved in tetrahydrofuran (1 ml), to which copper sulfate (7 mg, 0.044 mmol), sodium ascorbate (14 mg, 0.07 mmol) and water (0.2 ml) were added, followed by stirring at room temperature for 12 hours. Upon completion of the reaction, the reaction mixture was diluted with ethyl acetate, and washed with water. The residue of the organic layer was dried over anhydrous sodium sulfate, filtered and concentrated, purified by Prep HPLC, and neutralized by adding a sodium hydrogen carbonate aqueous solution to give a target compound (30.1 mg, 37%, yellow solid).

LC/MS (ESI) m/z: 980[M+H]$^+$

Example 26

A target compound was prepared in the same manner as described in Example 5.

Example 27

Preparation of N-((4,6-dimethyl-2-oxo-1,2-dihydropyridine-3-yl)methyl)-4'-((4-(2-((5-(3-(2-((2-(2,6-dioxopiperidine-3-yl)-1-oxoisoindoline-4-yl)amino)-2-oxoethoxy)propoxy)pentyl)amino)-2-oxoethyl)piperazine-1-yl)methyl)-5-(ethyl(tetrahydro-2H-pyran-4-yl)amino)-4-methyl-[1,1'-biphenyl]-3-carboxamide

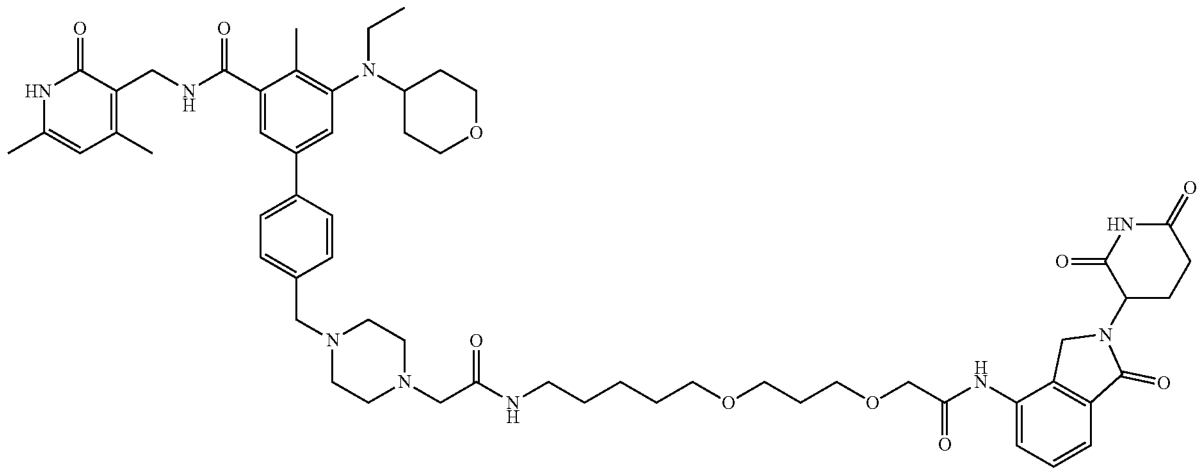 [SMILES: CCN(c1cc(-c2ccc(CN3CCN(CC(=O)NCCCCCOCCCOCC(=O)Nc4cccc5c4CN(C4CCC(=O)NC4=O)C5=O)CC3)cc2)cc(C(=O)NCc2c(C)cc(C)[nH]c2=O)c1C)C1CCOCC1]

Step 1: Preparation of 3-((5-(benzyloxy)pentyl)oxy)propane-1-ol

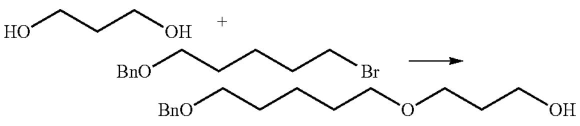

Propane-1,3-diol (3 g, 39.4 mmol) was dissolved in N,N-dimethylformamide (23 mL), to which NaH (0.378 g, 9.46 mmol) was added at 0° C., followed by stirring for 30 minutes. Then, (((5-bromopentyl)oxy)methyl)benzene (2.028 g, 7.88 mmol) was added to the mixture, and the mixture was stirred at room temperature for 16 hours. Upon completion of the reaction, the reaction mixture was diluted with dichloromethane, and washed with water and brine. The residue of the organic layer was dried over anhydrous sodium sulfate, filtered and concentrated, and then purified by MPLC to give a target compound (1.43 g, 72%).

LC/MS (ESI) m/z: 253[M+H]$^+$

Step 2: Preparation of tert-butyl 2-(3-((5-(benzyloxy)pentyl)oxy)propoxy)acetate

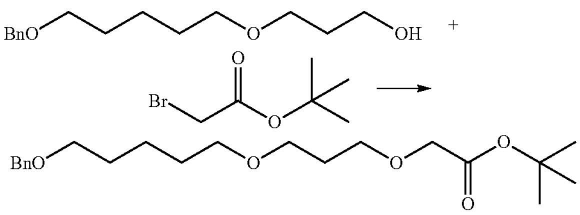

The compound prepared in step 1 (1.4319 g, 5.67 mmol) was dissolved in toluene (8 mL), to which tert-butyl bromoacetate (2.77 g, 14.19 mmol) and tetrabutylammonium bromide (0.36 g, 1.135 mmol) were added, and 35% sodium hydroxide aqueous solution (7.5 mL) was added at 0° C., followed by stirring at room temperature for 16 hours. Upon completion of the reaction, the reaction mixture was diluted with dichloromethane, and washed with water and brine. The residue of the organic layer was dried over anhydrous sodium sulfate, filtered and concentrated, and then purified by MPLC to give a target compound (1.71 g, 82%).

LC/MS (ESI) m/z: 367[M+H]$^+$

Step 3: Preparation of tert-butyl2-(3-((5-hydroxypentyl)oxy)propoxy)acetate

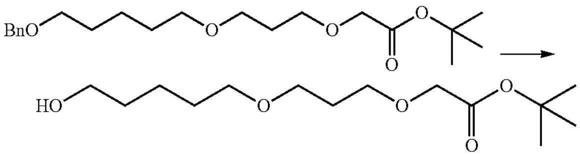

The compound prepared in step 2 (1.7121 g, 4.67 mmol) was dissolved in ethyl acetate (35 mL) and methanol (11 mL), to which Pd/C (0.621 g, 5.84 mmol) was added, followed by stirring at room temperature for 3 hours under a hydrogen atmosphere. Upon completion of the reaction, the reaction mixture was filtered through Celite. The separated filtrate was concentrated under reduced pressure to give a target compound, and the obtained compound was used in the next step without further purification.

LC/MS (ESI) m/z: 277[M+H]$^+$

Step 4: Preparation of tert-butyl2-(3-((5-bromopentyl)oxy)propoxy)acetate

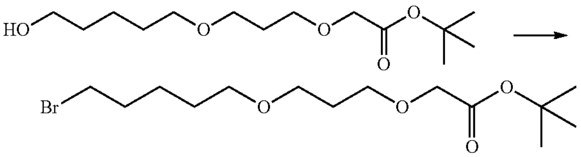

The compound prepared in step 3 (1.291 g, 4.67 mmol) was dissolved in dichloromethane (11 mL), to which carbon tetrabromide (1.859 g, 5.61 mmol) and triphenylphosphine (1.470 g, 5.61 mmol) were added at 0° C., followed by stirring for 30 minutes. Then, the reaction mixture was further stirred at room temperature for 4 hours. Upon completion of the reaction, the reaction mixture was concentrated under reduced pressure, and purified by MPLC to give a target compound (1.2 g, 77%).

LC/MS (ESI) m/z: 340[M+H]$^+$

Step 5: Preparation of tert-butyl2-(3-((5-azidopentyl)oxy)propoxy)acetate

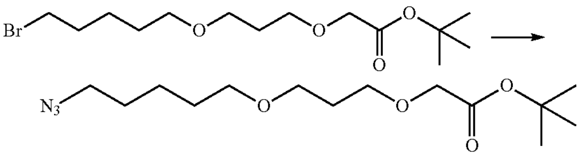

The compound prepared in step 4 (1.118 g, 3.30 mmol) was dissolved in N,N-dimethylformamide (11 mL), to which sodium azide (1.071 g, 16.48 mmol) was added, followed by stirring at room temperature for 4 hours. Upon completion of the reaction, the reaction mixture was diluted with dichloromethane, and washed with water and brine. The residue of the organic layer was dried over anhydrous sodium sulfate, filtered and concentrated, and then purified by MPLC to give a target compound (0.89 g, 91%).

LC/MS (ESI) m/z: 302[M+H]$^+$

Step 6: Preparation of tert-butyl2-(3-((5-aminopentyl)oxy)propoxy)acetate

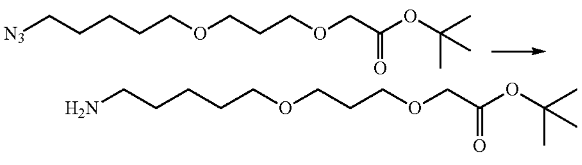

The compound prepared in step 5 (0.648 g, 2.150 mmol) was dissolved in ethyl acetate (10 mL), to which Pd/C (0.229 g, 2.150 mmol) was added, followed by stirring for 2 hours under a hydrogen atmosphere. Upon completion of the reaction, the reaction mixture was filtered through Celite. The separated filtrate was concentrated under reduced pressure to give a target compound, and the obtained compound was used in the next step without further purification.

LC/MS (ESI) m/z: 276[M+H]$^+$

Step 7: Preparation of tert-butyl 2-(3-((5-(2-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-biphenyl]-4-yl)methyl)piperazine-1-yl)acetamido)pentyl)oxy)propoxy)acetate

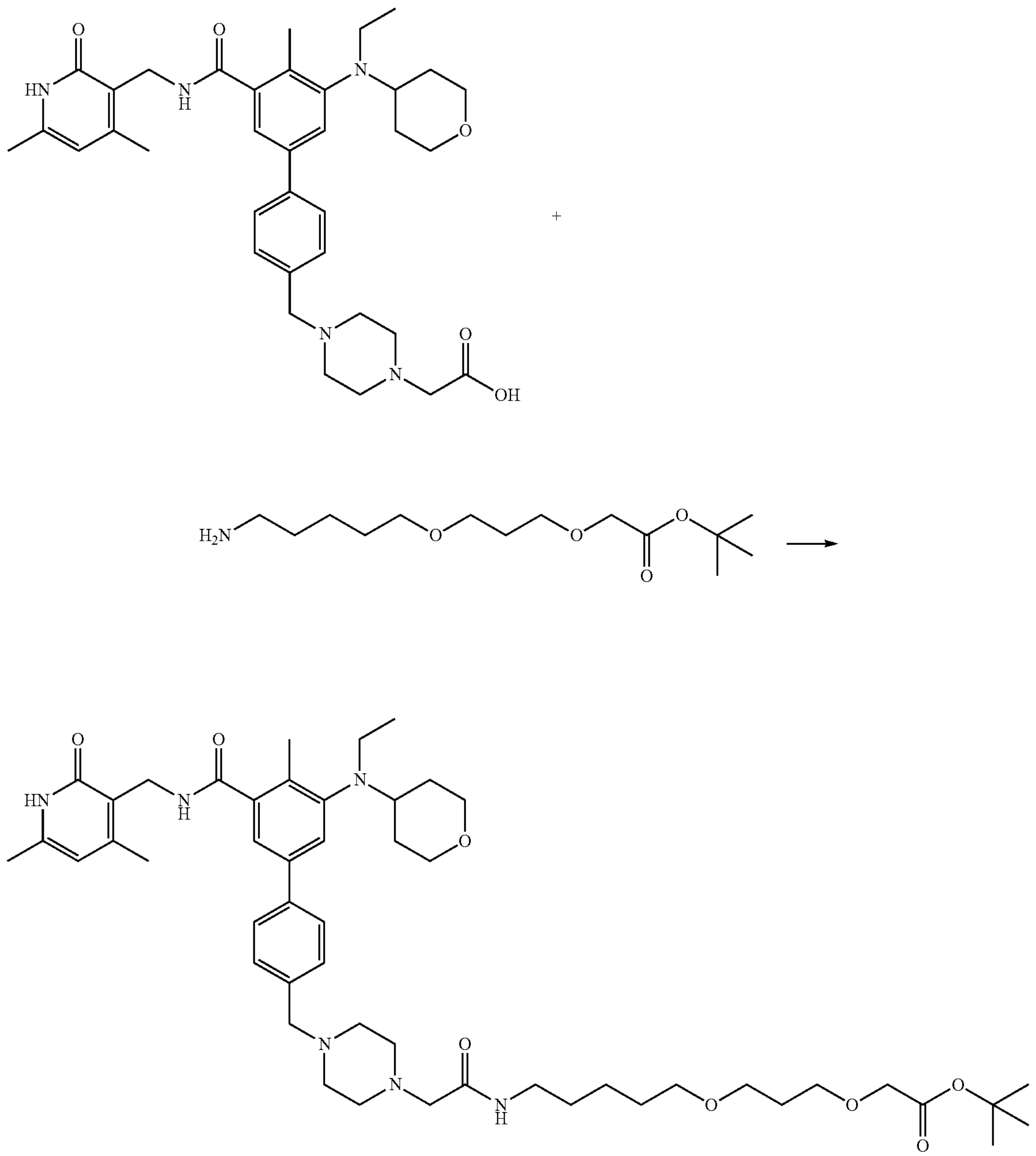

The compound (0.987 g, 1.568 mmol) prepared in [Example 1-Step 6] was dissolved in N,N-dimethylformamide (5 mL), to which the compound prepared in step 6 (0.4317 g, 1.568 mmol), N,N-diisopropylethylamine (1.36 mL, 7.84 mmol), HOBT (0.840 g, 5.49 mmol) and EDCI (0.451 g, 2.351 mmol) were added, followed by stirring at room temperature for 16 hours. Upon completion of the reaction, the reaction mixture was diluted with dichloromethane, and washed with water and brine. The residue of the organic layer was dried over anhydrous sodium sulfate, filtered and concentrated, and then purified by MPLC to give a target compound (0.45 g, 33%).

LC/MS (ESI) m/z: 888$[M+H]^+$

Step 8: Preparation of 2-(3-((5-(2-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-biphenyl]-4-yl)methyl)piperazine-1-yl)acetamido)pentyl)oxy)propoxy)acetate

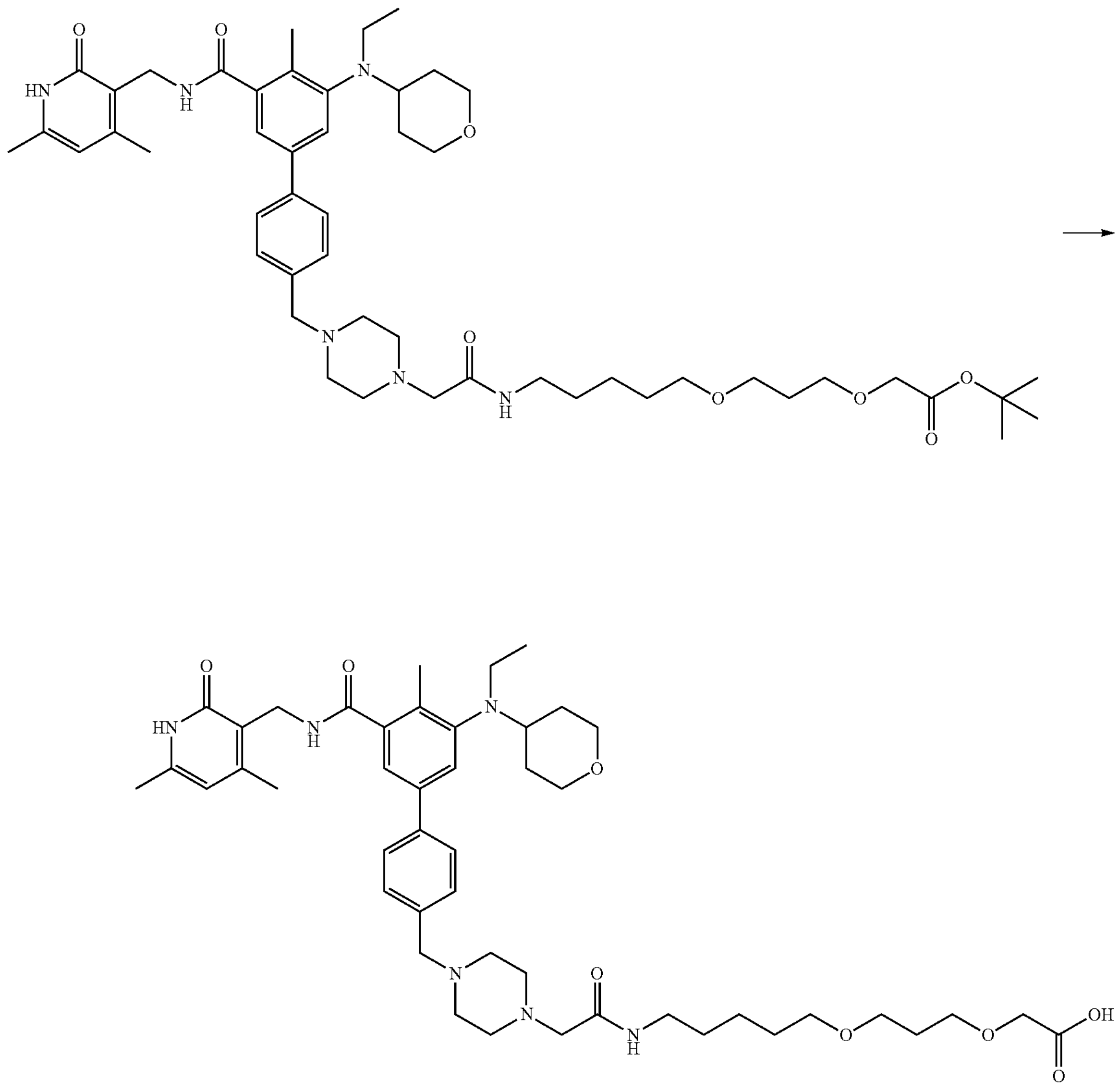

The compound prepared in step 7 (0.2 g, 0.225 mmol) was dissolved in dichloromethane (3 mL), to which 2,2,2-trifluoroacetic acid (1 mL, 12.98 mmol) was added, followed by stirring at room temperature for 1 hour. Upon completion of the reaction, the reaction mixture was concentrated under reduced pressure to give a target compound, and the obtained compound was used in the next step without further purification.

LC/MS (ESI) m/z: 832[M+H]+

Step 9: Preparation of N-((4,6-dimethyl-2-oxo-1,2-dihydropyridine-3-yl)methyl)-4'-((4-(2-((5-(3-(2-((2-(2,6-dioxopiperidine-3-yl)-1-oxoisoindoline-4-yl)amino)-2-oxoethoxy)propoxy)pentyl)amino)-2-oxoethyl)piperazine-1-yl)methyl)-5-(ethyl(tetrahydro-2H-pyran-4-yl)amino)-4-methyl-[1,1'-biphenyl]-3-carboxamide

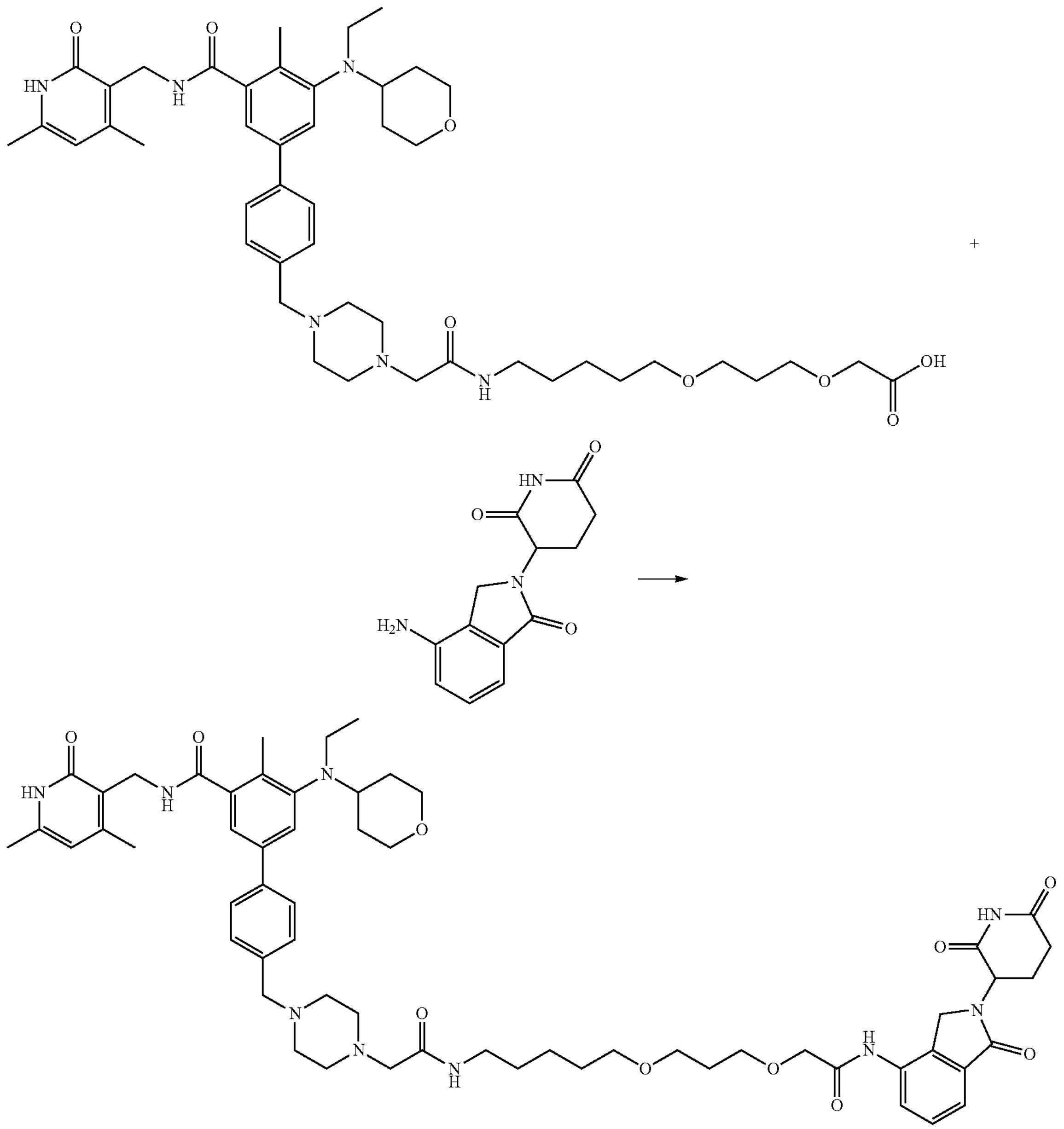 [SMILES: CCN(c1cc(-c2ccc(CN3CCN(CC(=O)NCCCCCOCCCOCC(=O)O)CC3)cc2)cc(C(=O)NCc2c(C)cc(C)[nH]c2=O)c1C)C1CCOCC1 ; Nc1cccc2c1CN(C1CCC(=O)NC1=O)C2=O ; CCN(c1cc(-c2ccc(CN3CCN(CC(=O)NCCCCCOCCCOCC(=O)Nc4cccc5c4CN(C4CCC(=O)NC4=O)C5=O)CC3)cc2)cc(C(=O)NCc2c(C)cc(C)[nH]c2=O)c1C)C1CCOCC1]

The compound prepared in step 8 (0.094 g, 0.113 mmol) was dissolved in N,N-dimethylformamide (2 mL), to which 3-(4-amino-1-oxoisoindoline-2-yl)piperidine-2,6-dione (0.032 g, 0.124 mmol), propylphosphonic anhydride solution in DMF (0.396 mL, 0.679 mmol) and pyridine (0.018 mL, 0.226 mmol) were added, followed by stirring at 80° C. for 4 hours. Upon completion of the reaction, the reaction mixture was diluted with dichloromethane, and washed with water and brine. The residue of the organic layer was dried over anhydrous sodium sulfate, filtered and concentrated, and then purified by MPLC to give a target compound (0.032 g, 27%, yellow solid).

LC/MS (ESI) m/z: 1073[M+H]+

Example 28

A target compound was prepared in the same manner as described in Example 27.

Example 29

Preparation of N-((4,6-dimethyl-2-oxo-1,2-dihydropyridine-3-yl)methyl)-4'-((4-(2-((2-(4-(2-((2-(2,6-dioxopiperidine-3-yl)-1,3-dioxoisoindoline-4-yl)amino)ethyl)piperazine-1-yl)ethyl)amino)-2-oxoethyl)piperazine-1-yl)methyl)-5-(ethyl(tetrahydro-2H-pyran-4-yl)amino)-4-methyl-[1,1'-biphenyl]-3-carboxamide

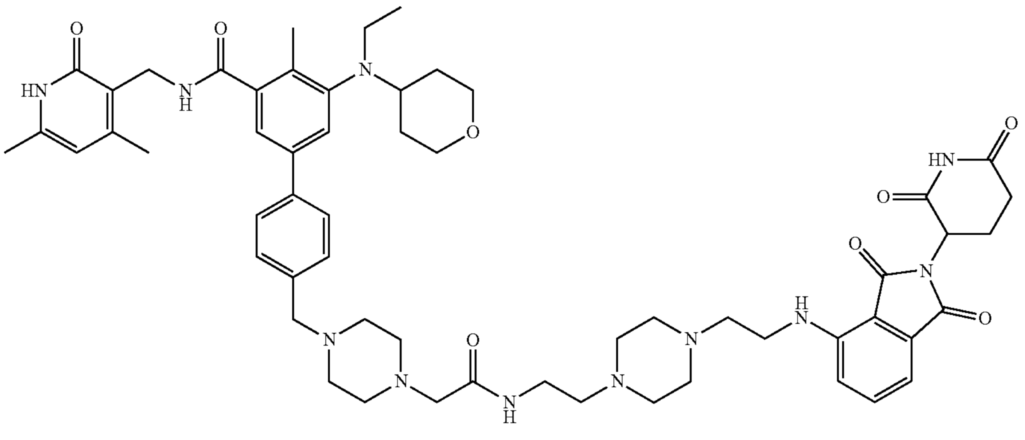 [SMILES: CCN(c1cc(-c2ccc(CN3CCN(CC(=O)NCCN4CCN(CCNc5cccc6c5C(=O)N(C5CCC(=O)NC5=O)C6=O)CC4)CC3)cc2)cc(C(=O)NCc2c(C)cc(C)[nH]c2=O)c1C)C1CCOCC1]

Step 1: Preparation of tert-butyl 4-(2-(2-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-biphenyl]-4-yl)methyl)piperazine-1-yl)acetamido)ethyl)piperazine-1-carboxylate

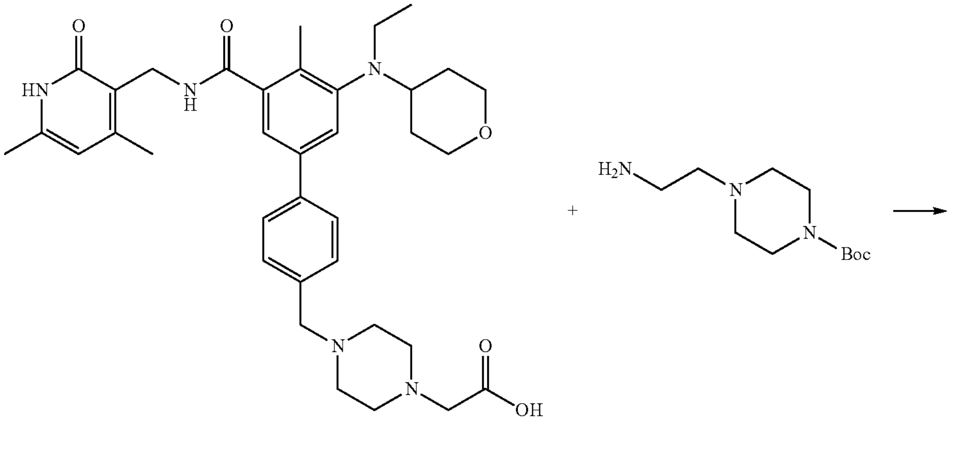

-continued

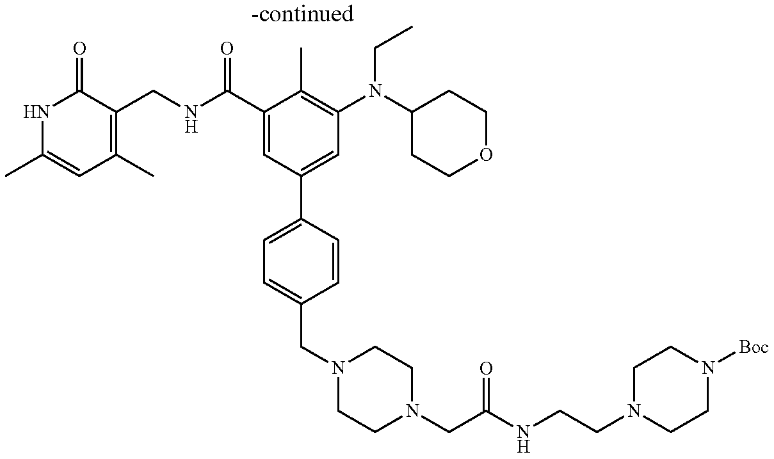

The compound (0.1 g, 0.159 mmol) prepared in [Example 1-Step 6] was dissolved in N,N-dimethylformamide (1.5 mL), to which tert-butyl4-(2-aminoethyl)piperazine-1-carboxylate (0.036 g, 0.159 mmol), N,N-diisopropylethylamine (0.139 mL, 0.794 mmol), HOBT (0.085 g, 0.556 mmol) and EDCI (0.046 g, 0.238 mmol) were added, followed by stirring at room temperature for 16 hours. Upon completion of the reaction, the reaction mixture was diluted with dichloromethane, and washed with water and brine. The residue of the organic layer was dried over anhydrous sodium sulfate, filtered and concentrated, and then purified by MPLC to give a target compound (0.082 g, 61%).

LC/MS (ESI) m/z: 842[M+H]$^+$

Step 2: Preparation of N-((4,6-dimethyl-2-oxo-1,2-dihydropyridine-3-yl)methyl)-5-(ethyl(tetrahydro-2H-pyran-4-yl)amino)-4-methyl-4'-((4-(2-oxo-2-((2-(piperazine-1-yl)ethyl)amino)ethyl)piperazine-1-yl)methyl)-[1,1'-biphenyl]-3-carboxamide 2,2,2-trifluoroacetic acid salt

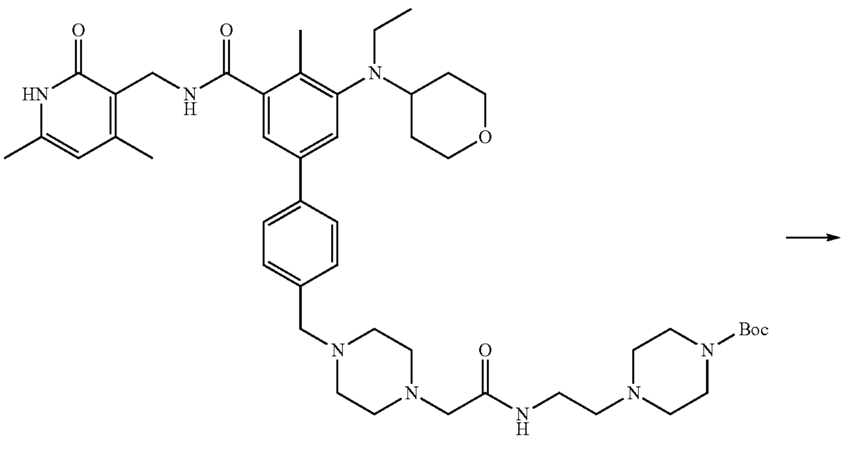

-continued

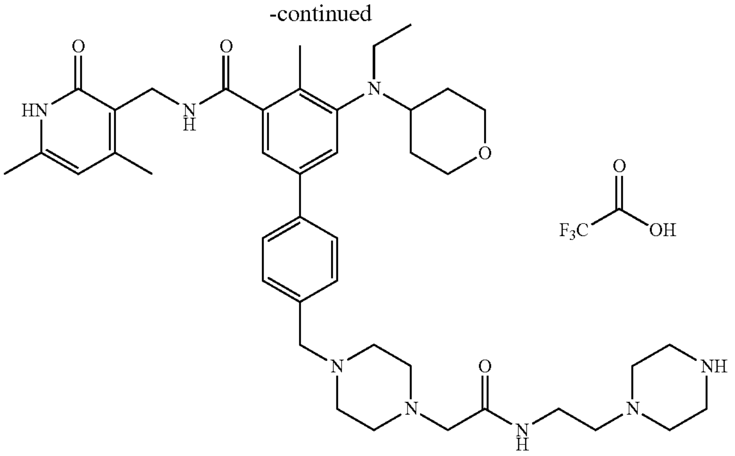

The compound prepared in step 1 (0.082 g, 0.097 mmol) was dissolved in dichloromethane (3 mL), to which 2,2,2-trifluoroacetic acid (1 mL, 12.98 mmol) was added, followed by stirring at room temperature for 1 hour. Upon completion of the reaction, the reaction mixture was concentrated under reduced pressure to give a target compound, and the obtained compound was used in the next step without further purification.

LC/MS (ESI) m/z: 832[M+H]$^+$

Step 3: Preparation of 4'-((4-(2-((2-(4-(2-aminoethyl)piperazine-1-yl)ethyl)amino)-2-oxoethyl)piperazine-1-yl)methyl)-N-((4,6-dimethyl-2-oxo-1,2-dihydropyridine-3-yl)methyl)-5-(ethyl(tetrahydro-2H-pyran-4-yl)amino)-4-methyl-[1,1'-biphenyl]-3-carboxamide

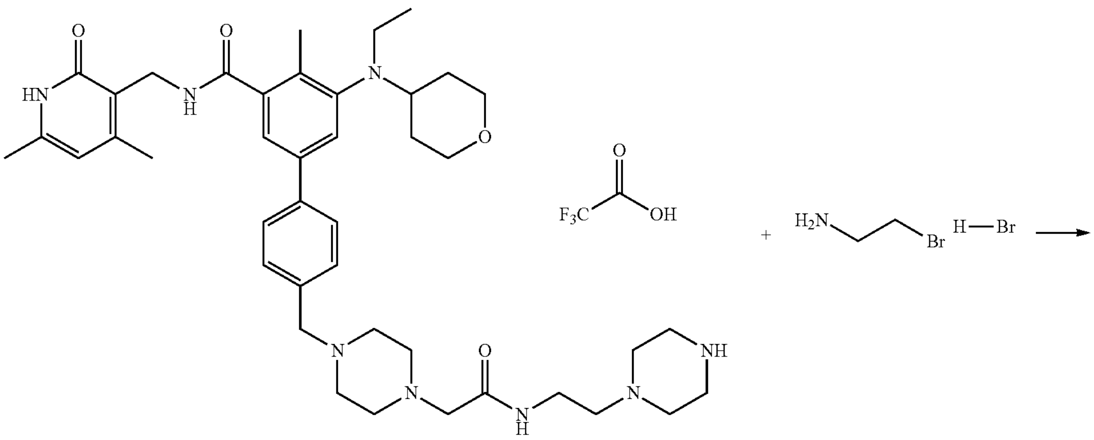

-continued

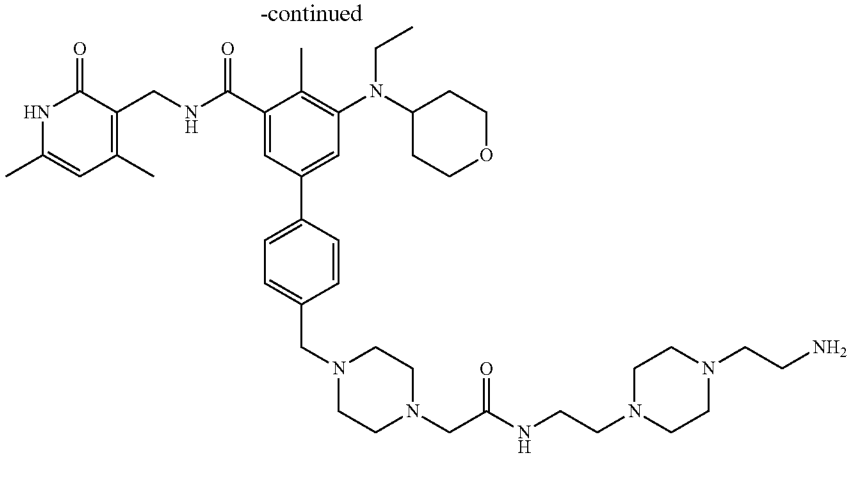

The compound prepared in step 2 (0.083 g, 0.097 mmol) was dissolved in N,N-dimethylformamide (1 mL), to which potassium carbonate (0.040 g, 0.291 mmol) and 2-bromoethylamine hydrobromide (0.024 g, 0.116 mmol) were added, followed by stirring at 70° C. for 1 hour. Upon completion of the reaction, the reaction mixture was diluted with dichloromethane, and washed with water and brine. The residue of the organic layer was dried over anhydrous sodium sulfate, filtered and concentrated, and then purified by MPLC to give a target compound (0.013 g, 18%).

LC/MS (ESI) m/z: 785[M+H]$^+$

Step 4: Preparation of N-((4,6-dimethyl-2-oxo-1,2-dihydropyridine-3-yl)methyl)-4'-((4-(2-((2-(4-(2-((2-(2,6-dioxopiperidine-3-yl)-1,3-dioxoisoindoline-4-yl)amino)ethyl)piperazine-1-yl)ethyl)amino)-2-oxoethyl)piperazine-1-yl)methyl)-5-(ethyl (tetrahydro-2H-pyran-4-yl)amino)-4-methyl-[1,1'-biphenyl]-3-carboxamide

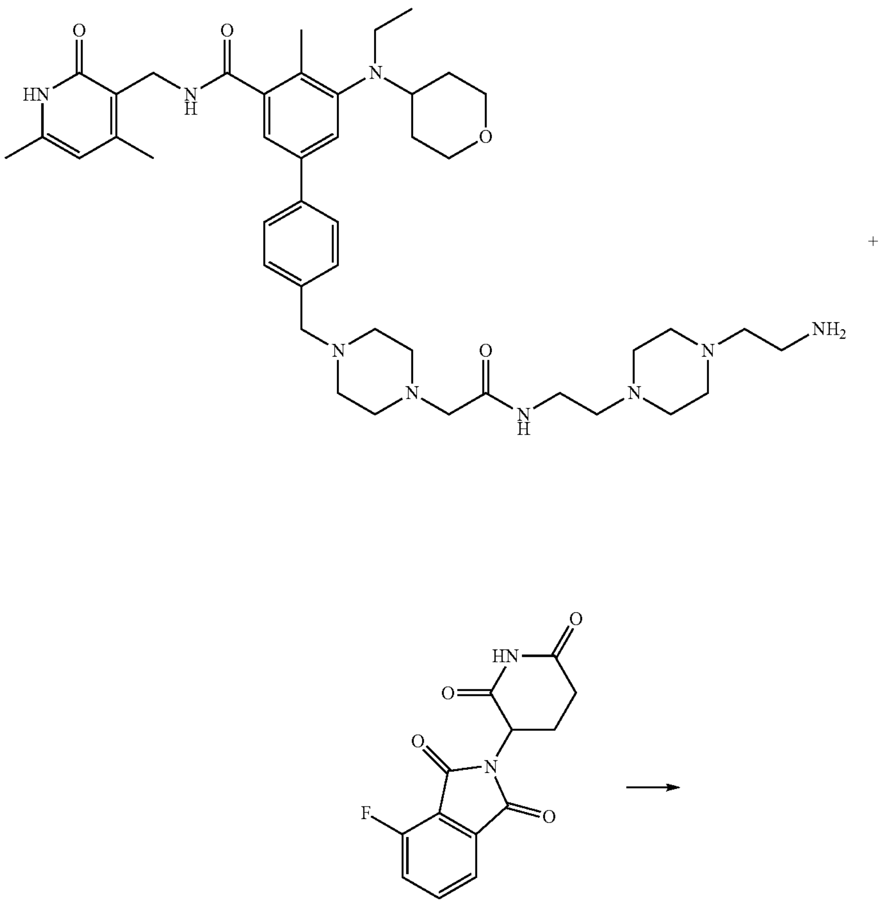

-continued

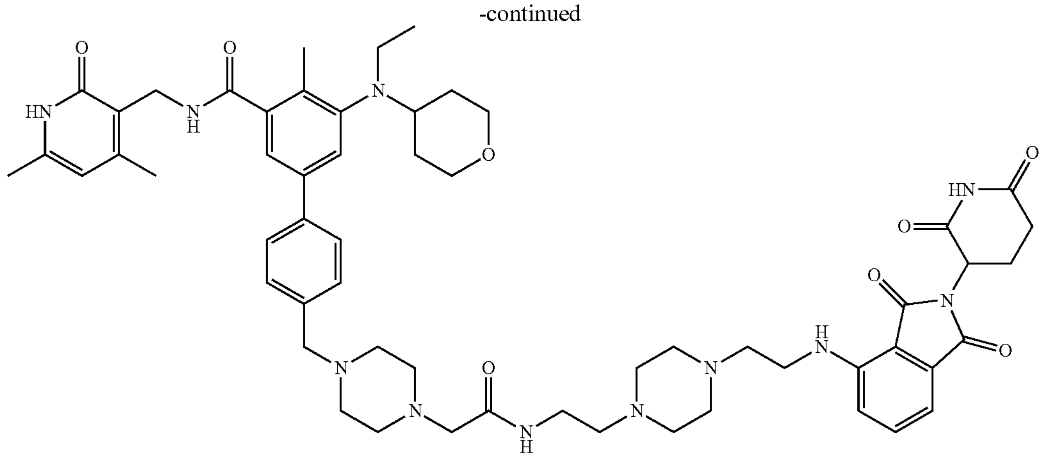

The compound prepared in step 3 (0.0139 g, 0.018 mmol) was dissolved in N-methyl-2-pyrrolidone (1 mL), to which 2-(2,6-dioxopiperidine-3-yl)-4-fluoroisoindoline-1,3-dione (4.90 mg, 0.018 mmol) and N,N-diisopropylethylamine (6.19 μl, 0.035 mmol) were added, followed by stirring at 90° C. for 16 hours. The residue of the organic layer was dried over anhydrous sodium sulfate, filtered and concentrated, purified by Prep HPLC, and neutralized by adding a sodium hydrogen carbonate aqueous solution to give a target compound (5 mg, 27%, yellow solid).

LC/MS (ESI) m/z: 1041[M+H]$^+$

Example 30

A target compound was prepared in the same manner as described in Example 29.

Example 31

Preparation of N-((4,6-dimethyl-2-oxo-1,2-dihydropyridine-3-yl)methyl)-4'-((4-(4-(1-(2-((2-(2,6-dioxopiperidine-3-yl)-1,3-dioxoisoindoline-4-yl)amino)-2-oxoethyl)-1H-1,2,3-triazole-4-yl)-butyl)piperazine-1-yl)methyl)-5-(ethyl(tetrahydro-2H-pyran-4-yl)amino)-4-methyl-[1,1'-biphenyl]-3-carboxamide

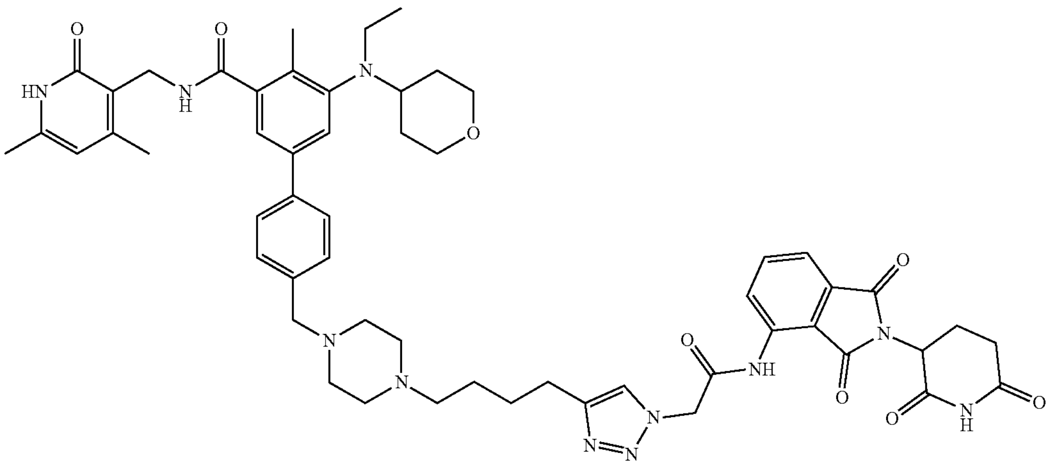 [SMILES: CCN(c1cc(-c2ccc(CN3CCN(CCCCc4cn(CC(=O)Nc5cccc6c5C(=O)N(C5CCC(=O)NC5=O)C6=O)nn4)CC3)cc2)cc(C(=O)NCc2c(C)cc(C)[nH]c2=O)c1C)C1CCOCC1]

Step 1: Preparation of N-(2-(2,6-dioxopiperidine-3-yl)-1,3-dioxoisoindoline-4-yl)-2-(4-(4-hydroxybutyl)-1H-1,2,3-triazole-1-yl)acetamide

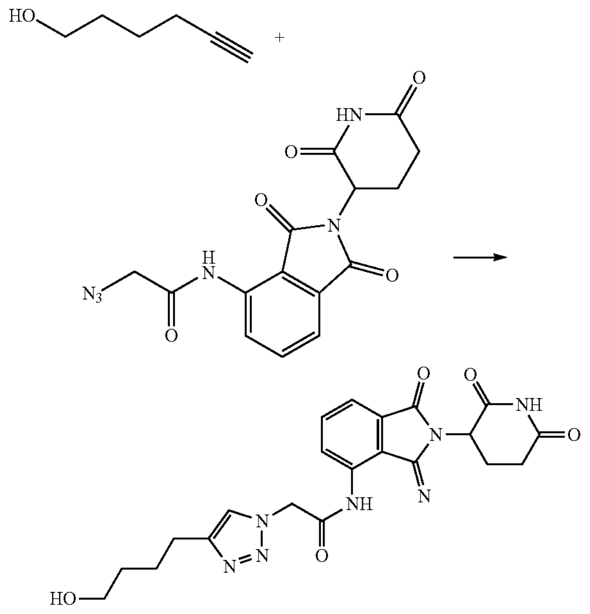

2-Azido-N-(2-(2,6-dioxopiperidine-3-yl)-1,3-dioxoisoindoline-4-yl)acetamide (50 mg, 0.14 mmol) and 5-hexyn-1-ol (15.1 mg, 0.154 mmol) were dissolved in tetrahydrofuran (1 ml), to which copper sulfate (15 mg, 0.094 mmol), sodium ascorbate (20 mg, 0.10 mmol) and water (0.2 ml) were added, followed by stirring at room temperature for 12 hours. Upon completion of the reaction, the reaction mixture was diluted with ethyl acetate, and washed with water. The residue of the organic layer was dried over anhydrous sodium sulfate, filtered and concentrated, and then purified by MPLC to give a target compound (43 mg, 67%, yellow solid).

LC/MS (ESI) m/z: 455[M+H]$^+$

Step 2: Preparation of 2-(4-(4-bromobutyl)-1H-1,2,3-triazole-1-yl)-N-(2-(2,6-dioxopiperidine-3-yl)-1,3-dioxoisoindoline-4-yl)acetamide

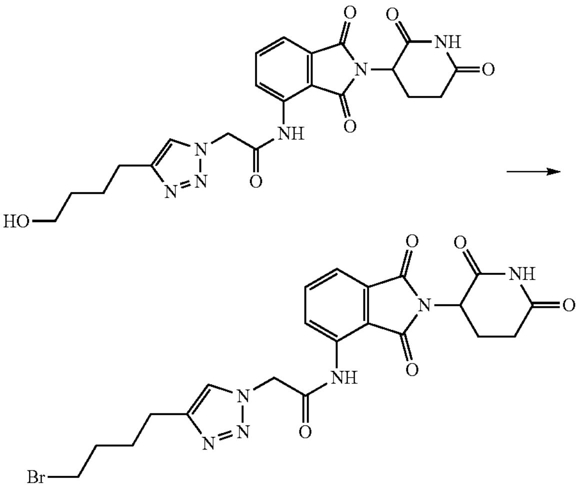

The compound prepared in step 1 (43 mg, 0.095 mmol) was dissolved in dichloromethane (1 ml), to which carbon tetrabromide (34.5 mg, 0.104 mmol) and triphenylphosphine (27.3 mg, 0.104 mmol) were added, followed by stirring at room temperature for 20 hours. Then, the reaction mixture was diluted with hexane, filtered and concentrated, and then purified by MPLC to give a target compound (34 mg, 70%, yellow solid).

LC/MS (ESI) m/z: 517[M+H]$^+$

Step 3: Preparation of N-((4,6-dimethyl-2-oxo-1,2-dihydropyridine-3-yl)methyl)-4'-((4-(4-(1-(2-((2-(2,6-dioxopiperidine-3-yl)-1,3-dioxoisoindoline-4-yl)amino)-2-oxoethyl)-1H-1,2,3-triazole-4-yl)-butyl)piperazine-1-yl)methyl)-5-(ethyl(tetrahydro-2H-pyran-4-yl)amino)-4-methyl-[1,1'-biphenyl]-3-carboxamide

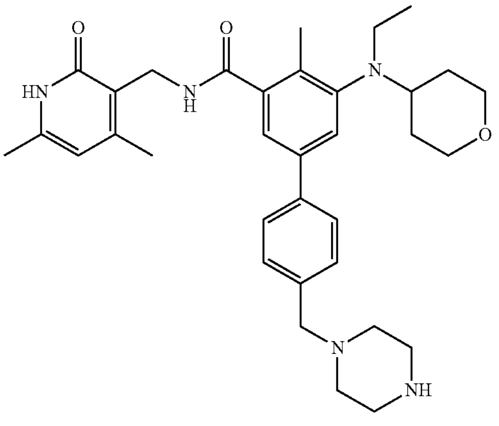

+

-continued

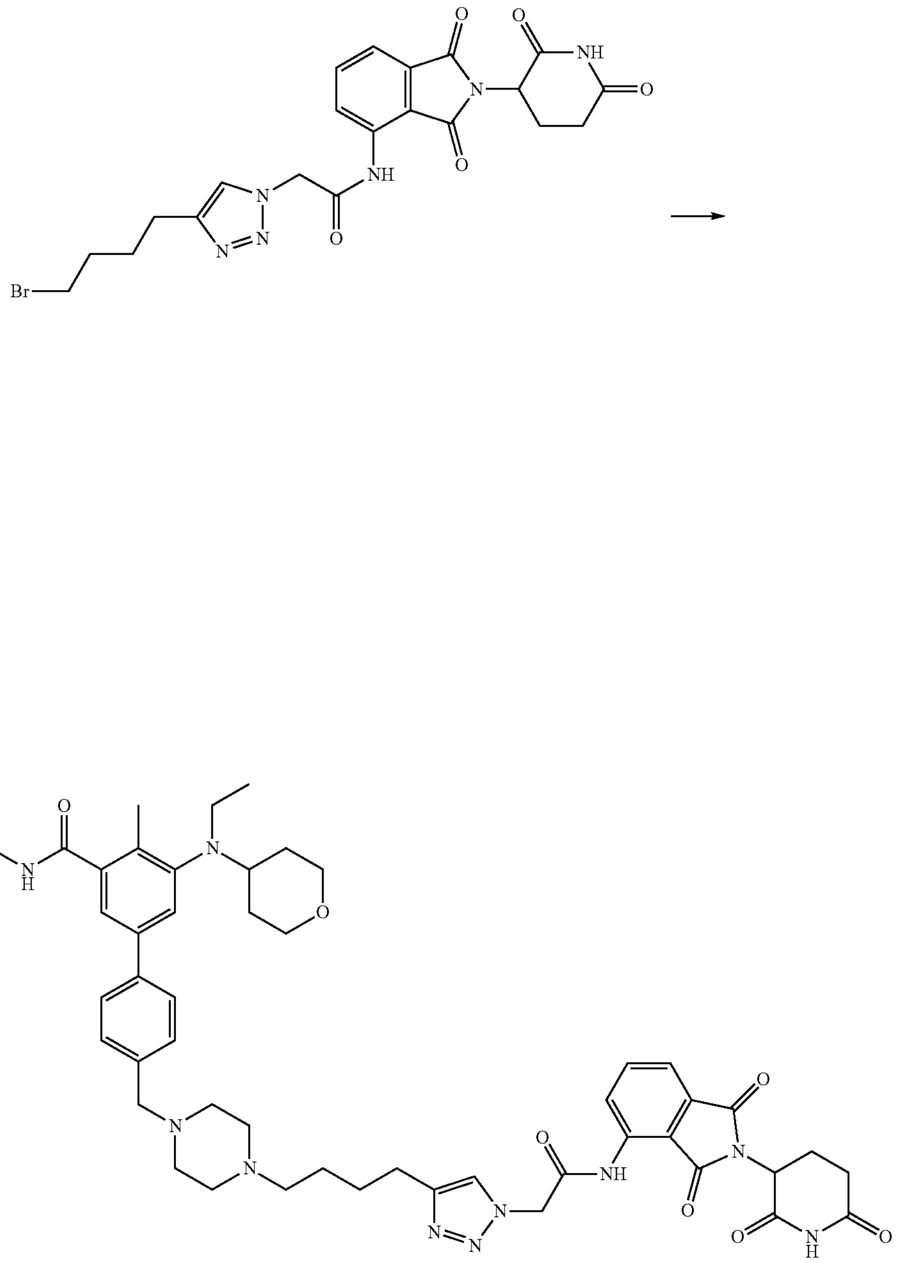

The compound (49.6 mg, 0.072 mmol) prepared in [Example 1—Step 4] was dissolved in N,N-dimethylformamide (1 ml), to which the compound (34 mg, 0.066 mmol) prepared in step 2 and potassium carbonate (45.4 mg, 0.33 mmol) were added, followed by stirring at 60° C. for 12 hours. Upon completion of the reaction, the reaction mixture was diluted with ethyl acetate, and washed with water and brine. The residue of the organic layer was dried over anhydrous sodium sulfate, filtered and concentrated, purified by Prep HPLC, and neutralized by adding a sodium hydrogen carbonate aqueous solution to give a target compound (2.9 mg, 4%, yellow solid).

LC/MS (ESI) m/z: 1008[M+H]+

Example 32

A target compound was prepared in the same manner as described in Example 25.

Example 33, 34

Target compounds were prepared in the same manner as described in Example 29.

Example 35

Preparation of N-((4,6-dimethyl-2-oxo-1,2-dihydropyridine-3-yl)methyl)-4'-((4-(2-(6-4((2-(2,6-dioxopiperidine-3-yl)-1,3-dioxoisoindoline-4-yl-amino)butyl)-2,6-diazaspiro[3.3]heptane-2-yl)-2-oxoethyl)piperazine-1-yl)methyl)-5-(ethyl-(tetrahydro-2H-pyran-4-yl)amino)-4-methyl-[1,1'-biphenyl]-3-carboxamide

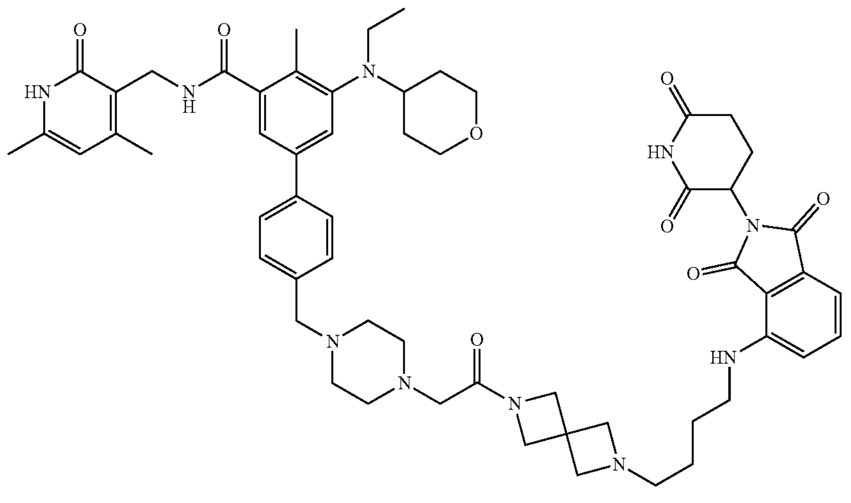 [SMILES: CCN(c1cc(-c2ccc(CN3CCN(CC(=O)N4CC5(CN(CCCCNc6cccc7c6C(=O)N(C6CCC(=O)NC6=O)C7=O)C5)C4)CC3)cc2)cc(C(=O)NCc2c(C)cc(C)[nH]c2=O)c1C)C1CCOCC1]

Step 1: Preparation of t-butyl 6-(4-(1,3-dioxoisoindoline-2-yl)butyl)-2,6-diazaspiro[3.3]heptane-2-carboxylate

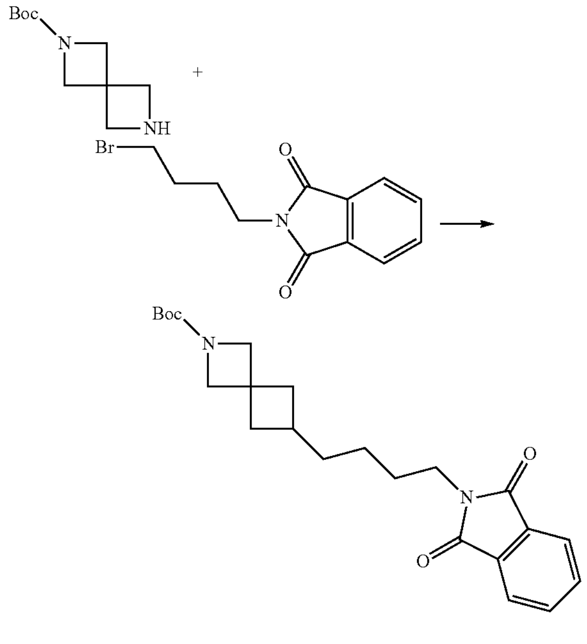

T-butyl 2,6-diazaspiro[3.3]heptane-2-carboxylate (0.1 g, 0.504 mmol) and 2-(4-bromobutyl)isoindoline-1,3-dione (0.185 g, 0.66 mmol) were dissolved in N,N-dimethylformamide (1.5 ml), to which potassium carbonate (0.209 g, 1.51 mmol) was added, followed by stirring at room temperature for 12 hours. Upon completion of the reaction, the reaction mixture was diluted with ethyl acetate, and washed with water and brine. The residue of the organic layer was dried over anhydrous sodium sulfate, filtered and concentrated, and then purified by MPLC to give a target compound (0.108 g, 54%, white solid).

LC/MS (ESI) m/z: 400$[M+H]^+$

Step 2: Preparation of t-butyl 6-(4-aminobutyl)-2,6-diazaspiro[3.3]heptane-2-carboxylate

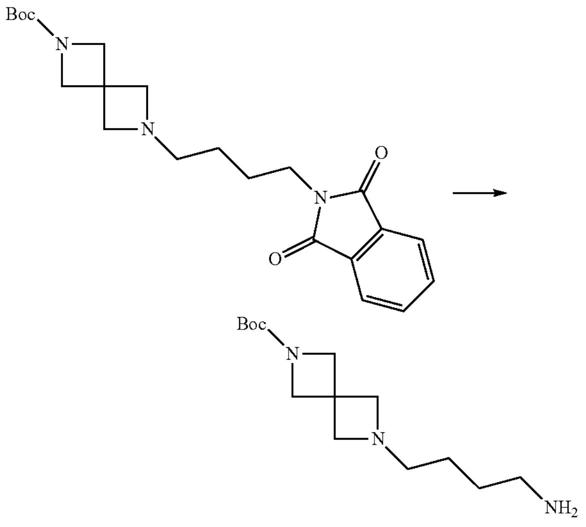

The compound prepared in step 1 (0.108 g, 0.27 mmol) was dissolved in ethanol (2.7 ml), to which hydrazinyl hydrate (0.066 ml, 1.35 mmol) was added, followed by stirring at room temperature for 12 hours.

Upon completion of the reaction, the reaction mixture was concentrated under reduced pressure, and then purified by MPLC to give a target compound (50 mg, 69%, yellow liquid).

LC/MS (ESI) m/z: 270[M+H]$^+$

Step 3: Preparation of t-butyl 6-(4-((2-(2,6-dioxopiperidine-3-yl)-1,3-dioxoisoindoline-4-yl)amino)butyl)-2,6-diazaspiro[3.3]heptane-2-carboxylate

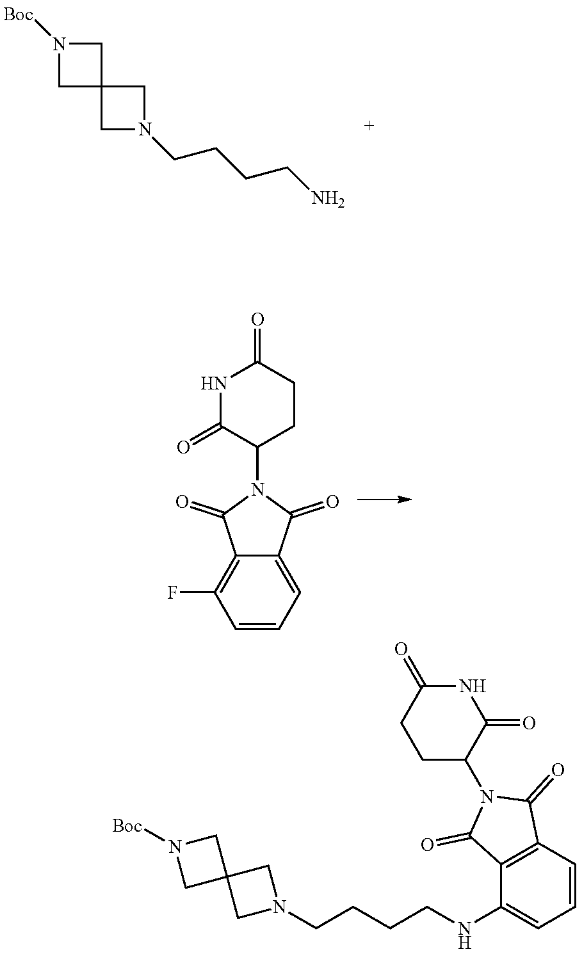

The compound prepared in step 2 (50 mg, 0.186 mmol) was dissolved in N-methyl-2-pyrrolidone (1 ml), to which 2-(2,6-dioxopiperidine-3-yl)-4-fluoroisoindoline-1,3-dione (51.3 mg, 0.186 mmol) and N,N-diisopropylethylamine (0.097 ml, 0.557 mmol) were added, followed by stirring at 110° C. for 12 hours. Upon completion of the reaction, the temperature of the reaction mixture was lowered to room temperature, diluted with ethyl acetate, and washed with water and brine. The residue of the organic layer was dried over anhydrous sodium sulfate, filtered and concentrated, and then purified by MPLC to give a target compound (41 mg, 42%, yellow solid).

LC/MS (ESI) m/z: 526[M+H]$^+$

Step 4: Preparation of 4-((4-(2,6-diazaspiro[3.3]heptane-2-yl)butyl)amino)-2-(2,6-dioxopiperidine-3-yl)isoindoline-1,3-dione 2,2,2-trifluoroacetate

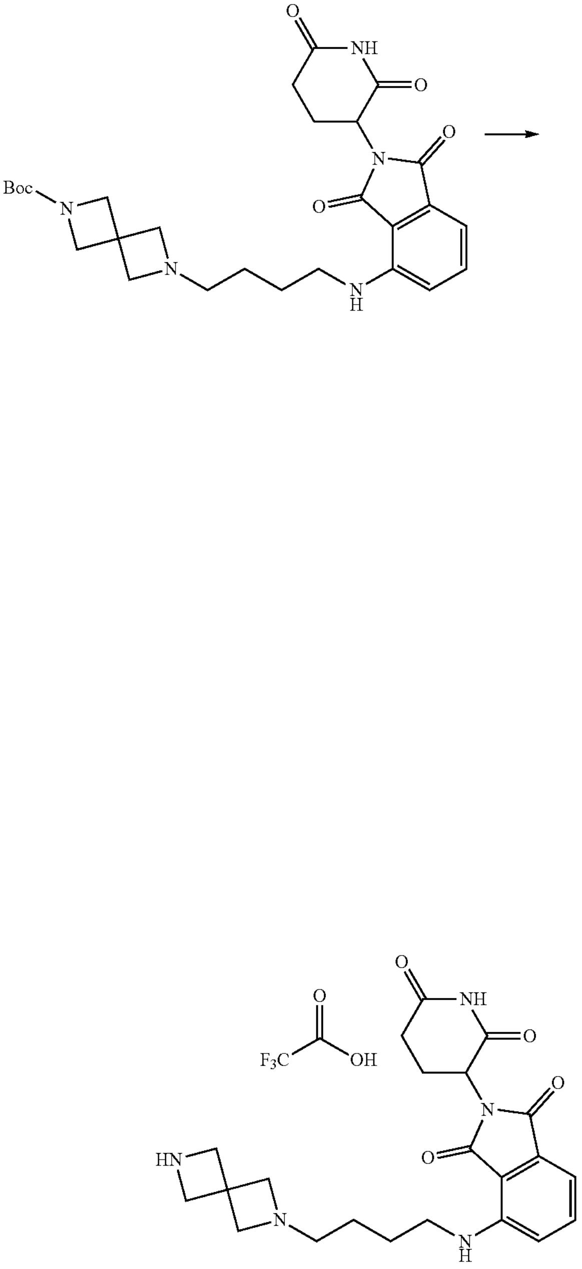

The compound prepared in step 3 (41 mg, 0.078 mmol) was dissolved in dichloromethane (1 ml), to which 2,2,2-trifluoroacetic acid (0.3 ml) was added, followed by stirring at room temperature for 3 hours. Upon completion of the reaction was completed, the reaction mixture was concentrated under reduced pressure to give a target compound, and the obtained compound was used in the next step without further purification.

LC/MS (ESI) m/z: 426[M+H]$^+$

Step 5: Preparation of N-((4,6-dimethyl-2-oxo-1,2-dihydropyridine-3-yl)methyl)-4'-((4-(2-(6-4((2-(2,6-dioxopiperidine-3-yl)-1,3-dioxoisoindoline-4-yl-amino)butyl)-2,6-diazaspiro[3,3]heptane-2-yl)-2-oxoethyl)piperazine-1-yl)methyl)-5-(ethyl-(tetrahydro-2H-pyran-4-yl)amino)-4-methyl-[1,1'-biphenyl]-3-carboxamide

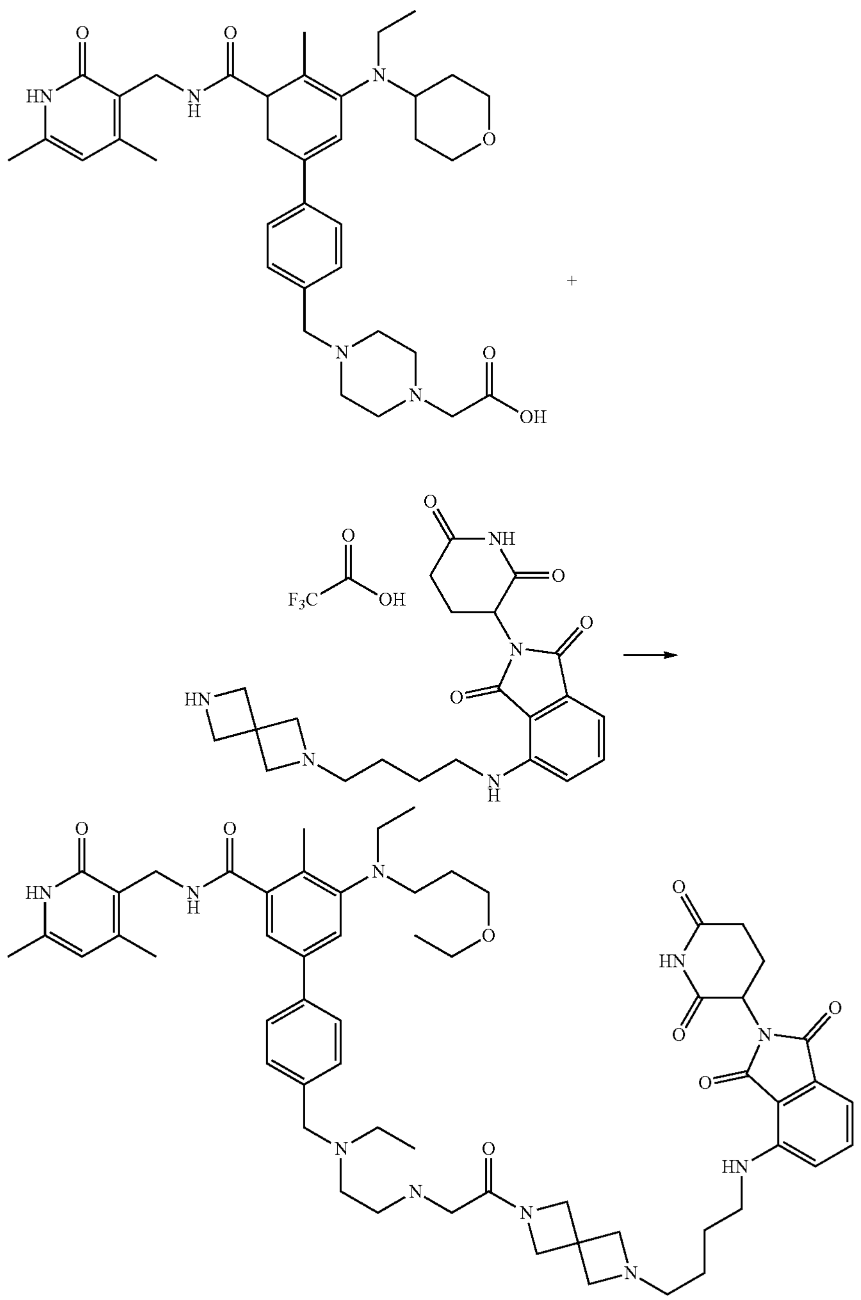

The compound prepared in step 4 (42.1 mg, 0.078 mmol) and the compound (49.1 mg, 0.078 mmol) prepared in [Example 1—Step 6] were dissolved in N,N-dimethylformamide (1 ml), to which EDC (22.4 mg, 0.117 mmol), HOBT (41.8 mg, 0.27 mmol) and N,N-diisopropylethylamine (0.068 ml, 0.39 mmol) were added, followed by stirring at room temperature for 16 hours. Upon completion of the reaction, the reaction mixture was diluted with ethyl acetate, and washed with water and brine. The residue of the organic layer was dried over anhydrous sodium sulfate, filtered and concentrated, purified by Prep HPLC, and neutralized by adding a sodium hydrogen carbonate aqueous solution to give a target compound (7 mg, 8%, yellow solid).

LC/MS (ESI) m/z: 1037$[M+H]^+$

Example 36

A target compound was prepared in the same manner as described in Example 35.

Example 37

Preparation of (2S,4R)-1-((S)-2-(tert-butyl)-18-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-biphenyl]-4-yl)methyl)piperazine-1-yl)-4,17-dioxo-6,10-dioxa-3,16-diazaoctadecanoyl)-4-hydroxy-N-(4-(4-methylthiazole-5-yl)benzyl)pyrrolidine-2-carboxamide

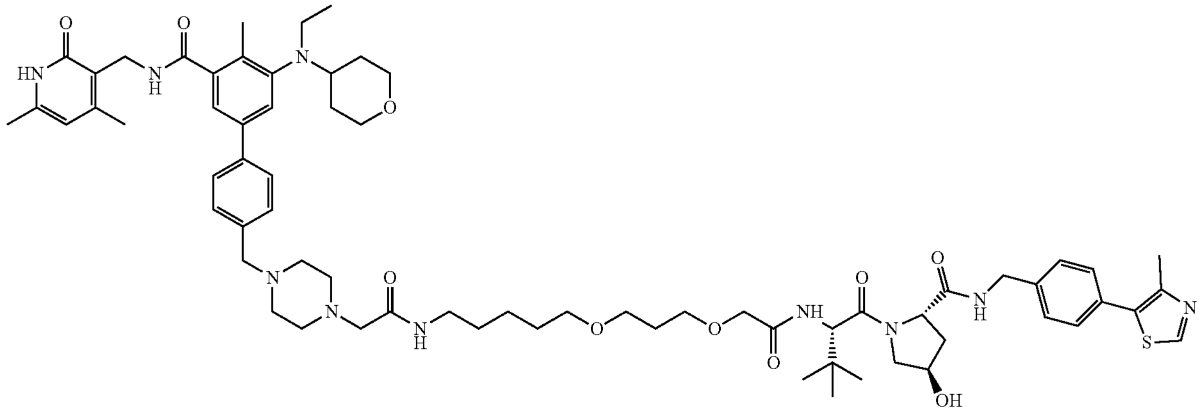 [SMILES: CCN(c1cc(-c2ccc(CN3CCN(CC(=O)NCCCCCOCCCOCC(=O)N[C@H](C(=O)N4C[C@H](O)C[C@H]4C(=O)NCc4ccc(-c5scnc5C)cc4)C(C)(C)C)CC3)cc2)cc(C(=O)NCc2c(C)cc(C)[nH]c2=O)c1C)C1CCOCC1]

Step 1: Preparation of 2-(3-((5-azidopentyl)oxy)propoxy)acetate

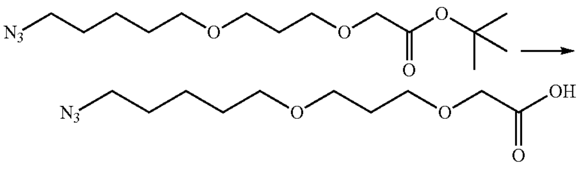

The compound (0.1 g, 0.332 mmol) prepared in [Example 27-Step 5] was dissolved in dichloromethane (2 mL), to which 2,2,2-trifluoroacetic acid (1 mL, 12.98 mmol) was added, followed by stirring at room temperature for 1 hour. Upon completion of the reaction, the reaction mixture was concentrated under reduced pressure to give a target compound, and the obtained compound was used in the next step without further purification.

LC/MS (ESI) m/z: 246[M+H]+

Step 2: Preparation of (2S,4R)-1-((S)-2-(2-(3-((5-azidopentyl)oxy)propoxy)acetamido)-3,3-dimethylbutanoyl)-4-hydroxy-N-(4-(4-methylthiazole-5-yl)benzyl)pyrrolidine-2-carboxamide

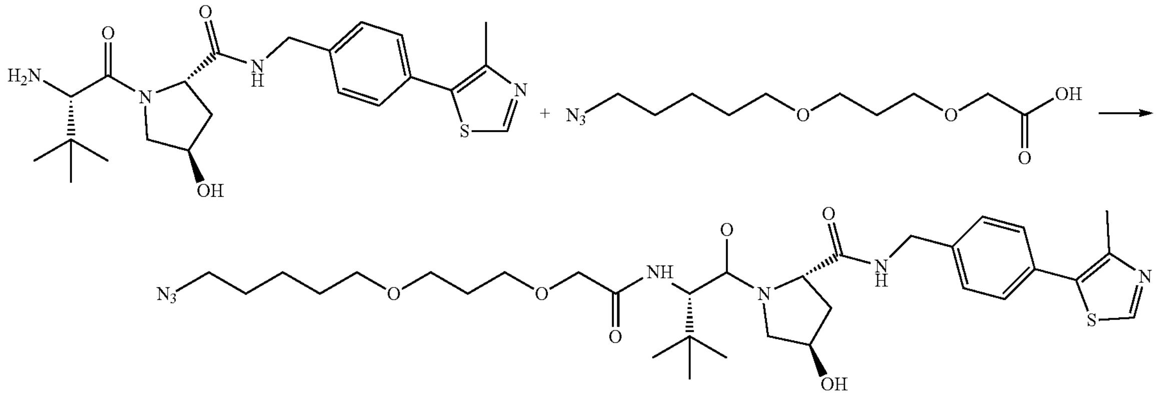

(2S,4R)-1-((S)-2-amino-3,3-dimethylbutanoyl)-4-hydroxy-N-(4-(4-methylthiazole-5-yl)benzyl)pyrrolidine-2-carboxamide (0.142 g, 0.330 mmol) was dissolved in N,N-dimethylformamide (3 mL), to which the compound prepared in step 1 (0.081 g, 0.330 mmol), N,N-diisopropylethylamine (0.288 mL, 1.651 mmol) and HATU (0.188 g, 0.495 mmol) were added, followed by stirring at room temperature for 16 hours. Upon completion of the reaction, the reaction mixture was diluted with dichloromethane, and washed with water and brine. The residue of the organic layer was dried over anhydrous sodium sulfate, filtered and concentrated, and then purified by MPLC to give a target compound (0.15 g, 71%).

LC/MS (ESI) m/z: 658[M+H]$^+$

Step 3: Preparation of (2S,4R)-1-((S)-2-(2-(3-((5-aminopentyl)oxy)propoxy)acetamido)-3,3-dimethylbutanoyl)-4-hydroxy-N-(4-(4-methylthiazole-5-yl)benzyl)pyrrolidine-2-carboxamide

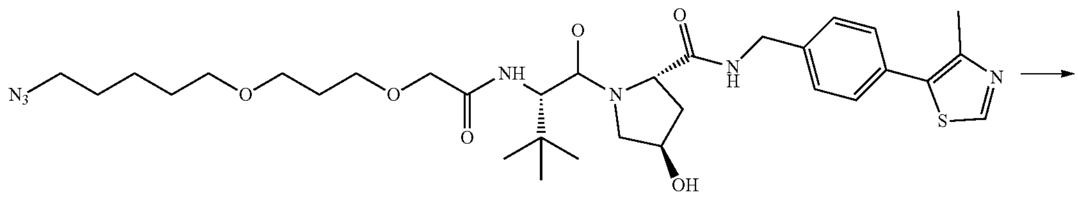

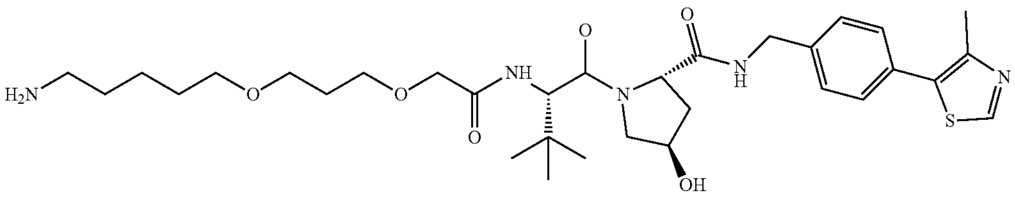

The compound prepared in step 2 (0.1538 g, 0.234 mmol) was dissolved in tetrahydrofuran (2 mL) and water (0.1 mL), to which triphenylphosphine (0.307 g, 1.169 mmol) was added, followed by stirring at room temperature for 16 hours. Upon completion of the reaction, the reaction mixture was diluted with dichloromethane, and washed with water and brine. The residue of the organic layer was dried over anhydrous sodium sulfate, filtered and concentrated, and then purified by MPLC to give a target compound (0.10 g, 73%).

LC/MS (ESI) m/z: 632[M+H]$^+$

Step 4: Preparation of (2S,4R)-1-((S)-2-(tert-butyl)-18-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-biphenyl]-4-yl)methyl)piperazine-1-yl)-4,17-dioxo-6,10-dioxa-3,16-diazaoctadecanoyl)-4-hydroxy-N-(4-(4-methylthiazole-5-yl)benzyl)pyrrolidine-2-carboxamide

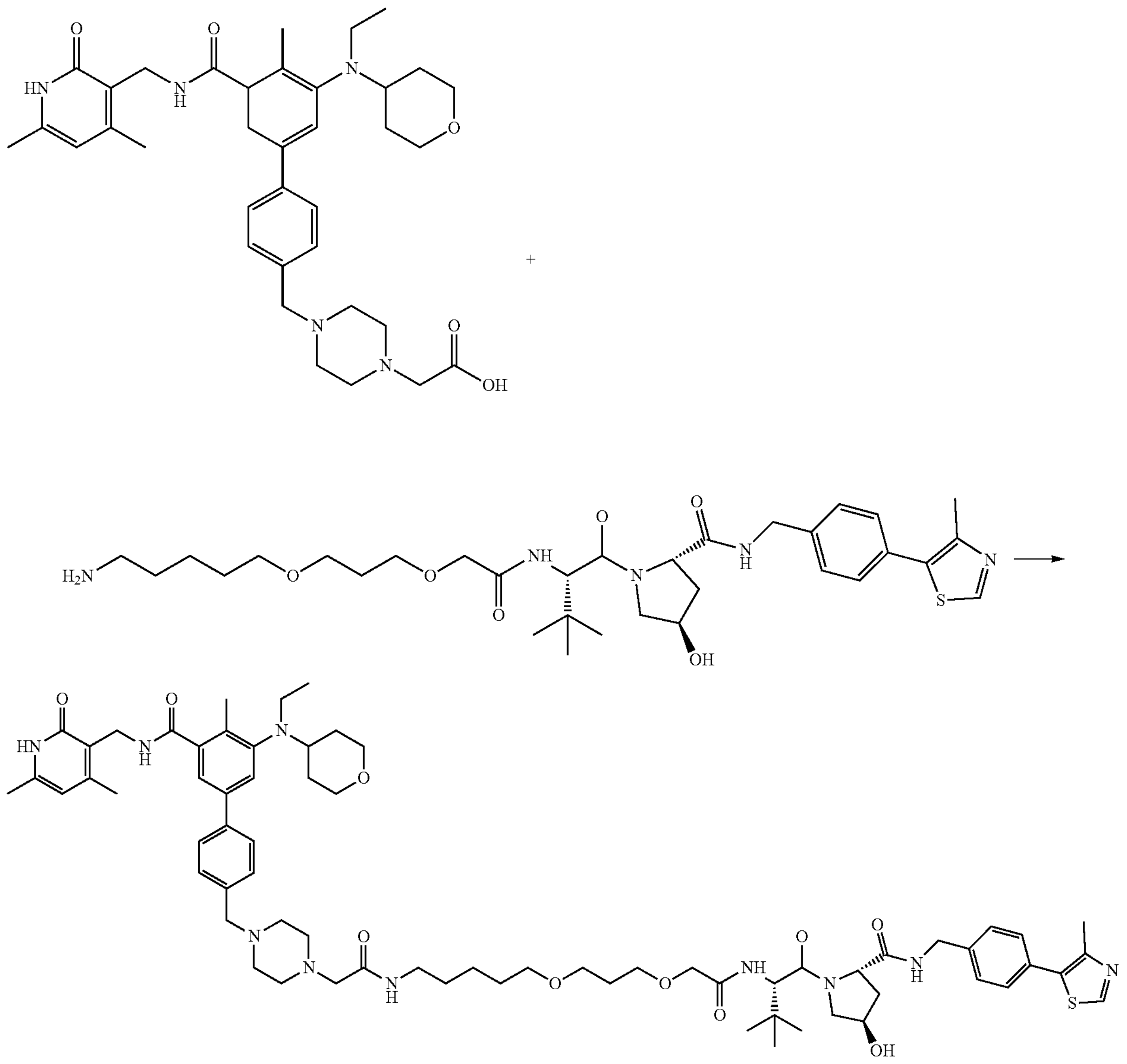

The compound (0.059 g, 0.079 mmol) prepared in [Example 1-Step 6] was dissolved in N,N-dimethylformamide (1 mL), to which the compound prepared in step 3 (0.05 g, 0.079 mmol), N,N-diisopropylethylamine (0.138 mL, 0.791 mmol) and HATU (0.045 g, 0.119 mmol) were added, followed by stirring at room temperature for 16 hours. Upon completion of the reaction, the reaction mixture was diluted with dichloromethane, and washed with water and brine. The residue of the organic layer was dried over anhydrous sodium sulfate, filtered and concentrated, and then purified by MPLC to give a target compound (5.2 mg, 5%, white solid).

LC/MS (ESI) m/z: $1244[M+H]^+$

Example 38, 39, 40, 41, 42, 43, 44, 45, 46

Target compounds were prepared in the same manner as described in Example 37.

Example 47

Preparation of (2S, 4R)-1-((S)-2-(3-(4-(4-((3'-(((4,6-dimethyl-2-oxo-1,2-dihydropyridine-3-yl)methyl) carbamoyl)-5'-(ethyl(tetrahydro-2H-pyran-4-yl) amino)-4'-methyl-[1,1'-biphenyl]-4-yl)methyl) piperazine-1-carbonyl)-1H-1,2,3-triazole-1-yl) propanamido)-3,3-dimethylbutanoyl)-4-hydroxy-N-(4-(4-methylthiazol-5-yl)benzyl)pyrrolidine-2-carboxamide

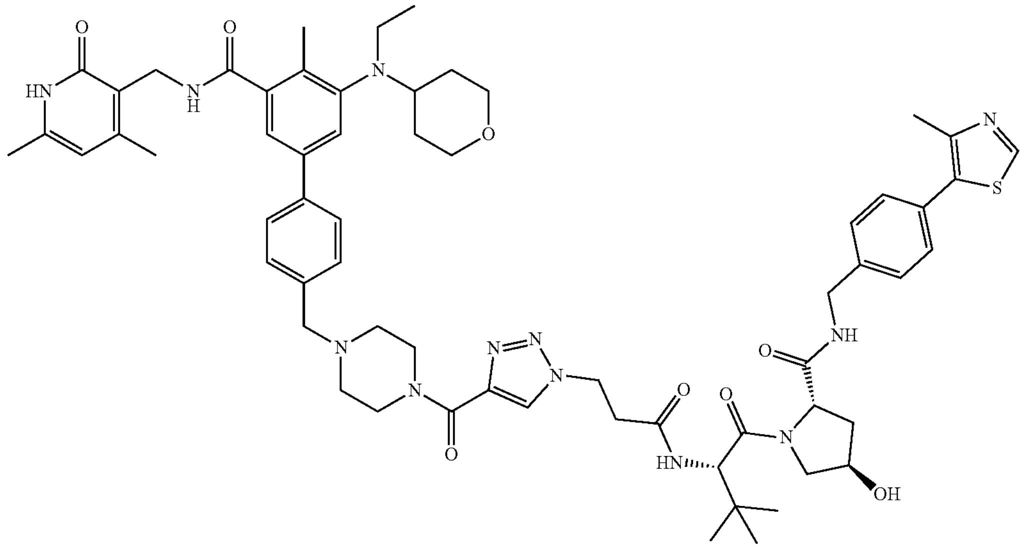 [SMILES: CCN(c1cc(-c2ccc(CN3CCN(C(=O)c4cn(CCC(=O)N[C@H](C(=O)N5C[C@H](O)C[C@H]5C(=O)NCc5ccc(-c6scnc6C)cc5)C(C)(C)C)nn4)CC3)cc2)cc(C(=O)NCc2c(C)cc(C)[nH]c2=O)c1C)C1CCOCC1]

Step 1: Preparation of (2S, 4R)-1-((S)-2-(3-azidopropanamido)-3,3-dimethylbutanoil)-4-hydroxy-N-(4-(4-methylthiazol-5-yl)benzyl)pyrrolidine-2-carboxamide

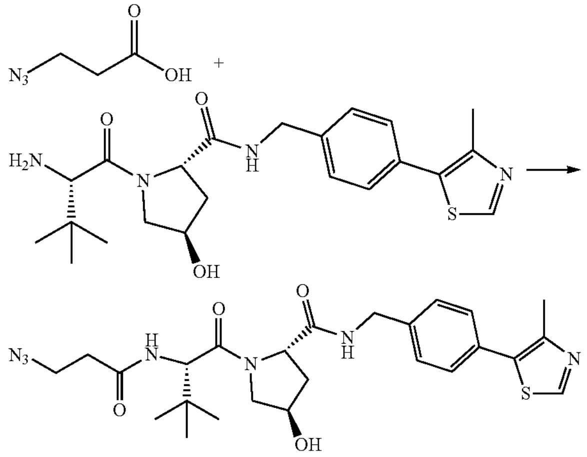

3-Azidopropanoic acid (0.088 g, 0.766 mmol) and (2S, 4R)-1-((S)-2-amino-3,3-dimethylbutanoyl)-4-hydroxy-N-(4-4-methylthiazol-5-yl)benzyl)pyrrolidine-2-carboxamide (0.3 g, 0.7 mmol) were dissolved in N,N-dimethylformamide (2 ml), to which N,N-diisopropylethylamine (0.1 ml, 0.57 mmol), EDC (0.216 g, 1.4 mmol) and HOBT (0.213 g, 1.4 mmol) were added, followed by stirring at room temperature for 16 hours. Upon completion of the reaction, the reaction mixture was diluted with ethyl acetate, and washed with water.

The residue of the organic layer was dried over anhydrous sodium sulfate, filtered and concentrated, and then purified by MPLC to give a target compound (0.239 g, 65%, white solid).

LC/MS (ESI) m/z: 528[M+H]$^+$

Step 2: Preparation of (2S, 4R)-1-((S)-2-(3-(4-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-biphenyl]-4-yl)methyl)piperazine-1-carbonyl)-1H-1,2,3-triazole-1-yl)propanamido)-3,3-dimethylbutanoyl)-4-hydroxy-N-(4-(4-methylthiazol-5-yl)benzyl)pyrrolidine-2-carboxamide

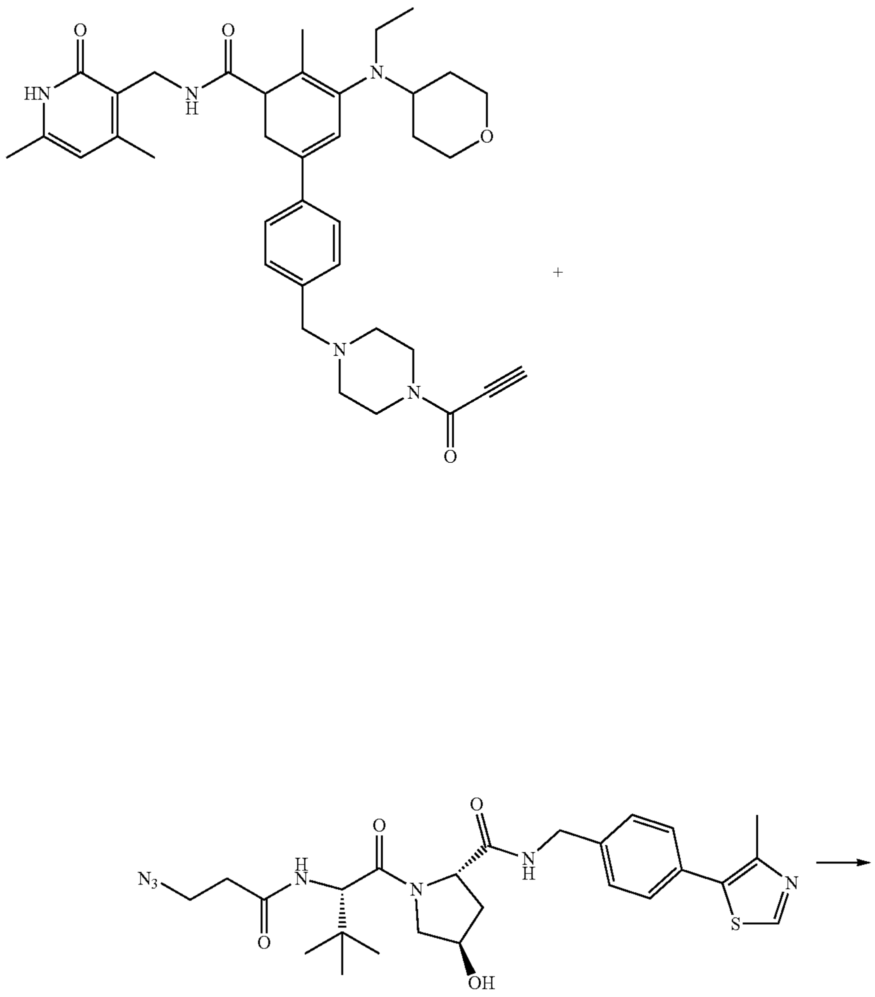

-continued

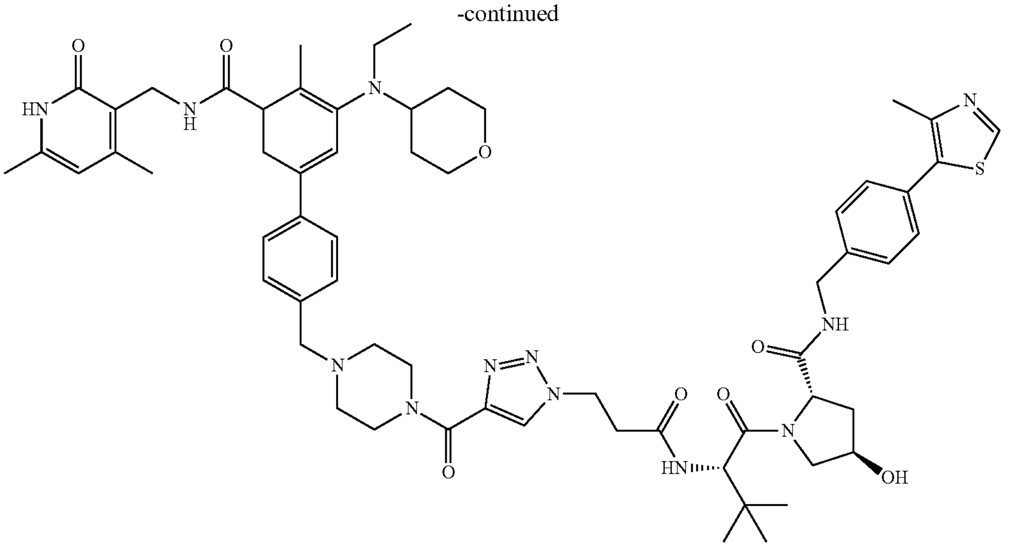

The compound prepared in step 1 (42.3 mg, 0.08 mmol) and the compound (50 mg, 0.08 mmol) prepared in [Example 25—Step 1] were dissolved in tetrahydrofuran (1 ml), to which copper sulfate (7 mg, 0.044 mmol), sodium ascorbate (14 mg, 0.07 mmol) and water (0.2 ml) were added, followed by stirring at room temperature for 12 hours. Upon completion of the reaction, the reaction mixture was diluted with ethyl acetate, and washed with water. The residue of the organic layer was dried over anhydrous sodium sulfate, filtered and concentrated, purified by Prep HPLC, and neutralized by adding a sodium hydrogen carbonate aqueous solution to give a target compound (29.7 mg, 32%, white solid).

LC/MS (ESI) m/z: 1151[M+H]$^+$

Example 48

A target compound was prepared in the same manner as described in Example 47.

Example 49

A target compound was prepared in the same manner as described in Example 37.

Example 50

Preparation of 4'-((4-(2-((6-((2S)-2-((25)-3-amino-2-hydroxy-4-phenylbutanamido)-4-methylpentanamido)hexyl)amino)-2-oxoethyl)piperazine-1-yl)methyl)-N-((4,6-dimethyl-2-oxo-1,2-dihydropyridine-3-yl)methyl)-5-(ethyl(tetrahydro-2H-pyran-4-yl)amino)-4-methyl-[1,1'-biphenyl]-3-carboxamide

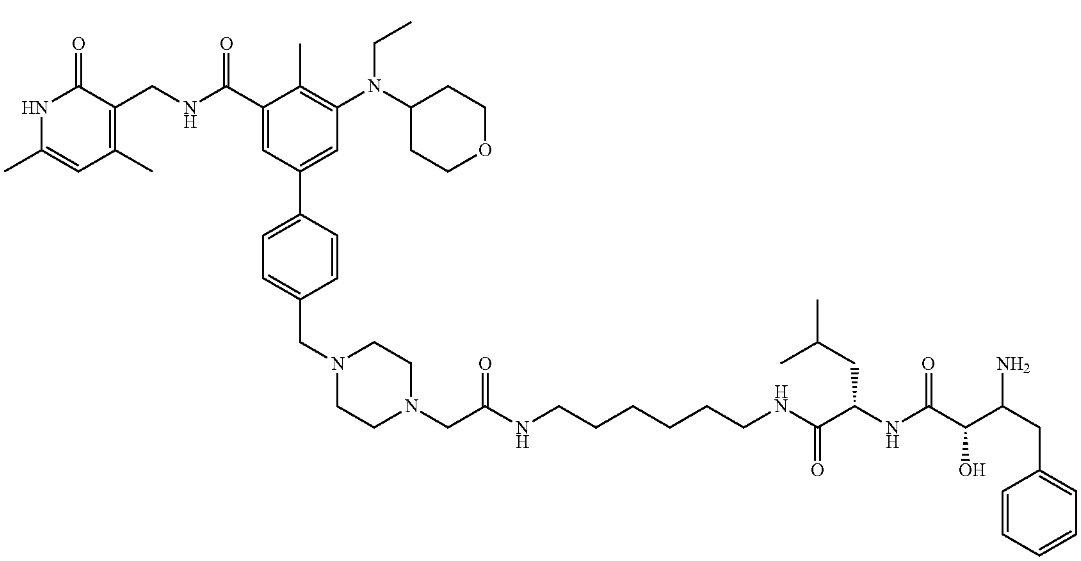 [SMILES: CCN(c1cc(-c2ccc(CN3CCN(CC(=O)NCCCCCCNC(=O)[C@H](CC(C)C)NC(=O)[C@@H](O)C(N)Cc4ccccc4)CC3)cc2)cc(C(=O)NCc2c(C)cc(C)[nH]c2=O)c1C)C1CCOCC1]

Step 1: Preparation of t-butyl (6-(2-(4-((3'-(((4,6-dimethyl-2-oxo-1,2-dihydropyridine-3-yl)methyl) carbamoyl)-5'-(ethyl(tetrahydro-2H-pyran-4-yl) amino)-4'-methyl-[1,1'-biphenyl]-4-yl)methyl) piperazine-1-yl)acetamido)hexyl)carbamate
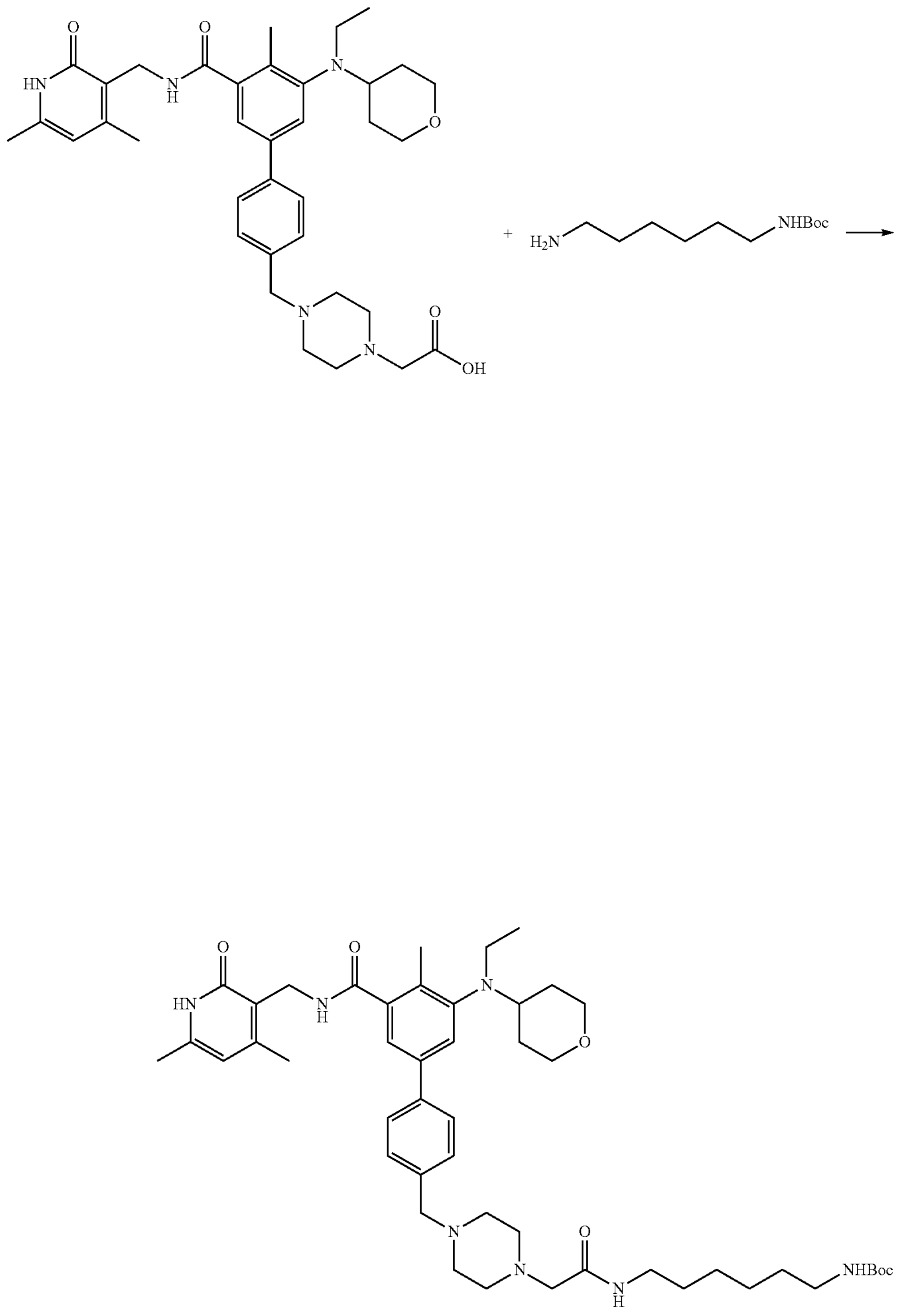

The compound (0.15 g, 0.202 mmol) prepared in [Example 1—Step 6] was dissolved in N,N-dimethylformamide (2 ml), to which N,N-diisopropylethylamine (0.17 ml, 1.0 mmol) and HATU (0.115 g, 0.3 mmol) were added, followed by stirring at room temperature for 16 hours. Upon completion of the reaction, the reaction mixture was diluted with ethyl acetate, and washed with water. The residue of the organic layer was dried over anhydrous sodium sulfate, filtered and concentrated, and then purified by MPLC to give a target compound (64 mg, 38%, white solid).

LC/MS (ESI) m/z: 828[M+H]+

Step 2: Preparation of 4'-((4-(2-((6-aminohexyl)amino)-2-oxoethyl)piperazine-1-yl)methyl)-N-((4,6-dimethyl-2-oxo-1,2-dihydropyridine-3-yl)methyl)-5-(ethyl(tetrahydro-2H-pyran-4-yl)amino)-4-methyl-[1,1'-biphenyl]-3-carboxamide

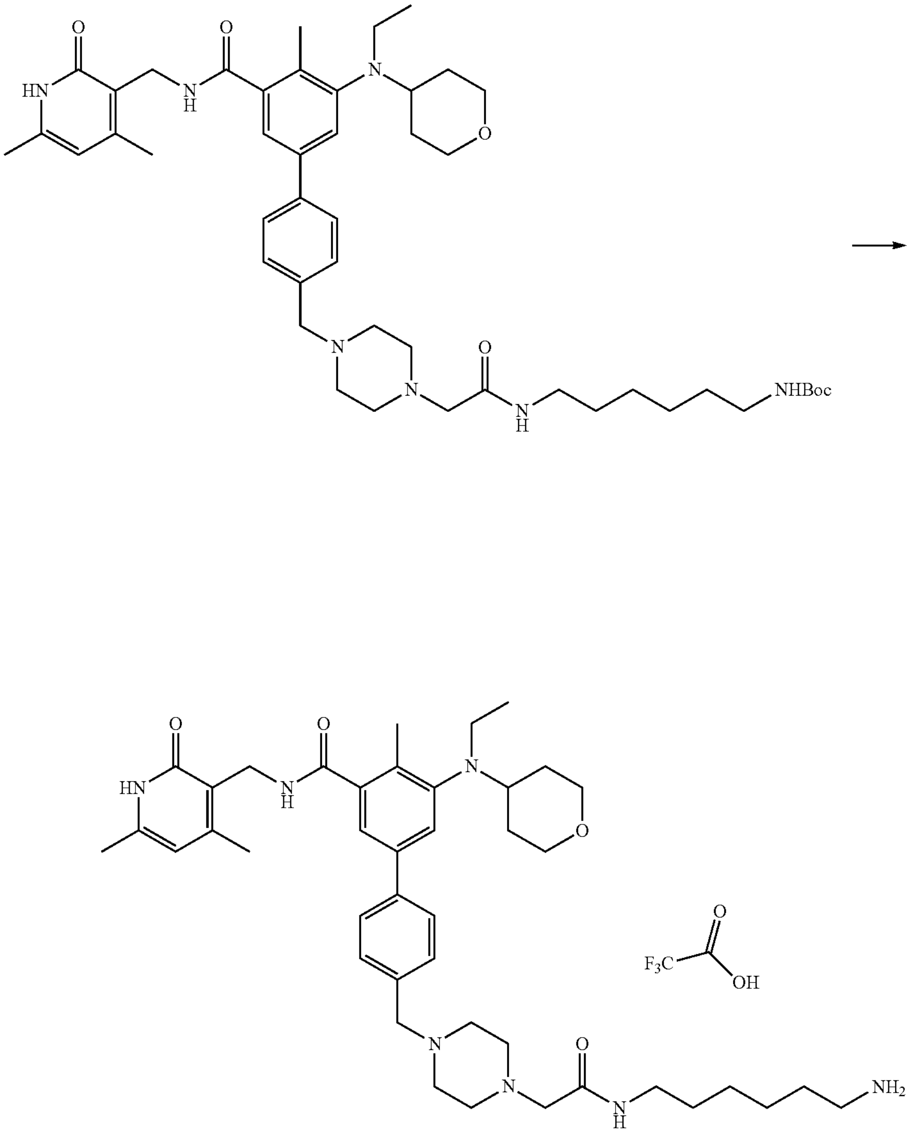

The compound prepared in step 1 (64 mg, 0.077 mmol) was dissolved in dichloromethane (1 ml), to which trifluoroacetic acid (0.2 ml) was added, followed by stirring at room temperature for 3 hours. Upon completion of the reaction, the reaction mixture was concentrated under reduced pressure to give a target compound, and the obtained compound was used in the next step without further purification.

LC/MS (ESI) m/z: 728[M+H]+

Step 3: Preparation of ((2R)-3-((t-butoxycarbonyl) amino)-2-hydroxy-4-penylbutanoyl)-L-leucine

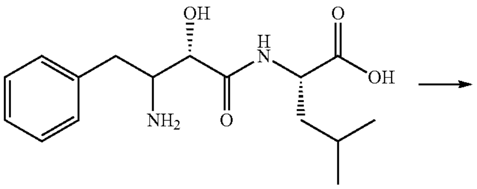

-continued

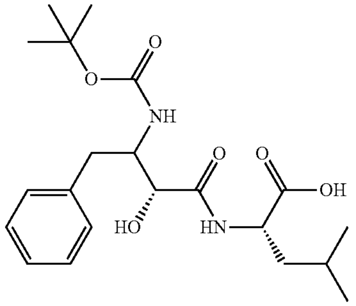

2-(3-Amino-2-hydroxy-4-phenylbutanamido)-4-methylpentanoic acid (3 g, 9.73 mmol) was dissolved in dichloromethane (32 ml), to which sodium carbonate (2.68 g, 25.3 mmol) and di-t-butyl dicarbonate (2.94 ml, 12.65 mmol) were added, followed by stirring at room temperature for 1 hour. Upon completion of the reaction, the reaction mixture was washed with water. The residue of the organic layer was dried over anhydrous sodium sulfate, filtered and concentrated, and then used in the next step without further purification.

LC/MS (ESI) m/z: 409[M+H]+

Step 4: Preparation of t-butyl ((35)-4-(((S)-1-((6-(2-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-biphenyl]-4-yl)methyl)piperazine-1-yl)acetamido)hexyl)amino)-4-methyl-1-oxopentane-2-yl)amino)-3-hydroxy-4-oxo-1-phenylbutane-2-yl)carbamate

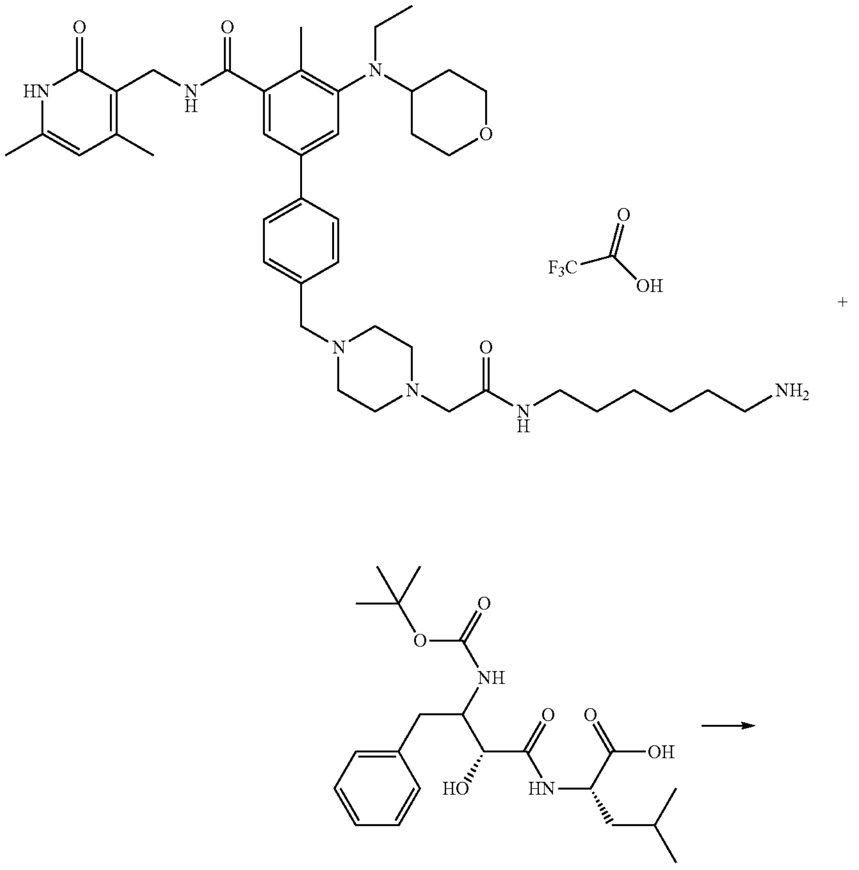

-continued

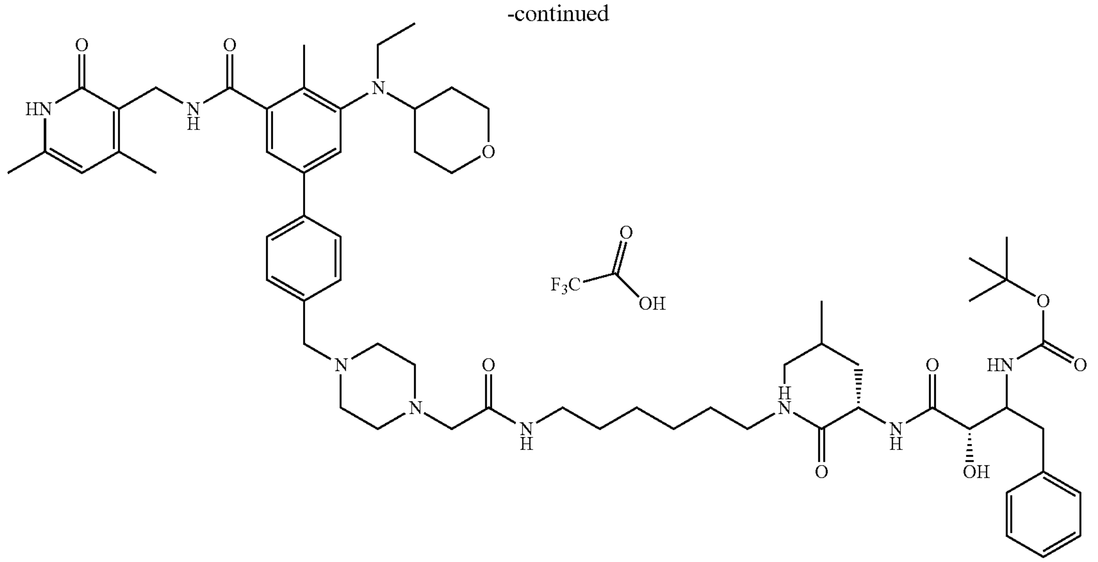

The compound prepared in step 2 (64.8 mg, 0.077 mmol) and the compound prepared in step 3 (47.2 mg, 0.116 mmol) were dissolved in N,N-dimethylformamide (1 ml), to which N,N-diisopropylethylamine (49.8 mg, 0.385 mmol), EDC (22.14 mg, 0.116 mmol) and HOBT (41.3 mg, 0.27 mmol) were added, followed by stirring at room temperature for 16 hours. Upon completion of the reaction, the reaction mixture was diluted with ethyl acetate, and washed with water. The residue of the organic layer was dried over anhydrous sodium sulfate, filtered and concentrated, and then purified by Prep HPLC to give a target compound (28 mg, 33%, white solid).

LC/MS (ESI) m/z: 1118[M+H]$^+$

Step 5: Preparation of 4'-((4-(2-((6-((2S)-2-((2S)-3-amino-2-hydroxy-4-phenylbutanamido)-4-methylpentanamido)hexyl)amino)-2-oxoethyl)piperazine-1-yl)methyl)-N-((4,6-dimethyl-2-oxo-1,2-dihydropyridine-3-yl)methyl)-5-(ethyl(tetrahydro-2H-pyran-4-yl)amino)-4-methyl-[1,1'-biphenyl]-3-carboxamide

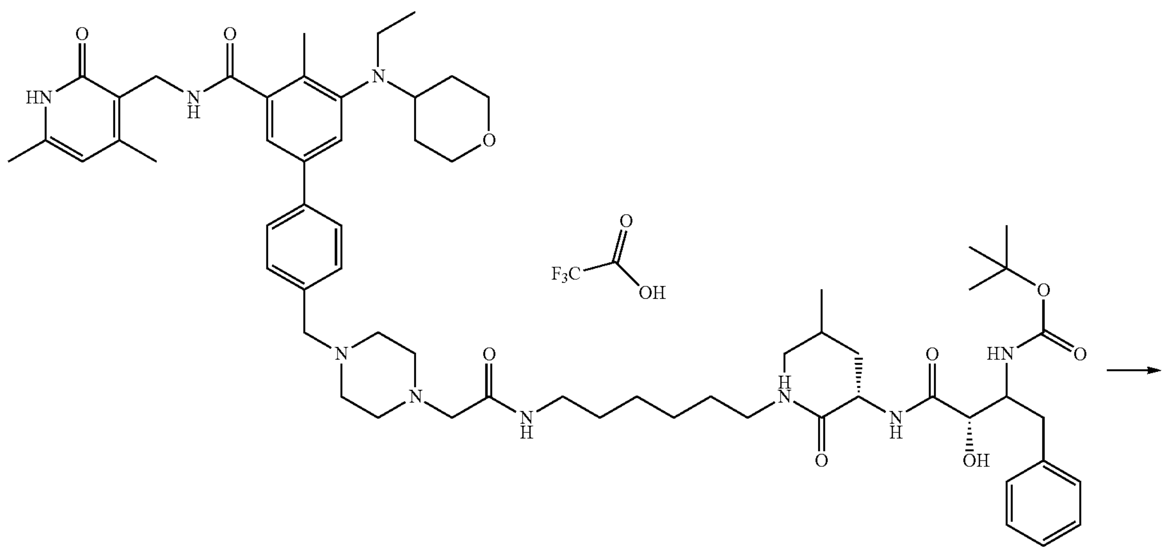

-continued

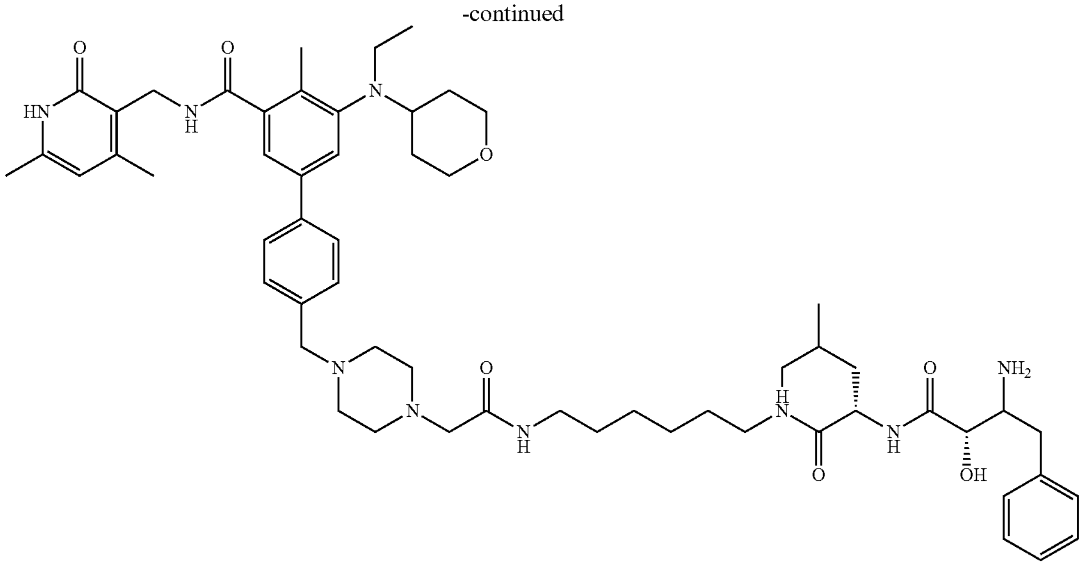

The compound prepared in step 4 (28 mg, 0.023 mmol) was dissolved in dichloromethane (1 ml), to which trifluoroacetic acid (0.3 ml) was added, followed by stirring at room temperature for 2 hours. Upon completion of the reaction, the reaction mixture was diluted with dichloromethane, neutralized by adding a sodium hydrogen carbonate aqueous solution, and washed with water. The residue of the organic layer was dried over anhydrous sodium sulfate, filtered and concentrated to give a target compound (11.5 mg, 49%, white solid).

LC/MS (ESI) m/z: 1018[M+H]$^+$

Chemical structures, compound names, analysis data, yields, and purification methods of the compounds prepared in Examples 1-50 are summarized and shown in Table 1 below.

TABLE 1

| | structure | name | $^1H$ NMR, MS | Yield (%) | HPLC r.t. (min) Purity |
|---|---|---|---|---|---|
| 1 | 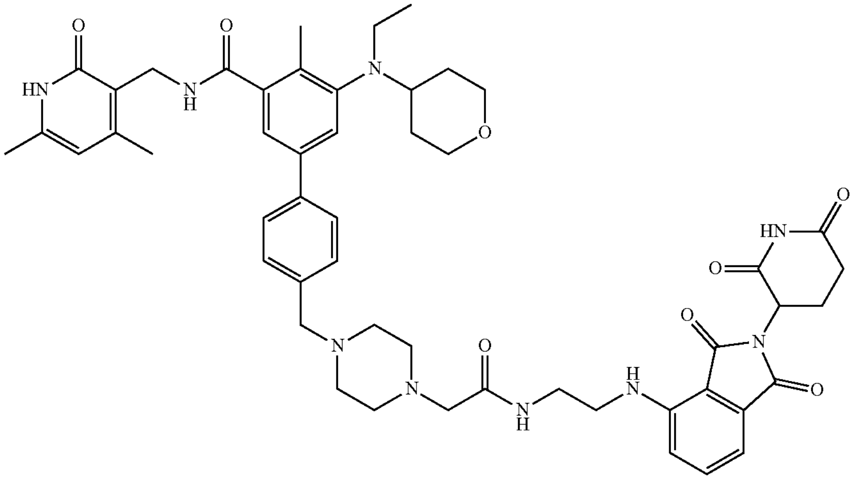 [SMILES: CCN(c1cc(-c2ccc(CN3CCN(CC(=O)NCCNc4cccc5c4C(=O)N(C4CCC(=O)NC4=O)C5=O)CC3)cc2)cc(C(=O)NCc2c(C)cc(C)[nH]c2=O)c1C)C1CCOCC1] | N-((4,6-dimethyl-2-oxo-1,2-dihydro-pyridine-3-yl)methyl)-4'-((4-(2-((2-((2-(2,6-dioxo-piperidine-3-yl)-1,3-dioxo isoindoline-4-yl)amino) ethyl)amino)-2-oxoethyl) piperazine-1-yl)methyl)-5-(ethyl(tetra-hydro-2H-pyran-4-yl)amino)-4-methyl-[1,1'-biphenyl]-3-carboxamide | $^1H$ NMR 400 MHz, DMSO δ 11.45 (br s, 1H), 11.09 (br s, 1H), 8.18 (t, J = 4.8 Hz, 1H), 7.88 (t, J = 5.7 Hz, 1H), 7.59-7.55 (m, 3H), 7.39 (s, 1H), 7.33 (d, J = 8.1 Hz, 2H), 7.21-7.19 (m, 2H), 7.02 (d, J = 7.0 Hz, 2H), 6.69 (t, J = 5.8 Hz, 1H), 5.85 (s, 1H), 5.04 (dd, J = 12.7, 5.2 Hz, 1H), 4.34 (d, J = 4.2 Hz, 1H), 4.28 (d, J = 4.9 Hz, 2H), 3.84-3.73 (m, 3H), 3.46 (s, 2H), 3.46-3.37 (m, 2H), 3.29-3.22 (m, 2H), 3.11-3.01 (m, 3H), 2.99-2.87 (m, 1H), 2.87 (s, 2H), 2.58-2.53 | 26 | (A) 4.4 06100% |

TABLE 1-continued
| | structure | name | $^1$H NMR, MS | Yield (%) | HPLC r.t. (min) Purity |
|---|---|---|---|---|---|
| | | | (m, 2H), 2.38-2.36 (m, 8H), 2.24 (s, 3H), 2.20 (s, 3H), 2.09 (s, 3H), 2.00-1.93 (m, 2H), 1.67-1.64 (m, 2H), 1.56-1.47 (m, 2H), 0.83 (t, J = 6.9 Hz, 3H); 929 [M + H] $^+$ | | |
| 2 | 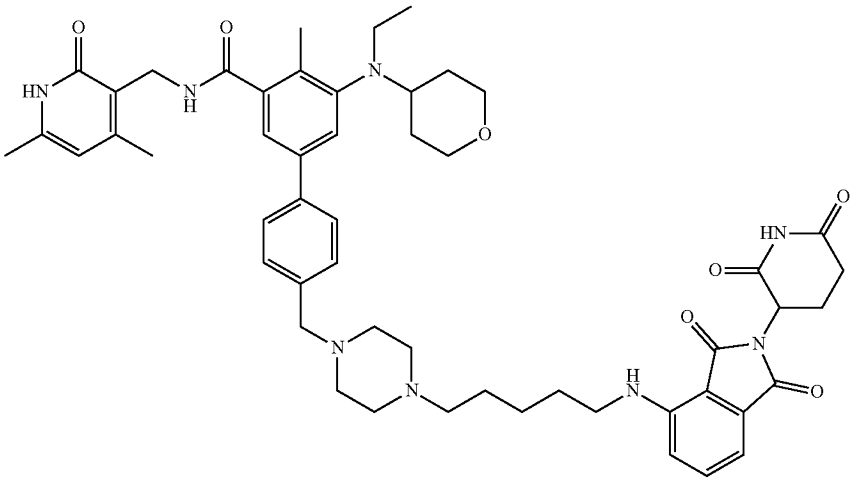 [SMILES: CCN(c1cc(-c2ccc(CN3CCN(CCCCCNc4cccc5c4C(=O)N(C4CCC(=O)NC4=O)C5=O)CC3)cc2)cc(C(=O)NCc2c(C)cc(C)[nH]c2=O)c1C)C1CCOCC1] | N-((4,6-dimethyl-2-oxo-1,2-dihydro-pyridine-3-yl)methyl)-4'-((4-(5-((2-(2,6-dioxo-piperidine-3-yl)-1,3-dioxoiso-indoline-4-yl)amino) pentyl) piperazine-1-yl)methyl)-5-(ethyl(tetra-hydro-2H-pyran-4-yl)amino)- | $^1$H NMR 400 MHz, $CDCl_3$ δ 11.25 (br s, 1H), 9.09 (br s, 1H), 7.49-7.42 (m, 3H), 7.32-7.31 (m, 3H), 7.13 (t, J = 5.8 Hz, 1H), 7.07 (d, J = 7.1 Hz, 1H), 6.86 (d, J = 8.6 Hz, 1H), 6.22 (t, J = 5.4 Hz, 1H), 5.89 (s, 1H), 4.89 (dd, J = 12.2, 5.3 Hz, 1H), | 10 | (B) 3.3 6298% |

TABLE 1-continued

| structure | name | $^1$H NMR, MS | Yield (%) | HPLC r.t. (min) Purity |
|---|---|---|---|---|
| | 4-methyl-[1,1'-biphenyl]-3-carboxamide | 4.59-4.49 (m, 2H), 3.94 (d, J = 11.3 Hz, 2H), 3.52 (s, 2H), 3.34-3.23 (m, 4H), 3.09 (q, J = 6.9 Hz, 2H), 3.04-2.97 (m, 1H), 2.87-2.65 (m, 4H), 2.48 (br s, 6H), 2.40 (s, 3H), 2.36-2.34 (m, 5H), 2.13 (s, 3H), 2.10-2.00 (m, 2H), 1.57-1.47 (m, 2H), 1.46-1.39 (m, 2H), 0.88 (t, J = 6.9 Hz, 3H); 914 [M + H] + | | |

TABLE 1-continued

| | structure | name | $^1$H NMR, MS | Yield (%) | HPLC r.t. (min) Purity |
|---|---|---|---|---|---|
| 3 | 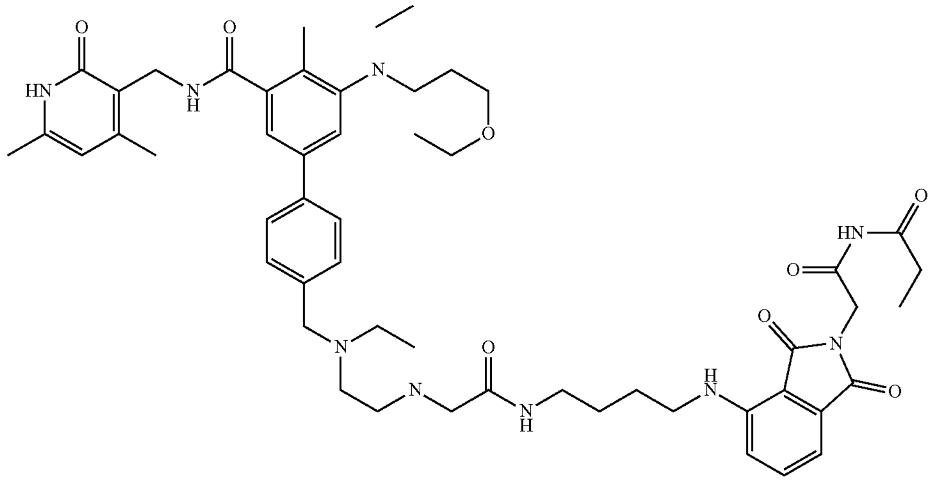 | N-((4,6-dimethyl-2-oxo-1,2-dihydro-pyridine-3-yl)methyl)-4'-((4-(2-((4-((2-(2,6-dioxo-piperidine-3-yl)-1,3-dioxoiso-indoline-4-yl)amino)butyl)amino)-2-oxoethyl)piperazine-1-yl)methyl)-5-(ethyl(tetra-hydro-2H-pyran-4-yl)amino)-4-methyl-[1,1'-biphenyl]-3-carboxamide | $^1$H NMR 400 MHz, $CDC1_3$ δ 10.75 (br s, 1H), 10.49 (br s, 1H), 7.50-7.44 (m, 3H), 7.32-7.30 (m, 3H), 7.25-7.23 (m, 2H), 7.15 (t, J = 5.9 Hz, 1 H), 7.08 (d, J = 7.0 Hz, 1H), 6.87 (d, J = 8.6 Hz, 1H), 6.20 (t, J = 5.6 Hz, 1H), 5.91 (s, 1H), 4.89 (dd, J = 11.9, 5.0 Hz, 1H), 4.61 (dd, J = 14.1, 6.6 Hz, 1H), 4.45 (dd, J = 14.1, 8.5 Hz, 1H), 3.94 (d, J = 11.2 Hz, 2H), 3.56-3.48 (m, 2H), 3.34-3.27 (m, 6H), 3.09 (q, J = 6.9 Hz, | 36 | (B) 3.4 0998% |

TABLE 1-continued
| | structure | name | $^1$H NMR, MS | Yield (%) | HPLC r.t. (min) Purity |
|---|---|---|---|---|---|
| | | | 2H), 3.04-2.98 (m, 3H), 2.87-2.72 (m, 4H), 2.54-2.48 (m, 8H), 2.42 (s, 3H), 2.35 (s, 3H), 2.18 (s, 3H), 2.13-2.07 (m, 1H), 1.70-1.63 (m, 4H), 0.89 (t, J = 7.0 Hz, 3H); 957 [M + H] $^+$ | | |
| 4 | 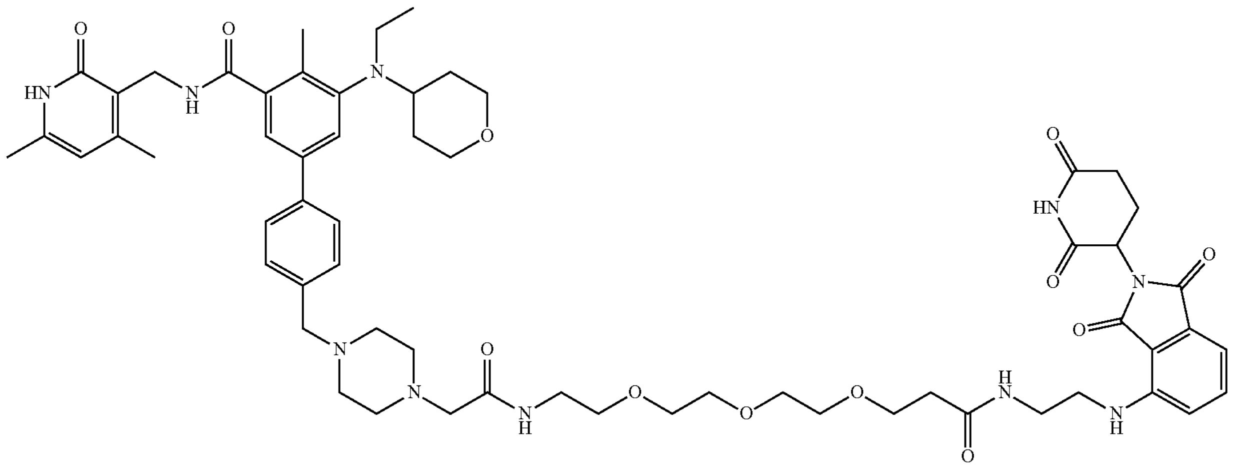 [SMILES: CCN(c1cc(-c2ccc(CN3CCN(CC(=O)NCCOCCOCCOCCC(=O)NCCNc4cccc5c4C(=O)N(C4CCC(=O)NC4=O)C5=O)CC3)cc2)cc(C(=O)NCc2c(C)cc(C)[nH]c2=O)c1C)C1CCOCC1] | N-((4,6-dimethyl-2-oxo-1,2-dihydro-pyridine-3-yl)methyl)-4'-((4-(18-((2-(2,6-dioxo-piperidine-3-yl)-1,3-dioxoiso-indoline-4-yl)amino)-2,15-dioxo-6,9,12-trioxa-3,16-diazaocta-decyl) piperazine-1-yl)methyl)-5-(ethyl(tetra- | $^1$H NMR 400 MHz, $CDCl_3$ δ 10.53 (br s, 1H), 9.99 (br s, 1H), 7.51-7.43 (m, 4H), 7.31-7.29 (m, 3H), 7.16 (t, J = 6.0 Hz, 1H), 7.15-7.08 (m, 2H), 7.01 (d, J = 8.5 Hz, 1H), 6.46 (br s, 1H), 5.91 (s, 1H), 4.87 (dd, J = 9.1, 5.3 Hz, 1H), 4.55 (d, J = | 57 | (B) 3.2 8298% |

TABLE 1-continued

| structure | name | $^1H$ NMR, MS | Yield (%) | HPLC r.t. (min) Purity |
|---|---|---|---|---|
| | hydro-2H-pyran-4-yl)amino)-4-methyl-[1,1'-biphenyl]-3-carboxamide | 8.7 Hz, 2H), 4.05-4.00 (m, 1H), 3.97 (d, J = 15.8 Hz, 2H), 3.67 (t, J = 5.8 Hz, 2H), 3.56-3.52 (m, 12H), 3.46-3.44 (m, 6H), 3.34-3.28 (m, 2H), 3.09 (q, J = 7.0 Hz, 2H), 3.04-2.97 (m, 3H), 2.85-2.63 (m, 4H), 2.54 (br s, 4H), 2.46-2.45 (m, 4H), 2.41 (s, 3H), 2.34 (s, 3H), 2.18 (s, 3H), 2.12-2.01 (m, 1H), 1.70-1.64 (m, 4H), 0.88 (t, J = 6.9 Hz, 3H); 1132 [M + H] + | | |

TABLE 1-continued

| | structure | name | $^1$H NMR, MS | Yield (%) | HPLC r.t. (min) Purity |
|---|---|---|---|---|---|
| 5 | 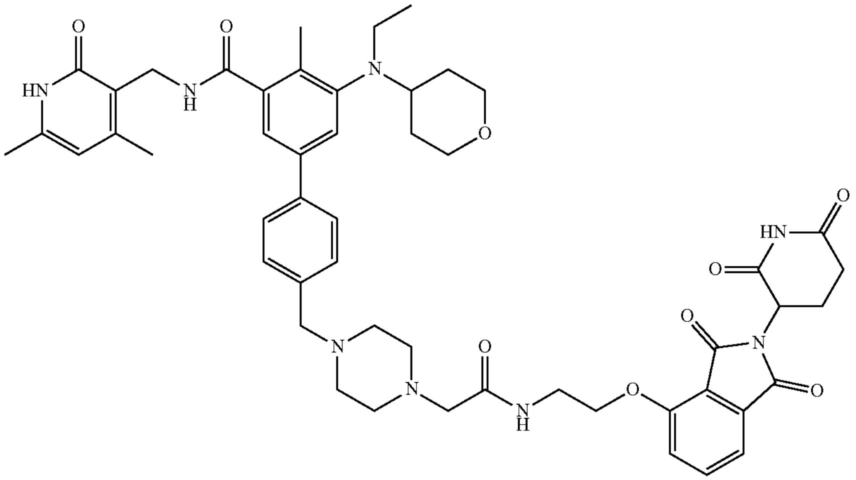 [SMILES: CCN(c1cc(-c2ccc(CN3CCN(CC(=O)NCCOc4cccc5c4C(=O)N(C4CCC(=O)NC4=O)C5=O)CC3)cc2)cc(C(=O)NCc2c(C)cc(C)[nH]c2=O)c1C)C1CCOCC1] | N-((4,6-dimethyl-2-oxo-1,2-dihydro-pyridine-3-yl)methyl)-4'-((4-(2-((2-((2-(2,6-dioxo-piperidine-3-yl)-1,3-dioxoiso-indoline-4-yl)oxy) ethyl)amino)-2-oxoethyl) piperazine-1-yl)methyl)-5-(ethyl(tetra-hydro-2H-pyran-4-yl)amino)-4-methyl-[1,1'-biphenyl]-3-carboxamide | $^1$H NMR 400 MHz, $CDC1_3$ δ 11.12 (br s, 1H), 10.80 (br s, 1H), 7.87-7.84 (m, 1H), 7.70-7.66 (m, 1H), 7.48-7.43 (m, 5H), 7.32 (s, 2H), 7.25-7.21 (m, 7H), 7.20 (d, J = 4.9 Hz, 1H), 5.91 (s, 1H), 4.96 (dd, J = 12.2, 5.2 Hz, 1H), 4.58 (dd, J = 14.2, 6.6 Hz, 1H), 4.41 (dd, J = 14.2, 5.8 Hz, 1H), 4.29-4.23 (m, 2H), 4.02 (p, J = 6.1 Hz, 1H), 3.95-3.88 (m, 2H), 3.67-3.57 (m, 2H), 3.51-3.46 (m, 1H), 3.34-3.27 (m, 2H), 3.08 (q, J = 6.9 Hz, 2H), 3.03-2.94 (m, 4H), 2.88-2.66 (m, 4H), 2.55 (br s, | 34 | (A) 4.2 8594% |

TABLE 1-continued

| | structure | name | $^1H$ NMR, MS | Yield (%) | HPLC r.t. (min) Purity |
|---|---|---|---|---|---|
| | | | 8H), 2.42 (s, 3H), 2.40 (s, 3H), 2.35-2.34 (m, 1H), 2.22-2.16 (m, 4H), 2.12-2.08 (m, 1H), 0.88 (t, J = 6.9 Hz, 3H); 930 [M + H] + | | |
| 6 | 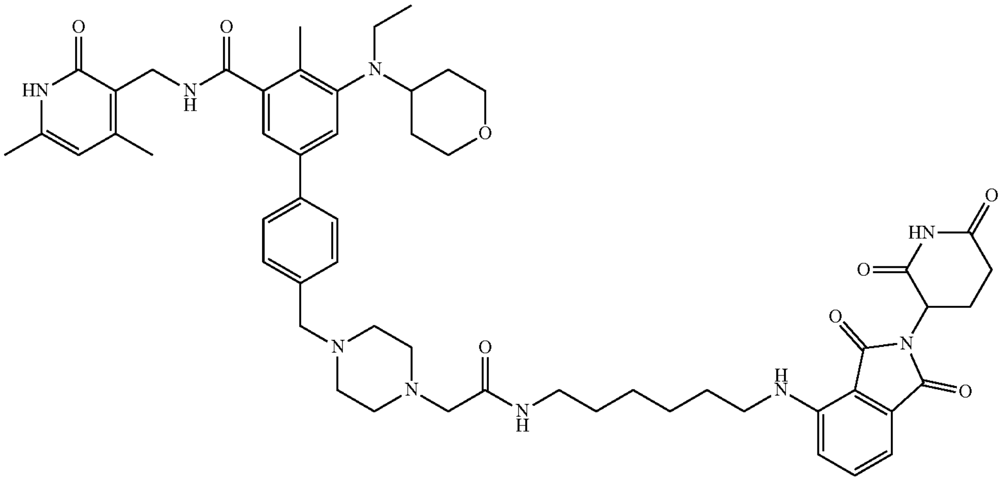 | N-((4,6-dimethyl-2-oxo-1,2-dihydro-pyridine-3-yl)methyl)-4'-((4-(2-((6-((2-(2,6-dioxo-piperidine-3-yl)-1,3-dioxoiso-indoline-4-yl)amino) hexyl)amino)-2-oxoethyl) piperazine-1-yl)methyl)-5-(ethyl(tetra-hydro-2H-pyran-4-yl)amino)-4-methyl-[1,1'-biphenyl]- | 1H NMR 400 MHz, $CDCl_3$ δ 10.72 (br s, 1H), 9.99 (br s, 1H), 7.51-7.44 (m, 3H), 7.32-7.30 (m, 3H), 7.25 (s, 1H), 7.19 (t, J = 6.0 Hz, 1H), 7.13 (t, J = 6.0 Hz, 1H), 7.08 (d, J = 7.1 Hz, 1H), 6.87 (d, J = 8.6 Hz, 1H), 6.21 (t, J = 5.4 Hz, 1H), 5.92 (s, 1H), 4.89 (dd, J = 12.0, 5.1 Hz, 1H), 4.57 (dd, J = 14.1, 6.2 Hz, 1H), | 61 | (B) 3.6 3297% |

TABLE 1-continued

| structure | name | $^1H$ NMR, MS | Yield (%) | HPLC r.t. (min) Purity |
|---|---|---|---|---|
| | 3-carboxamide | 4.51 (dd, J = 14.1, 5.9 Hz, 1H), 3.94 (d, J = 11.2 Hz, 2H), 3.53 (s, 2H), 3.48-3.23 (m, 6H), 3.10 (q, J = 7.0 Hz, 2H), 3.04-2.99 (m, 3H), 2.87-2.68 (m, 4H), 2.55 (br s, 4H), 2.50 (br s, 4H), 2.42 (s, 3H), 2.34 (s, 3H), 2.18 (s, 3H), 2.14-2.02 (m, 1H), 1.70-1.64 (m, 5H), 1.57-1.42 (m, 3H), 1.41-1.33 (m, 5H), 0.89 (t, J = 6.9 Hz, 3H); 985 [M + H]$^+$ | | |

TABLE 1-continued

| | structure | name | $^1H$ NMR, MS | Yield (%) | HPLC r.t. (min) Purity |
|---|---|---|---|---|---|
| 7 | 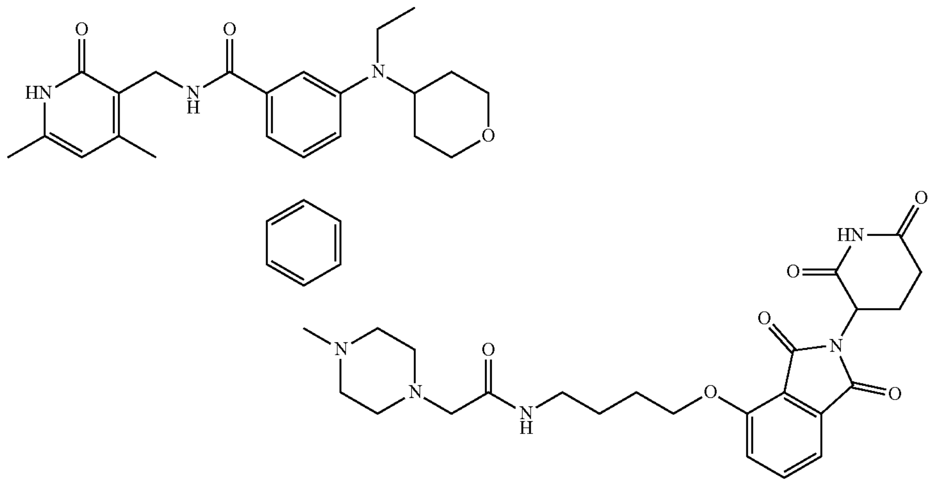 | N-((4,6-dimethyl-2-oxo-1,2-dihydro-pyridine-3-yl)methyl)-4'-((4-(2-((4-((2-(2,6-dioxo-piperidine-3-yl)-1,3-dioxoiso-indoline-4-yl)oxy) butyl)amino)-2-oxoethyl) piperazine-1-yl)methyl)-5-(ethyl(tetra-hydro-2H-pyran-4-yl)amino)-4-methyl-[1,1'-biphenyl]-3-carboxamide | $^1H$ NMR 400 MHz, $CDCl_3$ δ 10.82 (br s, 1H), 10.46 (br s, 1H), 7.68-7.64 (m, 1H), 7.44 (d, J = 7.8 Hz, 3H), 7.36-7.29 (m, 4H), 7.25-7.23 (m, 1H), 4.92 (dd, J = 12.5, 7.0 Hz, 1H), 4.57 (dd, J = 14.1, 7.8 Hz, 1H), 4.45 (dd, J = 14.1, 8.3 Hz, 1H), 4.20-4.17 (m, 2H), 3.94 (d, J = 11.3 Hz, 2H), 3.59-3.40 (m, 3H), 3.36-3.28 (m, 3H), 3.08 (q, J = 7.0 Hz, 2H), 3.06-2.95 (m, 3H), 2.87-2.61 (m, 3H), 2.56-2.51 (m, 7H), 2.41 (s, 3H), 2.36 (s, 3H), | 29 | (B) 3.3 2999% |

TABLE 1-continued

| | structure | name | $^1H$ NMR, MS | Yield (%) | HPLC r.t. (min) Purity |
|---|---|---|---|---|---|
| | | | 2.17 (s, 3H), 2.11-2.01 (m, 1H), 1.96-1.86 (m, 2H), 1.80-1.67 (m, 7H), 0.88 (t, J = 7.0 Hz, 3H); 958 $[M + H]^+$ | | |
| 8 | 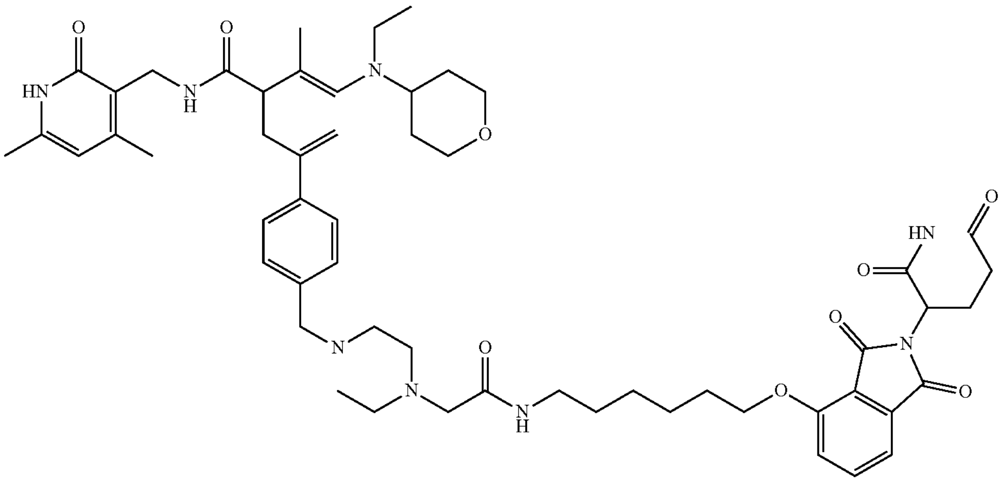 [SMILES: C=C(CC(C(=O)NCc1c(C)cc(C)[nH]c1=O)/C(C)=C/N(CC)C1CCOCC1)c1ccc(CNCCN(CC)CC(=O)NCCCCCCOc2cccc3c2C(=O)N(C(CCC=O)C(N)=O)C3=O)cc1] | N-((4,6-dimethyl-2-oxo-1,2-dihydro-pyridine-3-yl)methyl)-4'-((4-(2-((6-((2-(2,6-dioxo-piperidine-3-yl)-1,3-dioxo-isoindoline-4-yl)oxy) hexyl)amino)-2-oxoethyl) piperazine-1-yl)methyl)-5-(ethyl(tetra-hydro-2H-pyran-4-yl)amino)-4-methyl-[1,1'-biphenyl]-3-carboxamide | $^1H$ NMR (400 MHz, $CDCl_3$) δ10.55 (br s, 1H), 10.19 (br s, 1H), 7.68-7.64 (m, 1H), 7.46-7.43 (m, 3H), 7.32 (d, J = 7.2 Hz, 3H), 7.25-7.23 (m, 1H), 7.20 (d, J = 8.5 Hz, 2H), 7.12 (t, J = 5.9 Hz, 1H), 5.91 (s, 1H), 4.91 (dd, J = 12.4, 7.0 Hz, 1H), 4.55 (dd, J = 14.0, 7.8 Hz, 1H), 4.48 (dd, J = 14.1, 8.2 Hz, 1H), 4.16 (t, J = | 15 | (B) 3.5 1291% |

TABLE 1-continued

| structure | name | $^1H$ NMR, MS | Yield (%) | HPLC r.t. (min) Purity |
|---|---|---|---|---|
| | | 6.3 Hz, 2H), 4.03 (p, J = 6.1 Hz, 1H), 3.94 (d, J = 11.2 Hz, 2H), 3.55 (br s , 2H), 3.34-3.25 (m, 4H), 3.08 (q, J = 7.0 Hz, 2H), 3.04-2.99 (m, 3H), 2.87-2.66 (m, 4H), 2.56-2.50 (m, 7H), 2.41 (s, 3H), 2.34 (s, 3H), 2.18 (s, 3H), 2.10-2.02 (m, 1H), 1.90-1.83 (m, 2H), 1.70-1.62 (m, 4H), 1.57-1.51 (m, 2H), 1.44-1.35 (m, 3H), 0.89 (t, J = 7.0 Hz, 3H); 986 [M + H] + | | |

TABLE 1-continued

| | structure | name | $^1$H NMR, MS | Yield (%) | HPLC r.t. (min) Purity |
|---|---|---|---|---|---|
| 9 | 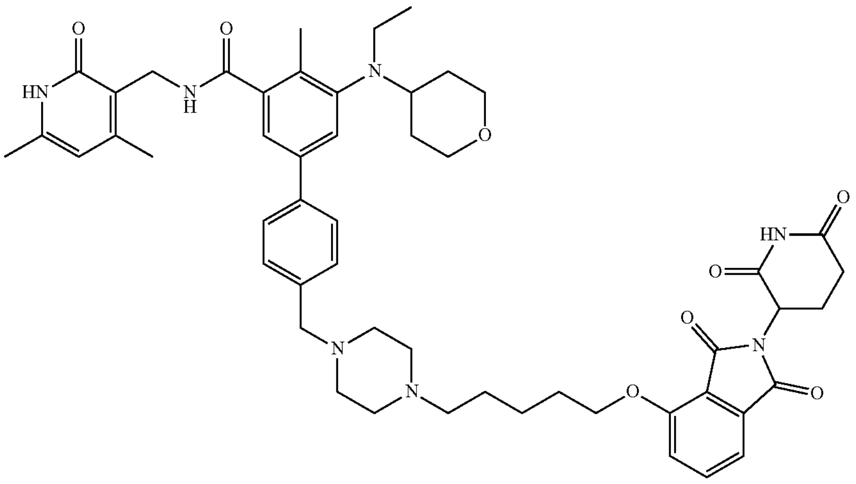 [SMILES: CCN(c1cc(-c2ccc(CN3CCN(CCCCCOc4cccc5c4C(=O)N(C4CCC(=O)NC4=O)C5=O)CC3)cc2)cc(C(=O)NCc2c(C)cc(C)[nH]c2=O)c1C)C1CCOCC1] | N-((4,6-dimethyl-2-oxo-1,2-dihydro-pyridine-3-yl)methyl)-4'-((4-(5-((2-(2,6-dioxo-piperidine-3-yl)-1,3-dioxo-isoindoline-4-yl)oxy) pentyl) piperazine-1-yl)methyl)-5-(ethyl(tetra-hydro-2H-pyran-4-yl)amino)-4-methyl-[1,1'-biphenyl]-3-carboxamide | $^1$H NMR 400 MHz, $CDCl_3$ δ 10.73 (br s, 1H), 9.30 (br s, 1H), 7.67-7.63 (m, 1H), 7.44 (d, J = 7.5 Hz, 3H), 7.32 (d, J = 8.2 Hz, 3H), 7.19 (d, J = 8.4 Hz, 1H), 7.14 (t, J = 5.9 Hz, 1H), 5.90 (s, 1H), 4.92 (dd, J = 12.5, 7.0 Hz, 1H), 4.57-4.49 (m, 2H), 4.17 (t, J = 6.2 Hz, 2H), 4.00 (p, J = 6.1 Hz, 1H), 3.94 (d, J = 11.2 Hz, 2H), 3.53 (s, 2H), 3.34-3.28 (m, 2H), 3.09 (q, J = 7.0 Hz, 2H), 3.04-2.98 (m, 1H), 2.86-2.64 (m, 4H), 2.50 (br s, 7H), 2.40 (s, 3H), 2.38-2.36 (m, 2H), 2.35 (s, 3H), 2.12 | 24 | (A) 4.4 04100% |

TABLE 1-continued

| | structure | name | $^1$H NMR, MS | Yield (%) | HPLC r.t. (min) Purity |
|---|---|---|---|---|---|
| | | | (s, 3H), 2.11-1.92 (m, 1H), 1.87 (p, J = 6.7 Hz, 2H), 1.70-1.64 (m, 4H), 1.54-1.52 (m, 3H), 0.89 (t, J = 7.0 Hz, 3H); 915 [M + H] $^+$ | | |
| 10 | 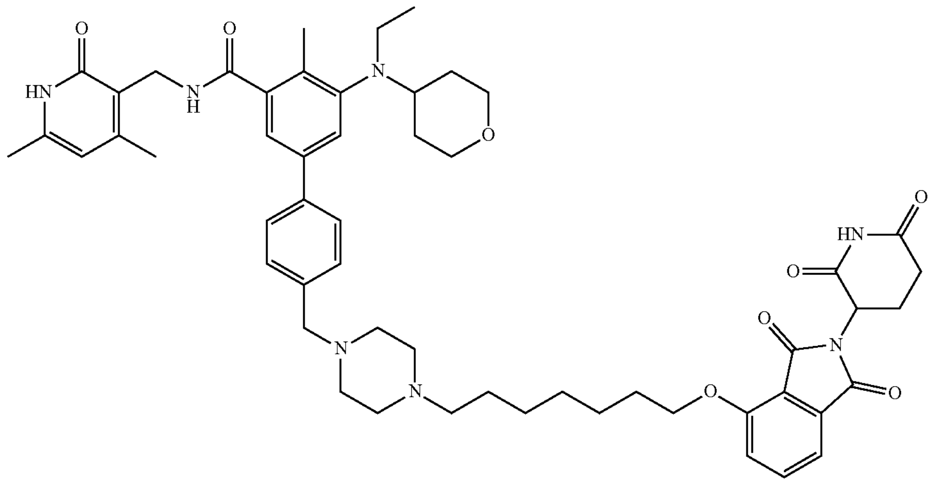 [SMILES: CCN(c1cc(-c2ccc(CN3CCN(CCCCCCCOc4cccc5c4C(=O)N(C4CCC(=O)NC4=O)C5=O)CC3)cc2)cc(C(=O)NCc2c(C)cc(C)[nH]c2=O)c1C)C1CCOCC1] | N-((4,6-dimethyl-2-oxo-1,2-dihydro-pyridine-3-yl)methyl)-4'-((4-(7-((2-(2,6-dioxo-piperidine-3-yl)-1,3-dioxo-isoindoline-4-yl)oxy) heptyl) piperazine-1-yl)methyl)-5-(ethyl(tetra-hydro-2H-pyran-4-yl)amino)-4-methyl-[1,1'-biphenyl]-3-carboxamide | $^1$H NMR (400 MHz, $CDCl_3$) δ 11.29 (br s, 1H), 10.08 (br s, 1H), 7.66 (t, J = 7.7 Hz, 1H), 7.43 (d, J = 7.6 Hz, 3H), 7.32-7.30 (m, 3H), 7.19 (d, J = 8.5 Hz, 1H), 7.14 (t, J = 5.8 Hz, 1H), 5.89 (s, 1H), 4.92 (dd, J = 11.3, 4.9 Hz, 1H), 4.54 (d, J = 5.8 Hz, 2H), 4.22-4.10 (m, 2H), 3.94 (d, J = 11.2 Hz, 2H), 3.66 (d, J = 13.0 Hz, 1H), | 12 | (A) 4.6 07100% |

TABLE 1-continued

| structure | name | $^1$H NMR, MS | Yield (%) | HPLC r.t. (min) Purity |
|---|---|---|---|---|
| | | 3.49 (d, J = 13.0 Hz, 1H), 3.31 (t, J = 10.2 Hz, 2H), 3.09 (q, J = 7.0 Hz, 2H), 3.03-2.98 (m, 1H), 2.86-2.62 (m, 4H), 2.52 (br s, 7H), 2.39-2.34 (m, 9H), 2.13-2.08 (m, 4H), 2.03-2.00 (m, 2H), 1.87-1.82 (m, 4H), 1.52-1.34 (m, 7H), 0.89 (t, J = 6.5 Hz, 3H); 943 [M + H] $^+$ | | |

TABLE 1-continued
| | structure | name | $^1$H NMR, MS | Yield (%) | HPLC r.t. (min) Purity |
|---|---|---|---|---|---|
| 11 | 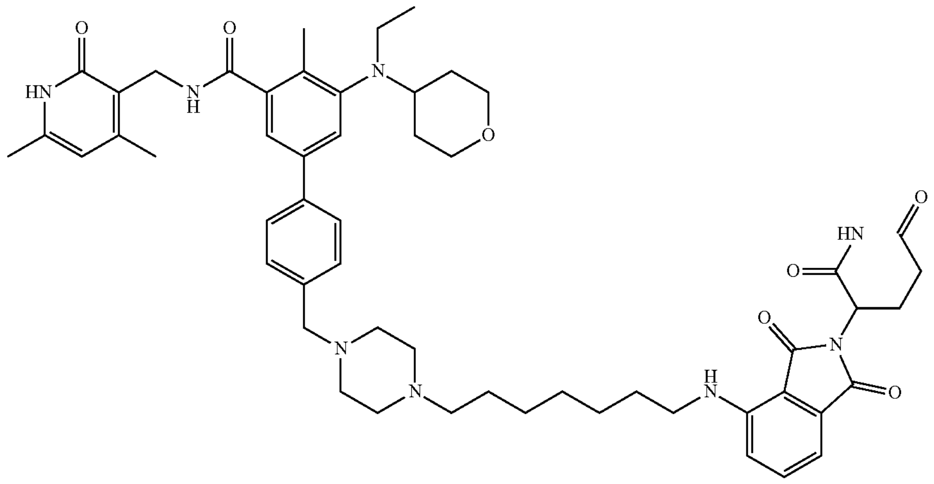 [SMILES: CCN(c1cc(-c2ccc(CN3CCN(CCCCCCCNc4cccc5c4C(=O)N(C(CCC=O)C(N)=O)C5=O)CC3)cc2)cc(C(=O)NCc2c(C)cc(C)[nH]c2=O)c1C)C1CCOCC1] | N-((4,6-dimethyl-2-oxo-1,2-dihydro-pyridine-3-yl)methyl)-4'-((4-(7-((2-(2,6-dioxo-piperidine-3-yl)-1,3-dioxo-isoindoline-4-yl) amino)heptyl) piperazine-1-yl)methyl)-5-(ethyl(tetra-hydro-2H-pyran-4-yl)amino)-4-methyl-[1,1'-biphenyl]-3-carboxamide | $^1$H NMR (400 MHz, $CDCl_3$) δ 11.04 (br s, 1H), 9.55 (br s, 1H), 7.51-7.41 (m, 3H), 7.35-7.29 (m, 3H), 7.15-7.05 (m, 2H), 6.87 (d, J = 8.5 Hz, 1H), 6.23 (t, J = 5.6 Hz, 1H), 5.91 (s, 1H), 4.89 (dd, J = 11.8, 5.4 Hz, 1H), 4.54 (d, J = 5.9 Hz, 2H), 3.98-3.91 (m, 2H), 3.68-3.49 (m, 3H), 3.36-3.23 (m, 4H), 3.09 (q, J = 6.9 Hz, 2H), 3.04-2.97 (m, 1H), 2.89-2.66 (m, 4H), 2.60-2.46 (m, 8H), 2.43-2.32 (m, 11H), 2.17-2.09 (m, 5H), 2.06-1.98 (m, 2H), 1.75-1.60 (m, 5H), 1.57-1.46 | 9 | (A) 4.7 13100% |

TABLE 1-continued

| | structure | name | $^1$H NMR, MS | Yield (%) | HPLC r.t. (min) Purity |
|---|---|---|---|---|---|
| | | | (m, 2H), 0.93-0.80 (m, 3H); 942 [M + H] $^+$ | | |
| 12 | 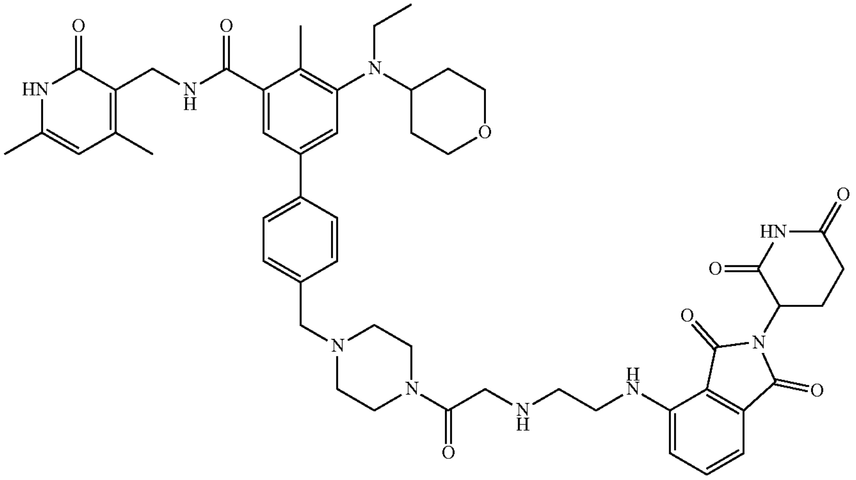 [SMILES: CCN(c1cc(-c2ccc(CN3CCN(C(=O)CNCCNc4cccc5c4C(=O)N(C4CCC(=O)NC4=O)C5=O)CC3)cc2)cc(C(=O)NCc2c(C)cc(C)[nH]c2=O)c1C)C1CCOCC1] | N-((4,6-dimethyl-2-oxo-1,2-dihydro-pyridine-3-yl)methyl)-4'-((4-((2-((2-(2,6-dioxo-piperidine-3-yl)-1,3-dioxo-isoindoline-4-yl)amino) ethyl)glycyl) piperazine-1-yl)methyl)-5-(ethyl(tetra-hydro-2H-pyran-4-yl)amino)-4-methyl-[1,1'-biphenyl]-3-carboxamide | $^1$H NMR (400 MHz, $CDCl_3$) δ 10.66 (br s, 1H), 9.89 (br s, 1H), 7.51-7.44 (m, 3H), 7.33-7.29 (m, 3H), 7.25-7.23 (m, 1H), 7.16 (t, J = 6.1 Hz, 1H), 7.09 (d, J = 7.1 Hz, 1H), 6.90 (d, J = 8.5 Hz, 1H), 6.59 (t, J = 5.4 Hz, 1H), 5.92 (s, 1H), 4.90 (dd, J = 12.0, 5.3 Hz, 1H), 4.59 (dd, J = 14.1, 6.2 Hz, 1H), 4.49 (dd, J = 14.1, 5.8 Hz, 1H), 3.98-3.92 (m, 2H), 3.72-3.59 (m, 3H), 3.57 (s, 2H), 3.47 (s, 2H), 3.43-3.29 (m, 6H), 3.10 (q, J = 7.0 Hz, 2H), | 27 | (A) 4.2 01100% |

TABLE 1-continued

| | structure | name | $^1$H NMR, MS | Yield (%) | HPLC r.t. (min) Purity |
|---|---|---|---|---|---|
| | | | 3.05-2.99 (m, 1H), 2.94 (t, J = 5.8 Hz, 2H), 2.86-2.66 (m, 4H), 2.51-2.46 (m, 2H), 2.44-2.38 (m, 6H), 2.36 (s, 3H), 2.18 (s, 3H), 2.11-2.00 (m, 3H), 0.90 (t, J = 7.0 Hz, 3H): 929 [M + H] $^+$ | | |
| 13 | 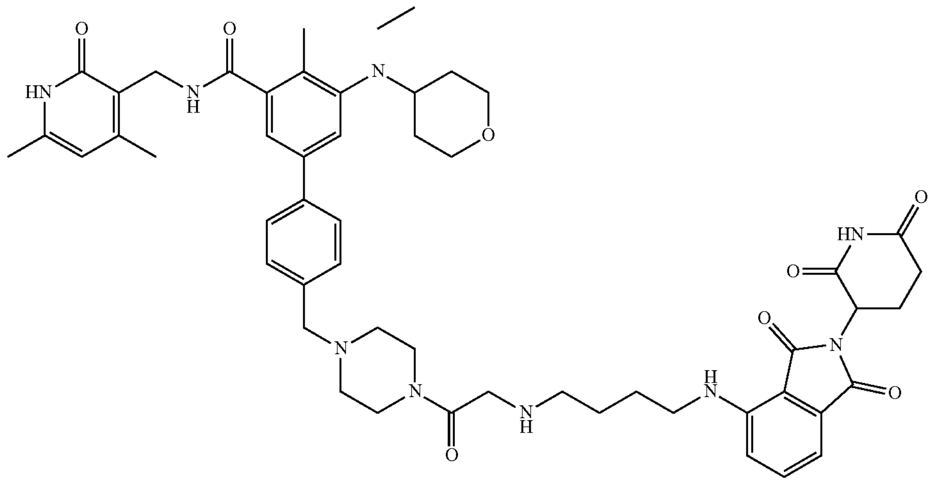 | N-((4,6-dimethyl-2-oxo-1,2-dihydro-pyridine-3-yl)methyl)-4'-((4-((4-((2-(2,6-dioxo-piperidine-3-yl)-1,3-dioxoiso-indoline-4-yl) amino)butyl) glycyl) piperazine-1-yl)methyl)-5-(ethyl(tetra-hydro-2H-pyran-4-yl)amino)-4-methyl-[1,1'- | $^1$H NMR (400 MHz, $CDCl_3$) δ 11.20 (br s, 1H), 9.65 (br s, 1H), 7.50-7.42 (m, 3H), 7.33-7.29 (m, 3H), 7.14 (t, J = 6.0 Hz, 1H), 7.07 (d, J = 7.1 Hz, 1H), 6.88 (d, J = 8.6 Hz, 1H), 6.28 (t, J = 5.6 Hz, 1H), 5.91 (s, 1H), 4.89 (dd, J = 12.0, 5.4 Hz, 1H), 4.54 (d, J = 5.9 Hz, 2H), 3.97-3.91 (m, 2H), 3.69-3.60 | 16 | (A) 4.3 1897% |

TABLE 1-continued

| structure | name | $^1$H NMR, MS | Yield (%) | HPLC r.t. (min) Purity |
|---|---|---|---|---|
| | biphenyl]-3-carboxamide | (m, 3H), 3.58-3.49 (m, 2H), 3.42-3.37 (m, 4H), 3.35-3.26 (m, 5H), 3.09 (q, J = 7.0 Hz, 2H), 3.04-2.96 (m, 1H), 2.88-2.64 (m, 7H), 2.49-2.44 (m, 2H), 2.43-2.38 (m, 6H), 2.34 (s, 3H), 2.16 (s, 3H), 2.12-2.07 (m, 2H), 2.05-1.98 (m, 2H), 1.67-1.58 (m, 2H), 0.89 (t, J = 6.8 Hz, 3H): 957 [M + H] $^+$ | | |

TABLE 1-continued

| | structure | name | $^1H$ NMR, MS | Yield (%) | HPLC r.t. (min) Purity |
|---|---|---|---|---|---|
| 14 | 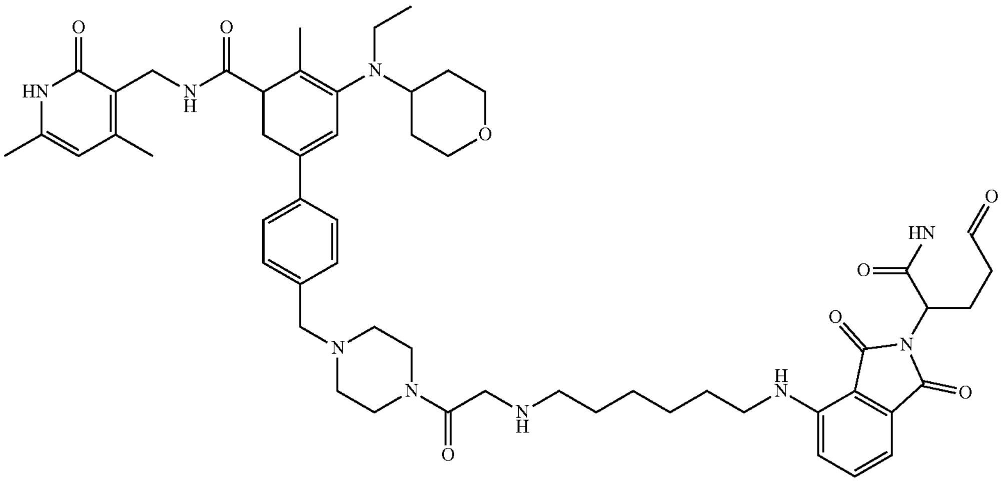 [SMILES: CCN(C1=C(C)C(C(=O)NCc2c(C)cc(C)[nH]c2=O)CC(c2ccc(CN3CCN(C(=O)CNCCCCCCNc4cccc5c4C(=O)N(C(CCC=O)C(N)=O)C5=O)CC3)cc2)=C1)C1CCOCC1] | N-((4,6-dimethyl-2-oxo-1,2-dihydro-pyridine-3-yl)methyl)-4'-((4-((6-((2-(2,6-dioxo-piperidine-3-yl)-1,3-dioxoiso-indoline-4-yl) amino)hexyl) glycyl) piperazine-1-yl)methyl)-5-(ethyl(tetra-hydro-2H-pyran-4-yl)amino)-4-methyl-biphenyl]-3-carboxamide | $^1H$ NMR (400 MHz, $CDCl_3$) δ 11.12 (br s, 1H), 9.21 (br s, 1H), 7.51-7.42 (m, 3H), 7.33-7.28 (m, 3H), 7.11 (t, J = 6.0 Hz, 1H), 7.07 (d, J = 7.1 Hz, 1H), 6.87 (d, J = 8.5 Hz, 1H), 6.22 (t, J = 5.6 Hz, 1H), 5.92 (s, 1H), 4.89 (dd, J = 12.0, 5.3 Hz, 1H), 4.54 (d, J = 6.0 Hz, 2H), 3.97-3.92 (m, 2H), 3.66-3.62 (m, 2H), 3.52 (s, 2H), 3.42-3.38 (m, 4H), 3.36-3.22 (m, 5H), 3.09 (q, J = 7.0 Hz, 2H), 3.05-2.97 (m, 1H), 2.89-2.69 (m, 4H), 2.64-2.58 (m, 2H), 2.48-2.38 (m, 8H), 2.34 (s, 3H), 2.17 | 18 | (A) 4.5 01100% |

TABLE 1-continued

| | structure | name | $^1$H NMR, MS | Yield (%) | HPLC r.t. (min) Purity |
|---|---|---|---|---|---|
| | | | (s, 3H), 2.13-2.08 (m, 2H), 2.05-1.99 (m, 4H), 1.74-1.62 (m, 2H), 1.55-1.49 (m, 2H), 1.45-1.38 (m, 2H), 0.89 (t, J = 6.9 Hz, 3H); 985 [M + H] + | | |
| 15 | 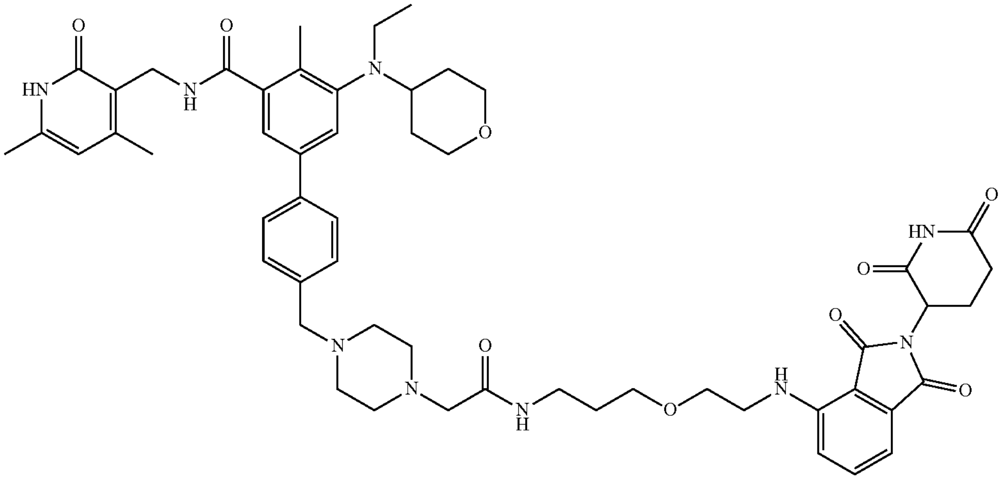 [SMILES: CCN(c1cc(-c2ccc(CN3CCN(CC(=O)NCCCOCCNc4cccc5c4C(=O)N(C4CCC(=O)NC4=O)C5=O)CC3)cc2)cc(C(=O)NCc2c(C)cc(C)[nH]c2=O)c1C)C1CCOCC1] | N-((4,6-dimethyl-2-oxo-1,2-dihydro-pyridine-3-yl)methyl)-4'-((4-(2-((3-(2-((2-(2,6-dioxo-piperidine-3-yl)-1,3-dioxoiso-indoline-4-yl)amino) ethoxy)propyl) amino)-2-oxoethyl) piperazine-1-yl)methyl)-5-(ethyl(tetra-hydro-2H-pyran-4-yl)amino)-4-methyl-[1,1'-biphenyl]-3- | 1H NMR (400MHz, $CDCl_3$) δ 10.76 (br s, 1H), 10.54 (br s, 1H), 7.52 (dd, J = 8.5, 7.2 Hz, 1H), 7.45 (d, J = 8.0 Hz, 2H), 7.40 (t, J = 5.9 Hz, 1H), 7.32-7.27 (m, 2H), 7.12 (d, J = 7.1 Hz, 1H), 6.93 (d, J = 8.5 Hz, 1H), 6.54 (t, J = 5.5 Hz, 1H), 5.93 (s, 1H), 4.89 (dd, J = 12.1, 5.3 Hz, 1H), 4.59-4.47 (m, 2H), 3.95 (d, J = 11.2 Hz, | 8 | (B) 3.4 3293% |

TABLE 1-continued

| structure | name | $^1$H NMR, MS | Yield (%) | HPLC r.t. (min) Purity |
|---|---|---|---|---|
| | carboxamide | 2H), 3.74-3.64 (m, 2H), 3.60-3.53 (m, 2H), 3.53-3.45 (m, 3H), 3.45-3.38 (m, 3H), 3.35-3.28 (m, 2H), 3.09 (q, J = 6.9 Hz, 2H), 3.05-2.95 (m, 3H), 2.88-2.64 (m, 4H), 2.60-2.50 (m, 4H), 2.49-2.40 (m, 5H), 2.36 (s, 3H), 2.23-2.17 (m, 3H), 2.13-2.01 (m, 2H), 1.86-1.78 (m, 2H), 1.74-1.64 (m, 6H), 0.89 (t, J = 6.9 Hz, 3H); 987 [M + H]$^+$ | | |

TABLE 1-continued

| | structure | name | $^1$H NMR, MS | Yield (%) | HPLC r.t. (min) Purity |
|---|---|---|---|---|---|
| 16 | 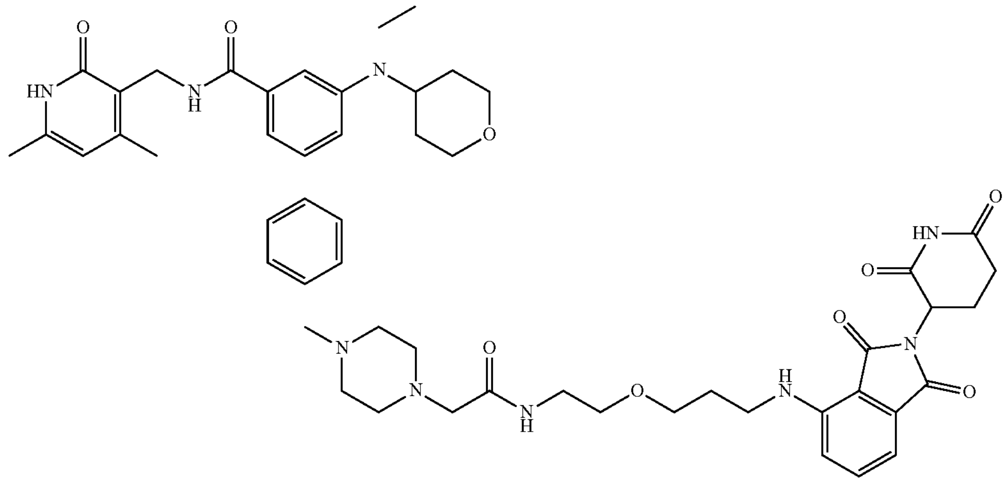 | N-((4,6-dimethyl-2-oxo-1,2-dihydro-pyridine-3-yl)methyl)-4'-((4-(2-((2-(3-((2-(2,6-dioxo-piperidine-3-yl)-1,3-dioxoiso-indoline-4-yl)amino)propoxy)ethyl)amino)-2-oxoethyl)piperazine-1-yl)methyl)-5-(ethyl(tetra-hydro-2H-pyran-4-yl)amino)-4-methyl-[1,1'-biphenyl]-3-carboxamide | $^1$H NMR (400 MHz, $CDCl_3$) δ 10.91 (br s, 1H), 10.65 (br s, 1H), 7.66-7.60 (m, 1H), 7.52 (dd, J = 8.6, 7.1 Hz, 1H), 7.44 (d, J = 8.0 Hz, 2H), 7.36 (t, J = 6.0 Hz, 1H), 7.30-7.27 (m, 2H), 7.22 (d, J = 7.9 Hz, 2H), 7.10 (d, J = 7.1 Hz, 1H), 6.94 (d, J = 8.5 Hz, 1H), 6.61 (t, J = 5.6 Hz, 1H), 5.93 (s, 1H), 4.88 (dd, J = 12.2, 5.4 Hz, 1H), 4.59 (dd, J = 14.2, 6.3 Hz, 1H), 4.48 (dd, J = 14.3, 5.7 Hz, 1H), 3.94 (d, J = 11.3 Hz, 2H), 3.60 (t, J = 5.6 Hz, 2H), 3.57-3.49 (m, 4H), 3.47-3.40 (m, 2H), | 42 | (B) 3.4 5995% |

TABLE 1-continued
| | structure | name | $^1$H NMR, MS | Yield (%) | HPLC r.t. (min) Purity |
|---|---|---|---|---|---|
| | | | 3.37-3.28 (m, 4H), 3.08 (q, J = 6.9 Hz, 2H), 3.04-2.97 (m, 3H), 2.87-2.67 (m, 4H), 2.59-2.50 (m, 4H), (m, 2.46-2.38 5H), 2.37 (s, 3H), 2.21 (s, 3H), 2.12-2.01 (m, 2H), 1.99-1.91 (m, 2H), 0.88 (t, J = 6.9 Hz, 3H); 987 [M + H] + | | |
| 17 | 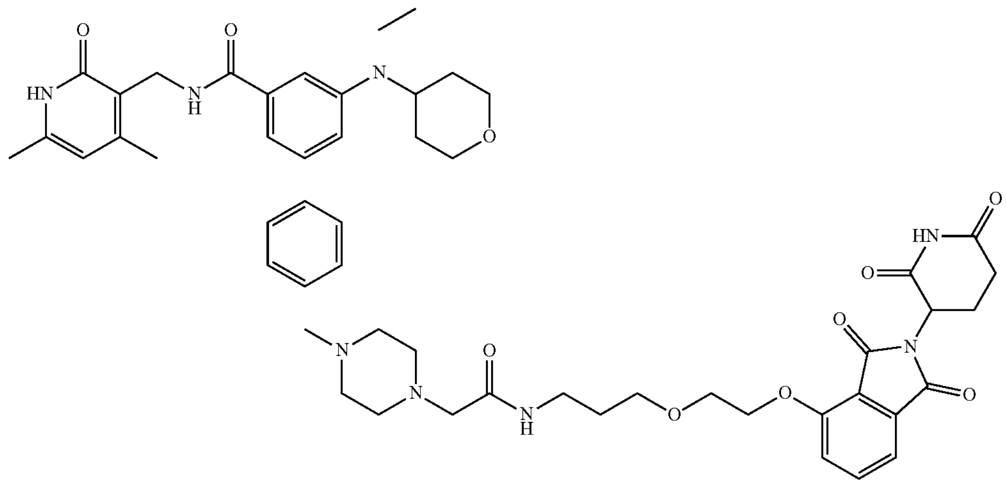 | N-((4,6-dimethyl-2-oxo-1,2-dihydro-pyridine-3-yl)methyl)-4'-((4-(2-((3-(2-((2-(2,6-dioxo-piperidine-3-yl)-1,3-dioxoiso-indoline-4-yl)oxy)ethoxy)propyl)amino)-2-oxoethyl)piperazine-1-yl)methyl)-5-(ethyl(tetra-hydro- | $^1$H NMR (400 MHz, $CDCl_3$) δ 10.61 (br s, 2H), 7.69 (dd, J = 8.4, 7.3 Hz, 1H), 7.47 (t, J = 7.5 Hz, 3H), 7.36 (t, J = 6.0 Hz, 1H), 7.32-7.2 6 (m, 4H), 7.22 (t, J = 6.0 Hz, 1H), 5.93 (s, 1H), 4.92 (dd, J = 12.1, 5.3 Hz, 1H), 4.60-4.4 6 (m, 2H), 4.35 (t, J = | 4 | (B) 3.2 7997% |

TABLE 1-continued

| structure | name | $^1H$ NMR, MS | Yield (%) | HPLC r.t. (min) Purity |
|---|---|---|---|---|
| | 2H-pyran-4-yl)amino)-4-methyl-[1,1'-biphenyl]-3-carboxamide | 4.8 Hz, 2H), 3.98-3.91 (m, 2H), 3.90-3.86 (m, 2H), 3.68-3.62 (m, 2H), 3.54-3.45 (m, 2H), 3.42-3.28 (m, 4H), 3.09 (q, J = 6.8 Hz, 2H), 3.04-2.96 (m, 3H), 2.88-2.63 (m, 4H), 2.63-2.46 (m, 6H), 2.46-2.39 (m, 4H), 2.36 (s, 3H), 2.20 (s, 3H), 2.12-2.01 (m, 2H), 1.85-1.77 (m, 2H), 0.89 (t, J = 7.0 Hz, 3H); 988 [M + H] + | | |

TABLE 1-continued

| | structure | name | $^1H$ NMR, MS | Yield (%) | HPLC r.t. (min) Purity |
|---|---|---|---|---|---|
| 18 | 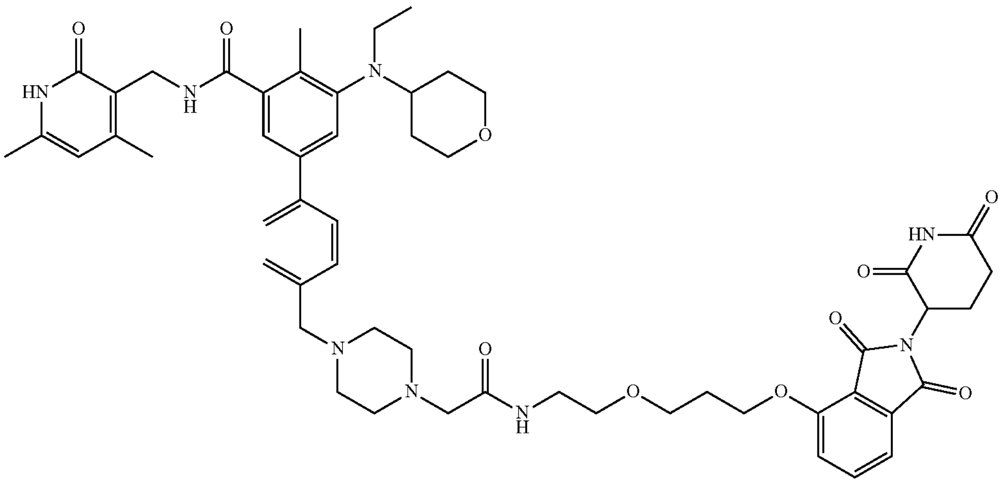 [SMILES: C=C(/C=C\C(=C)c1cc(C(=O)NCc2c(C)cc(C)[nH]c2=O)c(C)c(N(CC)C2CCOCC2)c1)CN1CCN(CC(=O)NCCOCCCOc2cccc3c2C(=O)N(C2CCC(=O)NC2=O)C3=O)CC1] | N-((4,6-dimethyl-2-oxo-1,2-dihydro-pyridine-3-yl)methyl)-4'-((4-(2-((2-(3-((2-(2,6-dioxo-piperidine-3-yl)-1,3-dioxoiso-indoline-4-yl)oxy)propoxy)ethyl)amino)-2-oxoethyl)piperazine-1-yl)methyl)-5-(ethyl(tetra-hydro-2H-pyran-4-yl)amino)-4-methyl-[1,1'-biphenyl]-3-carboxamide | $^1H$ NMR (400 MHz, $CDCl_3$) δ 10.92 (br s, 1H), 10.62 (br s, 1H), 7.69 (dd, J = 8.5, 7.3 Hz, 1H), 7.55 (t, J = 5.7 Hz, 1H), 7.49-7.44 (m, 3H), 7.33 (t, J = 6.1 Hz, 1H), 7.31-7.25 (m, 4H), 5.94 (s, 1H), 4.93 (dd, J = 12.4, 5.4 Hz, 1H), 4.60 (dd, J = 14.2, 6.3 Hz, 1H), 4.47 (dd, J = 14.2, 5.7 Hz, 1H), 4.31 (t, J = 6.6 Hz, 2H), 4.06-3.99 (m, 1H), 3.98-3.92 (m, 2H), 3.71-3.63 (m, 2H), 3.56-3.52 (m, 2H), 3.50-3.45 (m, 2H), 3.40 (s, 2H), 3.36- | 7 | (B) 3.2 6997% |

TABLE 1-continued
| | structure | name | $^1$H NMR, MS | Yield (%) | HPLC r.t. (min) Purity |
|---|---|---|---|---|---|
| | | | 3.28 (m, 2H), 3.08 (q, J = 6.9 Hz, 2H), 3.04-2.97 (m, 3H), 2.87-2.65 (m, 4H), 2.58-2.50 (m, 4H), 2.49-2.39 (m, 6H), 2.36 (s, 3H), 2.21 (s, 3H), 2.19-2.13 (m, 2H), 2.11-2.04 (m, 1H), 1.74-1.67 (m, 4H), 0.88 (t, J = 6.9 Hz, 3H); 988 [M + H] $^+$ | | |
| 19 | 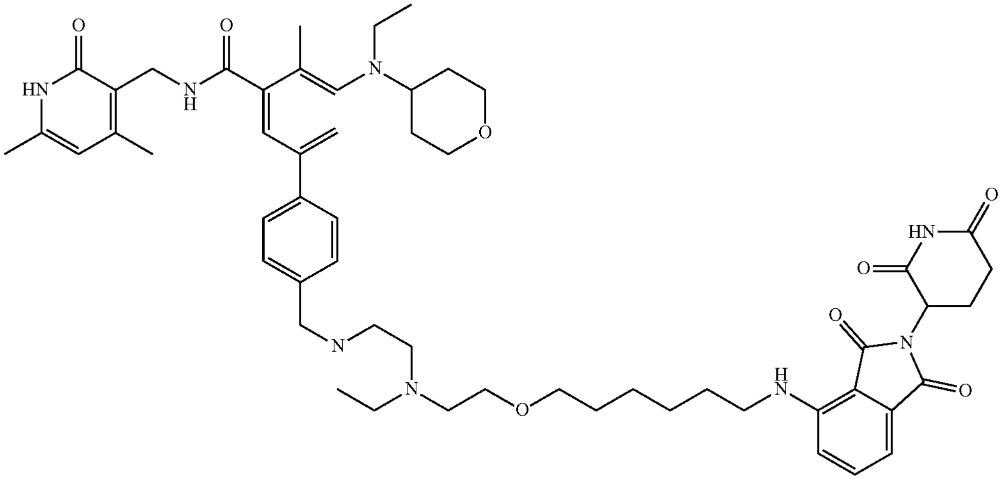 [SMILES: C=C(/C=C(C(=O)NCc1c(C)cc(C)[nH]c1=O)\C(C)=C\N(CC)C1CCOCC1)c1ccc(CNCCN(CC)CCOCCCCCCNc2cccc3c2C(=O)N(C2CCC(=O)NC2=O)C3=O)cc1] | N-((4,6-dimethyl-2-oxo-1,2-dihydro-pyridine-3-yl)methyl)-4'-((4-(2-((6-((2-(2,6-dioxo-piperidine-3-yl)-1,3-dioxoiso-indoline-4-yl)amino) hexyl)oxy) ethyl) piperazine-1-yl)methyl)-5-(ethyl(tetra-hydro- | $^1$H NMR (400 MHz, $CDCl_3$) δ 11.73 (br-s, 1H), 9.87 (s, 1H), 7.49-7.42 (m, 3H), 7.30 (d, J = 7.8 Hz, 3H), 7.16 (t, J = 5.76 Hz, 1H), 7.06 (d, J = 7.08 Hz, 1H), 6.86 (d, J = 8.52 Hz, 1H), 6.21 (t, J = 5.36 Hz, 1H), | 17 | (A) 4.7 7896% |

TABLE 1-continued

| structure | name | $^1$H NMR, MS | Yield (%) | HPLC r.t. (min) Purity |
|---|---|---|---|---|
| | 2H-pyran-4-yl)amino)-4-methyl-[1,1'-biphenyl]-3-carboxamide | 5.89 (s, 1H), 4.88 (dd, J = 12.06, 5.32 Hz, 1H), 4.54 (d, J = 5.84 Hz, 2H), 3.93 (d, J = 11.24 Hz, 2H), 3.56-3.51 (m, 4H), 3.41 (t, J = 6.44 Hz, 2H), 3.33-3.22 (m, 4H), 3.08 (q, J = 6.96 Hz, 2H), 3.02-2.97 (m, 1H), 2.86-2.69 (m, 3H), 2.61-2.52 (m, 8H), 2.39 (s, 3H), 2.32 (s, 3H), 2.12 (s, 3H), 2.10-2.01 (m, 2H), 1.69-1.55 (m, 9H), 1.40-1.35 (m, 4H), 0.87 (t, J = 6.88 Hz, 3H); LCMS $[M + H]^+$ 972. | | |

TABLE 1-continued

| | structure | name | $^1$H NMR, MS | Yield (%) | HPLC r.t. (min) Purity |
|---|---|---|---|---|---|
| 20 | 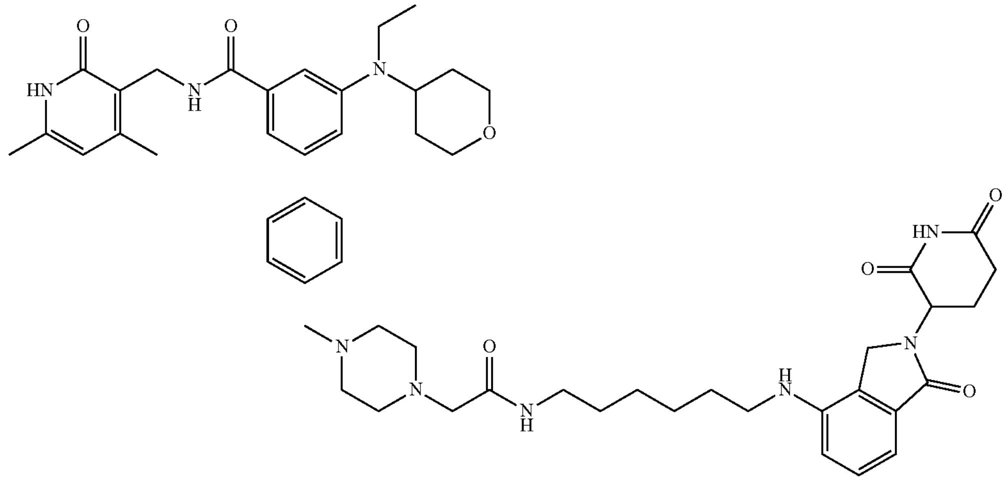 | N-((4,6-dimethyl-2-oxo-1,2-dihydro-pyridine-3-yl)methyl)-4'-((4-(2-((6-((2-(2,6-dioxo-piperidine-3-yl)-1-oxoiso-indoline-4-yl)amino) hexyl)amino)-2-oxoethyl) piperazine-1-yl)methyl)-5-(ethyl(tetra-hydro-2H-pyran-4-yl)amino)-4-methyl[1,1'-biphenyl]-3-carboxamide | 1H NMR (400 MHz, $CDCl_3$) δ 11.23 (s, 1H), 10.09 (s, 1H), 7.45 (d, J = 8.08 Hz, 2H), 7.35-7.22 (m, 5H), 7.20-7.13 (m, 2H), 6.76 (d, J = 7.96 Hz, 1H), 5.92 (s, 1H), 5.21 (dd, J = 13.24, 5.16 Hz, 1H), 4.60-4.47 (m, 2H), 4.29 (d, J = 15.56 Hz, 1H), 4.10 (d, J = 15.16 Hz, 1H), 3.94 (d, J = 11.24 Hz, 2H), 3.62 (br-s, 1H), 3.56-3.45 (m, 2H), 3.34-3.22 (m, 4H), 3.18 (br-s, 2H), 3.08 (q, J = 7.0 Hz, 2H), 3.04-2.97 (m, 3H), 2.81-2.77 (m, 2H), 2.53-2.47 | 13 | (A) 4.4 8995% |

TABLE 1-continued
| | structure | name | $^1$H NMR, MS | Yield (%) | HPLC r.t. (min) Purity |
|---|---|---|---|---|---|
| | | | (m, 5H), 2.41 (s, 3H), 2.33 (s, 3H), 2.28-2.23 (m, 1H), 2.16 (s, 3H), 2.14-2.13 (m, 1H), 1.77-1.59 (m, 8H), 1.56-1.47 (m, 2H), 1.45-1.39 (m, 2H), 1.38-1.34 (m, 2H), 0.88 (t, J = 6.92 Hz, 3H); LCMS $[M + H]^+$ 971. | | |
| 21 | 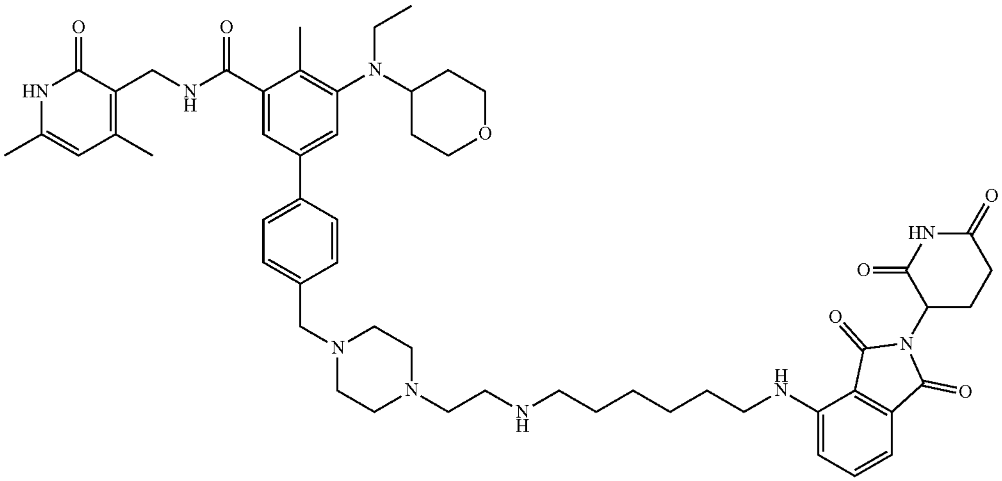 [SMILES: CCN(c1cc(-c2ccc(CN3CCN(CCNCCCCCCNc4cccc5c4C(=O)N(C4CCC(=O)NC4=O)C5=O)CC3)cc2)cc(C(=O)NCc2c(C)cc(C)[nH]c2=O)c1C)C1CCOCC1] | N-((4,6-dimethyl-2-oxo-1,2-dihydro-pyridine-3-yl)methyl)-4'-((4-(2-((6-((2-(2,6-dioxo-piperidine-3-yl)-1,3-dioxoiso-indoline-4-yl)amino)hexyl)amino)ethyl)piperazine-1-yl)methyl)-5-(ethyl(tetra-hydro-2H-pyran- | $^1$H NMR (400 MHz, $CDCl_3$) δ 7.50-7.41 (m, 3H), 7.32-7.28 (m, 3H), 7.16 (t, J = 5.9 Hz, 1H), 7.07 (d, J = 7.1 Hz, 1H), 6.86 (d, J = 8.6 Hz, 1H), 6.22 (t, J = 5.6 Hz, 1H), 5.90 (s, 1H), 4.91-4.85 (m, 1H), 4.59-4.49 (m, 2H), 3.97-3.91 (m, 2H), 3.50 | 11 | (B) 3.4 3293% |

TABLE 1-continued

| structure | name | $^1H$ NMR, MS | Yield (%) | HPLC r.t. (min) Purity |
|---|---|---|---|---|
| | 4-yl)amino)-4-methyl-[1,1'-biphenyl]-3-carboxamide | (s, 2H), 3.34-3.23 (m, 4H), 3.08 (q, J = 7.0 Hz, 2H), 3.02-2.96 (m, 1H), 2.87-2.67 (m, 6H), 2.64-2.60 (m, 2H), 2.55-2.44 (m, 7H), 2.39 (s, 4H), 2.33 (s, 3H), 2.15-2.08 (m, 4H), 2.04-1.98 (m, 1H), 1.73-1.61 (m, 7H), 1.55-1.48 (m, 2H), 1.45-1.34 (m, 4H), 0.88 (t, J = 6.9 Hz, 3H); 971 $[M + H]^+$ | | |

TABLE 1-continued
| | structure | name | $^1H$ NMR, MS | Yield (%) | HPLC r.t. (min) Purity |
|---|---|---|---|---|---|
| 22 | 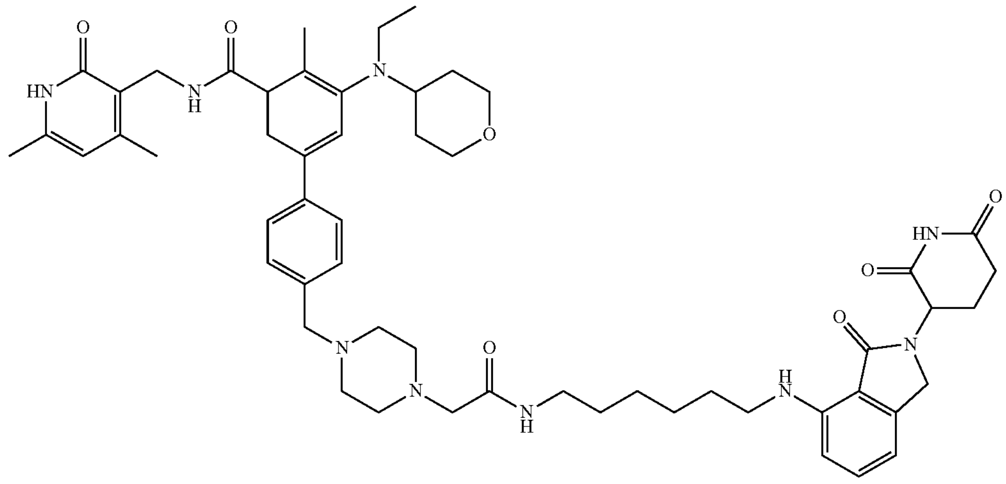 [SMILES: CCN(C1=C(C)C(C(=O)NCc2c(C)cc(C)[nH]c2=O)CC(c2ccc(CN3CCN(CC(=O)NCCCCCCNc4cccc5c4C(=O)N(C4CCC(=O)NC4=O)C5)CC3)cc2)=C1)C1CCOCC1] | N-((4,6-dimethyl-2-oxo-1,2-dihydro-pyridine-3-yl)methyl)-4'-((4-(2-((6-((2-(2,6-dioxo-piperidine-3-yl)-3-oxoiso-indoline-4-yl)amino) hexyl)amino)-2-oxoethyl) piperazine-1-yl)methyl)-5-(ethyl(tetra-hydro-2H-pyran-4-yl)amino)-4-methyl-[1,1'-biphenyl]-3-carboxamide | $^1H$ NMR (400 MHz, $CDC1_3$) δ 10.79 (br s, 1H), 10.15 (br s, 1H), 7.48-7.42 (m, 2H), 7.35-7.28 (m, 4H), 7.25-7.13 (m, 4H), 6.62-6.50 (m, 3H), 5.92 (s, 1H), 5.08 (dd, J = 13.4, 5.1 Hz, 1H), 4.57-4.50 (m, 2H), 4.41-4.32 (m, 1H), 4.26-4.16 (m, 1H), 3.98-3.90 (m, 2H), 3.55-3.43 (m, 2H), 3.36-3.18 (m, 6H), 3.09 (q, J = 6.6 Hz, 2H), 3.03-2.95 (m, 3H), 2.90-2.71 (m, 3H), 2.58-2.45 (m, 6H), 2.44-2.39 (m, 3H), 2.36-2.33 (m, 3H), 2.21-2.16 (m, 3H), 1.57-1.34 (m, 7H), | 9 | (B) 3.6 3998% |

TABLE 1-continued

| | structure | name | $^1$H NMR, MS | Yield (%) | HPLC r.t. (min) Purity |
|---|---|---|---|---|---|
| | | | 0.89 (t, J = 6.5 Hz, 3 H); 971 [M + H] + | | |
| 23 | 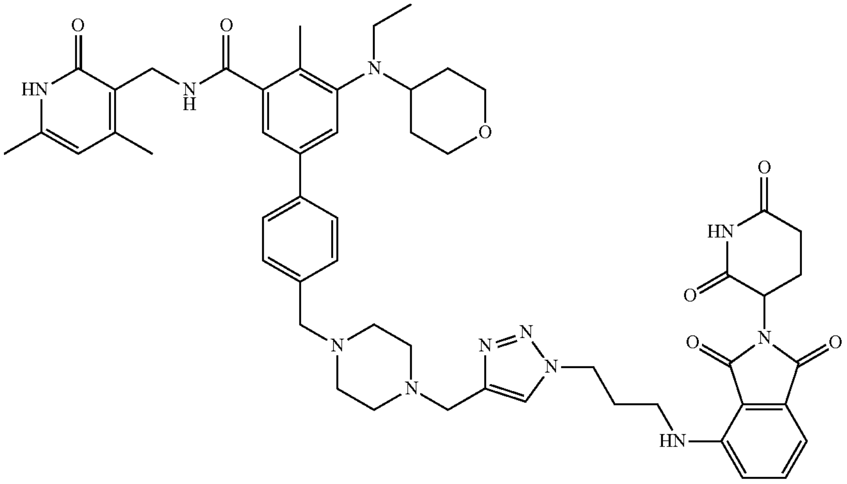 [SMILES: CCN(c1cc(-c2ccc(CN3CCN(Cc4cn(CCCNc5cccc6c5C(=O)N(C5CCC(=O)NC5=O)C6=O)nn4)CC3)cc2)cc(C(=O)NCc2c(C)cc(C)[nH]c2=O)c1C)C1CCOCC1] | N-((4,6-dimethyl-2-oxo-1,2-dihydro-pyridine-3-yl)methyl)-4'-((4-((1-(3-((2-(2,6-dioxo-piperidine-3-yl)-1,3-dioxoiso-indoline-4-yl)amino) propyl)-1H-1,2,3-triazole-4-yl)methyl) piperazine-1-yl)methyl)-5-(ethyl(tetra-hydro-2H-pyran-4-yl)amino)-4-methyl-[1,1'-biphenyl]-3-carboxamide | $^1$H NMR (400 MHz, $CDCl_3$) δ 11.31 (br-s, 1H), 9.93 (br-s, 1H), 7.50-7.41 (m, 4H), 7.30-7.23 (m, 4H), 7.11-1.05 (m, 2 H), 6.82 (d, J = 8.52 Hz, 1H), 6.26 (t, J = 5.8 Hz, 1H), 5.90 (s, 1H), 4.88 (dd, J = 12.14, 5.28 Hz, 1H), 4.60-4.49 (m, 2H), 4.46 (t, J = 6.84 Hz, 2H), 3.93 (d, J = 11.24 Hz, 2H), 3.71 (s, 2H), 3.52 (s, 2H), 3.33-3.28 (m, 4H), 3.08 (q, J = 7.0 Hz, 2H), 3.03-2.96 (m, 1H), | 23 | (A) 4.4 4896% |

TABLE 1-continued
| | structure | name | $^1H$ NMR, MS | Yield (%) | HPLC r.t. (min) Purity |
|---|---|---|---|---|---|
| | | | 2.87-2.66 (m, 3H), 2.53 (br-s, 6H), 2.40 (s, 3H), 2.38 (s, 3H), 2.32-2.24 (m, 2H), 2.14 (s, 3H), 2.12-2.08 (m, 1H), 1.69-1.64 (m, 4H), 1.27-1.23 (m, 2H), 0.88 (t, J = 6.88 Hz, 3H); LCMS $[M + H]^+$ 966. | | |
| 24 | 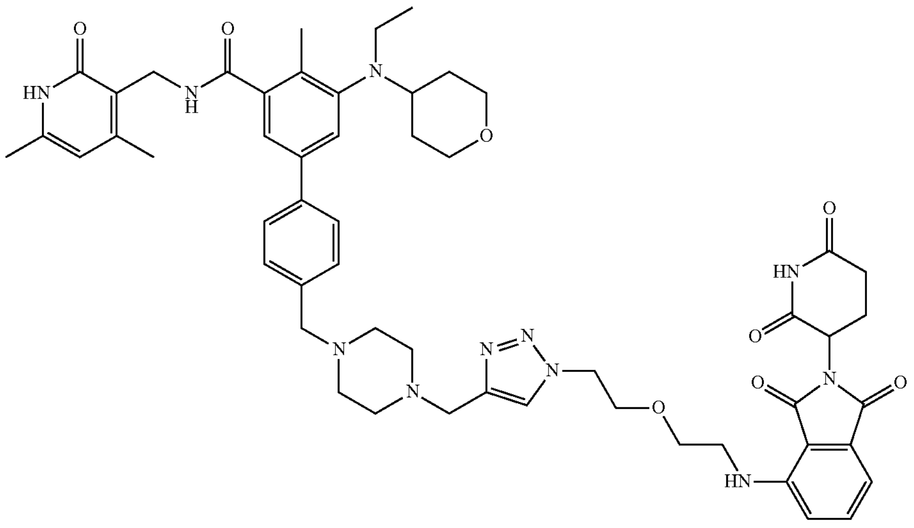 [SMILES: CCN(c1cc(-c2ccc(CN3CCN(Cc4cn(CCOCCNc5cccc6c5C(=O)N(C5CCC(=O)NC5=O)C6=O)nn4)CC3)cc2)cc(C(=O)NCc2c(C)cc(C)[nH]c2=O)c1C)C1CCOCC1] | N-((4,6-dimethyl-2-oxo-1,2-dihydro-pyridine-3-yl)methyl)-4'-((4-((1-(2-(2-((2-(2,6-dioxo-piperidine-3-yl)-1,3-dioxoiso-indoline-4-yl)amino) ethoxy)ethyl)-1H-1,2,3-triazole-4-yl)methyl) piperazine-1-yl)methyl)- | $^1H$ NMR (400 MHz, $CDCl_3$) δ 11.46 (br-s, 1H), 11.01 (br-s, 1H), 7.72 (s, 1H), 7.49 (t, J = 7.52 Hz, 1H), 7.42 (d, J = 8.12 Hz, 2H), 7.30-7.25 (m, 3H), 7.18 (t, J = 5.84 Hz, 1H), 7.12 (d, J = 7.08 Hz, 1H), 6.87 (d, J = 8.52 Hz, | 34 | (A) 4.4 8996% |

TABLE 1-continued

| structure | name | $^1$H NMR, MS | Yield (%) | HPLC r.t. (min) Purity |
|---|---|---|---|---|
| | 5-(ethyl(tetra-hydro-2H-pyran-4-yl)amino)-4-methyl-[1,1'-biphenyl]-3-carboxamide | 1H), 6.58 (t, J = 5.28 Hz, 1H), 5.89 (s, 1H), 4.89 (q, J = 5.8 Hz, 1H), 4.64-4.52 (m, 4H), 3.93 (d, J = 11.44 Hz, 2H), 3.89-3.86 (m, 2H), 3.76-3.58 (m, 4H), 3.50 (s, 2H), 3.41-3.38 (m, 2H), 3.33-3.31 (m, 2H), 3.01 (q, J = 5.56 Hz, 2H), 2.98-2.97 (m, 1H), 2.86-2.72 (m, 3H), 2.39 (s, 3H), 2.34 (s, 3H), 2.15-2.12 (m, 4H), 1.69-1.64 (m, 4H), 0.87 (t, J = 7.36 Hz, 3H); LCMS $[M + H]^+$ 996. | | |

TABLE 1-continued

| | structure | name | $^1H$ NMR, MS | Yield (%) | HPLC r.t. (min) Purity |
|---|---|---|---|---|---|
| 25 | 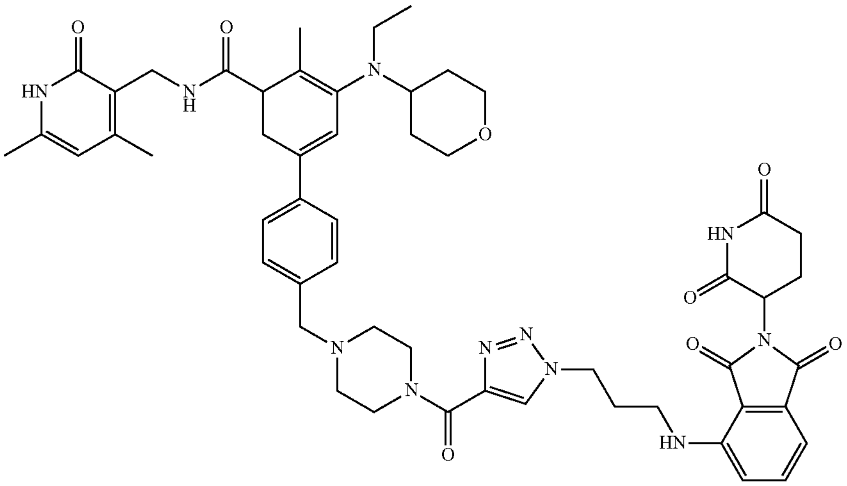 [SMILES: CCN(C1=C(C)C(C(=O)NCc2c(C)cc(C)[nH]c2=O)CC(c2ccc(CN3CCN(C(=O)c4cn(CCCNc5cccc6c5C(=O)N(C5CCC(=O)NC5=O)C6=O)nn4)CC3)cc2)=C1)C1CCOCC1] | N-((4,6-dimethyl-2-oxo-1,2-dihydro-pyridine-3-yl)methyl)-4'-((4-(1-(3-((2-(2,6-dioxo-piperidine-3-yl)-1,3-dioxoiso-indoline-4-yl)amino)propyl)-1H-1,2,3-triazol-4-carbonyl)piperazine-1-yl)methyl)-5-(ethyl(tetra-hydro-2H-pyran-4-yl)amino)-4-methyl-[1,1'-biphenyl]-3-carboxamide | $^1H$ NMR (400 MHz, $CDCl_3$) δ 11.66 (s, 1H), 9.36 (s, 1H), 8.76 (s, 1H), 8.18 (s, 1H), 7.47-7.39 (m, 3H), 7.32 (d, J = 8.16 Hz, 3H), 7.13 (t, J = 5.8 Hz, 1H), 7.08 (d, J = 7.12 Hz, 1H), 6.78 (d, J = 8.56 Hz, 1H), 6.40 (t, J = 5.08 Hz, 1H), 5.90 (s, 1H), 4.93-4.89 (m, 1H), 4.54 (d, J = 5.92 Hz, 2H), 4.51-4.46 (m, 2H), 4.28 (br-s, 2H), 3.93 (d, J = 11.24 Hz, 2H), 3.79 (br-s, 2H), 3.56 (s, 2H), 3.33-3.28 (m, 4H), 3.10 (q, J = | 37 | (A) 4.5 3297% |

TABLE 1-continued

| structure | name | $^1H$ NMR, MS | Yield (%) | HPLC r.t. (min) Purity |
|---|---|---|---|---|
| | | 6.8 Hz, 2H), 3.00-2.97 (m, 1H), 2.92-2.70 (m, 4H), 2.54-2.49 (m, 3H), 2.39 (s, 3H), 2.33 (s, 3H), 2.28-2.22 (m, 2H), 2.16-2.04 (m, 4H), 1.70-1.64 (m, 4H), 0.88 (t, J = 6.92 Hz, 3H); LCMS $[M + H]^+$ 980. | | |

TABLE 1-continued

| | structure | name | $^1H$ NMR, MS | Yield (%) | HPLC r.t. (min) Purity |
|---|---|---|---|---|---|
| 26 | 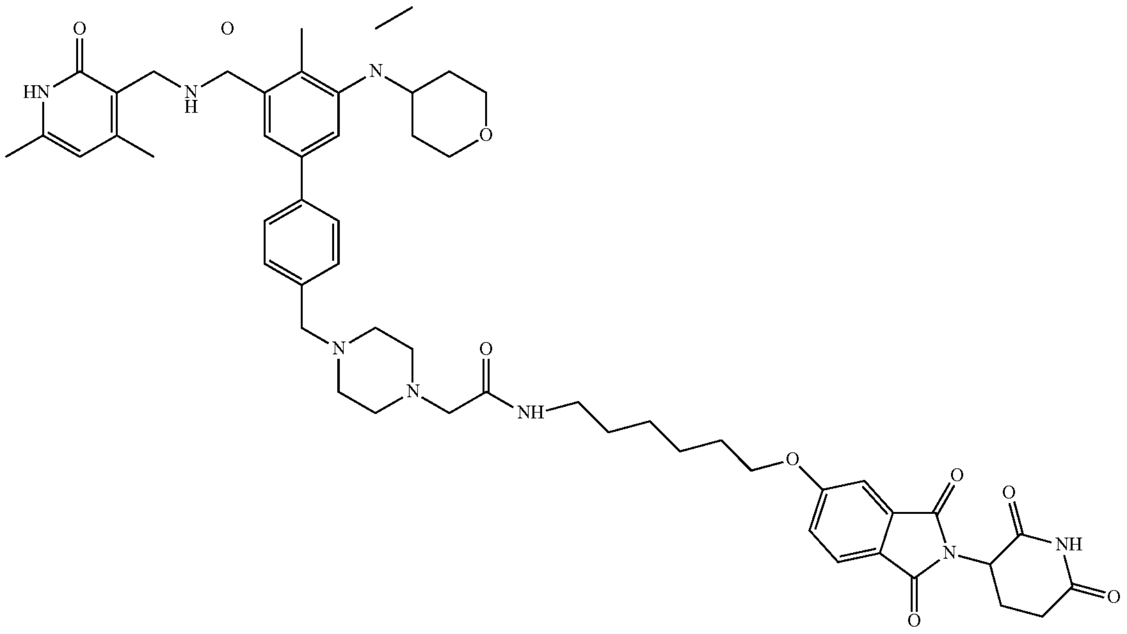 | N-((4,6-dimethyl-2-oxo-1,2-dihydro-pyridine-3-yl)methyl)-4'-((4-(2-((6-((2-(2,6-dioxo-piperidine-3-yl)-1,3-dioxoiso-indoline-5-yl)oxy)hexyl) amino)-2-oxoethyl) piperazine-1-yl)methyl)-5-(ethyl(tetra-hydro-2H-pyran-4-yl)amino)-4-methyl-[1,1'-biphenyl]-3-carboxamide | $^1H$ NMR (400 MHz, $CDCl_3$) δ 10.76 (br s, 1H), 9.51 (br s, 1H), 7.58 (d, J = 8.3 Hz, 1H), 7.45 (d, J = 8.1 Hz, 2H), 7.33-7.2 9 (m, 3H), 7.21 (t, J = 6.1 Hz, 1H), 7.13 (t, J = 6.0 Hz, 1H), 6.94 (d, J = 2.1 Hz, 1H), 6.73 (dd, J = 8.3, 2.2 Hz, 1H), 5.91 (s, 1H), 4.90 (dd, J = 12.1, 5.4 Hz, 1H), 4.78 (t, J = 5.5 Hz, 1H), 4.61-4.49 (m, 2H), 3.98-3.92 (m, 2H), 3.53-3.45 (m, 3H), 3.36-3.26 (m, 4H), 3.24-3.18 (m, 2H), 3.09 (q, J = 6.9 Hz, 2H), 3.04-2.95 (m, 3H), 2.88-2.65 (m, 4H), 2.59-2.43 (m, 7H), 2.41 (s, 3H), 2.33 | 56 | (B) 3.4 6599% |

TABLE 1-continued
| | structure | name | $^1$H NMR, MS | Yield (%) | HPLC r.t. (min) Purity |
|---|---|---|---|---|---|
| | | | (s, 3H), 2.18 (s, 3H), 2.12-2.05 (m, 1H), 1.74-1.66 (m, 4H), 1.57-1.50 (m, 2H), 1.47-1.33 (m, 4H), 0.88 (t, J = 7.0 Hz, 3H); 985 [M + H] + | | |
| 27 | 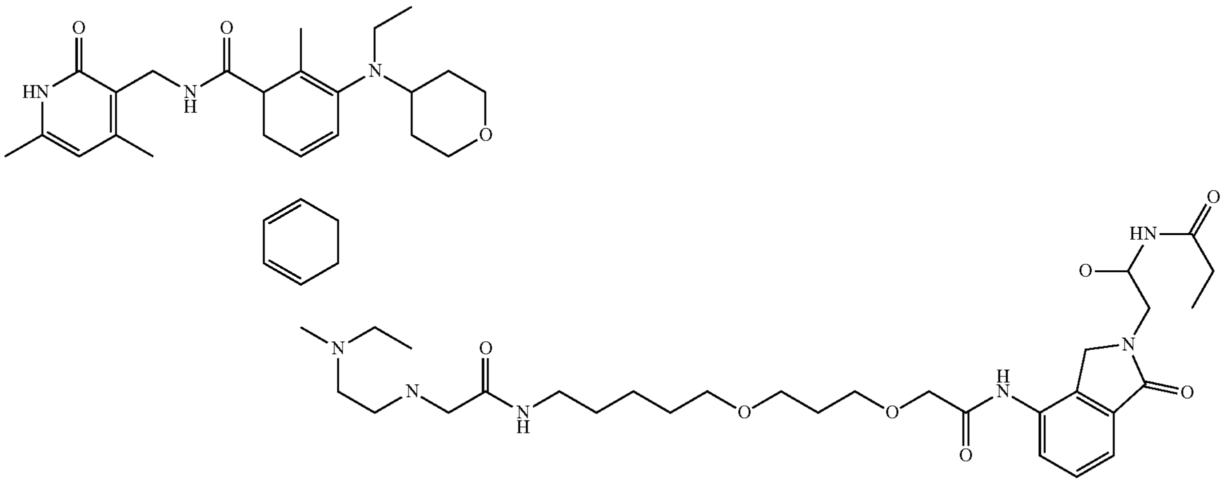 | N-((4,6-dimethyl-2-oxo-1,2-dihydro-pyridine-3-yl)methyl)-4'-((4-(2-((5-(3-(2-((2-(2,6-dioxo-piperidine-3-yl)-1-oxoiso-indoline-4-yl)amino)-2-oxoethoxy) propoxy) pentyl) amino)-2-oxoethyl) piperazine-1-yl) methyl)-5 (ethyl(tetra-hydro-2H-pyran-4- | $^1$H NMR (400 MHz, $CDCl_3$) δ 10.69 (br s, 1H), 9.88 (br s, 1H), 8.63 (s, 1H), 7.75 (d, J = 7.5 Hz, 1H), 7.67 (d, J = 7.9 Hz, 1H), 7.52-7.44 (m, 3H), 7.34-7.28 (m, 3H), 7.16 (t, J = 6.1 Hz, 1H), 7.10 (t, J = 6.0 Hz, 1H), 5.92 (s, 1H), 5.22 (dd, J = 13.3, 5.1 Hz, 1H), 4.61-4.47 (m, 2H), 4.43 (s, 2H), 4.10 (s, 2H), | 27 | (B) 3.2 3298 |

TABLE 1-continued

| structure | name | $^1H$ NMR, MS | Yield (%) | HPLC r.t. (min) Purity |
|---|---|---|---|---|
| | yl)amino)-4-methyl-[1,1'-biphenyl]-3-carboxamide | 4.07-3.98 (m, 1H), 3.97-3.91 (m, 2H), 3.71 (t, J = 6.1 Hz, 2H), 3.58-3.53 (m, 3H), 3.39 (t, J = 6.5 Hz, 2H), 3.35-3.28 (m, 2H), 3.22 (q, J = 6.9 Hz, 2H), 3.09 (q, J = 7.0 Hz, 2H), 3.04-2.96 (m, 3H), 2.90-2.75 (m, 2H) 2.57-2.46 (m, 6H), 2.41 (s, 3H), 2.37-2.28 (m, 4H), 2.23-2.15 (m, 4H), 1.95-1.88 (m, 2H), 1.74-1.67 (m, 4H), 1.53-1.41 (m, 4H), 1.34-1.24 (m, 5H), 0.89 (t, J = 7.0 Hz, 3H); 1073 [M + H] $^+$ | | |

TABLE 1-continued

| | structure | name | $^1$H NMR, MS | Yield (%) | HPLC r.t. (min) Purity |
|---|---|---|---|---|---|
| 28 | 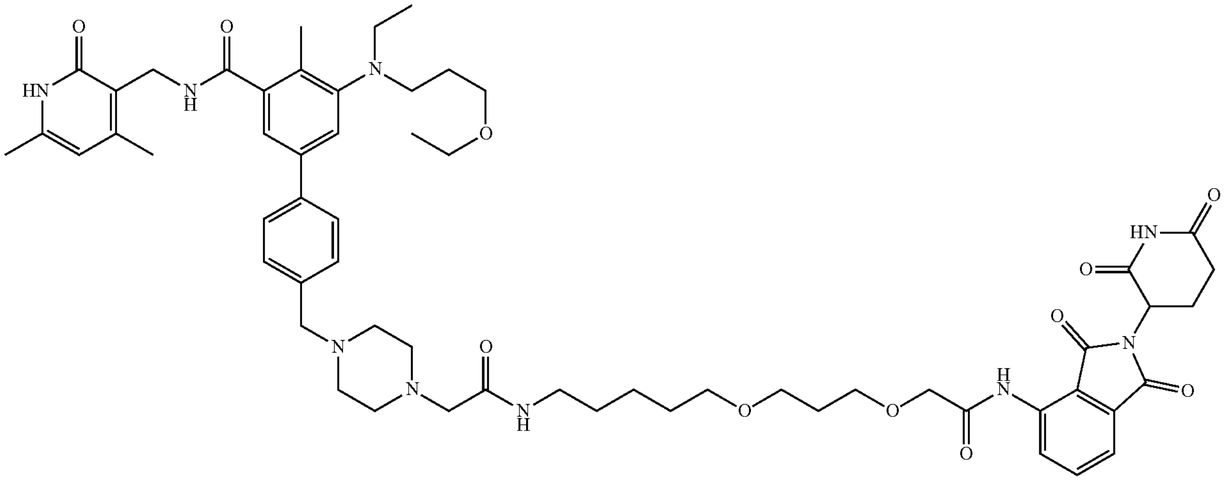 [SMILES: CCOCCCN(CC)c1cc(-c2ccc(CN3CCN(CC(=O)NCCCCCOCCCOCC(=O)Nc4cccc5c4C(=O)N(C4CCC(=O)NC4=O)C5=O)CC3)cc2)cc(C(=O)NCc2c(C)cc(C)[nH]c2=O)c1C] | N-((4,6-dimethyl-2-oxo-1,2-dihydro-pyridine-3-yl)methyl)-4'-((4-(2-((5-(3-(2-((2-(2,6-dioxo-piperidine-3-yl)-1,3-dioxoiso-indoline-4-yl)amino)-2-oxoethoxy) propoxy) pentyl) amino)-2-oxoethyl) piperazine-1-yl)methyl)-5-(ethyl(tetra-hydro-2H-pyran-4-yl)amino)-4-methyl-[1,1'-biphenyl]-3-carboxamide | $^1$H NMR (400 MHz, $CDCl_3$) δ 10.46 (s, 1H), 10.20 (br s, 1H), 10.08 (br s, 1H), 8.87 (d, J = 8.3 Hz, 1H), 7.74-7.69 (m, 1H), 7.56 (d, J = 7.3 Hz, 1H) 7.46? (d, J = 8.0 Hz, 2 H), 7.37-7.29 (m, 3H), 7.20 (t, J = 6.0 Hz, 1H) 7.09 (t, J = 6.0 Hz, 1H) 5.92 (s, 1H), 4.92 (dd, J = 12.4, 5.4 Hz, 1H), 4.54 (d, J = 6.0 Hz, 2H), 4.12 (s, 2H), 3.98-3.91 (m, 2H), 3.71 (t, J = 6.3 Hz, 2H), 3.60 (t, J = 6.3 Hz, 2H), 3.55 (s, 2H , 3.42 (t, J = 6.4 Hz, 2 H), 3.36-3.24 (m, 4H), 3.09 (q, J = 6.9 Hz, 2H), 3.04-2.6 (m, 3H), 2.90-2.68 | 28 | (B) 3.6 4299% |

TABLE 1-continued
| | structure | name | $^{1}$H NMR, MS | Yield (%) | HPLC r.t. (min) Purity |
|---|---|---|---|---|---|
| | | | (m, 4H), 2.59-2.46 (m, 7 H), 2.42 (s, 3H), 2.34 (s, 3H), 2.20 (s, 3H), 2.15-2.08 (m, 1H), 2.02-1.95 (m, 2H), 1.74-1.65 (m, 4H), 1.56-1.47 (m, 4 H), 1.41-1.29 (m, 3H), 0.89 (t, J = 6 Hz, 3 H); 1087 [M + H] + | | |
| 29 | 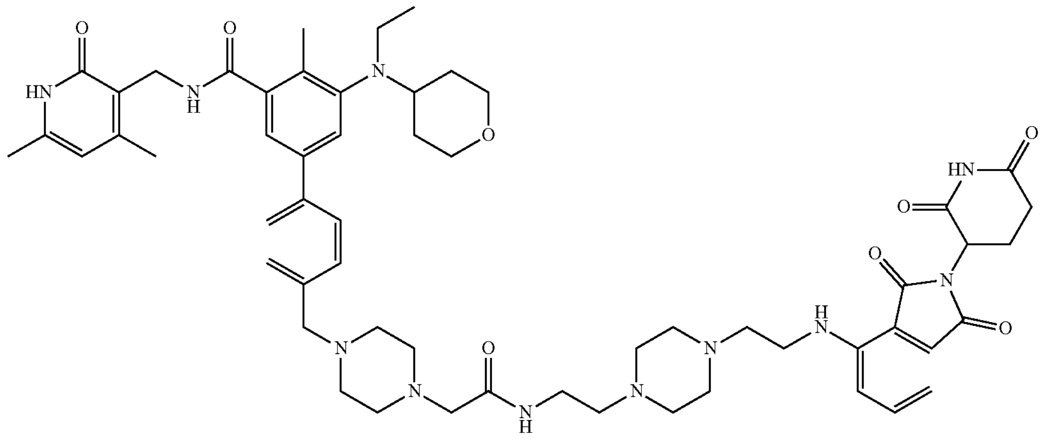 [SMILES: C=C/C=C(/NCCN1CCN(CCNC(=O)CN2CCN(CC(=C)/C=C\C(=C)c3cc(C(=O)NCc4c(C)cc(C)[nH]c4=O)c(C)c(N(CC)C4CCOCC4)c3)CC2)CC1)C1=CC(=O)N(C2CCC(=O)NC2=O)C1=O] | N-((4,6-dimethyl-2-oxo-1,2-dihydro-pyridine-3-yl)methyl)-4'-((4-(2-((2-(4-(2-((2-(2,6-dioxo-piperidine-3-yl)-1,3-dioxoiso-indoline-4-yl)amino) ethyl) piperazine-1-yl)ethyl) amino)-2-oxoethyl) piperazine-1-yl)methyl)-5- | $^{1}$H NMR (400 MHz, $CDCl_3$) δ 10.73 (br s, 1H), 10.50 (br s, 1H), 10.03 (br s, 1H), 7.59 (t, J = 5.2 Hz, 1H), 7.46-7.43 (m, 2H), 7.35-7.31 (m, 3H), 7.25-7.23 (m, 1H), 7.11-7.09 (m, 1H), 6.88 (d, J = 8.5 Hz, 1H), 6.65-6.61 (m, 1H), 5.92 (s, 1H), 4.89 (dd, J = | 27 | (A) 3.0 8296 |

TABLE 1-continued

| structure | name | $^1$H NMR, MS | Yield (%) | HPLC r.t. (min) Purity |
| --- | --- | --- | --- | --- |
| | (ethyl(tetra-hydro-2H-pyran-4-yl)amino)-4-methyl-[1,1'-biphenyl]-3-carboxamide | 12.3, 5.3 Hz, 1H), 4.54 (d, J = 6.0 Hz, 2H), 3.96-3.92 (m, 2H), 3.82 (t, J = 6.5 Hz, 1H), 3.55 (s, 2H), 3.39-3.28 (m, 7H), 3.09 (d, J = 7.0 Hz, 2H), 3.01 (s, 2H), 2.87-2.75 (m, 2H), 2.70-2.63 (m, 4H), 2.61-2.49 (m, 18H), 2.45-2.41 (m, 5H), 2.33 (s, 3H), 2.18 (s, 3H), 2.12-2.04 (m, 2H), 0.90 (t, J = 6.9 Hz, 3H); 1041 [M + H]$^+$ | | |

TABLE 1-continued

| | structure | name | $^1$H NMR, MS | Yield (%) | HPLC r.t. (min) Purity |
|---|---|---|---|---|---|
| 30 | 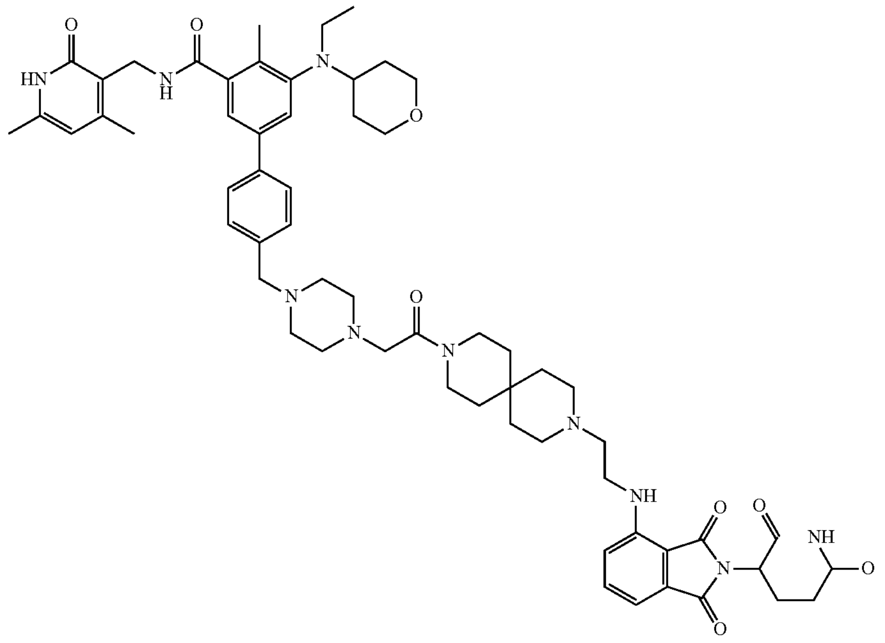 [SMILES: CCN(c1cc(-c2ccc(CN3CCN(CC(=O)N4CCC5(CCN(CCNc6cccc7c6C(=O)N(C(C=O)CCC(N)O)C7=O)CC5)CC4)CC3)cc2)cc(C(=O)NCc2c(C)cc(C)[nH]c2=O)c1C)C1CCOCC1] | N-((4,6-dimethyl-2-oxo-1,2-dihydro-pyridine-3-yl)methyl)-4'-((4-(2-(9-(2-((2-(2,6-dioxo-piperidine-3-yl)-1,3-dioxyiso-indoline-4-yl)amino) ethyl)-3,9-diazaspiro [5.5] undecane-3-yl)-2-oxoethyl) piperazine-1-yl)methyl)-5-(ethyl(tetra-hydro-2H-pyran-4-yl)amino)-4-methyl-[1,1'-biphenyl]-3-carboxamide | $^1$H NMR (400 MHz, $CDCl_3$) δ 10.80 (br s, 2H), 8.72 (br s, 1H), 7.74-7.68 (m, 1H), 7.66 (d, J = 7.1 Hz, 1H), 7.45-7.41 (m, 2H), 7.34-7.31 (m, 3H), 7.08 (d, J = 3.1 Hz, 1H), 6.87 (d, J = 8.5 Hz, 1H), 6.69 (t, J = 4.9 Hz, 1H), 5.90 (s, 1H), 4.91 (dd, J = 12.2, 5.4 Hz, 1H), 4.54 (d, J = 5.9 Hz, 2H), 3.97-3.92 (m, 2H), 3.81 (t, J = 6.6 Hz, 1H), 3.55 (s, 2H), 3.34-3.31 (m, 2H), 3.15 (d, J = 4.5 Hz, 2H) 3.09 (q, J = 7.0 Hz, 2H), 3.02-2.97 (m, 1H), 2.92-2.70 (m, 4H), 2.69-2.59 (m, 4H), 2.56-2.43 (m, 14H), | 15 | (B) 3.1 1594 |

TABLE 1-continued

| | structure | name | $^1H$ NMR, MS | Yield (%) | HPLC r.t. (min) Purity |
|---|---|---|---|---|---|
| | | | 2.40 (s, 3H), 2.33 (s, 3H), 2.16-2.09 (m, 5H), 1.49-1.39 (m, 8H), 0.89 (t, J = 7.0 Hz, 3 H); 1066 [M + H] $^+$ | | |
| 31 | 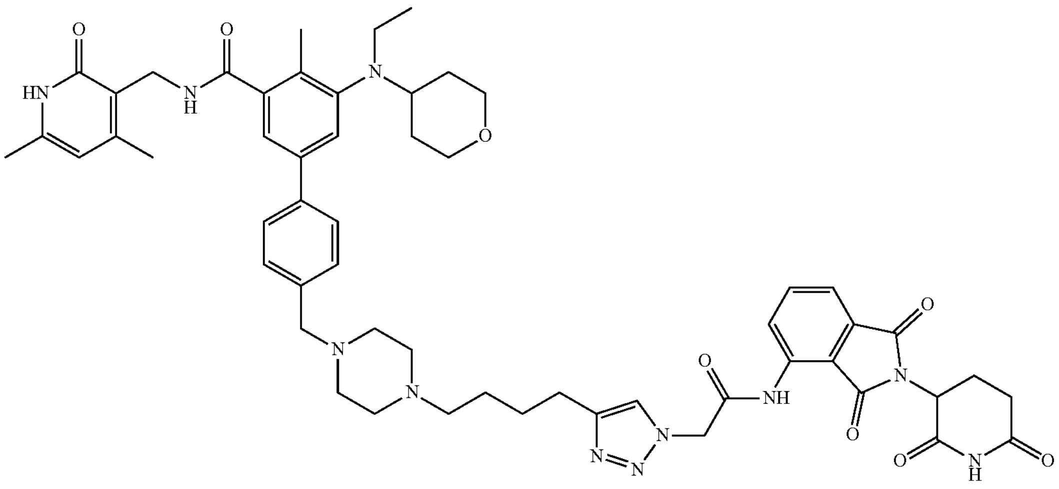 [SMILES: CCN(c1cc(-c2ccc(CN3CCN(CCCCc4cn(CC(=O)Nc5cccc6c5C(=O)N(C5CCC(=O)NC5=O)C6=O)nn4)CC3)cc2)cc(C(=O)NCc2c(C)cc(C)[nH]c2=O)c1C)C1CCOCC1] | N-((4, 6-dimethyl-2-oxo-1,2-dihydro-pyridine-3-yl)methyl)-4'-((4-(4-(1-(2-((2-(2,6-dioxo-piperidine-3-yl)-1,3-dioxoiso-indoline-4-yl)amino)-2-oxoethyl)-1H-1,2,3-triazole-4-yl)butyl) piperazine-1-yl)methyl)-5-(ethyl(tetra-hydro-2H-pyran-4-yl)amino)-4-methyl-[1,1'-biphenyl]-3-carboxamide | $^1H$ NMR (400 MHz, $CDCl_3$) δ 10.65 (br-s, 1H), 9.45 (s, 1H), 8.74 (d, J = 8.32 Hz, 1H), 7.71 (t, J = 7.48 Hz, 1H), 7.58-7.56 (m, 1H), 7.46-7.42 (m, 3H), 7.32-7.30 (m, 3H), 7.08 (t, J = 5.84 Hz, 1H), 5.90 (s, 1H), 5.39-5.34 (m, 2H), 5.13 (d, J = 17.4 Hz, 1H), 4.86-4.81 (m, 1H), 4.54 (d, J = 5.92 Hz, 2H), 3.94 (d, J = 11.28 Hz, 2H), 3.49 (s, 2H), | 4 | (A) 4.2 8899% |

TABLE 1-continued

| structure | name | $^1$H NMR, MS | Yield (%) | HPLC r.t. (min) Purity |
|---|---|---|---|---|
| | | 3.34-3.28 (m, 2H), 3.08 (q, J = 7.04 Hz, 2H), 3.04-2.96 (m, 1H), 2.85-2.61 (m, 6H), 2.51-2.40 (m, 10H), 2.33 (s, 3H), 2.21 (t, J = 7.52 Hz, 1H), 2.16 (s, 3H), 2.09-1.99 (m, 2H), 1.79-1.61 (m, 2H), 0.90-0.82 (m, 8H); LCMS [M + H] $^+$ 1008. | | |

TABLE 1-continued

| | structure | name | $^1$H NMR, MS | Yield (%) | HPLC r.t. (min) Purity |
|---|---|---|---|---|---|
| 32 | 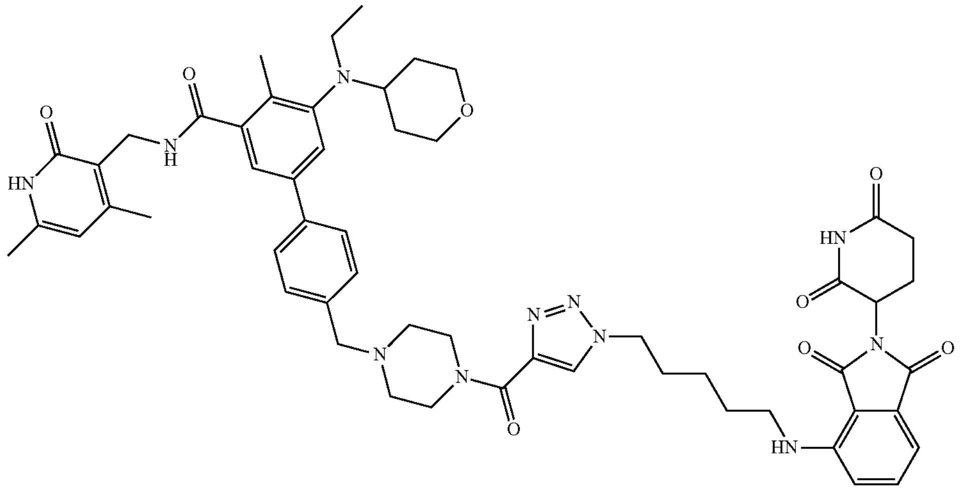 [SMILES: CCN(c1cc(-c2ccc(CN3CCN(C(=O)c4cn(CCCCCNc5cccc6c5C(=O)N(C5CCC(=O)NC5=O)C6=O)nn4)CC3)cc2)cc(C(=O)NCc2c(C)cc(C)[nH]c2=O)c1C)C1CCOCC1] | N-((4,6-dimethyl-2-oxo-1,2-dihydro-pyridine-3-yl)methyl)-4'-((4-(1-(5-((2-(2,6-dioxo-piperidine-3-yl)-1,3-dioxoiso-indoline-4-yl)amino)pentyl)-1H-1,2,3-triazol-4-carbonyl)piperazine-1-yl)methyl)-5-(ethyl(tetra-hydro-2H-pyran-4-yl)amino)-4-methyl-[1,1'-biphenyl]-3-carboxamide | $^1$H NMR (400 MHz, $CDCl_3$) δ 11.34 (br-s, 1H), 9.08 (br-s, 1H), 8.07 (s, 1H), 7.50-7.44 (m, 3H), 7.33 (d, J = 8.08 Hz, 3H), 7.27 (d, J = 1.56 Hz, 1H), 7.13 (t, J = 5.84 Hz, 1H), 7.08 (d, J = 7.08 Hz, 1H), 6.84 (d, J = 8.52 Hz, 1H), 6.19 (t, J = 5.56 Hz, 1H), 5.90 (s, 1H), 4.90 (dd, J = 11.96, 5.64 Hz, 1H), 4.54 (d, J = 5.88 Hz, 2H), 4.39 (t, J = 6.96 Hz, 2H), 4.2 (br-s, 2H), 3.94 (d, J = 11.36 Hz, 2H), 3.78 (br-s, 2H), 3.57 (s, 2H), 3.34-3.23 (m, 4H), 3.09 | 21 | (A) 4.7 5399% |

TABLE 1-continued

| structure | name | $^1H$ NMR, MS | Yield (%) | HPLC r.t. (min) Purity |
|---|---|---|---|---|
| | | (q, J = 7.04 Hz, 2H), 3.04-2.98 (m, 1H), 2.88-2.70 (m, 3H), 2.56-2.55 (m, 4H), 2.40 (s, 3H), 2.33 (s, 3H), 2.16 (s, 3H), 2.14-2.09 (m, 1H), 2.02-1.94 (m, 2H), 1.69-1.65 (m, 5H), 1.48-1.42 (m, 2H), 0.88 (t, J = 6.92 Hz, 4H); LCMS $[M + H]^+$ 1008. | | |

TABLE 1-continued

| | structure | name | $^1$H NMR, MS | Yield (%) | HPLC r.t. (min) Purity |
|---|---|---|---|---|---|
| 33 | 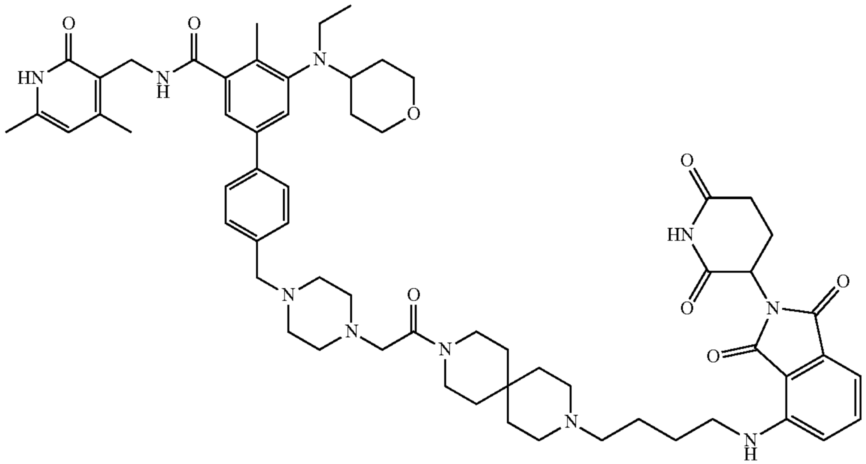 [SMILES: CCN(c1cc(-c2ccc(CN3CCN(CC(=O)N4CCC5(CCN(CCCCNc6cccc7c6C(=O)N(C6CCC(=O)NC6=O)C7=O)CC5)CC4)CC3)cc2)cc(C(=O)NCc2c(C)cc(C)[nH]c2=O)c1C)C1CCOCC1] | N-((4,6-dimethyl-2-oxo-1,2-dihydro-pyridine-3-yl)methyl)-4'-((4-(2-(9-(4-((2-(2,6-dioxo-piperidine-3-yl)-1,3-dioxoiso-indoline-4-yl)amino) butyl)-3,9-diazaspiro [5.5] undecane-3-yl)-2-oxoethyl) piperazine-1-yl)methyl)-5-(ethyl(tetra-hydro-2H-pyran-4-yl)amino)-4-methyl-[1,1'-biphenyl]-3-carboxamide | $^1$H NMR (400 MHz, $CDCl_3$) δ 10.26 (s, 1H), 8.72 (s, 1H), 7.52-7.43 (m, 3H), 7.36-7.30 (m, 3H), 7.10 (d, J = 7.1 Hz, 1H), 7.06 (t, J = 5.9 Hz, 1H), 6.88 (d, J = 8.5 Hz, 1H), 6.24 (t, J = 5.7 Hz, 1H), 5.90 (s, 1H), 4.90 (dd, J = 12.1, 5.3 Hz, 1H), 4.54 (d, J = 6.0 Hz, 2H), 3.98-3.91 (m, 2H), 3.57-3.48 (m, 5H), 3.36-3.27 (m, 4H), 3.16 (s, 2H), 3.09 (q, J = 7.0 Hz, 2H), 3.04-2.97 (m, 1H), 2.91-2.67 (m, 5H), 2.60-2.43 (m, 9H), 2.41 (s, 3H), 2.33 (s, 3H), 2.20-2.16 (m, 3H), 2.15-2.09 | 34 | (B) 3.2 4597% |

TABLE 1-continued

| | structure | name | $^1$H NMR, MS | Yield (%) | HPLC r.t. (min) Purity |
|---|---|---|---|---|---|
| | | | (m, 1H), 1.75-1.5 (m, 16H), 1.51-1.41 (m, 5H), 0.89 (t, J = 7.0 Hz, 3H); 1094 [M + H]$^+$ | | |
| 34 | 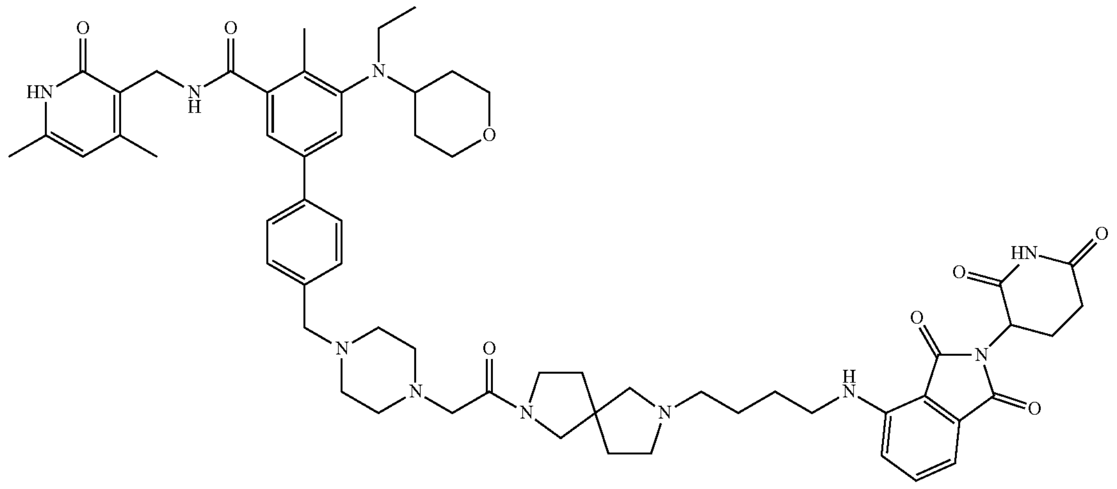 [SMILES: CCN(c1cc(-c2ccc(CN3CCN(CC(=O)N4CCC5(CCN(CCCCNc6cccc7c6C(=O)N(C6CCC(=O)NC6=O)C7=O)C5)C4)CC3)cc2)cc(C(=O)NCc2c(C)cc(C)[nH]c2=O)c1C)C1CCOCC1] | N-((4,6-dimethyl-2-oxo-1,2-dihydro-pyridine-3-yl)methyl)-4'-((4-(2-(7-(4-((2-(2,6-dioxo-piperidine-3-yl)-1,3-dioxoiso-indoline-4-yl)amino) butyl)-2,7-diazaspiro [4.4]nonane-2-yl)-2-oxoethyl) piperazine-1-yl)methyl)-5-(ethyl(tetra-hydro-2H-pyran-4-yl)amino)-4-methyl-[1,1'-biphenyl]-3-carboxamide | $^1$H NMR (400 MHz, $CDCl_3$) δ 10.60 (br s, 1H), 10.15 (br s, 1H), 7.56-7.40 (m, 3H), 7.37-7.29 (m, 3H), 7.24 (d, J = 1.8 Hz, 1H), 7.18-7.04 (m, 2H), 6.93-6.84 (m, 1H), 6.26 (t, J = 5.4 Hz, 1H), 5.91 (d, J = 2.8 Hz, 1H), 4.94-4.84 (m, 1H), 4.62-4.47 (m, 2H), 4.01-3.89 (m, 2H), 3.63-3.48 (m, 4H), 3.49-3.23 (m, 6H), 3.19-3.05 (m, 4H), 3.05-2.95 (m, 1H), 2.89-2.63 (m, 5H), | 37 | (B) 3.2 1299% |

TABLE 1-continued

| structure | name | $^1H$ NMR, MS | Yield (%) | HPLC r.t. (min) Purity |
|---|---|---|---|---|
| | | 2.63-2.37 (m, 13H), 2.37-2.31 (m, 3H), 2.27-2.19 (m, 1H), 2.17 (s, 3H), 2.13-2.03 (m, 1H), 2.00-1.64 (m, 13H), 0.89 (t, J = 6.9 Hz, 3H); 1066 $[M + H]^+$ | | |
| 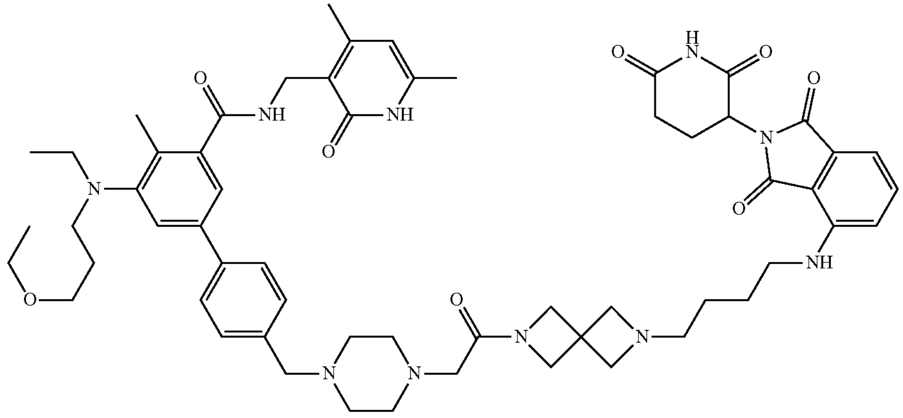 [SMILES: CCOCCCN(CC)c1cc(-c2ccc(CN3CCN(CC(=O)N4CC5(CN(CCCCNc6cccc7c6C(=O)N(C6CCC(=O)NC6=O)C7=O)C5)C4)CC3)cc2)cc(C(=O)NCc2c(C)cc(C)[nH]c2=O)c1C] | N-((4,6-dimethyl-2-oxo-1,2-dihydro pyridine-3-yl)methyl)-4'-((4-(2-(6-(4-((2-(2,6-dioxo-piperidine-3-yl)-1,3-dioxoiso-indoline-4-yl)amino) butyl)-2,6-diazaspiro [3.3]heptane-2-yl)-2-oxoethyl) piperazine-1-yl)methyl)-5-(ethyl(tetra-hydro-2H-pyran-4-yl)amino)- | $^1H$ NMR (400 MHz, $CDCl_3$) δ 11.03 (br-s, 1H), 9.43 (br-s, 1H), 7.49-7.43 (m, 3H), 7.32-7.30 (m, 3H), 7.12-7.07 (m, 2H), 6.86 (d, J = 8.52 Hz, 1H), 6.29 (t, J = 5.48 Hz, 1H), 5.90 (s, 1H), 4.89 (dd, J = 11.92, 5.64 Hz, 1H), 4.54 (d, J = 5.96 Hz, 2H), 4.29 (s, 2H), 4.05 (s, 2H), 3.94 | 8 | (A) 4.2 6492% |

TABLE 1-continued

| structure | name | $^1$H NMR, MS | Yield (%) | HPLC r.t. (min) Purity |
|---|---|---|---|---|
| | 4-methyl-[1,1'-biphenyl]-3-carboxamide | (d, J = 11.2 Hz, 2H), 3.51 (s, 2H), 3.34-3.24 (m, 8H), 3.08 (q, J = 7.0 Hz, 2H), 3.03-2.98 (m, 3H), 2.88-2.71 (m, 3H), 2.50 (br-s, 2H), 2.44-2.40 (m, 5H), 2.33 (s, 3H), 2.15 (s, 3H), 2.12-2.09 (m, 1H), 1.70-1.62 (m, 4H), 1.48-1.40 (m, 2H), 1.29-1.25 (m, 8H), 0.90-0.87 (m, 3H); LCMS [M + H] $^+$ 1037. | | |

TABLE 1-continued

| | structure | name | $^1$H NMR, MS | Yield (%) | HPLC r.t. (min) Purity |
|---|---|---|---|---|---|
| 36 | 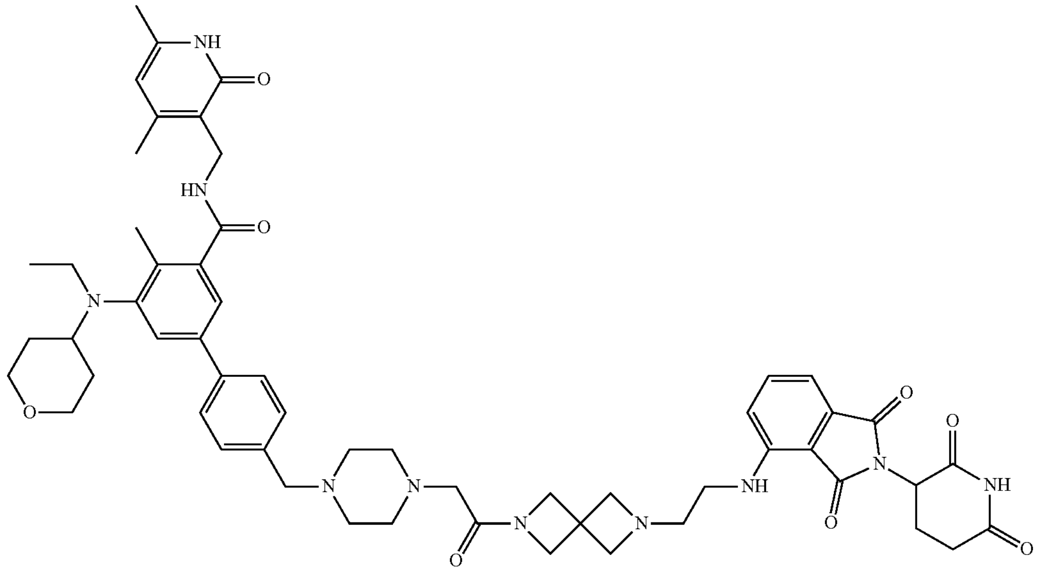 [SMILES: CCN(c1cc(-c2ccc(CN3CCN(CC(=O)N4CC5(CN(CCNc6cccc7c6C(=O)N(C6CCC(=O)NC6=O)C7=O)C5)C4)CC3)cc2)cc(C(=O)NCc2c(C)cc(C)[nH]c2=O)c1C)C1CCOCC1] | N-((4,6-dimethyl-2-oxo-1,2-dihydro-pyridine-3-yl)methyl)-4'-((4-(2-(6-(2-((2-(2,6-dioxo-piperidine-3-yl)-1,3-dioxoiso-indoline-4-yl)amino) ethyl)-2,6-diazaspiro [3.3]heptane-2-yl)-2-oxoethyl) piperazine-1-yl)methyl)-5-(ethyl(tetra-hydro-2H-pyran-4-yl)amino)-4-methyl-[1,1'-biphenyl]-3-carboxamide | $^1$H NMR (400 MHz, $CDCl_3$) δ 10.71 (br-s, 1H), 9.57 (br-s, 1H), 7.51-7.44 (m, 3H), 7.35-7.28 (m, 4H), 7.11-7.08 (m, 2H), 6.86 (d, J = 8.52 Hz, 1H), 6.46 (t, J = 5.32 Hz, 1H), 5.91 (s, 1H), 5.38-5.32 (m, 3H), 4.91 (dd, J = 12.24, 5.2 Hz, 1H), 4.55-4.53 (m, 3H), 4.33 (s, 2H), 4.04 (s, 2H), 3.94 (d, J = 11.36 Hz, 3H), 3.56-3.54 (m, 3H), 3.45-3.43 (m, 2H), 3.34-3.24 (m, 3H), 3.09 (q, J = 7.0 Hz, 3H), 3.00-2.98 (m, 3H), 2.89-2.74 (m, 3H), 2.70-2.67 | 27 | (A) 4.6 3892% |

TABLE 1-continued

| | structure | name | $^1$H NMR, MS | Yield (%) | HPLC r.t. (min) Purity |
|---|---|---|---|---|---|
| | | | (m, 2H), 2.41-2.33 (m, 8H), 2.23-2.16 (m, 7H), 2.13-2.08 (m, 1H), 2.01-1.99 (m, 2H), 0.88 (q, J = 5.36 Hz, 3H); LCMS [M + H] $^+$ 1009. | | |
| 37 | 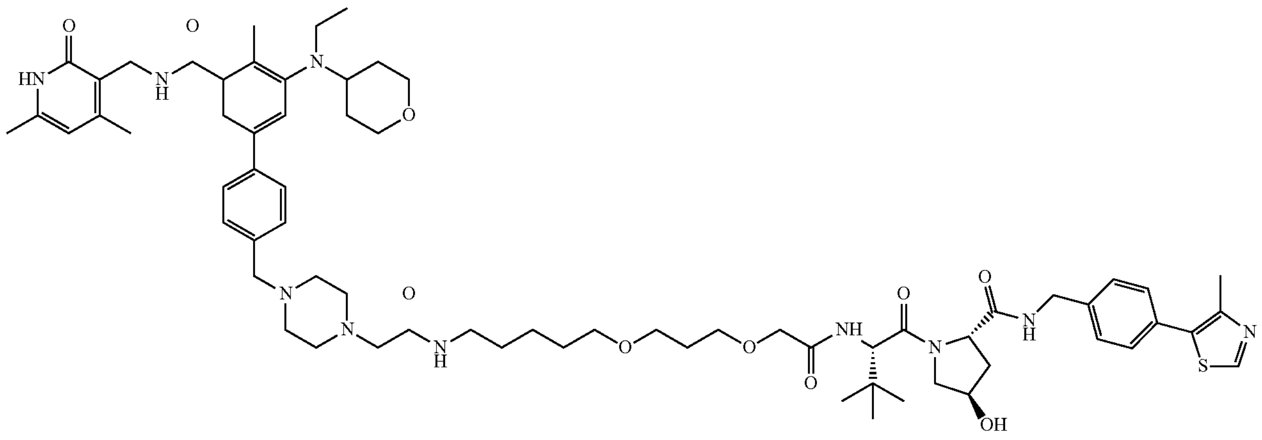 | (2S,4R)-1-((S)-2-(tert-butyl)-18-(4-((3'-(((4,6-dimethyl-2-oxo-1,2-dihydro-pyridine-3-yl)methyl) carbamoyl)-5'-(ethyl(tetra-hydro-2H-pyran-4-yl)amino)-4'-methyl-[1,1'-biphenyl]-4-yl) methyl) piperazine-1-yl)-4,17-dioxo-6,10-dioxa-3,16-diazaocta-decanoyl)-4-hydroxy-N-(4-(4- | $^1$H NMR (400 MHz, $CDCl_3$) δ 10.42 (br s, 1H), 8.68 (s, 1H), 7.54 (t, J = 6.0 Hz, 1H), 7.46 (d, J = 7.8 Hz, 2H), 7.38-7.28 (m, 6H), 7.25-7.22 (m, 1H), 7.19 (t, J = 6.0 Hz, 1H), 7.08 (t, J = 6.0 Hz, 1H), 5.90 (s, 1H), 4.71 (t, J = 8.0 Hz, 1H), 4.61-4.46 (m, 5H), 4.31 (dd, J = 14.9, 5.2 Hz, 1H), 4.10 (d, J = 11.3 Hz, 1H), 3.98-3.87 (m, 4H), 3.85- | 5 | (A) 4.7 3895% |

TABLE 1-continued

| structure | name | $^1$H NMR, MS | Yield (%) | HPLC r.t. (min) Purity |
|---|---|---|---|---|
| | methyl-thiazol-5-yl)benzyl) pyrrolidine-2-carboxamide | 3.77 (m, H), 3.63-3.53 (m, 15H), 3.46 (t, J = 6.1 Hz, 2H), 3.40-3.22 (m, 6H), 3.09 (q, J = 6.9 Hz, 2H), 3.04-2.96 (m, 3H), 2.60-2.42 (m, 11H), 2.40 (s, 3H), 2.35 (s, 3H), 2.19 (s, 3H), 2.13-2.04 (m, 1H), 1.87-1.80 (m, 2H), 1.75-1.64 (m, 5H), 1.59-1.47 (m, 4H), 1.39-1.30 (m, 2H), 0.99-0.85 (m, 12 H); 1244 [M + H] $^+$ | | |

TABLE 1-continued

| | structure | name | $^1$H NMR, MS | Yield (%) | HPLC r.t. (min) Purity |
|---|---|---|---|---|---|
| 38 | 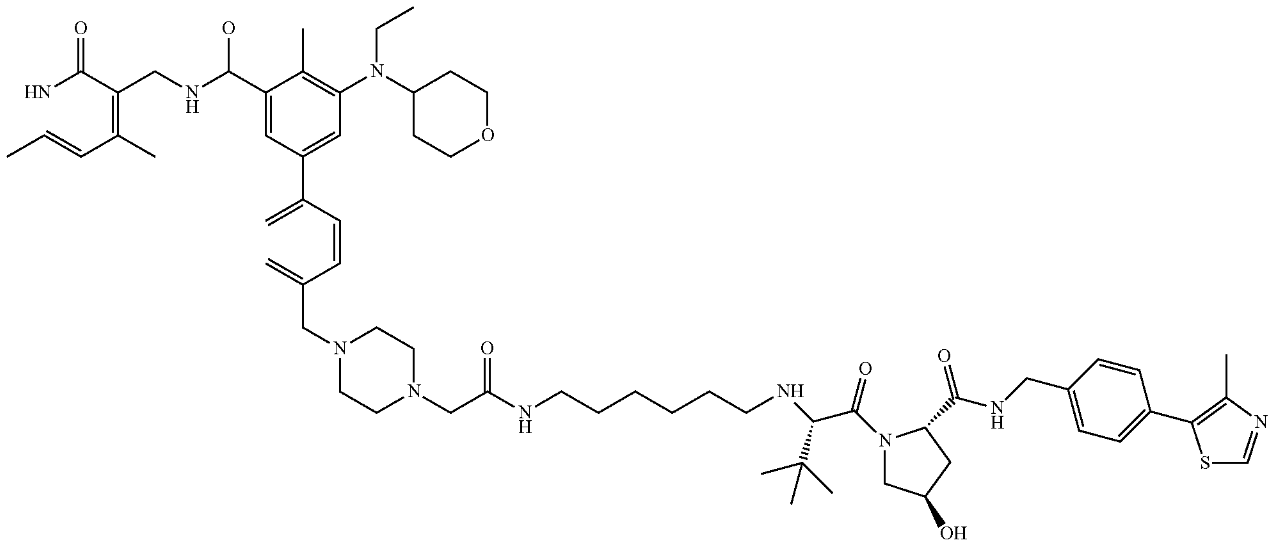 [SMILES: C=C(/C=C\C(=C)c1cc(C(O)NC/C(C(N)=O)=C(C)/C=C/C)c(C)c(N(CC)C2CCOCC2)c1)CN1CCN(CC(=O)NCCCCCCN[C@H](C(=O)N2C[C@H](O)C[C@H]2C(=O)NCc2ccc(-c3scnc3C)cc2)C(C)(C)C)CC1] | (2S,4R)-1-((S)-2-((6-(2-(4-((3'-(((4,6-dimethyl-2-oxo-1,2-dihydro-pyridine-3-yl) methyl) carbamoyl)-5'-(ethyl(tetra-hydro-2H-pyran-4-yl)amino)-4'-methyl-[1,1'-biphenyl]-4-yl)methyl) piperazine-1-yl)acetamido) hexyl) amino)-3,3-dimethyl-butanoyl)-4-hydroxy-N-(4-(4-methyl-thiazole-5-yl)benzyl) pyrrolidine-2-carboxamide | 1H NMR (400 MHz, $CDCl_3$) δ 11.59 (br s, 1H), 8.67 (s, 1H), 7.96 (dd, J = 6.8, 5.0 Hz, 1H), 7.43 (d, J = 7.9 Hz, 2H), 7.33-7.28 (m, 7H), 7.26-7.24 (m, 1H), 7.20 (t, J = 6.3 Hz, 1H), 7.09 (t, J = 5.9 Hz, 1H), 5.88 (s, 1H), 4.85 (dd, J = 8.1, 6.7 Hz, 1H), 4.61-4.52 (m, 3H), 4.45 (dd, J = 14.1, 5.5 Hz, 1H), 4.23 (dd, J = 14.8, 5.0 Hz, 1H), 4.05-3.90 (m, 3H), 3.70-3.57 (m, 2H), 3.53 (s, 2H), 3.35-3.14 (m, 4H), 3.11-3.05 (m, 3H), 3.03-2.94 (m, 3H), 2.63-2.43 (m, 12H), 2.37 (s, 3H), | 14 | (A) 4.3 4290% |

TABLE 1-continued
| | structure | name | $^1H$ NMR, MS | Yield (%) | HPLC r.t. (min) Purity |
|---|---|---|---|---|---|
| | | | 2.35-2.30 (m, 4H), 2.12 (s, 3H), 2.10-2.02 (m, 1H), 1.75-1.59 (m, 5H), 1.49-1.33 (m, 4H), 1.32-1.23 (m, 5H), 0.92-0.84 (m,12H); 1142 $[M + H]^+$ | | |
| 39 | 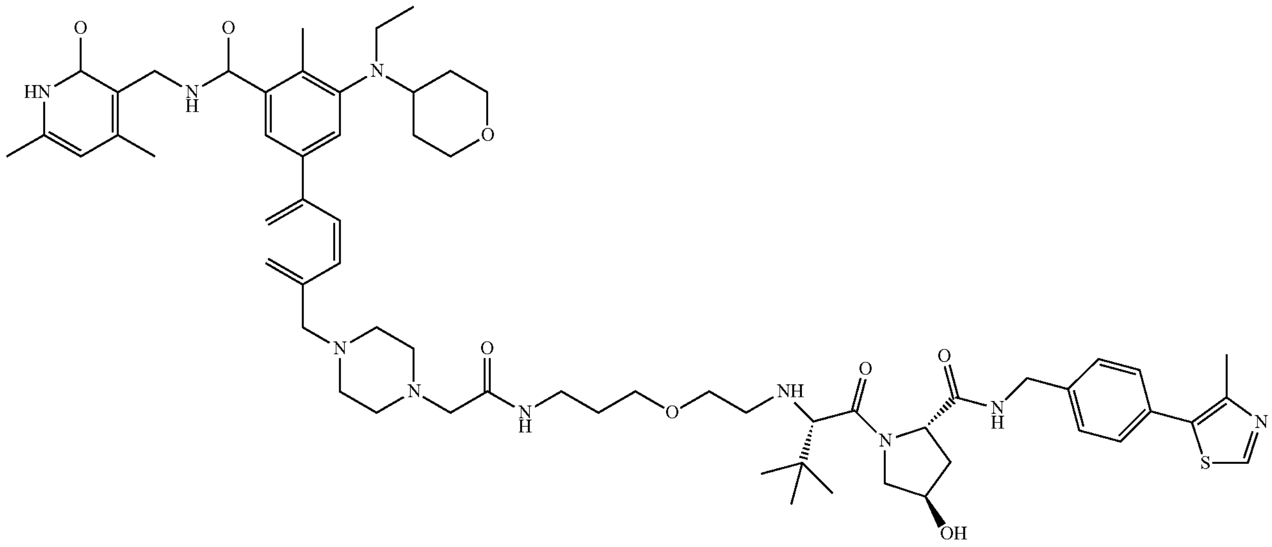 [SMILES: C=C(/C=C\C(=C)c1cc(C(O)NCC2=C(C)C=C(C)NC2O)c(C)c(N(CC)C2CCOCC2)c1)CN1CCN(CC(=O)NCCCOCCN[C@H](C(=O)N2C[C@H](O)C[C@H]2C(=O)NCc2ccc(-c3scnc3C)cc2)C(C)(C)C)CC1] | (2S,4R)-1-((S)-2-((2-(3-(2-(4-((3'-(((4,6-dimethyl-2-oxo-1,2-dihydro-pyridine-3-yl) methyl) carbamoyl)-5'-(ethyl(tetra-hydro-2H-pyran-4-yl)amino)-4'-methyl-[1,1'-biphenyl]-4-yl)methyl) piperazine-1-yl)acetamido) propoxy) ethyl)amino)-3,3- | $^1H$ NMR (400 MHz, $CDCl_3$) δ 10.71 (br s, 1H), 8.67 (s, 1H), 7.91 (t, J = 5.8 Hz, 1H), 7.45 (d, J = 7.9 Hz, 2H), 7.35-7.26 (m, 9H), 7.10 (t, J = 5.9 Hz, 1H), 5.89 (s, 1H), 4.86 (dd, J = 8.2, 6.7 Hz, 1H), 4.62-4.52 (m, 3H), 4.47 (dd, J = 14.1, 5.6 Hz, 1H), 4.25 (dd, J = 14.8, 5.0 Hz, 1H), 3.95 (d, J = 11.5 Hz, | 48 | (A) 4.3 2191% |

TABLE 1-continued

| structure | name | $^1H$ NMR, MS | Yield (%) | HPLC r.t. (min) Purity |
|---|---|---|---|---|
| | dimethyl-butanoyl)-4-hydroxy-N-(4-(4-methyl-thiazol-5-yl)benzyl) pyrrolidine-2-carboxamide | 2H), 3.78 (d, J = 10.9 Hz, 1H), 3.62-3.51 (m, 3H), 3.49-3.27 (m, 8H), 3.24 (s, 1H), 3.09 (q, J = 7.0 Hz, 2H), 3.05-2.93 (m, 3H), 2.77-2.67 (m, 1H), 2.67-2.58 (m, 1H), 2.58-2.42 (m, 11H), 2.39 (s, 3H), 2.35 (s, 3H), 2.16 (s, 3H), 2.10-2.00 (m, 1H), 1.78-1.62 (m, 9H), 0.95-0.80 (m, 12H): 1144 $[M + H]^+$ | | |

TABLE 1-continued

| | structure | name | $^1H$ NMR, MS | Yield (%) | HPLC r.t. (min) Purity |
|---|---|---|---|---|---|
| 40 | 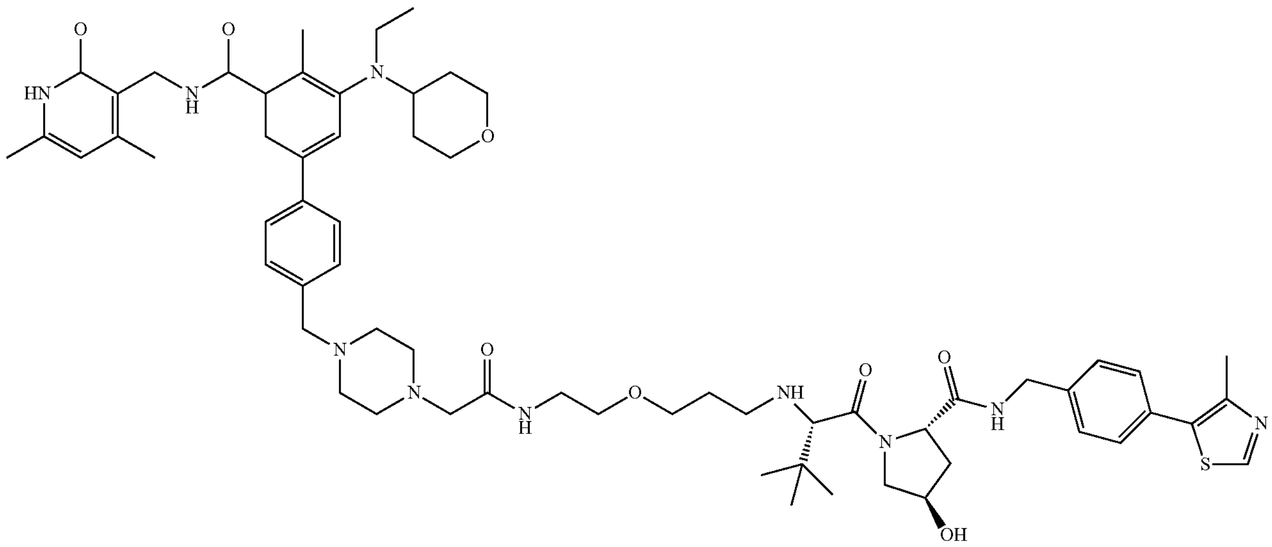 [SMILES: CCN(C1=C(C)C(C(O)NCC2=C(C)C=C(C)NC2O)CC(c2ccc(CN3CCN(CC(=O)NCCOCCCN[C@H](C(=O)N4C[C@H](O)C[C@H]4C(=O)NCc4ccc(-c5scnc5C)cc4)C(C)(C)C)CC3)cc2)=C1)C1CCOCC1] | (2S,4R)-1-((S)-2-((3-(2-(2-(4-((3'-(((4,6-dimethyl-2-oxo-1,2-dihydro-pyridine-3-yl) methyl) carbamoyl)-5'-(ethyl(tetra-hydro-2H-pyran-4-yl)amino)-4'-methyl-[1,1'-biphenyl]-4-yl)methyl) piperazine-1-yl)acetamido) ethoxy) propyl) amino)-3,3-dimethyl-butanoyl)-4-hydroxy-N-(4-(4-methyl-thiazol-5-yl)benzyl) pyrrolidine-2-carboxamide | $^1H$ NMR (400 MHz, $CDCl_3$) δ 10.93 (br s, 1H), 8.67 (s, 1H), 8.05 (t, J = 5.9 Hz, 1H), 7.45 (d, J = 7.9 Hz, 2H), 7.42-7.37 (m, 1H), 7.35-7.28 (m, 6H), 7.26-7.24 (m, 2H), 7.14 (t, J = 5.9 Hz, 1H), 5.88 (s, 1H), 4.87 (t, J = 7.5 Hz, 1H), 4.66-4.52 (m, 3H), 4.40 (dd, J = 14.2, 5.4 Hz, 1H), 4.21 (dd, J = 14.8, 4.9 Hz, 1H), 4.07-3.98 (m, 1H), 3.98-3.90 (m, 2H), 3.71 (d, J = 10.9 Hz, 1H), 3.60 (dd, J = 10.9, 4.1 Hz, 1H), 3.55 (s, 2H), 3.52-3.24 (m, 8H), 3.15-2.94 (m, 6H), 2.64-2.42 (m, 11H), 2.42- | 19 | (A) 4.3 0290% |

TABLE 1-continued

| | structure | name | $^1$H NMR, MS | Yield (%) | HPLC r.t. (min) Purity |
|---|---|---|---|---|---|
| | | | 2.26 (m, 7H), 2.15 (s, 3H), 2.10-2.01 (m, 1H), 1.82-1.49 (m, 9H), 0.94-0.81 (m, 12H); 1144 [M + H] $^+$ | | |
| 41 | 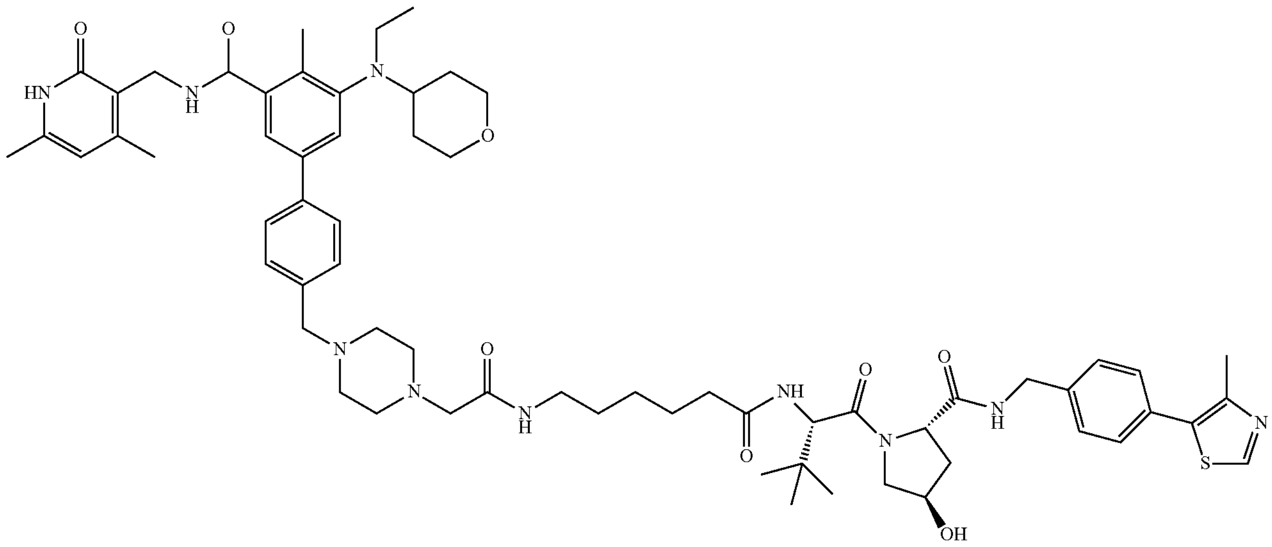 [SMILES: CCN(c1cc(-c2ccc(CN3CCN(CC(=O)NCCCCCC(=O)N[C@H](C(=O)N4C[C@H](O)C[C@H]4C(=O)NCc4ccc(-c5scnc5C)cc4)C(C)(C)C)CC3)cc2)cc(C(O)NCc2c(C)cc(C)[nH]c2=O)c1C)C1CCOCC1] | (2S,4R)-1-((S)-2-(6-(2-(4-((3'-(((4,6-dimethyl-2-oxo-1,2-dihydro-pyridine-3-yl) methyl) carbamoyl)-5'-(ethyl(tetra-hydro-2H-pyran-4-yl)amino)-4'-methyl-[1,1'-biphenyl]-4-yl)methyl) piperazine-1-yl)acetamido) hexan-amido)-3,3-dimethyl-butanoyl)-4-hydroxy-N-(4-(4-methyl-thiazole-5-yl) benzyl) pyrrolidine- | $^1$H NMR (400 MHz, $CDCl_3$) δ 10.47 (br s, 1H), 8.68 (s, 1H), 7.54 (t, J = 5.8 Hz, 1H), 7.45 (d, J = 8.0 Hz, 2H), 7.32 (dd, J = 7.6, 2.6 Hz, 5H), 7.19 (d, J = 1.7 Hz, 1H), 7.14 (t, J = 6.1 Hz, 1H), 7.02 (d, J = 6.0 Hz, 1H), 6.29 (d, J = 8.9 Hz, 1H), 5.91 (s, 1H), 4.72 (t, J = 8.1 Hz, 1H), 4.62-4.48 (m, 3H), 4.44 (dd, J = 14.1, 5.7 Hz, 1H), 4.30 (dd, J = 14.9, 5.1 Hz, 1H), 4.15-3.90 (m, 4H), 3.67-3.53 | 32 | (B) 3.4 0299% |

TABLE 1-continued
| | structure | name | $^1$H NMR, MS | Yield (%) | HPLC r.t. (min) Purity |
|---|---|---|---|---|---|
| | | 2-carboxamide | (m, 3H), 3.38-3.24 (m, 3H), 3.23-3.13 (m, 1H), 3.13-3.06 (m, 2H), 3.06-2.92 (m, 3H), 2.59-2.42 (m, 8H), 2.42-2.34 (m, 5H), 2.22-2.10 (m, 5H), 1.76-1.38 (m, 15H), 1.32-1.19 (m, 3H), 0.91 (d, J = 10.7 Hz, 12H): 1156 [M + H] + | | |
| 42 | 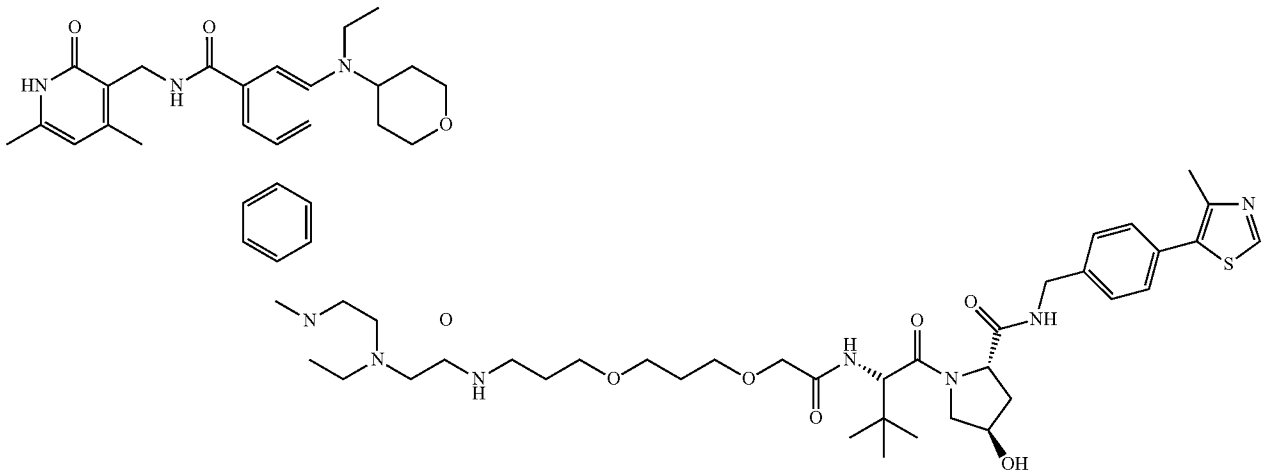 | (2S,4R)-1-((S)-2-(tert-butyl)-16-(4-((3'-(((4,6-dimethyl-2-oxo-1,2-dihydro-pyridine-3-yl)methyl) carbamoyl)-5'-(ethyl(tetra-hydro-2H-pyran-4-yl)amino)-4'-methyl-[1,1'-biphenyl]-4- | $^1$H NMR (400 MHz, $CDCl_3$) δ 11.30 (br-s, 1H), 8.67 (s, 1H), 7.58 (t, J = 5.8 Hz, 1H), 7.44 (d, J = 8.12 Hz, 2H), 7.34-7.29 (m, 8H), 7.25-7.22 (m, 1H), 7.13 (t, J = 5.88 Hz, 1H), 5.89 (s, 1H), 4.67 (t, J = 7.88 Hz, | 22 | (A) 4.6 5597% |

TABLE 1-continued

| structure | name | $^1$H NMR, MS | Yield (%) | HPLC r.t. (min) Purity |
|---|---|---|---|---|
| | yl)methyl) piperazine-1-yl)-4,15-dioxo-6,10-dioxa-3,14-diazahexa-decanoyl)-4-hydroxy-N-(4-(4-methyl-thiazol-5-yl)benzyl) pyrrolidine-2-carboxamide | 1H), 4.60-4.49 (m, 5H), 4.29 (dd, J = 14.98, 5.24 Hz, 1H), 4.03 (d, J = 11.24 Hz, 1H), 3.96-3.88 (m, 4H), 3.62 (dd, J = 11.12, 3.6 Hz, 1H), 3.57 (t, J = 6.16 Hz, 2H), 3.52 (s, 2H), 3.50-3.43 (m, 4H), 3.35-3.27 (m, 4H), 3.08 (q, J = 7.0 Hz, 2H), 3.02-2.95 (m, 3H), 2.49-2.42 (m, 11H), 2.39 (s, 3H), 2.34 (s, 3H), 2.15 (s, 3H), 2.10-2.05 (m, 1H), 1.89-1.82 (m, 2H), 1.76-1.64 (m, 6H), 0.97-0.94 (m, 9H), 0.88 (t, J = 6.96 Hz, 4H); LCMS $[M + H]^+$ 1215. | | |

TABLE 1-continued

| | structure | name | $^1H$ NMR, MS | Yield (%) | HPLC r.t. (min) Purity |
|---|---|---|---|---|---|
| 43 | 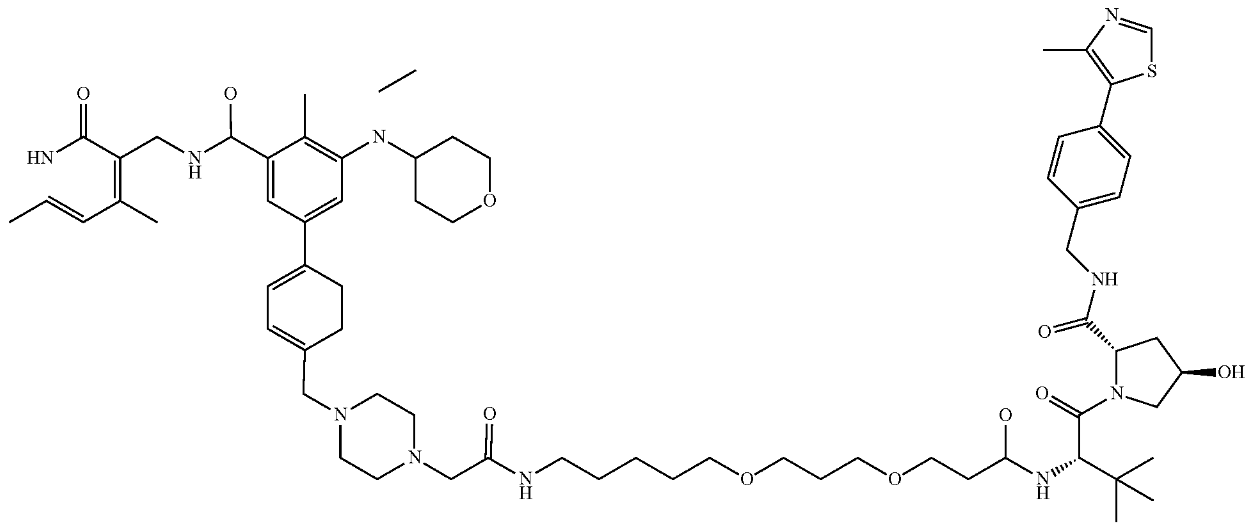 | (2S,4R)-1-((S)-2-(tert-butyl)-19-(4-((3'-(((4,6-dimethyl-2-oxo-1,2-dihydro-pyridine-3-yl)methyl) carbamoyl)-5'-(ethyl(tetra-hydro-2H-pyran-4-yl)amino)-4'-methyl-[1,1'-biphenyl]-4-yl)methyl) piperazine-1-yl)-4,18-dioxo-7,11-dioxa-3,17-diazanona-decanoyl)-4-hydroxy-N-(4-(4-methyl-thiazol-5-yl)benzyl) pyrrolidine-2-carboxamide | 1H NMR (400 MHz, $CDCl_3$) δ 11.05 (br-s, 1H), 8.67 (s, 1H), 7.45-7.35 (m, 4H), 7.33-7.31 (m, 7H), 7.25 (s, 1H), 7.17 (t, J = 6.0 Hz, 1H), 7.12 (t, J = 5.84 Hz, 1H), 5.89 (s, 1H), 4.70 (t, J = 8.0 Hz, 1H), 4.59-4.45 (m, 5H), 4.31 (dd, J = 14.94, 5.28 Hz, 1H), 4.12 (d, J = 11.44 Hz, 1H), 3.93 (d, J = 11.2 Hz, 2H), 3.59-3.53 (m, 5H), 3.46-3.39 (m, 4H), 3.36-3.22 (m, 5H), 3.08 (q, J = 7.04 Hz, 2H), 3.01-2.96 (m, 3H), 2.54 (br-s, 3H), 2.50-2.39 (m, 12H), | 14 | (A) 4.8 7397% |

TABLE 1-continued
| | structure | name | $^1H$ NMR, MS | Yield (%) | HPLC r.t. (min) Purity |
|---|---|---|---|---|---|
| | | | 2.33 (s, 3H), 2.15 (s, 3H), 2.12-2.07 (m, 1H), 1.80-1.75 (m, 3H), 1.69-1.64 (m, 4H), 1.56-1.48 (m, 4H), 1.37-1.27 (m, 3H), 0.93 (s, 9H), 0.90-0.86 (m, 4H); LCMS [M + H] + 1257. | | |
| 44 | 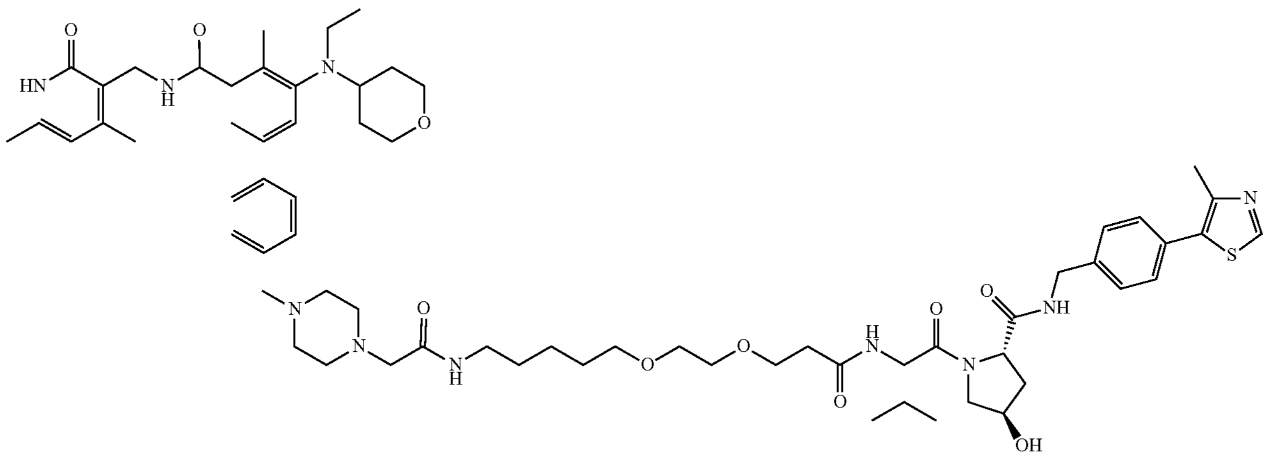 | (2S,4R)-1-((S)-2-(tert-butyl)-18-(4-((3'-(((4,6-dimethyl-2-oxo-1,2-dihydro-pyridine-3-yl)methyl)carbamoyl)-5'-(ethyl(tetra-hydro-2H-pyran-4-yl)amino)-4'-methyl-[1,1'-biphenyl]-4-yl)methyl)piperazine-1-yl)-4,17-dioxo-7,10- | $^1H$ NMR (400 MHz, $CDCl_3$) δ 11.27 (br-s, 1H), 8.67 (s, 1H), 7.49 (t, J = 5.84 Hz, 1H), 7.44 (d, J = 8.12 Hz, 2H), 7.35-7.27 (m, 8H), 7.25 (s, 1H), 7.18-7.11 (m, 2H), 5.89 (s, 1H), 4.70 (t, J = 8.0 Hz, 1H), 4.58-4.46 (m, 5H), 4.31 (dd, J = 14.98, 5.28 Hz, 1H), 4.14-4.08 (m, | 18 | (A) 4.6 7798% |

TABLE 1-continued

| structure | name | $^1H$ NMR, MS | Yield (%) | HPLC r.t. (min) Purity |
|---|---|---|---|---|
| | dioxa-3,16-diazaocta-decanoyl)-4-hydroxy-N-(4-(4-methyl-thiazole-5-yl)benzyl) pyrrolidine-2-carboxamide | 1H), 3.93 (d, J = 11.32 Hz, 2H), 3.62 (t, J = 5.68 Hz, 2H), 3.60-3.49 (m, 7H), 3.39 (t, J = 6.48 Hz, 2H), 3.33-3.21 (m, 4H), 3.08 (q, J = 7.04 Hz, 2H), 3.01-2.96 (m, 3H), 2.53 (br-s, 4H), 2.49-2.39 (m, 9H), 2.37 (s, 3H), 2.33 (s, 3H), 2.14 (s, 3H), 2.11-2.07 (m, 1H), 1.69-1.64 (m, 3H), 1.62-1.45 (m, 4H), 1.37-1.31 (m, 3H), 0.93 (s, 9H), 0.90-0.86 (m, 4H); LCMS $[M + H]^+$ 1243. | | |

TABLE 1-continued

| | structure | name | $^1$H NMR, MS | Yield (%) | HPLC r.t. (min) Purity |
|---|---|---|---|---|---|
| 45 | 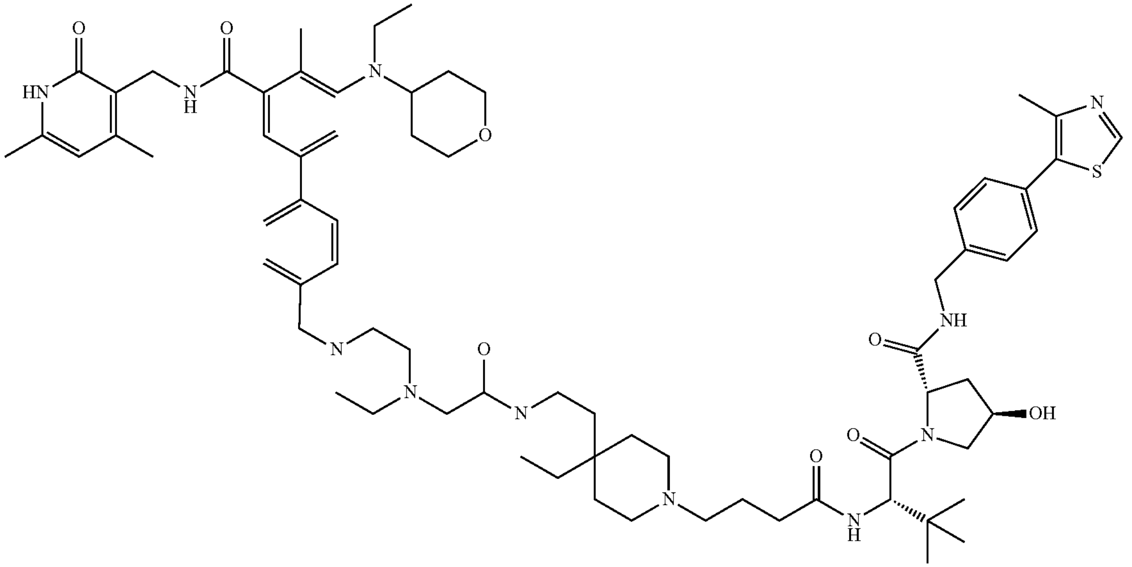 [SMILES: C=C(/C=C\C(=C)C(=C)/C=C(C(=O)NCc1c(C)cc(C)[nH]c1=O)\C(C)=C\N(CC)C1CCOCC1)CNCCN(CC)CC(O)NCCC1(CC)CCN(CCCC(=O)N[C@H](C(=O)N2C[C@H](O)C[C@H]2C(=O)NCc2ccc(-c3scnc3C)cc2)C(C)(C)C)CC1] | (2S,4R)-1-((S)-2-(4-(9-(2 (4-((3'-(((4,6-dimethyl-2-oxo-1,2-dihydro-pyridine-3-yl) methyl) carbamoyl)-5'-(ethyl(tetra-hydro-2H-pyran-4-yl)amino)-4'-methyl-[1,1'-biphenyl]-4-yl)methyl) piperazine-1-yl)acetyl)-3,9-diazaspiro [5.5] undecane-3-yl)butan-amido)-3,3-dimethyl-butanoyl)-4-hydroxy-N-(4-(4-methyl-thiazole-5-yl)benzyl) pyrrolidine-2-carboxamide | $^1$H NMR (400 MHz, $CDCl_3$) δ 11.35 (s, 1H), 8.68 (s, 1H), 7.47-7.41 (m, 2H), 7.38-7.27 (m, 8H), 7.11 (t, J = 5.9 Hz, 1H), 6.72 (d, J = 8.8 Hz, 1H), 5.89 (s, 1H), 4.71 (t, J = 8.0 Hz, 1H), 4.60-4.47 (m, 5H), 4.32 (dd, J = 15.0, 5.2 Hz, 1H), 4.12 (d, J = 11.4 Hz, 1H), 3.94 (d, J = 11.4 Hz, 2H), 3.62-3.42 (m, 7H), 3.37-3.25 (m, 2H), 3.14 (s, 2H), 3.09 (q, J = 7.0 Hz, 2H), 3.05-2.94 (m, 1H), 2.59-2.43 (m, 11H), 2.42-2.25 (m, 12H), | 31 | (B) 3.2 5598% |

TABLE 1-continued

| | structure | name | $^1$H NMR, MS | Yield (%) | HPLC r.t. (min) Purity |
|---|---|---|---|---|---|
| | | | 2.22 (t, J = 7.2 Hz, 3H), 2.18-2.09 (m, 4H), 1.80-1.57 (m, 7H), 1.56-1.47 (m, 4H), 1.46-1.35 (m, 4H), 0.97-0.86 (m, 12H); 1265 [M + H] $^+$ | | |
| 46 | 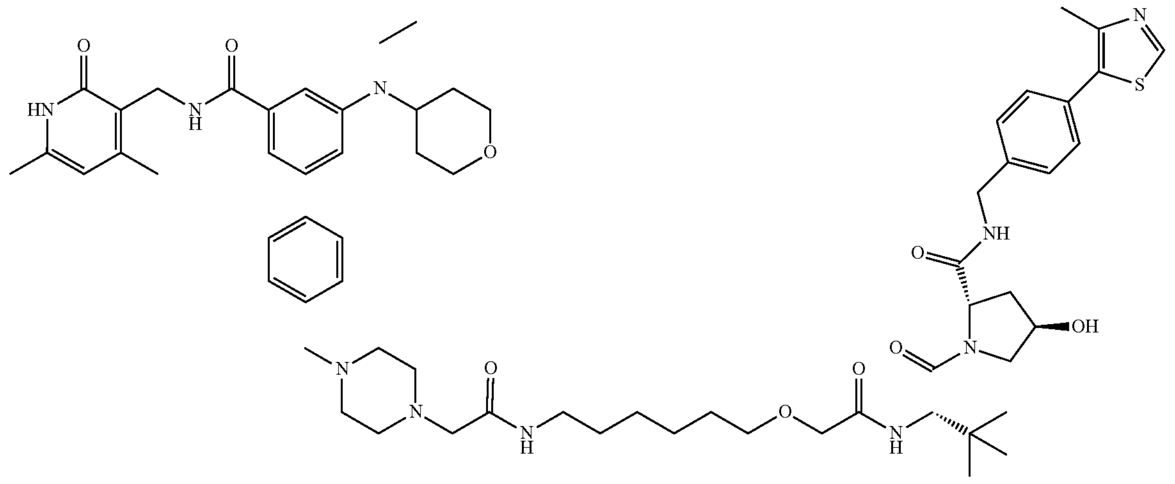 | (2S,4R)-1-((S)-2-(2-((6-(2-(4-((3'-(((4,6-dimethyl-2-oxo-1,2-dihydro-pyridine-3-yl)methyl) carbamoyl)-5'-(ethyl(tetra-hydro-2H-pyran-4-yl)amino)-4'-methyl-[1,1'-biphenyl]-4-yl)methyl) piperazine-1-yl)acetamido) hexyl) oxy) acetamido)-3,3-dimethyl-butanoyl)-4-hydroxy-N-(4-(4- | $^1$H NMR (400 MHz, $CDCl_3$) δ 11.13 (s, 1H), 8.67 (s, 1H), 7.62 (t, J = 6.0 Hz, 1H), 7.48-7.42 (m, 2H), 7.36-7.28 (m, 7H), 7.2 6-7.21 (m, 2H), 7.19-7.08 (m, 2H), 5.90 (s, 1H), 4.70 (t, J = 7.9 Hz, 1H), 4.61-4.44 (m, 5H), 4.30 (dd, J = 15.0, 5.3 Hz, 1H), 4.06 (d, J = 11.3 Hz, 1H), 3.98-3.89 (m, 3H), 3.88-3.81 (m, | 40 | (B) 3.5 15100% |

TABLE 1-continued

| structure | name | $^1$H NMR, MS | Yield (%) | HPLC r.t. (min) Purity |
| --- | --- | --- | --- | --- |
| | methyl-thiazole-5-yl)benzyl) pyrrolidine-2-carboxamide | 1H), 3.62 (dd, J = 11.2, 3.7 Hz, 1H), 3.55-3.41 (m, 4H), 3.35-3.21 (m, 4H), 3.09 (q, J = 7.0 Hz, 2H), 3.05-2.92 (m, 3H), 2.58-2.41 (m, 12H), 2.39 (s, 3H), 2.37-2.28 (m, 4H), 2.16 (s, 3H), 2.12-2.04 (m, 1H), 1.73-1.63 (m, 4H), 1.63-1.54 (m, 2H), 1.53-1.44 (m, 2H), 1.40-1.28 (m, 4H), 0.95 (s, 9H), 0.88 (t, J = 7.0 Hz, 3H); 1156 [M + H] $^+$ | | |

TABLE 1-continued

| | structure | name | $^1$H NMR, MS | Yield (%) | HPLC r.t. (min) Purity |
|---|---|---|---|---|---|
| 47 | 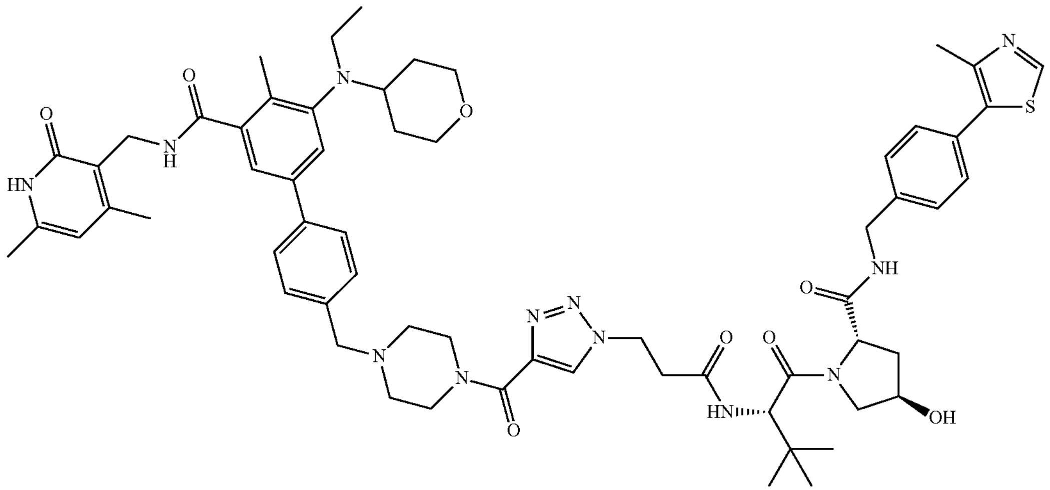 [SMILES: CCN(c1cc(-c2ccc(CN3CCN(C(=O)c4cn(CCC(=O)N[C@H](C(=O)N5C[C@H](O)C[C@H]5C(=O)NCc5ccc(-c6scnc6C)cc5)C(C)(C)C)nn4)CC3)cc2)cc(C(=O)NCc2c(C)cc(C)[nH]c2=O)c1C)C1CCOCC1] | (2S,4R)-1-((S)-2-(3-(4-(4-((3'-(((4,6-dimethyl-2-oxo-1,2-dihydro-pyridine-3-yl) methyl) carbamoyl)-5'-(ethyl(tetra-hydro-2H-pyran-4-yl)amino)-4'-methyl-[1,1'-biphenyl]-4-yl)methyl) piperazine-1-carbonyl)-1H-1,2,3-triazol-1-yl)propan-amido)-3,3-dimethyl-butanoyl)-4-hydroxy-N-(4-(4-methyl-thiazole-5-yl)benzyl) pyrrolidine-2-carboxamide | $^1$H NMR (400 MHz, $CDC1_3$) δ 11.13 (br-s, 1H), 8.65 (s, 1H), 8.00 (s, 1H), 7.83-7.81 (m, 1H), 7.53 (t, J = 5.6 Hz, 1H), 7.37-7.25 (m, 11H), 5.85 (s, 1H), 4.80 (t, J = 8.28 Hz, 1H), 4.62-4.49 (m, 5H), 4.45-4.41 (m, 2H), 4.29-4.26 (m, 2H), 4.18-4.08 (m, 3H), 3.94-3.90 (m, 2H), 3.63-3.57 (m, 3H), 3.51 (s, 2H), 3.32-3.24 (m, 2H), 3.08 (q, J = 7.04 Hz, 2H), 3.03-2.98 (m, 1H), 2.92-2.84 (m, 1H), 2.64-2.59 (m, 1H), 2.48 (s, 3H), 2.44-2.35 (m, | 32 | (A) 4.5 6499% |

TABLE 1-continued

| | structure | name | $^1$H NMR, MS | Yield (%) | HPLC r.t. (min) Purity |
|---|---|---|---|---|---|
| | | | 10H), 2.27-2.21 (m, 1H), 2.07 (s, 3H), 1.69-1.63 (m, 4H), 0.92 (s, 9H), 0.87 (t, J = 6.88 Hz, 3H); LCMS [M + H] + 1151. | | |
| 48 | 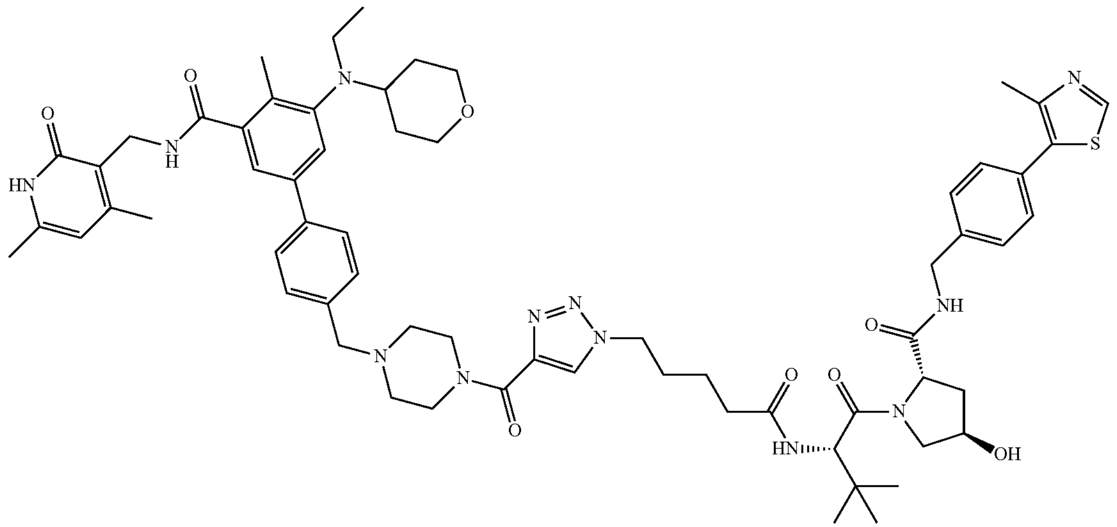 [SMILES: CCN(c1cc(-c2ccc(CN3CCN(C(=O)c4cn(CCCCC(=O)N[C@H](C(=O)N5C[C@H](O)C[C@H]5C(=O)NCc5ccc(-c6scnc6C)cc5)C(C)(C)C)nn4)CC3)cc2)cc(C(=O)NCc2c(C)cc(C)[nH]c2=O)c1C)C1CCOCC1] | (2S,4R)-1-((S)-2-(5-(4-(4-((3'-(((4,6-dimethyl-2-oxo-1,2-dihydro-pyridine-3-yl) methyl) carbamoyl)-5'-(ethyl(tetra-hydro-2H-pyran-4-yl)amino)-4'-methyl-[1,1'-biphenyl]-4-yl)methyl) piperazine-1-carbonyl)-1H-1,2,3-triazol-1-yl)pentan-amido)-3,3-dimethyl-butanoyl)-4-hydroxy-N- | $^1$H NMR (400 MHz, $CDCl_3$) δ 11.30 (br-s, 1H), 8.66 (s, 1H), 8.30 (s, 1H), 7.80 (t, J = 5.76 Hz, 1H), 7.44 (d, J = 8.12 Hz, 2H), 7.33-7.15 (m, 8H), 7.17 (t, J = 5.84 Hz, 1H), 6.84 (d, J = 9.08 Hz, 1H), 5.88 (s, 1H), 4.68-4.60 (m, 2H), 4.54-4.40 (m, 5H), 4.33-4.18 (m, 4H), 4.12-4.08 (m, 2H), 3.93 (d, J = 11.2 Hz, | 31 | (A) 4.6 3799% |

TABLE 1-continued

| structure | name | $^1$H NMR, MS | Yield (%) | HPLC r.t. (min) Purity |
| --- | --- | --- | --- | --- |
| | (4-(4-methyl-thiazole-5-yl)benzyl) pyrrolidine-2-carboxamide | 2H), 3.69-3.56 (m, 5H), 3.33-3.28 (m, 2H), 3.09 (q, J = 7.0 Hz, 2H), 3.04-2.97 (m, 1H) 2.49-2.41 (m, 7H), 2.38 (s, 3H), 2.34 (s, 3H), 2.30-2.23 (m, 3H), 2.19-2.12 (m, 4H), 1.84-1.65 (m, 6H), 1.55-1.49 (m, 1H), 0.97 (s, 9H), 0.89 (t, J = 6.92 Hz, 3H); LCMS [M + H]$^+$ 1179. | | |

TABLE 1-continued

| | structure | name | $^1$H NMR, MS | Yield (%) | HPLC r.t. (min) Purity |
|---|---|---|---|---|---|
| 49 | 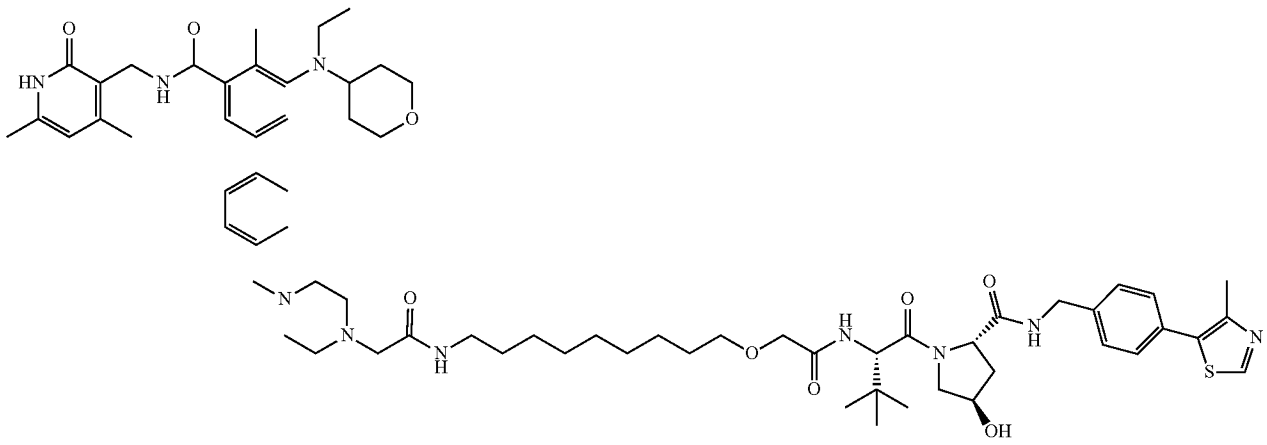 | (2S,4R)-1-((S)-2-(2-((9-(2-(4-((3'-(((4,6-dimethyl-2-oxo-1,2-dihydro-pyridine-3-yl)methyl)carbamoyl)-5'-(ethyl(tetra-hydro-2H-pyran-4-yl)amino)-4'-methyl-[1,1'-biphenyl]-4-yl)methyl)piperazine-1-yl)acetamido)nonyl)oxy)acetamido)-3,3-dimethyl-butanoyl)-4-hydroxy-N-(4-(4-methyl-thiazole-5-yl)benzyl)pyrrolidine-2-carboxamide | $^1$H NMR (400 MHz, $CDCl_3$) δ 10.34 (br s, 1H), 8.68 (s, 1H), 7.50 (t, J = 6.0 Hz, 1H), 7.48-7.43 (m, 2H), 7.37-7.2 9 (m, 7H), 7.26-7.22 (m, 1H), 7.17 (t, J = 6.0 Hz, 1H), 7.08 (t, J = 6.0 Hz, 1H), 5.90 (s, 1H), 4.71 (t, J = 7.9 Hz, 1H), 4.60-4.42 (m, 5H), 4.31 (dd, J = 14.9, 5.2 Hz, 1H), 4.12 (d, J = 11.3 Hz, 1H), 3.99-3.91 (m, 2H), 3.89 (d, J = 4.9 Hz, 2H), 3.67-3.56 (m, 2H), 3.53 (s, 2H), 3.46 (t, J = 6.6 Hz, 2H), 3.38-3.19 (m, 5H), 3.09 (q, J = 6.9 Hz, 2H), 3.05-2.95 | 58 | (B) 3.7 8299% |

TABLE 1-continued

| | structure | name | $^1$H NMR, MS | Yield (%) | HPLC r.t. (min) Purity |
|---|---|---|---|---|---|
| | | | (m, 3H), 2.60-2.43 (m, 11H), 2.41 (s, 3H), 2.35 (s, 3H), 2.19 (s, 3H), 2.12-2.02 (m, 1H), 1.79-1.41 (m, 17H), 1.39-1.31 (m, 2H), 0.92 (d, J = 21.1 Hz, 12H); 1242 [M + H]$^+$ | | |
| 50 | 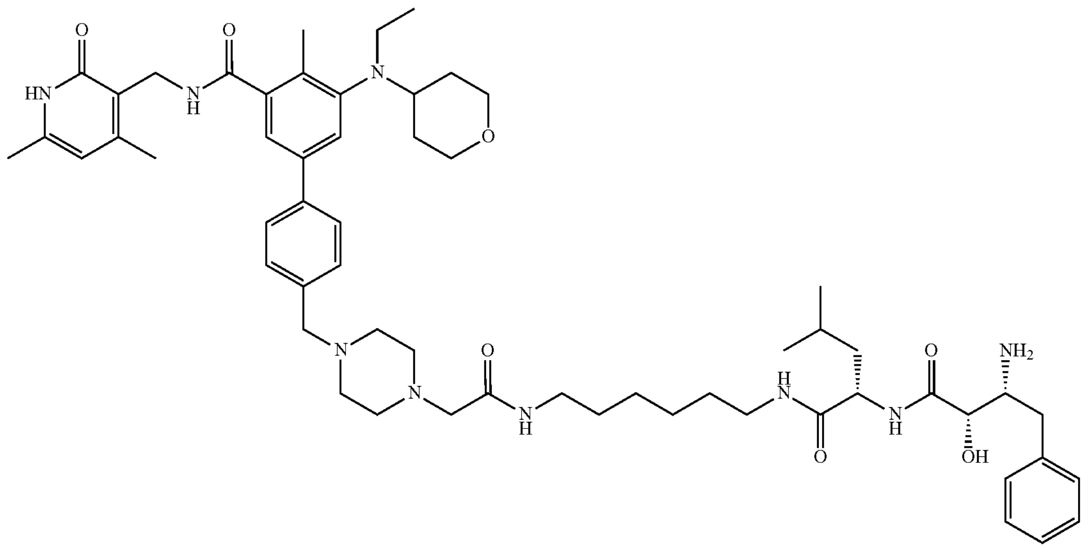 | 4'-((4-(2-((6-((S)-2-((2S,3R)-3-amino-2-hydroxy-4-phenylbutan-amido)-4-methylpentan-amido)hexyl) amino)-2-oxoethyl) piperazine-1-yl)methyl)-N-((4,6-dimethyl-2-oxo-1,2-dihydro-pyridine-3-yl)methyl)-5-(ethyl (tetrahydro-2H-pyran-4-yl)amino)-4-methyl- | $^1$H NMR (400 MHz, $CDCl_3$) δ 11.72 (br-s, 1H), 7.63 (d, J = 8.64 Hz, 1H), 7.43 (d, J = 8.0 Hz, 2H), 7.32-7.27 (m, 5H), 7.21-7.16 (m, 4H), 7.13 (t, J = 5.8 Hz, 1H), 6.79 (t, J = 5.48 Hz, 1H), 5.90 (s, 1H), 4.57-4.43 (m, 3H), 3.99 (d, J = 2.32 Hz, 1H), 3.93 (d, J = | 49 | (A) 4.371, 98% |

TABLE 1-continued

| structure | name | $^1H$ NMR, MS | Yield (%) | HPLC r.t. (min) Purity |
| --- | --- | --- | --- | --- |
| | [1,1'-biphenyl]-3-carboxamide | 11.12 Hz, 2H), 3.54 (s, 2H), 3.51-3.48 (m, 1H), 3.32-3.14 (m, 5H), 3.10-3.05 (m, 3H), 3.04-2.91 (m, 4H), 2.60-2.49 (m, 7H), 2.39 (s, 3H), 2.33 (s, 3H), 2.14 (s, 3H), 1.73-1.54 (m, 7H), 1.44-1.42 (m, 4H), 1.24 (br-s, 6H), 0.90-0.86 (m, 9H); LCMS $[M + H]^+$ 1018. | | |

<Experimental Example 1> Confirmation of Proteolytic Effect in Colorectal Cancer Cells (In Vitro)

In order to confirm the proteolytic effect of the compound represented by formula 1 or formula 2 according to the present invention, the following experiment was performed, and specifically, the proteolytic effect of the compounds of Examples 1-50 on colorectal cancer cells was evaluated.

Particularly, $5\times10^5$ LS174T cells were placed in each 6-well plate, and after 8 hours of stabilization, each well was treated with the example compound at the final concentrations of 25 nM, 50 nM, 100 nM, and 1000 nM. One well was treated with DMSO at the same percentage. After 72 hours of the treatment, the cells were collected and lysed using RIPA buffer (50 mM Tris, pH 7.5, 150 mM NaCl, 1% Triton X-100, 0.1% SDS, mM EDTA, 0.5% deoxycholate, and protease inhibitor cocktail), followed by sonication (30 sec on/30 sec off, 5 cycles) to prepare a cell lysate. Western blotting was performed after the protein quantification through cell lysate BCA using the cell lysate, and the results are shown in table 2.

TABLE 2

| Example | %, degradation at 1 uM | Grade |
|---|---|---|
| 1 | 8.15 | D |
| 2 | 18.10 | D |
| 3 | 13.61 | D |
| 4 | 0 | D |
| 5 | 0 | D |
| 6 | 61.64 | B |
| 7 | 22.74 | D |
| 8 | 2.91 | D |
| 9 | 10.58 | D |
| 10 | 0 | D |
| 11 | 12.87 | D |
| 12 | 16.89 | D |
| 13 | 29.35 | C |
| 14 | 6.21 | D |
| 15 | 0 | D |
| 16 | 5.51 | D |
| 17 | 3.25 | D |
| 18 | 16.74 | D |
| 19 | 9.07 | D |
| 20 | 58.73 | B |
| 21 | 83.09 | A |
| 22 | 0 | D |
| 23 | 1.52 | D |
| 24 | 0 | D |
| 25 | 7.41 | D |
| 26 | 9.54 | D |
| 27 | 2.27 | D |
| 28 | 0 | D |
| 29 | 0 | D |
| 30 | 95.65 | A |
| 31 | 0 | D |
| 32 | 31.67 | C |
| 33 | 80.85 | A |
| 34 | 0 | D |
| 35 | 0 | D |
| 36 | 0 | D |
| 37 | 92.73 | A |
| 38 | 9.97 | D |
| 39 | 0 | D |
| 40 | 0 | D |
| 41 | 8.36 | D |
| 42 | 0 | D |
| 43 | 67.12 | B |
| 44 | 73.57 | B |
| 45 | 76.02 | A |
| 46 | 83.76 | A |
| 47 | 0 | D |
| 48 | 5.74 | D |

TABLE 2-continued

| Example | %, degradation at 1 uM | Grade |
|---|---|---|
| 49 | 96.49 | A |
| 50 | 0 | D |

In Table 2, the grade is the percent value of the protein degradation for each section when treated with 1 μM, and the values for each grade are as follows.

A: >75%, B: 50-75%, C: 25-50%, D: <25%

As shown in table 2, the compounds of the present invention were excellent in the effect of degrading EZH2 protein when treated to colorectal cancer cells. In particular, it was found that the compounds of Examples 21, 30, 33, 37, 45, 48 and 49 exhibit excellent effects.

In addition, as shown in FIGS. 1 to 5, the novel compound according to the present invention is a Degraducer compound that induces degradation of EZH2, the target protein, and significantly induces degradation of the target protein through UPS (Ubiquitin Proteasome System). Therefore, it can be seen that the pharmaceutical composition for preventing or treating EZH2-related diseases or conditions containing the compound as an active ingredient has a preventive or ameliorating effect on the diseases.

<Experimental Example 2> Evaluation of EZH2 Proteolytic Activity Using Nano-BiT Assay System In order to evaluate the EZH2 proteolytic activity of the compound according to the present invention, the following experiment was performed.

Specifically, the CRISPR/Cas9 technique was used to construct a stable cell line of HiBiT-EZH2. After the transfection of EZH2 targeted CRISPR/Cas9 vector and single-stranded oligo-deoxynucleotide (ssODN) containing HiBiT nucleotide sequence into HEK293T cells, cell stabilization was performed for 2-3 days. After harvesting the cells, the cell solution was prepared at a concentration of 1 cell/100 ul, and 100 ul of the cell solution was dispensed into each well of a 96-well plate and seeded so that a single cell could proliferate in each well. After proliferating the cells for 2-3 weeks, some of the proliferated cells from one cell were recovered and gDNA was extracted. To confirm that the HiBiT sequence was correctly inserted into the EZH2 target, deep sequencing was performed to select the cells containing the HiBiT sequence, and after further verification through Sanger sequencing, the final EZH2-HiBiT HEK293T cells were obtained.

Figure 6:
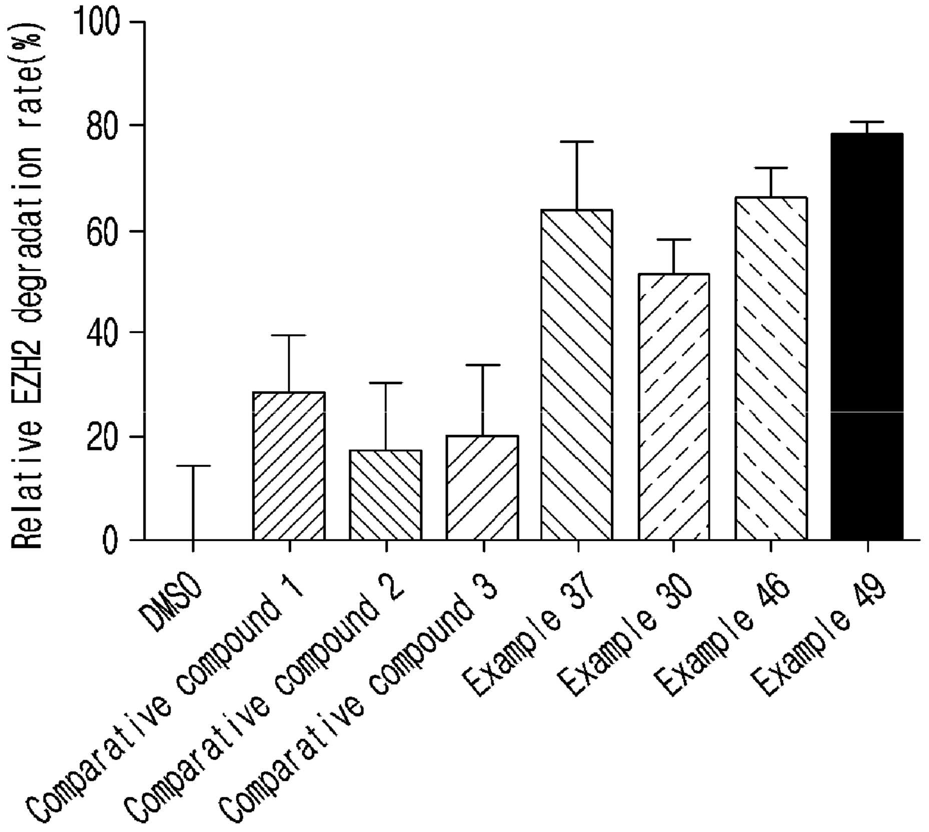
FIG. 6 is a graph evaluating the EZH2 proteolytic activity using Nano-BiT assay system.

$1\times10^3$ of the obtained cells were placed in a 96-well white plate, and after 18 hours of stabilization, each well was treated with the example compound at a final concentration of 1 μM. The control group was treated with the same concentration of DMSO which was used as the solvent of the example compound. After 72 hours of the treatment, an assay was performed using Nano-Glo HiBiT Lytic Detection System (N3040, Promega). After removing the medium, 100 μL of lysis buffer, 1 μL of LgBiT protein and 1 μL of substrate buffer were added to each well. Then, the plate was reacted in a shaking incubator at 700 rpm for 2 minutes, and then the mixture of each well was pipetted to mix well. Thereafter, the plate was reacted at room temperature for 10 minutes while light was blocked, and luminescence was measured. The results are shown in table 3 and FIG. 6.

TABLE 3

| Substance | Relative EZH2 degradation rate, 1 μM(%) Average | Standard Deviation (n = 3) |
|---|---|---|
| DMSO | 0 | 13.8 |
| Comparative compound 1 | 27.8 | 11.2 |
| Comparative compound 2 | 16.2 | 13.9 |
| Comparative compound 3 | 19.2 | 14.6 |
| Example 37 | 62.9 | 13.8 |
| Example 30 | 50.7 | 7.7 |
| Example 46 | 65.8 | 5.9 |
| Example 49 | 77.8 | 2.7 |

As shown in table 3, the example compounds of the present invention (Examples 37, 30, 46 and 49) exhibited significantly better EZH2 proteolytic ability compared to comparative compound 1

(
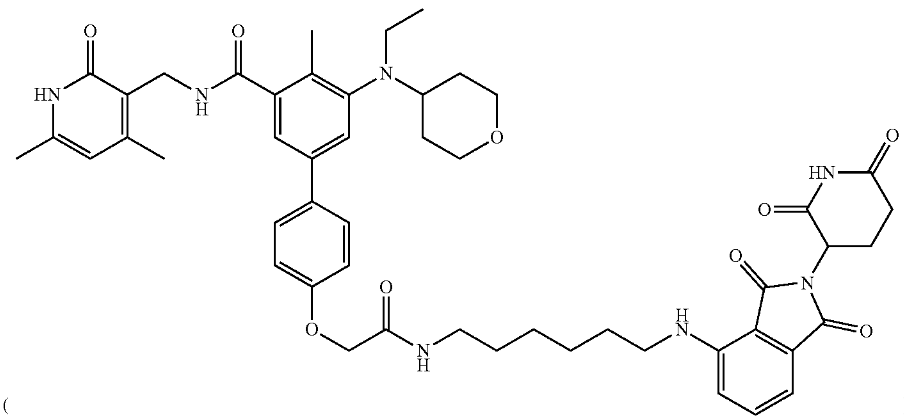
), comparative compound 2

(
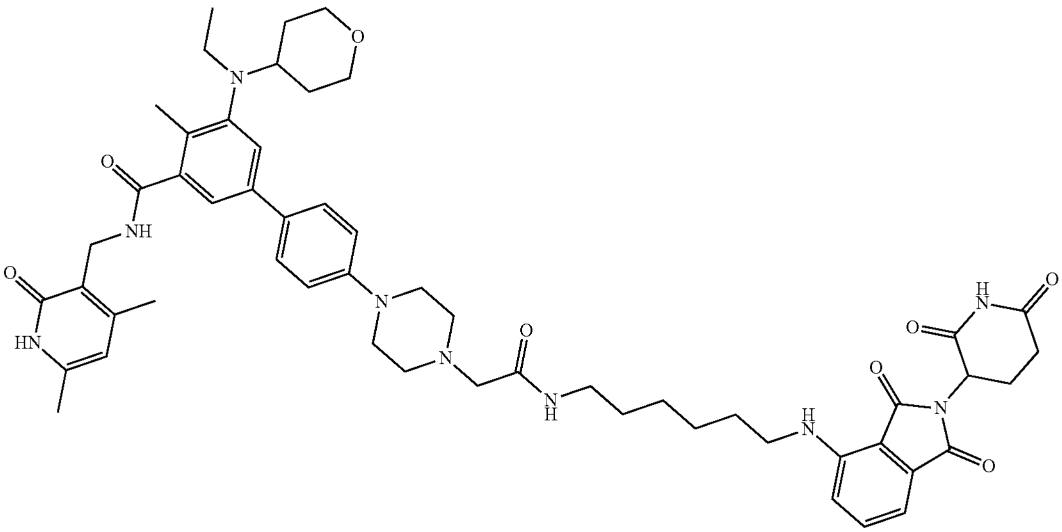
), and comparative compound 3

(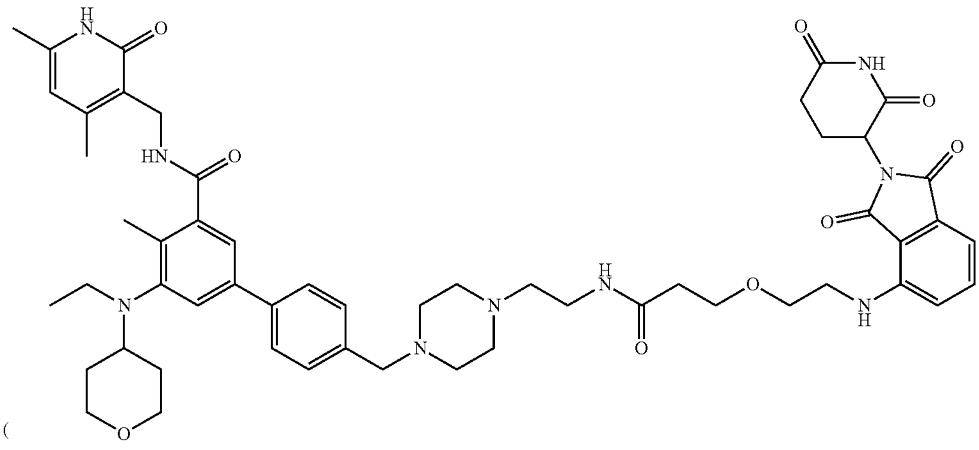), the EZH2 proteolytic PROTAC patented substances of other companies. Therefore, it was confirmed that the example compounds according to the present invention have EZH2 proteolytic activity, and can be effectively used for the treatment of EZH2-related diseases and cancers, in particular, cancers in which EZH2 is overexpressed.

What is claimed is:

1. A compound represented by Formula 2, a stereoisomer thereof, a solvate thereof, a hydrate thereof or a pharmaceutically acceptable salt thereof:

[Formula 2]

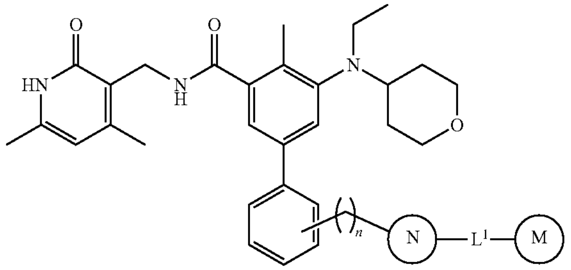

wherein in Formula 2:

n is an integer of 1;

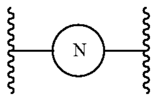

is

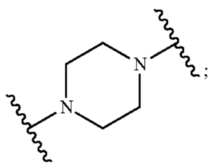 [SMILES: *N1CCN(*)CC1];

$L^1$ is

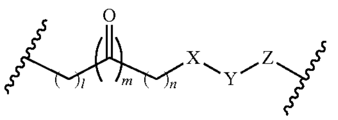

or

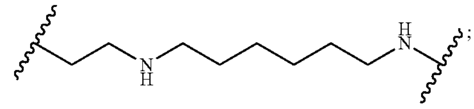 [SMILES: *CCNCCCCCCN*];

and

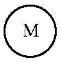

is

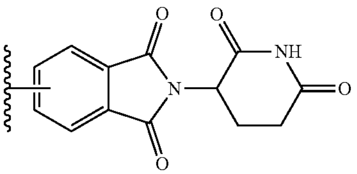 or

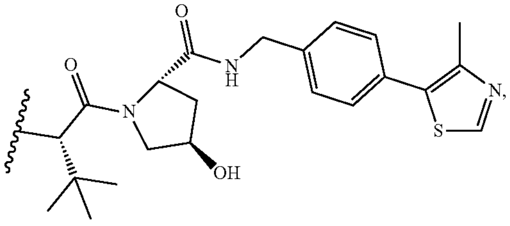, wherein in $L^1$:

l is 1, m is 1, and n is 0;

X is —NH— or

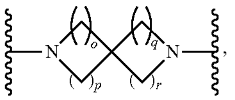

wherein each of o, p, q and r is 2;

Y is unsubstituted or oxo-substituted $C_{9-12}$ alkylene, wherein the carbon of alkylene can be substituted with —O—, when X is —NH—, or Y is unsubstituted or oxo-substituted $C_{2-4}$ alkylene, wherein the carbon of alkylene can be substituted with —O—, when X is

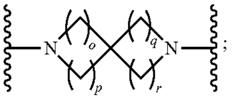

and

Z is —NH—.

2. The compound, the stereoisomer thereof, the solvate thereof, the hydrate thereof or the pharmaceutically acceptable salt thereof according to claim 1, wherein $L^1$ is

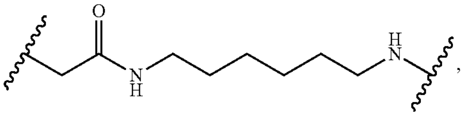

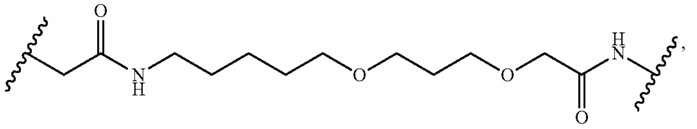 [SMILES: *CC(=O)NCCCCCCCCCOCC(=O)N*]

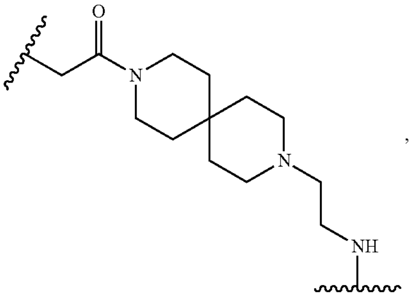

,

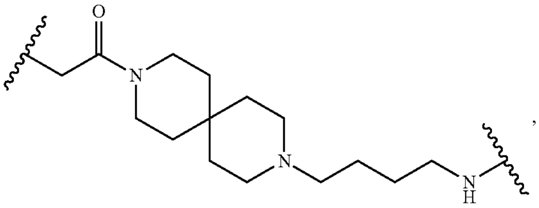

,

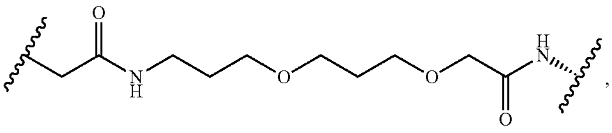

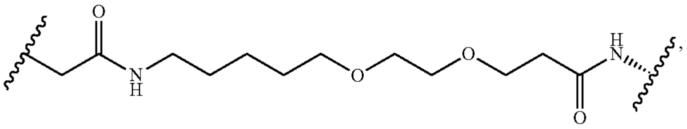

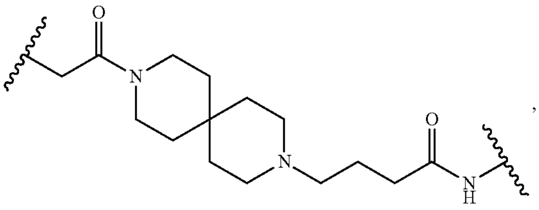

,

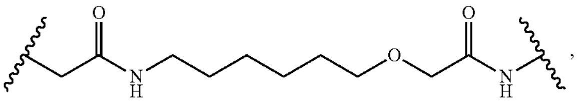

, or

-continued

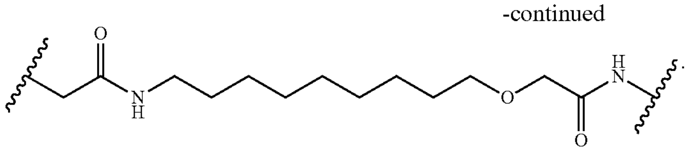

3. The compound, the stereoisomer thereof, the solvate thereof, the hydrate thereof or the pharmaceutically acceptable salt thereof according to claim 1, wherein the compound represented by Formula 2 is

(21) N-((4,6-dimethyl-2-oxo-1,2-dihydropyridine-3-yl)methyl)-4'-((4-(2-((6-((2-(2,6-dioxopiperidine-3-yl)-1,3-dioxoisoindoline-4-yl)amino)hexyl)amino)ethyl)piperazine-1-yl)methyl)-5-(ethyl(tetrahydro-2H-pyran-4-yl)amino)-4-methyl-[1,1'-biphenyl]-3-carboxamide,

(30) N-((4,6-dimethyl-2-oxo-1,2-dihydropyridine-3-yl)methyl)-4'-((4-(2-(9-(2-((2-(2,6-dioxopiperidine-3-yl)-1,3-dioxoisoindoline-4-yl)amino)ethyl)-3,9-diazaspiro[5.5]undecane-3-yl)-2-oxoethyl)piperazine-1-yl)methyl)-5-(ethyl(tetrahydro-2H-pyran-4-yl)amino)-4-methyl-[1,1'-biphenyl]-3-carboxamide,

(33) N-((4,6-dimethyl-2-oxo-1,2-dihydropyridine-3-yl)methyl)-4'-((4-(2-(9-(4-((2-(2,6-dioxopiperidine-3-yl)-1,3-dioxoisoindoline-4-yl)amino)butyl)-3,9-diazaspiro[5.5]undecane-3-yl)-2-oxoethyl)piperazine-1-yl)methyl)-5-(ethyl(tetrahydro-2H-pyran-4-yl)amino)-4-methyl-[1,1'-biphenyl]-3-carboxamide,

(37) (2S,4R)-1-((S)-2-(tert-butyl)-18-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-biphenyl]-4-yl)methyl)piperazine-1-yl)-4,17-dioxo-6,10-dioxa-3,16-diazaoctadecanoyl)-4-hydroxy-N-(4-(4-methylthiazole-5-yl)benzyl)pyrrolidine-2-carboxamide,

(44) (2S,4R)-1-((S)-2-(tert-butyl)-18-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-biphenyl]-4-yl)methyl)piperazine-1-yl)-4,17-dioxo-7,10-dioxa-3,16-diazaoctadecanoyl)-4-hydroxy-N-(4-(4-methylthiazole-5-yl)benzyl)pyrrolidine-2-carboxamide,

(45) (2S,4R)-1-((S)-2-(4-(9-(2-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-biphenyl]-4-yl)methyl)piperazine-1-yl)acetyl)-3,9-diazaspiro[5.5]undecane-3-yl)butanamido)-3,3-dimethylbutanoyl)-4-hydroxy-N-(4-(4-methylthiazole-5-yl)benzyl)pyrrolidine-2-carboxamide

(46) (2S,4R)-1-((S)-2-(2-((6-(2-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-biphenyl]-4-yl)methyl)piperazine-1-yl)acetamido)hexyl)oxy)acetamido)-3,3-dimethylbutanoyl)-4-hydroxy-N-(4-(4-methylthiazole-5-yl)benzyl)pyrrolidine-2-carboxamide, or

(49) (2S,4R)-1-((S)-2-(2-((9-(2-(4-((3'-(((4,6-dimethyl-2-oxo-1,2-dihydropyridine-3-yl)methyl)carbamoyl)-5'-(ethyl(tetrahydro-2H-pyran-4-yl)amino)-4'-methyl-[1,1'-biphenyl]-4-yl)methyl)piperazine-1-yl)acetamido)nonyl)oxy)acetamido)-3,3-dimethylbutanoyl)-4-hydroxy-N-(4-(4-methylthiazole-5-yl)benzyl)pyrrolidine-2-carboxamide.

4. A method for treating cancer comprising administering a compound represented by Formula 2 of claim 1, a stereoisomer thereof, a solvate thereof, a hydrate thereof or a pharmaceutically acceptable salt thereof to a subject in need thereof, wherein the cancer is a cancer in which EZH2 is overexpressed.

5. The method for treating cancer according to claim 4, wherein the cancer is at least one selected from pseudomyxoma, intrahepatic biliary tract cancer, hepatoblastoma, liver cancer, thyroid cancer, colon cancer, testis cancer, myelodysplastic syndrome, glioblastoma, oral cancer, lib cancer, mycosis fungoides, acute myeloid leukemia, acute lymphoid leukemia, basal cell carcinoma, ovarian epithelial cancer, ovarian germ cell cancer, male breast cancer, brain cancer, pituitary adenoma, multiple myeloma, gallbladder cancer, biliary tract cancer, colorectal cancer, chronic myelogenous leukemia, chronic lymphocytic leukemia, retinoblastoma, choroidal melanoma, ampullar of vater cancer, bladder cancer, peritoneal cancer, parathyroid cancer, adrenal cancer, nasal cavity cancer, non-small cell lung cancer, tongue cancer, astrocytoma, small cell lung cancer, pediatric brain cancer, pediatric lymphoma, pediatric leukemia, small intestine cancer, meningioma, esophageal cancer, glioma, renal pelvic cancer, kidney cancer, heart cancer, duodenal cancer, malignant soft tissue cancer, malignant bone cancer, malignant lymphoma, malignant mesothelioma, malignant melanoma, eye cancer, vulvar cancer, ureteral cancer, urethral cancer, primary site unknown cancer, gastric lymphoma, stomach cancer, gastric carcinoid tumor, gastrointestinal stromal tumor, Wilms cancer, breast cancer, sarcoma, penile cancer, pharyngeal cancer, gestational trophoblastic disease, cervical cancer, endometrial cancer, uterine sarcoma, prostate cancer, metastatic bone cancer, metastatic brain cancer, mediastinal cancer, rectal cancer, rectal carcinoma, vaginal cancer, spinal cord cancer, acoustic tumor, pancreatic cancer, salivary gland cancer, Kaposi's sarcoma, Paget's disease, tonsil cancer, squamous cell carcinoma, lung adenocarcinoma, lung cancer, lung squamous cell carcinoma, skin cancer, anal cancer, rhabdomyosarcoma, laryngeal cancer, pleura cancer, blood cancer and thymus cancer.

6. The method for treating cancer according to claim 4, wherein the compound represented by Formula 2 selectively degrades EZH2.

7. A method for selectively degrading EZH2 protein comprising administering a compound represented by Formula 2 of claim 1, a stereoisomer thereof, a solvate thereof, a hydrate thereof or a pharmaceutically acceptable salt thereof to a subject in need thereof.

* * * * *